US011160488B2

(12) United States Patent
Neitz et al.

(10) Patent No.: US 11,160,488 B2
(45) Date of Patent: Nov. 2, 2021

(54) REAGENTS AND METHODS FOR MODULATING CONE PHOTORECEPTOR ACTIVITY

(71) Applicants: UNIVERSITY OF WASHINGTON, Seattle, WA (US); UNIVERSITY OF FLORIDA RESEARCH FOUNDATION, INCORPORATED, Gainesville, FL (US)

(72) Inventors: Jay Neitz, Seattle, WA (US); Maureen Neitz, Seattle, WA (US); James A. Kuchenbecker, Seattle, WA (US); William W. Hauswirth, Gainesville, FL (US)

(73) Assignees: Universty of Washington, Seattle, WA (US); University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/939,674

(22) Filed: Mar. 29, 2018

(65) Prior Publication Data
US 2018/0344197 A1 Dec. 6, 2018

Related U.S. Application Data

(63) Continuation of application No. 14/837,448, filed on Aug. 27, 2015, now abandoned, which is a continuation of application No. 14/075,415, filed on Nov. 8, 2013, now Pat. No. 9,198,595, which is a continuation of application No. 13/395,609, filed as application No. PCT/US2010/048964 on Sep. 15, 2010, now abandoned.

(60) Provisional application No. 61/242,587, filed on Sep. 15, 2009.

(51) Int. Cl.
| *A61B 5/0496* | (2006.01) |
| *C12N 7/00* | (2006.01) |
| *C12N 15/86* | (2006.01) |
| *A61B 5/00* | (2006.01) |
| *C12N 15/85* | (2006.01) |
| *A61N 5/06* | (2006.01) |
| *A61K 48/00* | (2006.01) |
| *C07K 14/005* | (2006.01) |
| *A61B 5/398* | (2021.01) |

(52) U.S. Cl.
CPC ............ *A61B 5/398* (2021.01); *A61B 5/0036* (2018.08); *A61B 5/0048* (2013.01); *A61B 5/4836* (2013.01); *A61B 5/4848* (2013.01); *A61B 5/6821* (2013.01); *A61B 5/7225* (2013.01); *A61K 48/0058* (2013.01); *A61K 48/0075* (2013.01); *A61N 5/0622* (2013.01); *C07K 14/005* (2013.01); *C12N 7/00* (2013.01); *C12N 15/85* (2013.01); *C12N 15/86* (2013.01); *A61N 2005/0652* (2013.01); *A61N 2005/0661* (2013.01); *A61N 2005/0663* (2013.01); *C12N 2750/14132* (2013.01); *C12N 2750/14143* (2013.01); *C12N 2799/025* (2013.01); *C12N 2830/008* (2013.01); *C12N 2830/42* (2013.01); *C12N 2840/44* (2013.01)

(58) Field of Classification Search
None
See application file for complete search history.

(56) References Cited

U.S. PATENT DOCUMENTS

| 4,874,237 | A | 10/1989 | Cringle |
| 5,436,146 | A | 7/1995 | Shenk et al. |
| 5,753,500 | A | 5/1998 | Shenk et al. |
| 6,040,183 | A | 3/2000 | Ferrari et al. |
| 6,093,570 | A | 7/2000 | Ferrari et al. |
| 6,153,436 | A | 11/2000 | Hermonat et al. |
| 6,482,634 | B1 | 11/2002 | Wilson et al. |
| 6,548,286 | B1 | 4/2003 | Samulski et al. |
| 7,972,278 | B2 | 7/2011 | Graham et al. |
| 8,075,137 | B2 | 12/2011 | Klistorner et al. |
| 8,118,752 | B2 | 2/2012 | Hetling et al. |
| 8,343,067 | B2 | 1/2013 | Jones et al. |
| 9,198,595 | B2 | 12/2015 | Neitz et al. |
| 2002/0168342 | A1 | 11/2002 | Wang et al. |
| 2007/0188710 | A1 | 8/2007 | Hetling et al. |
| 2009/0128776 | A1 | 5/2009 | Keating et al. |
| 2010/0091242 | A1 | 4/2010 | Baglini et al. |
| 2011/0001465 | A1 | 1/2011 | Sung et al. |
| 2011/0116046 | A1 | 5/2011 | Haeri et al. |
| 2012/0172419 | A1 | 7/2012 | Neitz et al. |
| 2013/0031709 | A1 | 2/2013 | Chen et al. |
| 2015/0025939 | A1 | 9/2015 | Chalberg et al. |

FOREIGN PATENT DOCUMENTS

| JP | 2002363107 A | 12/2002 |
| WO | 02/082904 | 10/2002 |
| WO | 2015/142941 A1 | 9/2015 |

OTHER PUBLICATIONS

Alexander et al. Nat. Med. 2007, 13(6)685-687.*
Michaelides et al, Eye 2005, 19:2-10).*
Mancuso, et al., (2005) Annual Meeting of the Association for Research in Vision and Ophthalmology, Ft. Lauderdale, FL, 46 (Supp S): 4565.
Mancuso, et al. (2007) Journal of Optical Society of America A: Optics and Image Science and Vision, 24(5):1411-1416.
Mauck, et al. (2008) Visual Neuroscience, 25(3):273-282.
Li, et al. (2008) Cone-specific expression using a human red opsin promoter in recombinant AAV, Vision Research, 48(3):332-338.

(Continued)

*Primary Examiner* — James D Schultz
(74) *Attorney, Agent, or Firm* — McDonnell Boehner Hulbert & Berghoff LLP

(57) ABSTRACT

The present invention provides reagents and methods for modulating cone photoreceptor activity, and devices for assessment of cone photoreceptor activity.

5 Claims, 8 Drawing Sheets

Specification includes a Sequence Listing.

(56) References Cited

OTHER PUBLICATIONS

Kuchenbecker, et al. (2008) Visual Neurosceince, 25 (3): 301-306.
Cai, et al., (2010) FASEB Journal, 24(4): 1178-1191.
Komaromy, et al. (2010) Human Molecular Genetics, 19(13): 2581-2593.
Mancuso, et al., (2009) Nature, 461(7265): 784.
Pang, et al. (2006) Molecular Therapy, 13(3): 565-572.
Lai, et al. (2007) Survey of ophthalmology, 52(1): 61-96.
Sutter, E. E. (1991). The Fast m-Transform: A Fast Computation of Cross-Correlations with Binary m-Sequences. SIAM Journal on Computing, 20(4),686-694.
Swanson, W. H., Ueno, T., Smith, V. C., & Pokorny, J. (1987). Temporal modulation sensitivity and pulse-detection thresholds for chromatic and luminance perturbations. Journal of the Optical Society of America A-Optics, Image Science and Vision, 4(10), 13.
Lindenberg, T., Horn, F. K., & Korth, M. (2003). Cyclic summation versus m-sequence technique in the multifocal ERG. Graefes Archive of Clinical Experimental Ophthalmology , 241(6),505-510.
Wiesel, T.N. & Hubel, D.H. Single-cell responses in striate cortex of kittens deprived of vision in one eye. J Neurophysiol. 26, 1003-1017 (1963).
Jacobs, G.H. A perspective on color vision in platyrrhine monkeys. Vision Res. 38, 3307-3313 (1998).
Reffin, J.P., Astell, S. & Mollon, J.D. Trials of a computer-controlled colour vision test that preserves the advantages of pseudo-isochromatic plates, in Colour Vision Deficiencies X69-76 (Kluwer Academic Publishers, Dordrecht, 1991).
Regan, B.C., Reffin, J.P. & Mollon, J.D. Luminance noise and the rapid determination of discrimination ellipses in colour deficiency. Vision Res. 34, 1279-1299 (1994).
Mancuso, K., Neitz, M. & Neitz, J. An adaptation of the Cambridge Colour Test for use with animals. Vis. Neurosci. (2006).
Nathans, J., Piantanida, T.P., Eddy, R.L., Shows, T.B. & Hogness, D.S. Molecular genetics of inherited variation in human color vision. Science 232, 203-210 (1986).
Shapley, R. Specificity of cone connections in the retina and color vision. Focus on "Specificity of cone inputs to macaque retinal ganglion cells". J Neurophysiol. 95, 587-588 (2006).
DeValois, R.L. & DeValois, K.K. A multi-stage color model. Vision Res. 33, 1053-1065 (1993).
Jacobs, G.H., Williams, G.A., Cahill, H. & Nathans, J. Emergence of Novel Color Vision in Mice Engineered to Express a Human Cone Photopigment. Science 315, 1723-1725 (2007).
Makous, W. Comment on "Emergence of Novel Color Vision in Mice Engineered to Express a Human Cone Photopigment". Science 318, 196 (2007).
Maguire, A.M. et al. Safety and efficacy of gene transfer for Leber's congenital amaurosis. N. Engl. J Med. 358, 2240-2248 (2008).

Bainbridge, J.W. & Ali, R.R. Success in sight: The eyes have it! Ocular gene therapy trials for LCA look promising. Gene Ther. 15, 1191-1192 (2008).
Cideciyan, A.V. et al. Human gene therapy for RPE65 isomerase deficiency activates the retinoid cycle of vision but with slow rod kinetics. Proc. Natl. Acad. Sci. USA 105, 15112-15117 (2008).
Wang, Y. et al. A locus control region adjacent to the human red and green visual pigment genes. Neuron 9, 429-440 (1992).
Nathans, J., Thomas, D. & Hogness, D.S. Molecular genetics of human color vision: the genes encoding blue, green, and red pigments. Science 232, 193-202 (1986).
Neitz, M., Neitz, J. & Jacobs, G.H. Spectral tuning of pigments underlying red green color vision. Science 252, 971-974 (1991).
Buning, H., Perabo, L., Coutelle, 0., Quadt-Humme, S. & Hallek, M. Recent developments in adeno-associated virus vector technology. J Gene Med. 10, 717-733 (2008).
ISR PCT/US2010/048964, dated Jun. 17, 2011.
Mauck, et al. "Longitudinal in vivo Characterization of Expression of Viral Delivered Genes for L-opsin and Green Fluorescent Protein in Cone Photoreceptors of Gerbils," Invest Opthalmol Vis Sci 2006, 47:E-abstract 4071.
Mancuso, et al., "Colorblindness Cure: Gene Therapy Confers a New Sensation," Invest Opthalmol Vis Sci 2008,49: E-abstract 3252.
International Search Report for PCT/US15/21087, dated Aug. 12, 2015.
Written Opinion of the International Search Authority for PCT/US15/21087, dated Aug. 12, 2015.
Alexander et al. (2007) "Restoration of cone vision in a mouse model of achromatopsia" Nature Medicine 13:685-687 [published online May 2007].
Chiu et al. (1994) "Blue cones and cone bipolar cells share transcriptional specificity as determined by expression of human blue visual pigment-derived transgenes" J. Neurosci. 14(6):3426-3436.
Glushakova et al. (2006) "Human Blue-Opsin Promoter Preferentially Targets Reporter Gene Expression to Rat S-Cone Photoreceptors" Invest. Opthalmol. Vis. Sci. 47:3505-3513.
Gunther et al. (2006) "A novel mutation in the short-wavelength-sensitive cone pigment gene associated with a tritan color vision defect" Vis. Neurosci. 23(3-4):403-409.
Komaromy et al. (2008) "Targeting gene expression to cones with human cone opsin promoters in recombinant AAV" Gene Therapy 15:1049-1055 [published online Mar. 13, 2008].
Shaaban et al. (1998) "Transgenic Mice Expressing a Functional Human Photopigment" Invest. Ophthalmol. Vis. Sci. 39:1036-1043.
Ueyama et al. (2009) "Analysis of introns and promoters of L/M visual pigment genes in relation to deutan color-vision deficiency with an array of normal gene orders" J. Hum. Genet. 54(9):525-530.
Khani et al., Inv. Opth. Vis. Sci. (2007) vol. 48(9), pp. 3954-3961.
Mancuso et al., 2007, [Abstract] Journal of Vision, vol. 7(15): 15a.

* cited by examiner a b c d e f

Figure 6

|  |  | Typical SNR | Highest SNR |
|---|---|---|---|
| GRN | Ring 2 | 82.98129 | 139.6429 |
|  | Ring 3 | 34.42575 | 47.00658 |
|  | Ring 4 | 33.5582 | 49.9321 |
| RED | Ring 2 | 47.16825 | 87.55556 |
|  | Ring 3 | 20.84694 | 34.38312 |
|  | Ring 4 | 16.75357 | 20.45714 |

REAGENTS AND METHODS FOR MODULATING CONE PHOTORECEPTOR ACTIVITY

RELATED APPLICATIONS

This application is a Continuation of U.S. patent application Ser. No. 14/837,448 filed Aug. 27, 2015, which is a continuation of U.S. patent application Ser. No. 14/075,415 filed Nov. 8, 2013 now U.S. Patent No. 9198595 issued Dec. 1, 2015, which is a continuation of U.S. patent application Ser. No. 13/395,609 filed Mar. 12, 2012, which is a U.S. National Phase of International Application No. PCT/US2010/048964, filed Sep. 15, 2010, which claims priority to U.S. Provisional Application No. 61/242,587, filed Sep. 15, 2009, the disclosures of which are hereby incorporated by reference in their entireties.

STATEMENT OF U.S. GOVERNMENT SUPPORT

This work was supported by the National Institutes of Health grants R01EY016861, R01EY11123, and P30EY01730. The U.S. government has certain rights in the invention.

BACKGROUND

Classic visual deprivation experiments have led to the expectation that neural connections established during development would not appropriately process an input that was not present from birth. Therefore, it was believed that treatment of congenital vision disorders would be ineffective unless administered to the very young.

SUMMARY OF THE INVENTION

In a first aspect, the present invention provides methods for cone cell gene therapy in a primate, comprising administering to the eye of a primate in need of cone cell gene therapy a recombinant gene delivery vector comprising:
(a) a promoter region, wherein the promoter region is specific for retinal cone cells; and
(b) a gene encoding a therapeutic, wherein the gene is operatively linked to the promoter region;
wherein in vivo expression of the therapeutic in cone cells of the primate serves to treat the primate in need of cone cell gene therapy.

The method of this aspect of the invention can be used, for example, to treat a cone cell disorder, including but not limited to color blindness, blue cone monochomacy, achromatopsia, incomplete achromatopsia, rod-cone degeneration, retinitis pigmentosa (RP), macular degeneration, cone dystrophy, blindness, Stargardt's Disease, and Leber's congenital amaurosis. In one embodiment, the methods restore visual capacity in the primate; in another embodiment, the primate is able to visualize new colors as a result of the therapy. In another embodiment, the primate has a vision disorder in which its photoreceptors are healthy. In a further embodiment, the primate is an adult primate.

In another aspect, the present invention provides isolated nucleic acid expression vector comprising:
(a) a promoter region, wherein the promoter region is specific for primate retinal cone cells; and
(b) a gene encoding a therapeutic, wherein the gene is operatively linked to the promoter region. In various embodiments, the vectors further comprise an enhancer element upstream of the promoter, wherein the gene is operatively linked to the enhancer element, and/or an intron comprising a splice donor/acceptor region, wherein the intron is located downstream of the promoter region and is located upstream of the gene. The vectors can be used, for example, in the methods of the invention.

In another aspect, the present invention provides color multi-focal electroretinogram (mf-ERG) comprising:
(a) an electroretinogram (ERG) comprising
 (i) a recording electrode that is (A) designed for placement on at least one of a cornea and a sclera of at least one eye of a subject and (B) arranged to output at least one signal generated by the at least one eye; and
 (ii) a computing system communicatively coupled to the recording electrode, the computing system comprising (A) at least one processor and (B) data storage containing instructions executable by the at least one processor to carry out a set of functions, the set of functions including processing and saving the at least one signal generated by the at least one eye;
(b) a retinal stimulator comprising matched light sources selected from the group consisting of red, green, blue, and ultraviolet light sources, wherein the matched light sources are connected to the ERG and in operation can be independently frequency modulated at rates between about 1 Hz and about 60 Hz, inclusive, wherein the stimulator in operation is capable of stimulating a retinal field of a subject throughout an operating radius of at least about 70 degrees;
(c) one or more constant current integrated circuit chips arranged to drive the stimulator; and
(d) a pulse-frequency modulator connected to the retinal stimulator, wherein in operation the pulse-frequency modulator is capable of controlling individual stimulator segments while keeping relative spectral content of the light constant. In various preferred embodiments, the matched light sources are paired red and green light sources; triplets of red, green, and blue light sources; or quartets of red, green, blue, and ultraviolet light sources. In another preferred embodiment the retinal stimulator comprises a concave surface comprising a series of trapezoidal-shaped circuit boards placed edge-to-edge, wherein the concave surface positions the matched light sources so in operation they are held equidistantly from and pointing toward a single focal point where a subject's pupil can be positioned.

BRIEF DESCRIPTION OF THE FIGURES

FIG. 6. The signal to noise ratio (SNR) for as a function of degrees of eccentricity for a typical (averaged) subject and for the highest subject recorded.

DETAILED DESCRIPTION OF THE INVENTION

Figure 1:
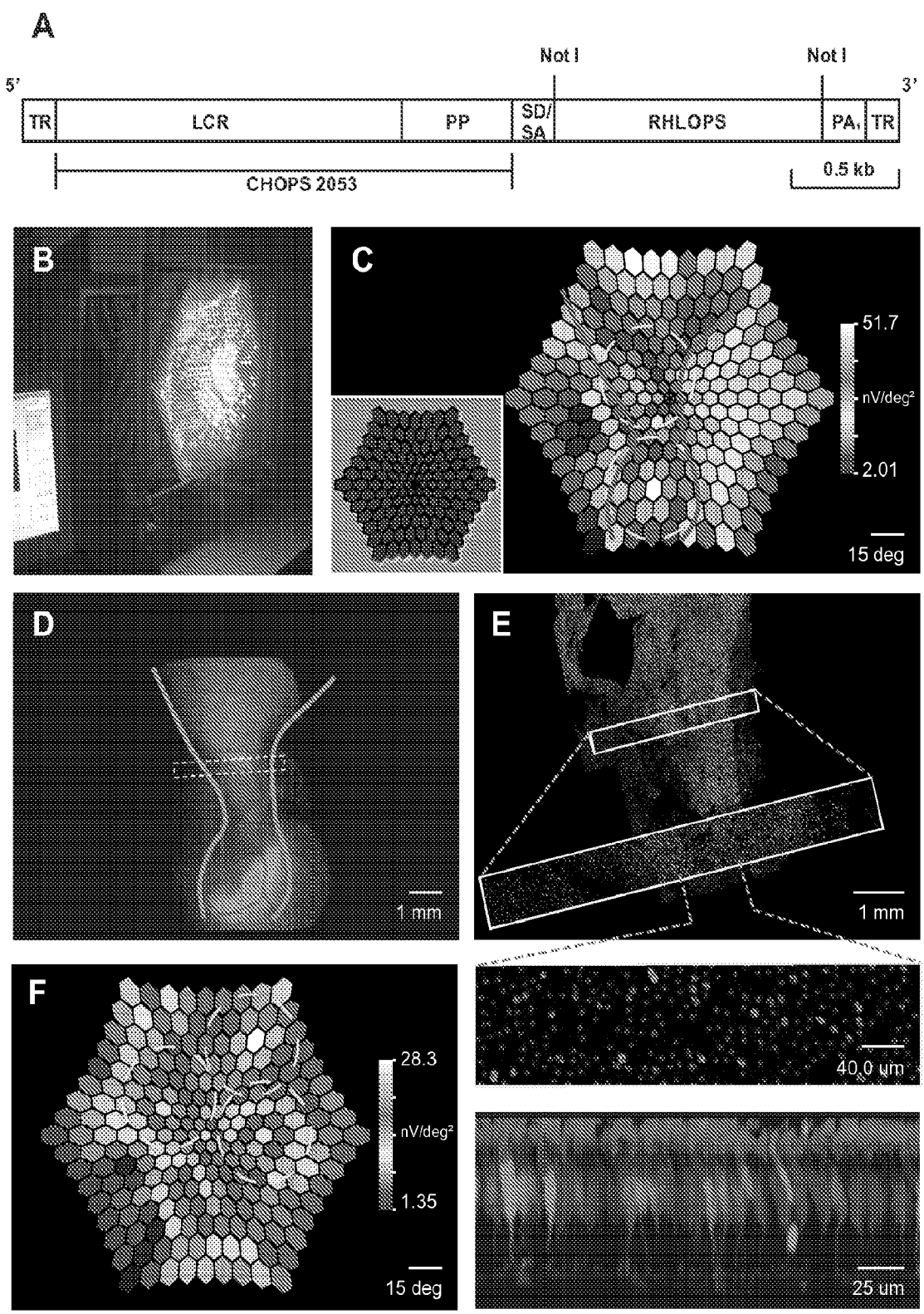
FIG. 1. rAAV2/5 vector produced functional L-opsin in primate retina. a) Molecular map; TR=terminal repeats; LCR=locus control region; PP=proximal promoter; SD/SA=splice donor/acceptor; RHLOPS=recombinant human L opsin cDNA; $PA_1$=polyadenylation signal. b) Red light Multi-focal electroretinogram (Mf-ERG) stimulus. c) mf-ERG 40 weeks after two injections (yellow circles) of a mixture of L-opsin- and green fluorescent protein (GFP)-coding viruses. Grey lines show borders of highest response; for comparison, inset=mfERG 16 weeks post-injection; there was no reliable signal from L-opsin, unchanged from baseline. High responses in far peripheral retina were measured reliably and may have originated from offshoot of one of the injections. d) Fluorescence photographs from a similar retinal area as c; grey lines from c were copied in d. e) Confocal microscopy revealed a mosaic pattern of GFP expression in 5-12% of cones. Because GFP-coding virus was diluted to ⅓ compared to L-opsin virus, an estimated 15-36% of cones in behaviourally tested animals express L-opsin. f) Mf-ERG from a behaviourally tested animal 70 weeks after 3 injections of L-opsin virus.

In a first aspect, the present invention provides methods for cone cell gene therapy in a primate, comprising administering to the eye of a primate in need of cone cell gene therapy a recombinant gene delivery vector comprising:

(a) a promoter region, wherein the promoter region is specific for retinal cone cells; and (b) a gene encoding a therapeutic, wherein the gene is operatively linked to the promoter region;

wherein in vivo expression of the therapeutic in cone cells of the primate serves to treat the primate in need of cone cell gene therapy.

Cone cells are photoreceptor cells in the retina of the eye that function best in relatively bright light. The cone cells gradually become sparser towards the periphery of the retina. The methods of the present invention can be used for treatment of any condition that can be addressed, at least in part, by gene therapy of retinal cone photoreceptor cells. The inventors have demonstrated effective treatment of congenital vision disorders in adult primates, a result that is completely unexpected in the art.

In one preferred embodiment, the gene therapy serves to treat a cone cell disorder. As used herein, a "cone cell disorder" is any disorder impacting retinal cone cells, including but not limited to color blindness, blue cone monochomacy, achromatopsia, incomplete achromatopsia, rod-cone degeneration, retinitis pigmentosa (RP), macular degeneration, cone dystrophy, blindness, Stargardt's Disease, and Leber's congenital amaurosis.

The gene encoding a therapeutic to be expressed in the cone cells can comprise or consist of any gene or cDNA that encodes a polypeptide or RNA-based therapeutic (siRNA, antisense, ribozyme, shRNA, etc.) that can be used as a therapeutic for treating a cone cell disorder. In a preferred embodiment, the primate is of the Parvorder Catarrhini. As is known in the art, Catarrhini is one of the two subdivisions of the higher primates (the other being the New World monkeys), and includes Old World monkeys and the apes, which in turn are further divided into the lesser apes or gibbons and the great apes, consisting of the orangutans, gorillas, chimpanzees, bonobos, and humans. In a further preferred embodiment, the primate is a human.

A "promoter" is a DNA sequence that directs the binding of RNA polymerase and thereby promotes RNA synthesis, i.e., a minimal sequence sufficient to direct transcription. Any suitable promoter region can be used in the gene therapy vectors, so long as it specifically promotes expression of the gene in retinal cone cells. In a preferred embodiment, the promoter specifically promotes expression of the gene in primate retinal cone cells; more preferably in Catarrhini retinal cone cells; even more preferably in human retinal cone cells. As used herein, "specifically" means that the promoter predominately promotes expression of the gene in retinal cone cells compared to other cell types, such that at least 80%, and preferably 85%, 90%, 91%, 92%, 93%, 94%, 95%, 96%, 97%, 97%, 98%, 99%, 99.5%, or more of expression of the gene after delivery of the vector to the eye will be in cone cells. Exemplary suitable promoter regions include the promoter region for any cone-specific gene, such as the L opsin promoter (SEQ ID NO:1), the M opsin promoter (SEQ ID NO:2), and the S opsin promoter (SEQ ID NO:3), or portions thereof suitable to promote expression in a cone-specific manner. Any suitable method for identifying promoter sequences capable of driving expression in primate cone cells can be used to identify such promoters, as will be understood by those of skill in the art based on the teachings herein.

In a preferred embodiment, the gene delivery vector further comprises an enhancer element upstream of the promoter, wherein the gene is operatively linked to the enhancer element. Enhancers are cis-acting elements that stimulate transcription of adjacent genes. Any suitable enhancer element can be used in the gene therapy vectors, so long as it enhances expression of the gene when used in combination with the promoter. In a preferred embodiment, the enhancer element is specific for retinal cone cells; more preferably, it is specific for primate retinal cone cells; more preferably in Catarrhini retinal cone cells; even more preferably in human retinal cone cells. As used herein, "specifically" means that the enhancer predominately enhances expression of the gene in retinal cone cells compared to other cell types, such that at least 80%, and preferably 85%, 90%, 91%, 92%, 93%, 94%, 95%, 96%, 97%, 97%, 98%, 99%, 99.5%, or more of expression of the gene after delivery of the vector to the eye will be in cone cells. Exemplary suitable enhancer regions comprise or consist of the enhancer region for any cone-specific gene, such as the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO:4), or other portions thereof suitable to promote expression in a cone-specific manner. Any suitable method for identifying enhancer sequences capable of driving expression in primate cone cells can be used to identify such enhancers, as will be understood by those of skill in the art based on the teachings herein.

The length of the promoter and enhancer regions can be of any suitable length for their intended purpose, and the spacing between the promoter and enhancer regions can be any suitable spacing to promote cone-specific expression of the gene product. In various preferred embodiments, the enhancer is located 0-1500; 0-1250; 0-1000; 0-750; 0-600; 0-500; 0-400; 0-300; 0-200; 0-100; 0-90; 0-80; 0-70; 0-60; 0-50; 0-40; 0-30; 0-20; or 0-10 nucleotides upstream of the promoter. The promoter can be any suitable distance upstream of the encoded gene.

In a further preferred embodiment that can be combined with any other embodiment in any aspect of the present invention, the enhancer comprises or consists of a sequence selected from the group consisting of the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO:4), or other portions thereof suitable to promote expression in a cone-specific manner, and the promoter comprises or consists of a sequence selected from the group consisting of L opsin promoter (SEQ ID NO: 1), the M opsin promoter (SEQ ID NO:2), and the S opsin promoter (SEQ ID NO:3).

In a further preferred embodiment, the gene delivery vector further comprises an intron comprising a splice donor/acceptor region, wherein the intron is located downstream of the promoter region and is located upstream of the gene. Any intron can be used, so long as it comprises a splice donor/acceptor region recognized in primate cone cells, so that the intron can be spliced out of the resulting mRNA product. In one embodiment, the intron comprises or consists of an SV40 intron according to SEQ ID NO:5. In various preferred embodiments, the 3' end of the intron is 0-20; 0-15; 0-10; 0-9; 0-8; 0-7; 0-6; or 0-5 nucleotides upstream of the gene, and its 5' end is 0-20; 0-15; 0-10; 0-9; 0-8; 0-7; 0-6; or 0-5 nucleotides downstream of the proximal promoter region.

The gene is operatively linked to the promoter region and the enhancer element, such that the promoter and enhancer elements are capable of driving expression of the gene or cDNA in cone cells of the subject.

The gene encoding a therapeutic to be expressed in the cone cells can be any gene or cDNA that encodes a polypeptide or RNA-based therapeutic (siRNA, antisense, ribozyme, shRNA, etc.) that can be used as a therapeutic for treating a cone cell disorder, or as a means to otherwise enhance vision, including but not limited to promoting tetrachromatic color vision. In various preferred embodiments, the gene encodes a therapeutic protein selected from the group consisting of (a) SEQ ID NO: 7 (SEQ ID NO: 6)*Homo sapiens* opsin 1 (cone pigments), short-wave-sensitive (OPN1SW), mRNA NCBI Reference Sequence: NM_001708.2;

(b) SEQ ID NO: 9 (SEQ ID NO: 8) *Homo sapiens* opsin 1 (cone pigments), medium-wave-sensitive (OPN1MW), mRNA NCBI Reference Sequence: NM_000513.2;

(c) SEQ ID NO: 11 (SEQ ID NO: 10)*Homo sapiens* opsin 1 (cone pigments), long-wave-sensitive (OPN1LW), mRNA NCBI Reference Sequence: NM_020061.4;

(d) SEQ ID NO: 13 (SEQ ID NO: 12) ATP binding cassette retina gene (ABCR) gene (NM_000350);

(e) SEQ ID NO: 15 (SEQ ID NO: 14) retinal pigmented epithelium-specific 65 kD protein gene (RPE65) (NM_000329);

(f) SEQ ID NO: 17 (SEQ ID NO: 16) retinal binding protein 1 gene (RLBP1) (NM_000326);

(g) SEQ ID NO: 19 (SEQ ID NO: 18) peripherin/retinal degeneration slow gene, (NM_000322);

(h) SEQ ID NO: 21 (SEQ ID NO: 20) arrestin (SAG) (NM_000541);

(i) SEQ ID NO: 23 (SEQ ID NO: 22) alpha-transducin (GNAT1) (NM_000172);

(j) SEQ ID NO: 24 guanylate cyclase activator 1A (GUCA1A) (NP_000400.2);

(k) SEQ ID NO: 25 retina specific guanylate cyclase (GUCY2D), (NP_000171.1);

(l) SEQ ID NO: 26 & 27 alpha subunit of the cone cyclic nucleotide gated cation channel (CNGA3) (NP_001073347.1 or NP_001289.1);

(m) SEQ ID NO: 28 Human cone transducin alpha subunit (incomplete achromotopsia);

(n) SEQ ID NO: 29 cone cGMP-specific 3',5'-cyclic phosphodiesterase subunit alpha', protein (cone dystrophy type 4);

(o) SEQ ID NO: 30 retinal cone rhodopsin-sensitive cGMP 3',5'-cyclic phosphodiesterase subunit gamma, protein (retinal cone dystrophy type 3A);

(p) SEQ ID NO: 31 cone rod homeobox, protein (Cone-rod dystrophy);

(q) SEQ ID NO: 32 cone photoreceptor cyclic nucleotide-gated channel beta subunit, protein (achromatopsia);

(r) SEQ ID NO: 33 cone photoreceptor cGMP-gated cation channel beta-subunit, protein (total color blindness, for example, among Pingelapese Islanders);

(s) SEQ ID NO: 35 (SEQ ID NO: 34) retinitis pigmentosa 1 (autosomal dominant) (RP1);

(t) SEQ ID NO: 37 (SEQ ID NO: 36) retinitis pigmentosa GTPase regulator interacting protein 1 (RPGRIP1);

(u) SEQ ID NO: 39 (SEQ ID NO: 38) PRP8;

(v) SEQ ID NO: 41 (SEQ ID NO: 40) centrosomal protein 290 kDa (CEP290);

(w) SEQ ID NO: 43 (SEQ ID NO: 42) IMP (inosine 5'-monophosphate) dehydrogenase 1 (IMPDH1), transcript variant 1;

(x) SEQ ID NO: 45 (SEQ ID NO: 44) aryl hydrocarbon receptor interacting protein-like 1 (AIPL1), transcript variant 1;

(y) SEQ ID NO: 47 (SEQ ID NO: 46) retinol dehydrogenase 12 (all-trans/9-cis/11-cis) (RDH12);

(z) SEQ ID NO: 49 (SEQ ID NO: 48) Leber congenital amaurosis 5 (LCA5), transcript variant 1; and (aa) exemplary OPN1LW/OPN1MW2 polymorphs (compared to OPN1LW (L opsin) polypeptide sequence; the amino acid to the left of the number is the residue present in the L opsin sequence; the number is the reside number in L opsin, and the reside to the right of the number is the variation from L opsin. Polymorphs according to these embodiments may comprise one or more of the amino acid substitutions in Table 1 below:

TABLE 1

| (i) | Thr65Ile |
| (ii) | Ile111Val |
| (iii) | Ser116Tyr |
| (iv) | Leu153Met |
| (v) | Ile171Val |
| (vi) | Ala174Val |
| (vii) | Ile178Val |
| (viii) | Ser180Ala |
| (ix) | Ile230Thr |
| (x) | Ala233Ser |
| (xi) | Val236Met |
| (xii) | Ile274Val |
| (xiii) | Phe275Leu |
| (xiv) | Tyr277Phe |
| (xv) | Val279Phe |
| (xvi) | Thr285Ala |
| (xvii) | Pro298Ala |
| (xviii) | Tyr309Phe. |

The proteins recited in (a)-(c) and (aa) are all involved in color vision. The exemplary polymorphs include ones at positions 65, 116, 180, 230, 233, 277, 285, and 309 that affect the spectra of the pigments in cone cells expressing them. Positions 274, 275, 277, 279, 285, 298 and 309 together distinguish L opsin from M opsin.

The proteins recited (d)-(z) are exemplary eye disease-associated gene, such as in retinitis pigmentosa (polypeptides "e"-"l", "s"-"y"), incomplete achromatopsia (polypeptide "m"), Stargardt's (polypeptide "d"); Leber congenital amaurosis (polypeptide "z"); cone dystrophy, such as cone dystrophy type 4 (polypeptide "n"); retinal cone dystrophy; for example, retinal cone dystrophy type 3A (polypeptide "o"); Cone-rod dystrophy (polypeptide "p"); achromatopsia (polypeptide 37 q'); and total color blindness, for example, among Pingelapese Islanders (polypeptide "r").

Exemplary nucleic acids encoding these polypeptides are shown by SEQ ID NO in parenthesis. Thus, in a further preferred embodiment, the genes comprise or consist of a nucleic acid sequence according to one or more of the nucleic acid sequences recited above. In a further preferred embodiment, the vector comprises the sequence shown in SEQ ID NO: 50

Any suitable gene therapy vector that can be used for cone cell delivery can be used in the methods of the present invention; the vector may comprise single or double stranded nucleic acid; preferably single stranded or double stranded DNA. In a preferred embodiment that can be combined with any of the above embodiments, the gene delivery vector comprises a recombinant adeno-associated virus (AAV) gene delivery vector. Prior to the present invention, rAAV vectors had not been shown capable of transducing primate cone cells. In this embodiment, the gene delivery vector is bounded on the 5' and 3' end by functional AAV inverted terminal repeat (ITR) sequences. By "functional AAV ITR sequences" is meant that the ITR sequences function as intended for the rescue, replication and packaging of the AAV virion. Hence, AAV ITRs for use in the vectors of the invention need not have a wild-type nucleotide sequence, and may be altered by the insertion, deletion or substitution of nucleotides or the AAV ITRs may be derived from any of several AAV serotypes. The rAAV vector may be derived from an adeno-associated virus serotype, including without limitation, AAV-1, AAV-2, AAV-3, AAV-4, AAV-5, AAV-6, AAV-7, AAV-8, etc. Preferred AAV vectors have the wild type REP and CAP genes deleted in whole or part, but retain functional flanking ITR sequences. In a further preferred embodiment, the AAV vector comprises rAAV2/5, a "pseudotyped" version of AAV2 created by using rep from AAV2 and cap from AAV5 or AAV2, AAV3. AAV4, AAV6, AAV7, AAV8 together with a plasmid containing a vector based on AAV2. Preferably, the rAAV is replication defective, in that the AAV vector cannot independently further replicate and package its genome. For example, when cone cells are transduced with rAAV virions, the gene is expressed in the transduced cone cells, however, due to the fact that the transduced cone cells lack AAV rep and cap genes and accessory function genes, the rAAV is not able to replicate.

Recombinant AAV (rAAV) virions encapsidating the vectors recited above for use in transducing cone cells may be produced using standard methodology. In one embodiment, an AAV expression vector according to the invention is introduced into a producer cell, followed by introduction of an AAV helper construct, where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety.

Any suitable method for producing viral particles for delivery can be used, including but not limited to those described in the examples that follow. Any concentration of viral particles suitable to effectively transducer cone cells can be administered to the eye. In one preferred embodiment, viral particles are delivered in a concentration of at least $10^{10}$ vector genome containing particles per mL; in various preferred embodiments, the viral particles are delivered in a concentration of at least $7.5\times10^{10}$; $10^{11}$; $5\times10^{11}$; $10^{12}$; $5\times10^{12}$; $10^{13}$; $1.5\times10^{13}$; $3\times10^{13}$; $5\times10^{13}$; $7.5\times9\times10^{13}$; or $9\times10^{13}$ vector genome containing particles per mL. Similarly, any total number of viral particles suitable to provide appropriate transduction of retinal cone cells can be administered to the primate's eye. In various preferred embodiments, at least $10^{10}$; $5\times10^{10}$; $10^{11}$; $5\times10^{11}$; $10^{12}$; $1.5\times10^{12}$; $3\times10^{12}$; $5\times10^{12}$; $7.5\times10^{12}$; $10^{13}$; $1.5\times10^{13}$; or $2.7\times10^{13}$ viral particles are injected per eye. Any suitable number of administrations of the vector to the primate eye can be made. In one embodiment, the methods comprise a single administration; in other embodiments, multiple administrations are made over time as deemed appropriate by an attending clinician.

The viral stock for delivery to the primate eye can be treated as appropriate for delivery. The viral stock can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide.

In a further preferred embodiment that can be combined with any other embodiment, the methods of the invention restore visual capacity in the primate. As used herein, "restoring visual capacity" means that some benefit to vision is provided, including but not limited to a reduction or slowing of vision loss; improved visual acuity; decrease in abnormal sensitivity to bright lights; and/or an increase in one or more visual attributes, such as improved color perception (ie: monochromatic to dichromatic vision; dichromatic to trichromatic vision; trichromatic to tetrachromatic vision; etc.). The primate is preferably of the Parvorder Catarrhini, and more preferably is a human.

In a further preferred embodiment that can be combined with all of the above embodiments, the primate suffers from color blindness, and the primate is able to visualize new colors as a result of the therapy. In this embodiment, it is preferred that the enhancer (if present) comprises or consists of a sequence selected from the group consisting of the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO:4), or other portions thereof suitable to promote expression in a cone-specific manner, and the promoter comprises or consists of a sequence selected from the group consisting of L opsin promoter (SEQ ID NO: 1), the M opsin promoter (SEQ ID NO:2), and the S opsin promoter (SEQ ID NO:3), while the gene encodes one or more polypeptides comprising or consisting of a sequence selected from the group consisting of SEQ ID NO: 7 (OPN1SW), SEQ ID NO: 9 (OPN1MW), SEQ ID NO: 11 (OPN1LW), mRNA; and exemplary OPN1LW/OPN1MW2 polymorphs as described in Table 1 above. It is further preferred that the vector comprises a rAAV vector as described above.

The color blindness may be acquired or inherited, and can be full (monochromatic) or partial. In a preferred embodiment, the primate has partial color blindness selected from the group consisting of red-green and blue-yellow color blindness. The partial color blindness can comprise, for example, dichromacy or anomalous trichromasy. These methods result in the primate improved color perception (ie: monochromatic to dichromatic vision; dichromatic to trichromatic vision; trichromatic to tetrachromatic vision; etc.). The primate is preferably of the Parvorder Catarrhini, and more preferably is a human.

As described in detail below, the methods may be used to improve color perception in primates from dichromatic to trichromatic. Dichromats who are missing either the L- or the M-photopigment fail to distinguish from grey:colours near the so-called 'spectral neutral point' located in the bluegreen region of color space (near dominant wavelength of 490 nm) and complementary colors near the 'extra-spectral neutral point' in the red-violet region (near dominant wavelength of 499 nm), Co-expressing the L-opsin transgene within a subset of endogenous M-cones shifted their spectral sensitivity to respond to long wavelength light, thus producing two distinct cone types absorbing in the middle-to-long wavelengths, as required for trichromasy. These results demonstrate that gene therapy changed the spectral sensitivity of a subset of the cones, and the results further demonstrate the unexpected result that adult monkeys gained new color vision capacities because of the gene therapy.

In a further preferred embodiment of all of the above embodiments, the primate has a vision disorder in which its photoreceptors are healthy, such as color blindness. As used herein, "healthy" means that the cells being treated are functioning but simply do not provide for the desired color perception, in contrast to gene therapy in which the target cells are degenerating or dying. The studies reported herein are the first to use gene therapy in primates to address a vision disorder in which all photoreceptors are intact and healthy, making it possible to assess the full potential of gene therapy to restore visual capacities. The methods of the present invention thus will allow many opportunities for functions to be added or restored in the eye.

In a further preferred embodiment that can be combined with any of the other embodiments herein, the primate is an adult primate, such as an adult human (ie: at least 16 years of age; preferably at least 18 years of age or 21 years of age). Classic visual deprivation experiments have led to the expectation that neural connections established during development would not appropriately process an input that was not present from birth. Therefore, it was believed that treatment of congenital vision disorders would be ineffective unless administered to the very young. The present study thus provides significantly unexpected results in curing a visual disorder in an adult primate.

Those of skill in the art will readily appreciate, based on the teachings herein, the variety of treatment modalities that can be accomplished using the methods of the invention. In one embodiment, the gene encodes ABCR and is administered to the eye of a primate with Stargardt disease. In other embodiments, the gene encodes:

one or more of polypeptides "e"-"l" and "s"-"y" in Table 1, and is administered to the eye of a primate with retinitis pigmentosa;

polypeptide "m" in Table 1, and is administered to the eye of a primate with incomplete achromatopsia;

polypeptide "z" in Table 1, and is administered to the eye of a primate with Leber congenital amaurosis;

polypeptide "n" in Table 1, and is administered to the eye of a primate with cone dystrophy, such as cone dystrophy type 4;

polypeptide "o" in Table 1, and is administered to the eye of a primate with retinal cone dystrophy, for example, retinal cone dystrophy type 3A;

polypeptide "p" in Table 1, and is administered to the eye of a primate with cone-rod dystrophy;

polypeptide "q" in Table 1, and is administered to the eye of a primate with achromatopsia; and/or polypeptide "r" in Table 1, and is administered to the eye of a primate with total color blindness, for example, a native of the Pingelapese Islands.

Any suitable means for delivery of the gene therapy vector to the eye can be used, including but not limited to administering in a contact lens fluid, contact lens cleaning and rinsing solutions, eye drops, surgical irrigation solutions, ophthalmological devices, injection, iontophoresis, topical instillation on the eye, and topical instillation. The topical instillation can be administered, for example, in the form of a liquid solution, a paste, of a hydrogel. The topical instillation can be embedded, for example, in a foam matrix or supported in a reservoir. The injection into the primate eye can be, for example, an intracameral injection, an intracorneal injection, a subconjonctival injection, a subtenon injection, a subretinal injection, an intravitreal injection, and an injection into the anterior chamber.

The primate's progress in response to the treatment may be monitored by any suitable means. In embodiments where the methods are used to treat color blindness, monitoring or progress may comprise, for example, use of standard color vision tests, or the wide-field color multifocal electroretinogram (mf-ERG) system described below to detect spectral sensitivity shifts in the primate's vision. Thus, in another aspect, the present invention provides methods for use of the electroretinogram disclosed herein for monitoring changes in vision perception, such as color perception, of a primate undergoing gene therapy to treat a visual disorder. All embodiments of the methods disclosed above can be combined with all embodiments of the electroretinogram disclosed below.

In a second aspect, the present invention provides isolated nucleic acid expression vectors comprising:

(a) a promoter region, wherein the promoter region is specific for primate retinal cone cells; and (b) a gene encoding a therapeutic, wherein the gene is operatively linked to the promoter region.

All terms in this second aspect have the same meaning as disclosed above for the first aspect of the invention. Similarly, all embodiments and combinations thereof disclosed above in the first aspect of the invention can be used in this second aspect of the invention. The inventors have demonstrated effective treatment of congenital vision disorders in adult primates using the recombinant vectors of the invention, a result that is completely unexpected in the art.

Any suitable promoter region can be used in the isolated nucleic acid expression vector, so long as it specifically promotes expression of the gene in retinal cone cells. In a preferred embodiment, the promoter specifically promotes expression of the gene in Catarrhini retinal cone cells; even more preferably in human retinal cone cells. Exemplary suitable promoter regions include the promoter region for any cone-specific gene, such as the L opsin promoter (SEQ ID NO: 1), the M opsin promoter (SEQ ID NO: 2), and the S opsin promoter (SEQ ID NO: 3), or portions thereof suitable to promote expression in a cone-specific manner.

In a preferred embodiment, the isolated nucleic acid expression vector further comprises an enhancer element upstream of the promoter, wherein the gene is operatively linked to the enhancer element. Any suitable enhancer element can be used in the gene therapy vectors, so long as it enhances expression of the gene when used in combination with the promoter. In a preferred embodiment, the enhancer element is specific for retinal cone cells; more preferably, it is specific for primate retinal cone cells; more preferably in Catarrhini retinal cone cells; even more preferably in human retinal cone cells. Exemplary suitable enhancer regions comprise or consist of the enhancer region for any cone-specific gene, such as the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO: 4), or other portions thereof suitable to promote expression in a cone-specific manner.

The length of the promoter and enhancer regions can be of any suitable length for their intended purpose, and the spacing between the promoter and enhancer regions can be any suitable spacing to promote cone-specific expression of the gene product. In various preferred embodiments, the enhancer is located 0-1500; 0-1250; 0-1000; 0-750; 0-600; 0-500; 0-400; 0-300; 0-200; 0-100; 0-90; 0-80; 0-70; 0-60; 0-50; 0-40; 0-30; 0-20; or 0-10 nucleotides upstream of the promoter. The promoter can be any suitable distance upstream of the encoded gene.

In a further preferred embodiment that can be combined with any other embodiment in any aspect of the present invention, the enhancer comprises or consists of a sequence selected from the group consisting of the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO: 4), or other portions thereof suitable to promote expression in a cone-specific manner, and the promoter comprises or consists of a sequence selected from the group consisting of L opsin promoter (SEQ ID NO: 1), the M opsin promoter (SEQ ID NO: 2), and the S opsin promoter (SEQ ID NO: 3).

In a further preferred embodiment, the isolated nucleic acid expression vector further comprises an intron comprising a splice donor/acceptor region, wherein the intron is located downstream of the promoter region and is located upstream of the gene. Any intron can be used, so long as it comprises a splice donor/acceptor region recognized in primate cone cells, so that the intron can be spliced out of the resulting mRNA product. In one embodiment, the intron comprises or consists of an SV40 intron according to SEQ ID NO: 5. In various preferred embodiments, the 3' end of the intron is 0-20; 0-15; 0-10; 0-9; 0-8; 0-7; 0-6; or 0-5 nucleotides upstream of the gene, and its 5' end is 0-20; 0-15; 0-10; 0-9; 0-8; 0-7; 0-6; or 0-5 nucleotides downstream of the proximal promoter region.

The gene is operatively linked to the promoter region and the enhancer element, such that the promoter and enhancer elements are capable of driving expression of the gene or cDNA in cone cells of the subject.

The gene encoding a therapeutic to be expressed in the cone cells can be any gene or cDNA that encodes a polypeptide or RNA-based therapeutic (siRNA, antisense, ribozyme, shRNA, etc.) that can be used as a therapeutic for treating a cone cell disorder, or as a means to otherwise enhance vision, including but not limited to promoting tetrachromatic color vision. In various preferred embodiments, the gene encodes a therapeutic protein comprising or consisting of those disclosed above in the methods of the first aspect of the invention.

In a further preferred embodiment, the vector comprises the sequence shown in SEQ ID NO: 50, which details the vector used in at least some of the examples that follow.

In a further preferred embodiment that can be combined with any of the above embodiments, the gene delivery vector comprises a recombinant adeno-associated virus (AAV) gene delivery vector. In a further preferred embodiment, the AAV vector comprises rAAV2/5. Preferably, the rAAV is replication defective, in that the AAV vector cannot independently further replicate and package its genome. For example, when cone cells are transduced with rAAV virions, the gene is expressed in the transduced cone cells, however, due to the fact that the transduced cone cells lack AAV rep and cap genes and accessory function genes, the rAAV is not able to replicate.

In a third aspect, the present invention provides a formulation comprising packaged viral particles containing the nucleic acid expression vectors of the second aspect of the invention. In one preferred embodiment, viral particles are present in a concentration of at least $10^{10}$ vector genome containing particles per mL; in various preferred embodiments, the viral particles are delivered in a concentration of at least $7.5 \times 10^{10}$; $10^{11}$; $5 \times 10^{11}$; $10^{12}$; $5 \times 10^{12}$; $10^{13}$; $1.5 \times 10^{13}$; $3 \times 10^{13}$; $5 \times 10^{13}$; $7.5 \times 9 \times 10^{13}$; or $9 \times 10^{13}$ vector genome containing particles per mL. The formulation may further comprise pharmaceutically-acceptable carriers, diluents and reagents as described above in the first aspect of the invention. The formulation may be in the form of a liquid solution, a paste, a hydrogel, or may be embedded within a substrate, including but not limited to a foam matrix or supported in a reservoir.

In a fourth aspect, the present invention provides recombinant host cells transfected or transduced with the nucleic acid expression vector of the second aspect of the invention. The cells may be of any type that can be transfected with the expression vector. In one embodiment where the expression vector is a rAAV vector, the cells comprise producer cells transduced with a replication incompetent rAAV expression vector according to the second aspect of the invention, form which viral particles can be obtained by introduction of an AAV helper construct as described above and as is well known in the art.

In a fifth aspect, the present invention provides a color multifocal electroretinogram system, comprising:

(a) an electroretinogram (ERG) comprising
 (i) a recording electrode that is (A) designed for placement on at least one of a cornea and a sclera of at least one eye of a subject and (B) arranged to output at least one signal generated by the at least one eye; and
 (ii) a computing system communicatively coupled to the recording electrode, the computing system comprising (A) at least one processor and (B) data storage containing instructions executable by the at least one processor to carry out a set of functions, the set of functions including processing and saving the at least one signal generated by the at least one eye;

(b) a retinal stimulator comprising matched light sources selected from the group consisting of red, green, blue, and ultraviolet light sources, wherein the matched light sources are connected to the ERG and in operation can be independently frequency modulated at rates between about 1 Hz and about 60 Hz, inclusive, wherein the stimulator in operation is capable of stimulating a retinal field of a subject throughout an operating radius of at least about 70 degrees;

(c) one or more constant current integrated circuit chips arranged to drive the stimulator; and (d) a pulse-frequency modulator connected to the retinal stimulator, wherein in operation the pulse-frequency modulator is capable of controlling individual stimulator segments while keeping relative spectral content of the light constant.

The electroretinograms of the present invention can be used, for example, in characterizing the topography of expression of the different opsin transgenes in the eyes of living subjects treated with gene therapy, and thus can be used with the gene therapy methods of the invention disclosed above.

As used here, a "matched" light source is one that includes light stimulus of different wavelengths, wherein the number of pixels is approximately the same, or is the same, at each wavelength. One non-limiting example is a matched light source stimulus containing 1024 doublet pixels each containing a red (653 nm, half-bandwidth 22 nm) and a green (527 nm, half-bandwidth 33 nm) LED, with a resulting matched light source with 2,048 paired green and red LEDs.

In various preferred embodiments, the stimulator in operation is capable of stimulating a retinal field of a subject throughout an operating radius of at least about 80, 90, 100, 110, 120, 130, 140, 150, or more degrees.

In one preferred embodiment, the matched light sources are paired red and green light sources. In another preferred embodiment, the matched light sources are triplets of red, green, and blue light sources. In a further preferred embodiment, the matched light sources are quartets of red, green, blue, and ultraviolet light sources.

Any suitable matched light source can be used. In one preferred embodiment, the matched light sources comprise matched light emitting diodes (LEDs).

In another preferred embodiment, that can be combined with any of the embodiments herein, the retinal stimulator comprises a concave surface comprising a series of trapezoidal-shaped circuit boards placed edge-to-edge, wherein the concave surface positions the matched light sources so in operation they are held equidistantly from and pointing toward a single focal point where a subject's pupil can be positioned. This embodiment helps to limit SNR fall-off in peripheral retinal regions. Any suitable concave surface can be used; in a preferred embodiment, the concave surface comprises a geodesic dome.

In a further embodiment that can be combined with any of the above embodiments, the set of functions executable by the processor further comprises coding and decoding topographical regions on the recording electrode using a cyclic summation technique.

In a further preferred embodiment that can be combined with any of the embodiments herein, the ERG further comprises an amplifier; and wherein the computing system is communicatively coupled to the amplifier.

Further embodiments and details of the color multifocal electroretinogram system are provided in the Examples that follow.

In a further aspect, the present invention provides methods for determining a location of functioning opsin expression in a subject, comprising use of the mf-ERG of any embodiment or combination of embodiments of the fifth aspect of the invention, wherein the recording electrode is placed on at least one of a cornea and a sclera of at least one eye of a subject; stimulating the subject's retinal field with the retinal stimulator; and determining responses of different areas of the subject's retina to different stimulation frequencies to generate a map of retinal responses, wherein the map provides a location of functioning opsin expression in a subject. In one preferred embodiment, the subject has been treated according to the gene therapy methods for color blindness disclosed above according to any embodiment or combination of embodiments of the first aspect of the invention.

Unless the context clearly dictates otherwise, embodiments in one aspect of the invention may be used in other aspects of the invention, and can be combined with each other.

Example 1

Red-green colour blindness, which results from the absence of either the long- (L) or middle- (M) wavelength-sensitive visual photopigments, is the most common single locus genetic disorder. Here, the possibility of curing colour blindness using gene therapy was explored in experiments on adult monkeys that had been colour blind since birth. A third type of cone pigment was added to dichromatic retinas, providing the receptoral basis for trichromatic colour vision. This opened a new avenue to explore the requirements for establishing the neural circuits for a new dimension of colour sensation. Classic visual deprivation experiments' have led to the expectation that neural connections established during development would not appropriately process an input that was not present from birth. Therefore, it was believed that treatment of congenital vision disorders would be ineffective unless administered to the very young. Here, however, addition of a third opsin in adult red-green colour-deficient primates was sufficient to produce trichromatic colour vision behaviour. Thus, trichromacy can arise from a single addition of a third cone class and it does not require an early developmental process. This provides a positive outlook for the potential of gene therapy to cure adult vision disorders.

Gene therapy was performed on adult squirrel monkeys (Saimiri sciureus) that were missing the L opsin gene. In this species, some females have trichromatic colour vision while males are red-green colour blind. Serotype 2/5 recombinant adeno-associated virus (rAAV) containing a human L-opsin gene under control of the L/M opsin enhancer and promoter (FIG. 1a) was delivered to the photoreceptor layer via subretinal injections. Transcriptional regulatory elements were chosen to direct expression preferentially in M cones, but not short- (S) wavelength-sensitive cones or rods[3]. To provide the receptoral basis for trichromacy, animals received three 100 μL injections (containing a total of $2.7 \times 10^{13}$ viral particles) in each eye which produced a relatively uniform, third submosaic of approximately 15-36% of M cones that coexpressed the transgene (FIG. 1e, f).

Prior to treatment, monkeys were trained to perform a computer-based colour vision test, the Cambridge Colour Test[4,5], which was modified for use with animals[6] (FIG. 2a). Dichromats who are missing either the L- or M-photopigment fail to distinguish from grey: colours near the so-called "spectral neutral point" located in the blue-green region of colour space (near dominant wavelength (DW) 490 nm) and complementary colours near the "extra-spectral neutral point," in the red-violet region (near DW=−499 nm). While trichromats have four main hue percepts—blue, yellow, red, and green—dichromats have only two percepts, nominally blue and yellow. Before treatment, two dichromatic monkeys completed three colour vision tests consisting of 16 hues (FIG. 2b, c). Four-to-six months was required to test all 16 hues; thus, baseline results represent testing conducted for more than a year. As predicted, prior to treatment monkeys had low thresholds (averaging <0.03 units in u', v' colour space) for colours that represent blues and yellows to their eyes, but always failed to discriminate the blue-green (DW=490 nm) and red-violet hues (DW=−499 nm) with thresholds extrapolated from psychometric functions being orders of magnitude higher (FIG. 2b, c). Results were highly repeatable, with no improvement between the first and third tests, making us confident that animals would not spontaneously improve in the absence of treatment.

Co-expressing the L-opsin transgene within a subset of endogenous M-cones shifted their spectral sensitivity to respond to long wavelength light, thus producing two distinct cone types absorbing in the middle-to-long wavelengths, as required for trichromacy. The spectral sensitivity shift was readily detected using a custom-built wide-field colour multifocal electroretinogram (mf-ERG) system (FIG. 1b, c, f) (see ref 7 for details). In preliminary experiments, validity of the colour mf-ERG was tested using an animal that had received a mixture of the L-opsin-coding virus plus an identical virus, except that a green fluorescent protein (GFP) gene replaced the L-opsin gene. As reported previously, faint GFP fluorescence was first detected at 9 weeks post-injection, and it continued to increase in area and intensity through 24 weeks[8]. While faint signs of GFP were first detectable at 9 weeks, L-opsin levels sufficient to produce suprathreshold mf-ERG signals were still not present at 16 weeks post-injection (FIG. 1c, inset). After GFP fluorescence became robust, the red light mf-ERG, which indicates responses from the introduced L-opsin, showed highly elevated response amplitudes in two areas (FIG. 1c) corresponding to locations of subretinal injections (FIG. 1d).

The two dichromatic monkeys who participated in behavioural tests of colour vision were treated with only L-opsin-coding virus. While the elongated pattern produced by two injections in FIGS. 1c and d allowed mf-ERG validation, the treatment goal was to produce a homogeneous region, as resulted from 3 injections shown in f, where the highest mf-ERG response covered about 80° of central retina, roughly the area for which humans have good red-green discrimination. These results demonstrate that gene therapy changed the spectral sensitivity of a subset of the cones. A priori, there were two possibilities for how a change in spectral sensitivity might change colour vision behaviour: 1) animals may have an increase in sensitivity to long-wavelength light, but if the neural circuitry for extracting colour information from the nascent "M+L cone" submosaic was absent, they would remain dichromatic, the hallmark of which is having two hues that are indistinguishable from grey (FIG. 2d). The spectral neutral point for individuals that have only S- and M-cones, (e.g. monkeys 1 and 2 pre-therapy), occurs near dominant wavelength (DW)=495 nm. At the limit, an increase in spectral sensitivity would shift the monkeys' neutral point toward that of individuals with only S and L cones, near DW=505 nm (dashed blue lines, FIG. 2d). 2) The second, more engaging possibility was that treatment would be sufficient to expand sensory capacity in monkeys, providing them with trichromatic vision. In this case, the animals' post-therapy results would appear similar to FIG. 2e, obtained from a trichromatic female control monkey.

Daily testing continued after treatment. After about 20 weeks post-injection (arrow, FIG. 3a), the trained monkeys' thresholds for blue-green and red-violet (DWs=490 and −499 nm, respectively, FIG. 3b, c) improved, reducing to an average of 0.08 units in u', v' colour space, indicating that they gained trichromatic vision. This time point corresponded to the same period in which robust levels of transgene expression were reported in the squirrel monkey[8]. A trichromatic female monkey and untreated dichromatic monkeys were tested in parallel. As expected, the female had low thresholds for all colours, averaging <0.03 units in u', v' colour space, but the untreated dichromats always failed to discriminate DWs=490 nm (triangle, FIG. 3a) and −499 nm, indicating a clear difference between treated and untreated monkeys.

Early experiments in which we obtained negative results served as "sham controls," demonstrating that acquiring a new dimension of colour vision requires a shift in spectral sensitivity that results from expression of an L pigment in a subset of M cones. Using similar subretinal injection procedures, we delivered fewer viral particles of an L-opsin-coding rAAV2/5 virus with an extra 146 base pair (bp) segment near the splice donor/acceptor site that had been carried over from the cloning vector and that was absent in the GFP-coding rAAV2/5 virus. The 146 bp segment contained an ATG and a duplicate mRNA start site that may have interfered with expression (see Full Methods online). Three monkeys received injections of this vector, containing an average of $1.7 \times 10^{12}$ virus particles per eye, and no reliable changes in spectral sensitivity were measured using the ERG. One animal was also tested behaviourally and his colour vision was unchanged from baseline 1 year after injection. In subsequent experiments reported here, we removed the extra 146 bp segment and also increased the amount of viral particles delivered per eye by approximately 16-fold, to $2.7 \times 10^{13}$. Negative results from earlier injections demonstrated that the subretinal injection procedure itself does not produce changes in the ERG or in colour vision.

Figure 2:
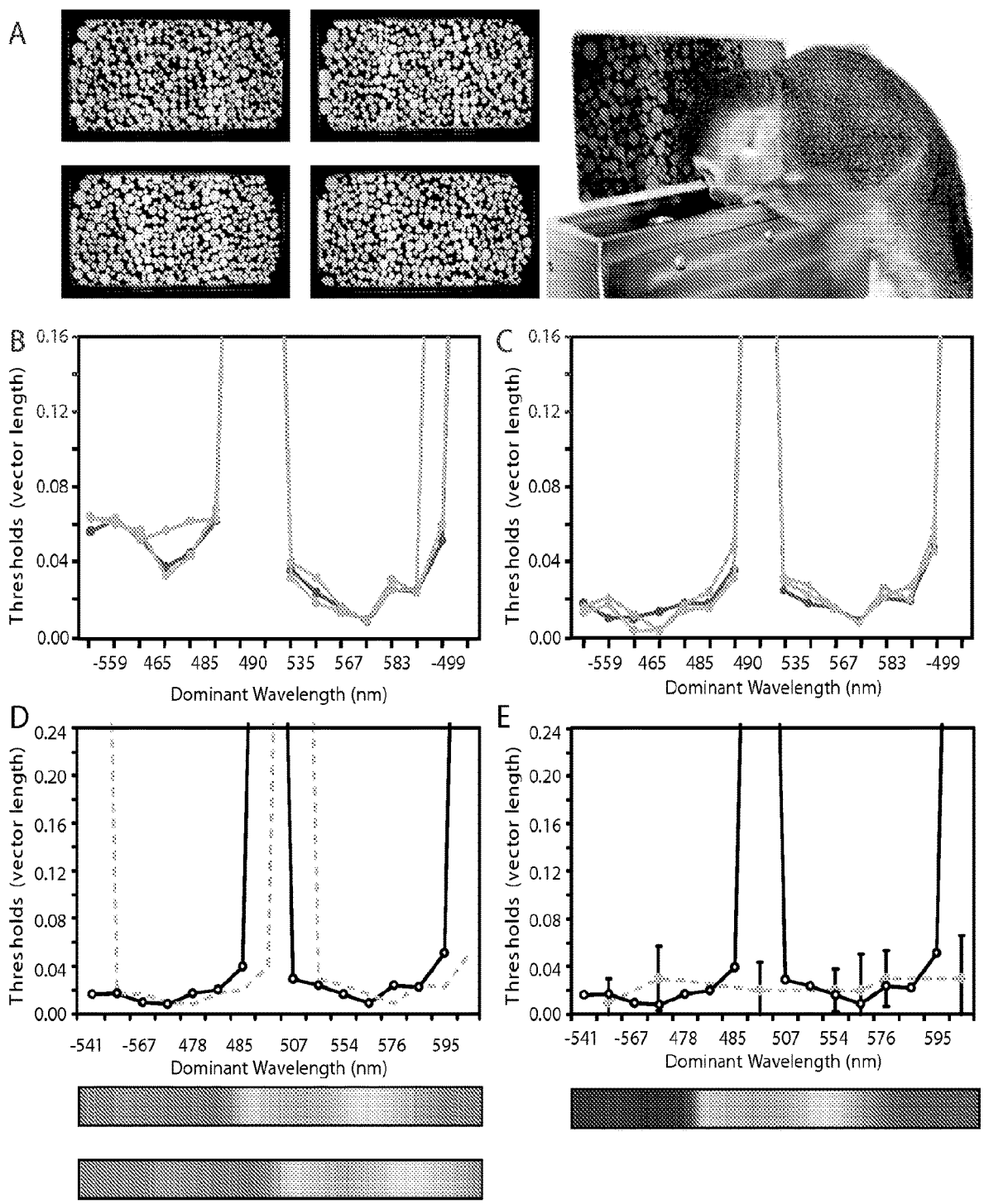
FIG. 2. Pre-therapy colour vision and possible treatment outcomes. a) Colour vision stimuli examples. b) Pre-therapy results, monkey 1. Hues tested are represented as dominant wavelengths (DWs) rather than u', v' coordinates. If a hue could not be reliably distinguished at even the highest saturation, the extrapolated threshold approached infinity. c) Pre-therapy results, monkey 2. d)-e), Possible experimental outcomes: Monkeys could have a relative increase in long-wavelength sensitivity, but remain dichromatic (dashed lines, d); theoretical colour spectrum appearances for a dichromat and a possible "spectral shift" are shown. Alternatively, dichromatic monkeys could become trichromatic. Results from a trichromatic female control monkey are plotted (dashed line, e; error bars=SEM and n varied from 7-11).
Figure 3:
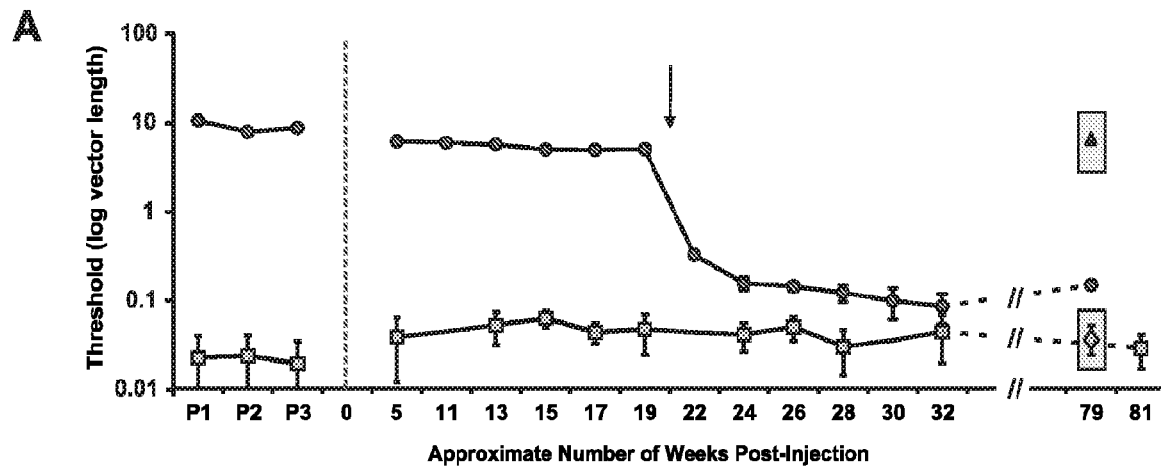
FIG. 3. Gene therapy produced trichromatic colour vision. a) Time course of thresholds for the blue-green confusion colour, DW=490 nm (circles), and a yellowish colour, DW=554 nm (squares). A logarithmic scale was used to fit high thresholds for DW=490 nm; significant improvement occurred after 20 weeks. Enclosed data points=untreated dichromatic monkey thresholds, DW=490 nm (triangle) and DW=554 nm (diamond). b)-c) Comparison of pre-therapy (open circles, solid line) and post-therapy thresholds (solid dots, dashed line). Enclosed data points are DW=490 nm thresholds when tested against a red-violet background (DW=−499 nm); pink triangles=trichromatic female control thresholds. Error bars=SEM; n varied from 7-11.
Figure 3:
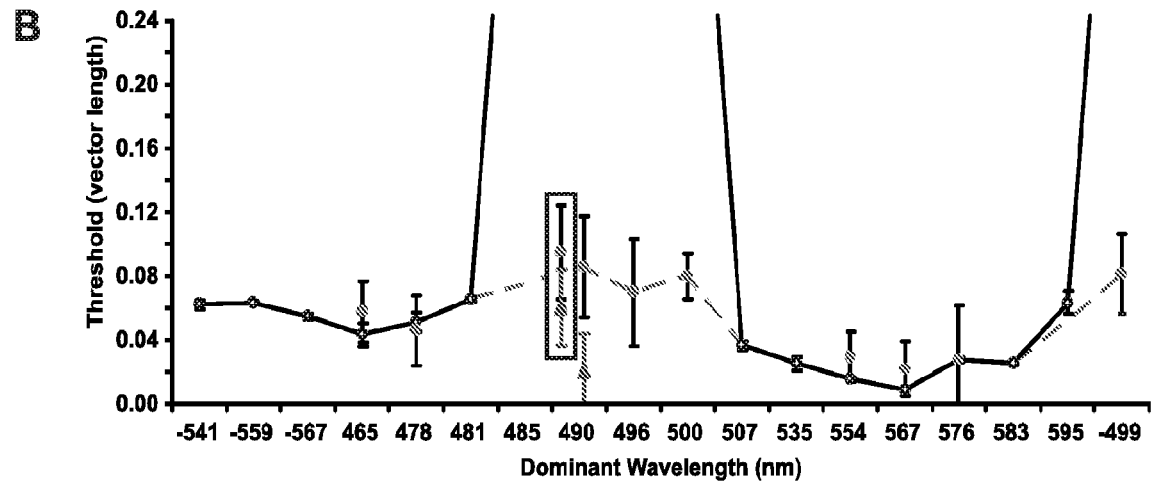
Figure 3:
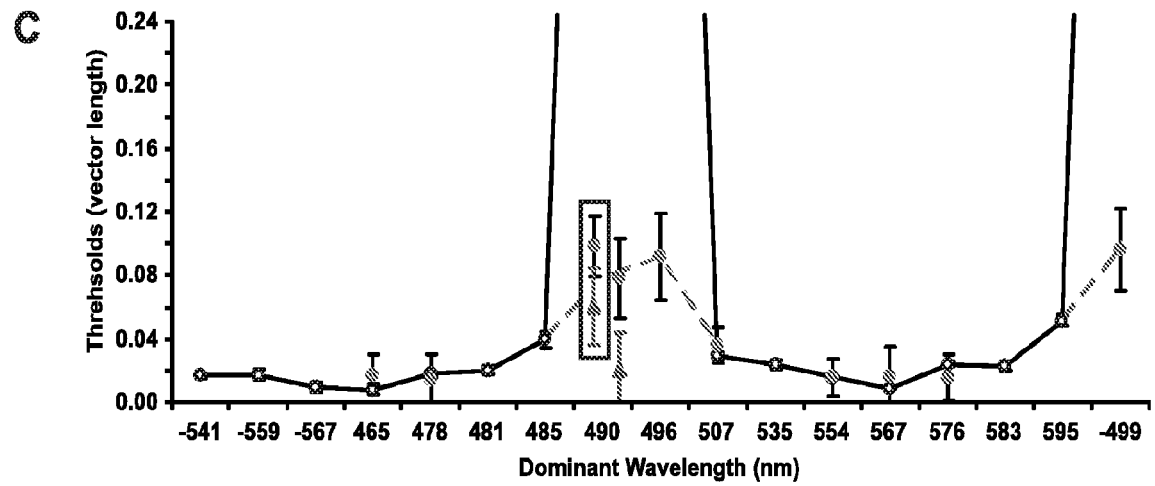
Figure 4:
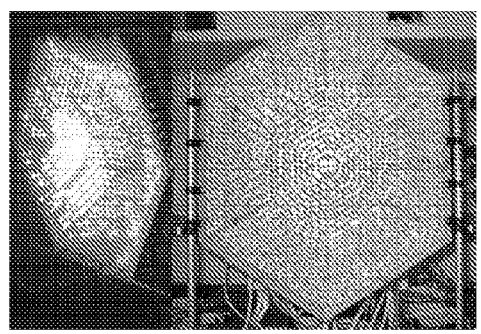
FIG. 4. a) The geodesic dome was created by placing trapezoidal-shaped circuit boards edge-to-edge. This structure holds the light emitting diodes (LEDs) so they converge on a single focal point. b) The circuit board takes the incoming control signals from the Retis-can mf-ERG and reroutes and modifies them to work with the new dome. The most frequent integrated circuit on the board are the constant current devices. c) The spectral composition of the red LED. d) The spectral composition of the green LED. e) The spectral sensitivity curves for the human M- (solid line) and L- (dashed line) cone photoreceptors. f) The activation of M-opsin (solid line) and the L-opsin (dashed line) in response to both the red and green LEDs.
Figure 4:
Figure 4:
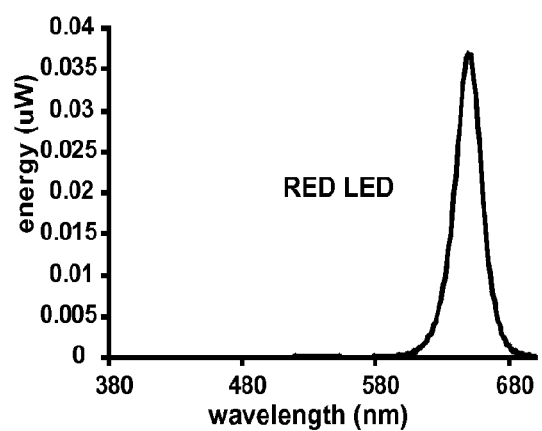
Figure 4:
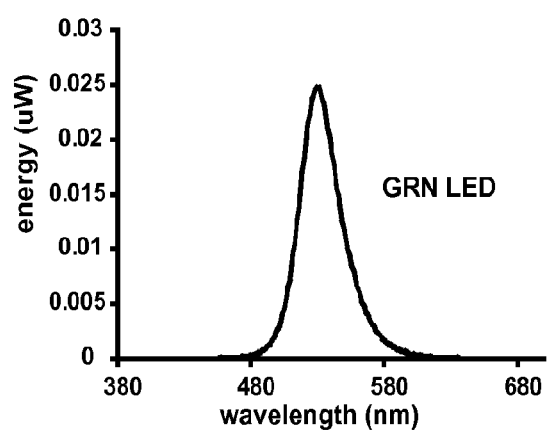
Figure 4:
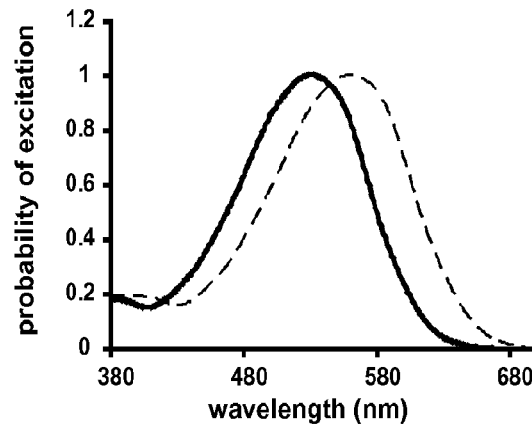
Figure 4:
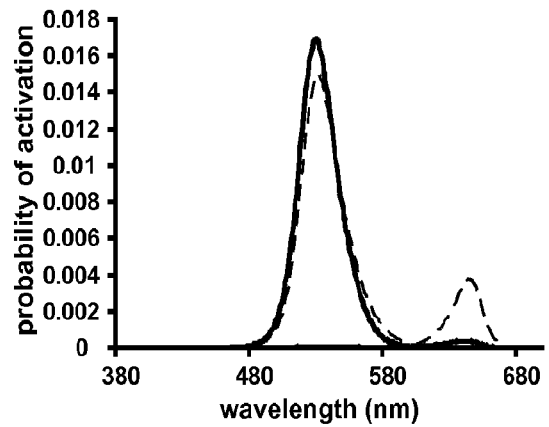
Figure 5:
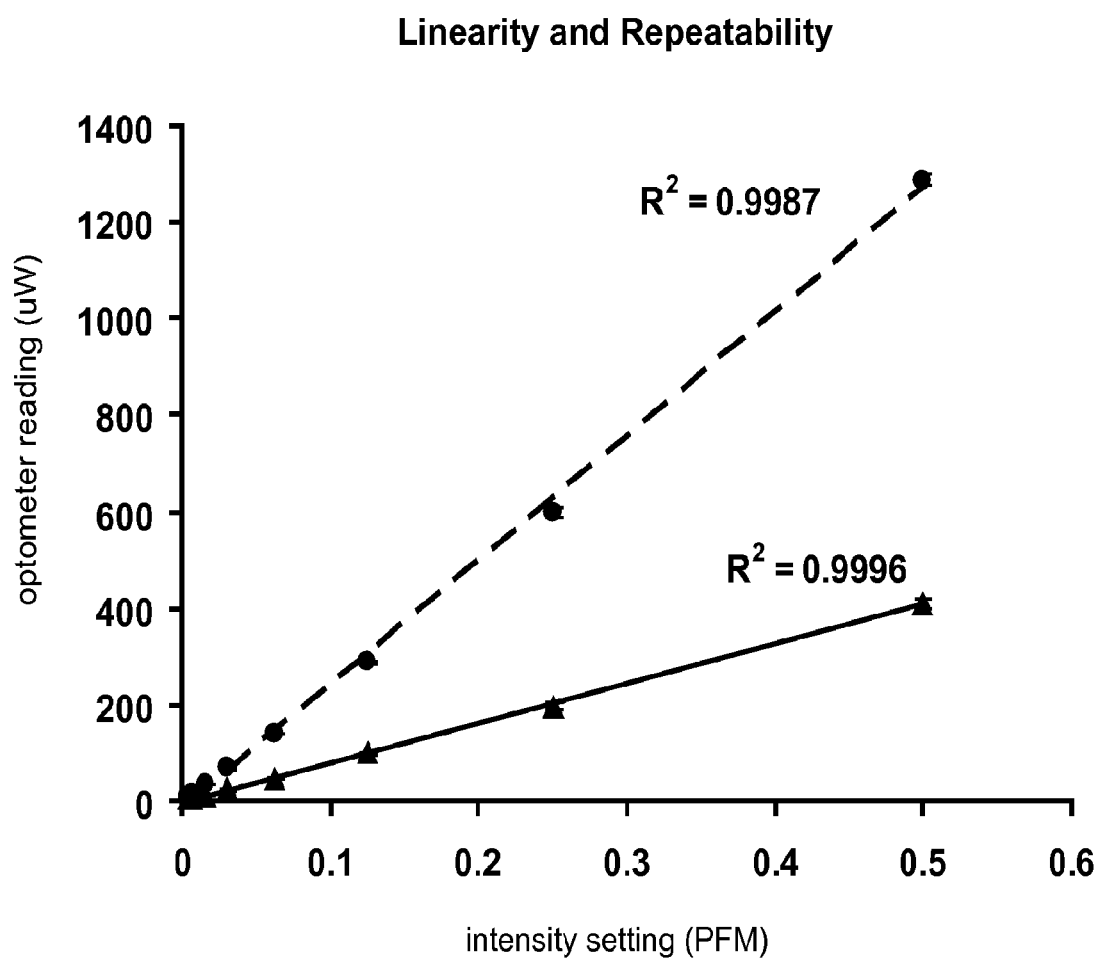
FIG. 5. Circles and dashed line represent the red LED out-puts in microwatts as a function of intensity; triangles and solid line represent the green LED outputs. Each data point represents an average of 3 measurements. Error bars are three standard deviations (99.7% confidence interval). To measure linearity, r2 values were computed for both the red and green LEDs.
Figure 7:
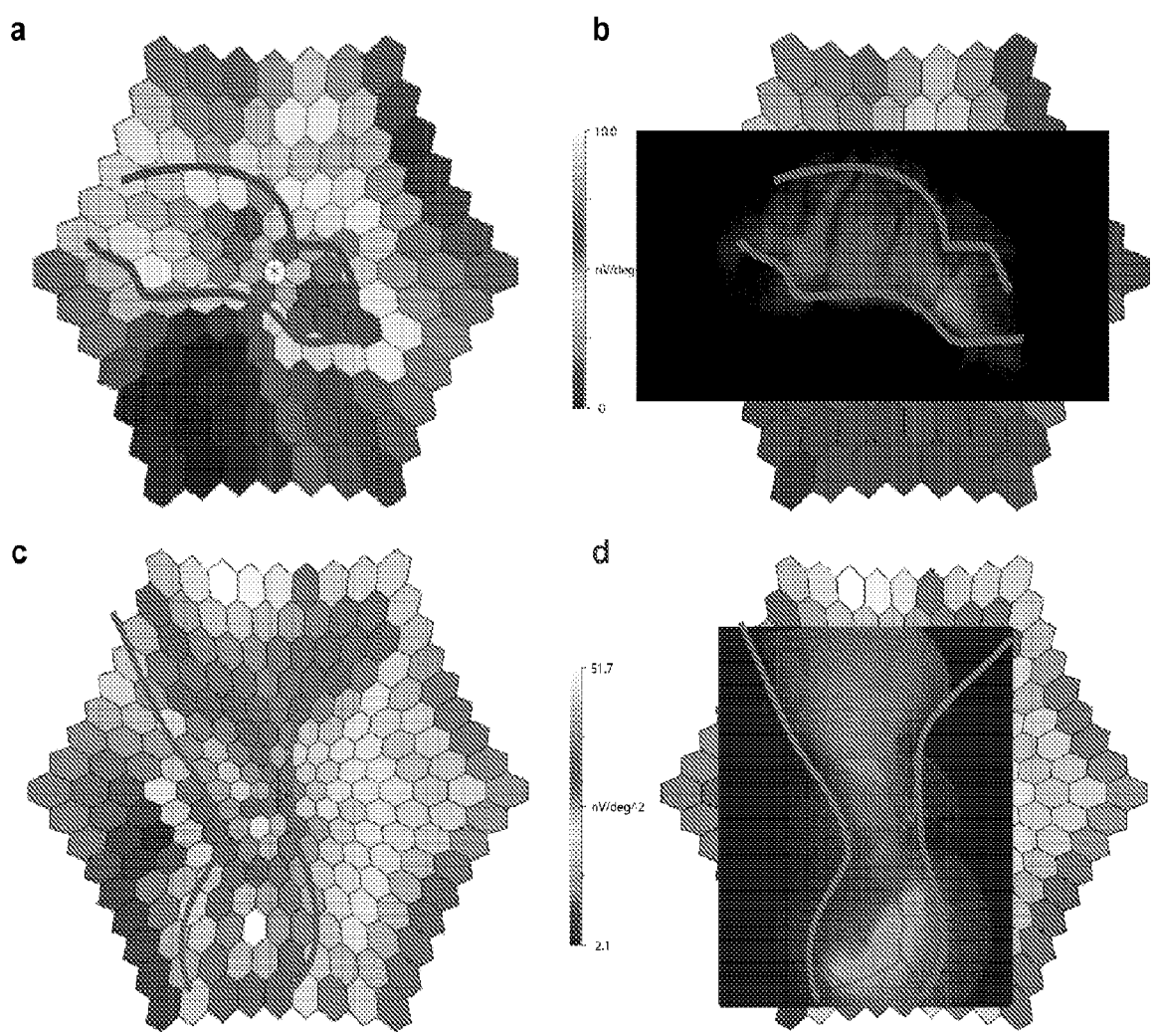
FIG. 7. a) Gerbil mf-ERG data in response to the L-cone isolating red stimulus. Locations of the retina that show a large amount of activity in response to stimulation by the red LEDs are indicated in red, while those areas that show the lowest amount of activation are indicated in blue (see scale). Gray lines show borders of the region where the mfERG response was highest. b) GFP fluorescence fundus image from the gerbil, scaled to the appropriate size, overlaid on the red-light mf-ERG data. The gray lines from (a) were copied into (b) to illustrate that areas of increased mf-ERG response corresponded to the same locations where robust GFP fluorescence was present. c) Red-light mf-ERG data from the squirrel monkey, which received two injections of the virus mixture, one superiorly and one inferiorly. d) A montage of GFP fluorescence images from the squirrel monkey, scaled to the appropriate size, overlaid on the mfERG data.
Figure 8:
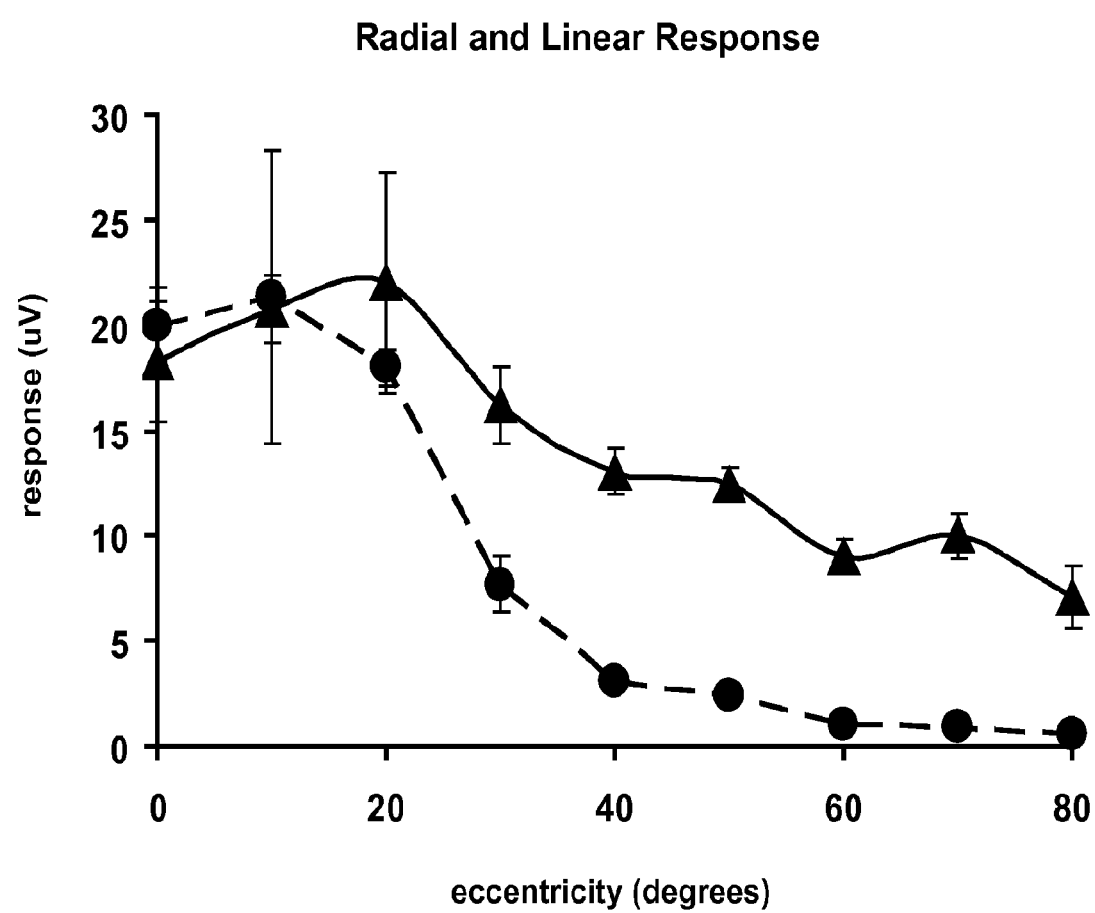
FIG. 8. The circles represent ERG response from LEDs that were moved on a linear path while the subject fixated forward. By 30 degrees, the signal is already less than half. In contrast, the triangles represent ERG response from LEDs that were fixed on a boom and rotated so that the LEDs always pointed at the pupil. Under this experimental protocol, −3 dB occurs first at 60 degrees.

The change in spectral sensitivity measured with the mf-ERG is necessary but not sufficient to produce a new colour vision capacity. For example, individuals with L but no M cones (termed deuteranopes) have a relatively enhanced sensitivity to red light but they are still as dichromatic as individuals with M but no L cones (protanopes), in that they are unable to distinguish particular "colours" from grey. To verify that the behavioural change observed in animals expressing the L pigment transgene was not purely a shift in spectral sensitivity (see FIG. 2d), monkey 1 was also tested on DWs=496 and 500 nm, and monkey 2 was tested on DWs 496 and 507 nm. Together, these DWs span the possible confusion points for deuteranopes and protanopes and for any intermediate dichromatic forms that could arise from expressing combinations of L and M pigments. As shown in FIGS. 3b and c, both monkeys' measured thresholds for these additional hues were similar to their thresholds for DW=490 nm, demonstrating they now lacked a spectral neutral point and have become truly trichromatic. Furthermore, treated monkeys were able to discriminate blue-green (DW=490 nm) when it was tested against a red-violet background (DW=−499 nm), instead of the grey background, indicating that the monkeys' newly-acquired "green" and "red" percepts were distinct from one another. The treated monkeys' improvement in colour vision has remained stable for over 2 years and we plan to continue testing the animals to evaluate long term treatment effects.

Classic experiments in which visual deprivation of one eye during development caused permanent vision loss' led to the idea that inputs must be present during development for the formation of circuits to process them. From the clear change in behaviour associated with treatment, compared both between and within subjects, we conclude that adult monkeys gained new colour vision capacities because of gene therapy. These startling empirical results provide insight into the evolutionary question of what changes in the visual system are required for adding a new dimension of colour vision. Previously, it seemed possible that a transformation from dichromacy to trichromacy would require evolutionary/developmental changes, in addition to acquiring a third cone type. For example, L and M opsin-specific genetic regulatory elements might have been required to direct the opsins into distinct cone types[9] that would be recognized by L and M cone-specific retinal circuitry[10], and to account for cortical processing, multi-stage circuitry[11] might have evolved specifically for the purpose of trichromacy. However, our results demonstrate that trichromatic colour vision behaviour requires nothing more than a third cone type. As an alternative to the idea that the new dimension of colour vision arose by acquisition of a new L vs. M pathway, it is possible that it exploited the pre-existing blue-yellow circuitry. For example, if addition of the third cone class split the formerly S vs. M receptive fields into two types with differing spectral sensitivities, this would obviate the need for neural rewiring as part of the process of adopting new colour vision.

Some form of inherent plasticity in the mammalian visual system can be inferred from the acquisition of novel colour vision, as was also demonstrated in genetically engineered mice[12]; however, the point has been made that such plasticity need not imply that any rewiring of the neural circuitry has occurred[13]. Similarly, given the fact that new colour vision behaviour in adult squirrel monkeys corresponded to the same time interval as the appearance of robust levels of transgene expression, we conclude that rewiring of the visual system was not associated with the change from dichromatic to trichromatic vision.

Treated adult monkeys unquestionably respond to colours previously invisible to them. The internal experiences associated with the dramatic change in discrimination thresholds measured here cannot be determined; therefore, we cannot know whether the animals experience new internal sensations of "red" and "green." Nonetheless, we do know that evolution acts on behaviour, not on internalized experiences, and we suggest that gene therapy recapitulated what occurred during evolution of trichromasy in primates. These experiments demonstrate that a new colour vision capacity, as defined by new discrimination abilities, can be added by taking advantage of pre-existing neural circuitry and, internal experience aside, full colour vision could have evolved in the absence of any other change in the visual system except the addition of a third cone type.

Gene therapy trials are underway for Leber's congenital amaurosis[14-16]. Thus far, treatment has been administered to individuals who have suffered retinal degeneration from the disease. The experiments reported here are the first to use gene therapy in primates to address a vision disorder in which all photoreceptors are intact and healthy, making it possible to assess the full potential of gene therapy to restore visual capacities. Treatment allowing monkeys to see new colours in adulthood provides a striking counter-example to what occurs under conditions of monocular deprivation. For instance, it is impossible to restore vision in an adult who had grown up with a unilateral cataract. Future technologies will allow many opportunities for functions to be added or restored in the eye. While some changes may produce outcomes analogous to monocular deprivation, we predict that others, like gene therapy for red-green colour blindness, will provide vision where there was previously blindness.

Methods Summary for Example 1

Viral Vector.

CHOPS2053 was a 2.1 kb fragment containing the locus control region (LCR) and proximal promoter (PP) upstream of the human X-chromosome opsin gene array[9,17]. These elements (also known as pR2.1) have been shown to target transgene expression to mammalian L/M cones[3,18]. RHLOPS was a 1.2 kb fragment containing recombinant human L opsin cDNA. A clone of the human L opsin cDNA[19], known as hs7, was generously provided by J. Nathans. The QuickChange kit (Stratagene) was used to convert codon 180 so that it would encode a human L pigment maximally sensitive to 562 nm[20]. The virus was made using the genome from rAAV serotype 2 and the capsid from serotype 5, and the preparation had $9 \times 10^{13}$ DNase-resistant vector genome containing particles per mL. To prevent vector aggregation, 0.014% Tween 20 was added to the final vector preparation. A total of $2.7 \times 10^{13}$ viral particles was injected per eye.

An earlier version of the L-opsin coding rAAV2/5 used in previous unsuccessful experiments contained an extra 146 base pair segment between the splice donor/acceptor site and the translational start codon of the L-opsin gene that had been carried over from the cloning vector. Because we were concerned that this fragment may have interfered with transgene expression, a second version of L-opsin rAAV2/5 in which the extra 146 bp had been removed was used in later experiments described here. In addition to modifying the vector, we also increased the amount of viral particles delivered per eye by approximately 16-fold, from $1.7 \times 10^{12}$ to $2.7 \times 10^{13}$. Thus, we cannot conclude from this set of experiments what exact titer of viral particles was required to produce the effects on color vision behaviour, or exactly what effects, if any, the extra 146 bp had on transgene expression in earlier unsuccessful attempts.

The single-stranded DNA genome of conventional rAAV vectors, including rAAV2/5 used here, is devoid of Rep coding sequences. Thus, the vector genome is stabilized predominantly in an episomal form; however, the potential for integration exists[21]. According to NIH guidelines, the viral vector used here is rated biosafety level 1 (BSL1), and animal biosafety level 1 (ABSL1) meaning no special precautions were required in handling the virus or animals treated with the virus. Following treatment, squirrel monkeys had an increase in AAV antibody titers, ranging from 4-12 fold. Antibody titers remained unchanged in untreated control animals who were housed with treated animals.

Subretinal Injections.

Subretinal injections were performed by a vitreo-retinal surgeon (T. B. C.) using a KDS model 210 syringe pump under a stereomicroscope. A 500 µL Hamilton Gastight (#1750TTL) Luer Lock syringe was connected to 88.9 cm of 30 gauge teflon tubing with male Luer Lock adapters at both ends (Hamilton 30TF double hub), which was then connected to a 30 gauge Becton Dickinson Yale regular bevel cannula (ref #511258) that was manually bent to produce a 135° angle 1.5 mm from the tip. All components were sterilized prior to use. The syringe and tubing were filled with sterile lactated Ringers solution to produce a dead volume of approximately 210 µL. Just prior to injection, 300 µL of rAAV was withdrawn using a rate of 100 µL/min.

Squirrel monkeys were anesthetized using intramuscular injections of ketamine (15 mg/kg) and xylazine (2 mg/kg); atropine (0.05 mg/kg) was also given to reduce airway secretions. The eye was dilated with 2-3 drops of tropicamide (1%) and treated with 1 drop each of betadine (5%), vigamox (0.5%), and proparacaine (1%). Subconjunctival injection of 0.1 mL of lidocaine (2%) was given and the anterior portion of the eye was exposed by performing a temporal canthotomy followed by limited conjuntival peritomy. Eyelids were held open with a speculum designed for premature infants. A temporal sclerotomy was made 1 mm posterior to the limbus with a 27 gauge needle, through which the injection cannula was inserted. Three subsequent 100 µL injections were made at different subretinal locations using an infusion rate of 1060 µL/min. Post-procedure, 0.05 mL each of decadron (10 mg/mL), kenalog (40 mg/mL), and cephazolin (100 mg/mL) were injected subconjunctivaly; 1 drop each of betadine (5%) and vigamox (0.5%) and a 0.6 cm strip of tobradex (0.3% tobramycin, 0.1% dexamethasone) ointment were applied topically; 10-20 mL of subcutaneous fluids (sterile lactated Ringers) were also given. Subsequent administration of steroids and analgesics were administered as needed post-procedure for potential inflammation or discomfort.

Confocal Microscopy.

The animal in FIG. 1c and d succumbed to respiratory illness, unrelated to gene therapy, approximately 2 years and 3 months post-injection. The retina was fixed in 4% paraformaldehyde in phosphate buffered saline (PBS), and rinsed in PBS with 10% and 30% sucrose. It was sequentially incubated with 10% Normal Donkey Serum, rabbit monoclonal antibody to M/L opsin (Chemicon AB5405), and a Cy3 (red) conjugated donkey anti-rabbit antibody (Jackson Immunoresearch). Confocal images were analyzed using ImageJ (rsbweb.nih.gov). In the middle panel of FIG. 1e, magenta dots mark cone locations, and the red anti-M/L-opsin antibody staining was removed to show GFP-expressing (green) cells more clearly.

Behavioural Colour Vision Assessment.

A three-alternative forced-choice paradigm in which position and saturation of the stimulus was randomized between trials was used. Monkeys had to discriminate the location of a coloured patch of dots that varied in size and brightness, surrounded by similarly varying grey dots. When animals touched the coloured target, a positive tone sounded and a juice reward was given; the next stimulus appeared immediately. (The squirrel monkey shown in FIG. 2c is drinking a reward from a previous trial.) If the wrong position was chosen, a negative tone sounded, and a 2-3 sec "penalty time" occurred before the next trial.

For each hue, monkeys were tested on up to 11 different saturations ranging from 0.01 to 0.11 in u', v' colour space (CIE 1976) and a threshold was calculated, which was taken as the saturation required to reach a criterion of 57% correct, the value determined to be significantly greater than chance (33% correct, $P=0.05$); see ref 6 for full details.

REFERENCES FOR EXAMPLE 1

1. Wiesel, T. N. & Hubel, D. H. Single-cell responses in striate cortex of kittens deprived of vision in one eye. *J. Neurophysiol.* 26, 1003-1017 (1963).
2. Jacobs, G. H. A perspective on color vision in platyrrhine monkeys. *Vision Res.* 38, 3307-3313 (1998).
3. Li, Q., Timmers, A. M., Guy, J., Pang, J. & Hauswirth, W. W. Cone-specific expression using a human red opsin promoter in recombinant AAV. *Vision Res.* 48(2007).
4. Reffin, J. P., Astell, S. & Mollon, J. D. Trials of a computer-controlled colour vision test that preserves the advantages of pseudo-isochromatic plates. in *Colour Vision Deficiencies X* 69-76 (Kluwer Academic Publishers, Dordrecht, 1991).
5. Regan, B. C., Reffin, J. P. & Mollon, J. D. Luminance noise and the rapid determination of discrimination ellipses in colour deficiency. *Vision Res.* 34, 1279-1299 (1994).
6. Mancuso, K., Neitz, M. & Neitz, J. An adaptation of the Cambridge Colour Test for use with animals. *Vis. Neurosci.* (2006).
7. Kuchenbecker, J., Sahay, M., Tait, D. M., Neitz, M. & Neitz, J. Topography of the long- to middle-wavelength sensitive cone ratio in the human retina assessed with a wide-field color multifocal electroretinogram. *Vis. Neurosci.* 25, 301-306 (2008).
8. Mancuso, K. et al. Recombinant adeno-associated virus targets passenger gene expression to cones in primate retina. *J. Opt. Soc. Am. A Opt. Image Sci. Vis.* 24, 1411-1416 (2007).
9. Nathans, J., Piantanida, T. P., Eddy, R. L., Shows, T. B. & Hogness, D. S. Molecular genetics of inherited variation in human color vision. *Science* 232, 203-210 (1986).
10. Shapley, R. Specificity of cone connections in the retina and color vision. Focus on "Specificity of cone inputs to macaque retinal ganglion cells". *J. Neurophysiol.* 95, 587-588 (2006).
11. DeValois, R. L. & DeValois, K. K. A multi-stage color model. *Vision Res.* 33, 1053-1065 (1993).
12. Jacobs, G. H., Williams, G. A., Cahill, H. & Nathans, J. Emergence of Novel Color Vision in Mice Engineered to Express a Human Cone Photopigment. *Science* 315, 1723-1725 (2007).
13. Makous, W. Comment on "Emergence of Novel Color Vision in Mice Engineered to Express a Human Cone Photopigment". *Science* 318, 196 (2007).
14. Maguire, A. M. et al. Safety and efficacy of gene transfer for Leber's congenital amaurosis. *N. Engl. J. Med.* 358, 2240-2248 (2008).
15. Bainbridge, J. W. & Ali, R. R. Success in sight: The eyes have it! Ocular gene therapy trials for LCA look promising. *Gene Ther.* 15, 1191-1192 (2008).
16. Cideciyan, A. V. et al. Human gene therapy for RPE65 isomerase deficiency activates the retinoid cycle of vision but with slow rod kinetics. *Proc. Natl. Acad. Sci. U.S.A.* 105, 15112-15117 (2008).
17. Wang, Y. et al. A locus control region adjacent to the human red and green visual pigment genes. *Neuron* 9, 429-440 (1992).
18. Mauck, M. C., Mauncuso, K., Kuchenbecher, J., Connor, T. B., Hauswirth, W. W., Neitz, J., Neitz, M. Longitudinal evaluation of expression of virally delivered transgenes in gerbil cone photoreceptors. *Vis. Neurosci.* 25, 273-282 (2008).
19. Nathans, J., Thomas, D. & Hogness, D. S. Molecular genetics of human color vision: the genes encoding blue, green, and red pigments. *Science* 232, 193-202 (1986).
20. Neitz, M., Neitz, J. & Jacobs, G. H. Spectral tuning of pigments underlying red-green color vision. *Science* 252, 971-974 (1991).
21. Biining, H., Perabo, L., Coutelle, O., Quadt-Humme, S. & Hallek, M. Recent developments in adeno-associated virus vector technology. *J. Gene Med.* 10, 717-733 (2008).

Example 2: Description and Validation of New LED-Based, Wide-Field, Color Mf-ERG The electroretinogram (ERG) is an electrophysiologic recording technique used to measure electrical activity of the entire retina. The electrochemical potential of retinal cells change in response to light, which in turn induces voltage on an electrode placed on the cornea and/or sclera. The first ERGs were recorded by a Swedish physiologist working in the mid-1800's in amphibian retina. Since this time the technique has been widely incorporated in clinical practice as a diagnostic tool. Marriage of physiology to engineering has led to a variety of stimuli and analysis paradigms which can tease out specific cellular responses or region specific information. The latter has been motivated by the fact that the topographical organization of the retina plays an important role in disease with different diseases being characterized by different affected retinal areas. Early attempts to evaluate the function of specific retinal regions using the ERG illuminated only a small patch of retina, however, such "focal ERGs" have the drawback that light reflected from the focal area onto other retinal regions produces an ERG response that cannot be uncoupled from that produced by the region of interest. The other problem is that obtaining any type of a topographical map of retinal function using the mono-focal approach is prohibited by the time required to obtain ERGs serially from many different retinal regions. Both problems have been solved with the development of the multifocal- (mf-) ERG, pioneered by Erich Sutter in the early 1990s (Sutter, 1991). Mf-ERGs perform a series of individual focal ERG experiments simultaneously by taking advantage of either (1) correlation techniques or (2) frequency encoding. In this way, a complete topographical map of electrical responses over a large retinal region is obtained in a relatively short period of time.

The typical ERG apparatus for mf-ERGs stimulates a hexagonal patch of retina with a 20 degree radius and uses video display. More recently a display that employs white light emitting diodes (LEDs) was designed for use with a frequency encoding method for obtaining mf-ERGs. Having a stimulus that could reach further into the periphery would be useful in the early detection of retinal diseases that progress from peripheral to central retina. Additionally, individuals with normal trichromatic color vision express three distinct photopigments, or opsins, in separate classes of cone photoreceptor: short- (S-), middle- (M-), and long- (L-) wavelength sensitive. The S-cones are maximally sensitive to short wavelengths of light near 420 nm; M-cones have their maximal response near 530 nm; and the L-cones are most sensitive near 560 nm. Thus, an mf-ERG stimulus containing LEDs of different wavelengths would have applications in characterizing the topography of expression of the different opsin transgenes in the eyes of living subjects treated with gene therapy.

In particular, in gene therapy treatments administering recombinant adeno-associated virus (rAAV) carrying a human L-opsin gene M-opsin gene or S-opsin gene to primates that have two cone types to produce trichromatic color vision. As such, a non-invasive objective method is needed to determine the locations of functioning opsin expression in vivo.

Here we describe a wide-field color mf-ERG capable of stimulating a radius greater than 70 degrees. The wide field mf-ERG has a colored LED-based stimulus that incorporates a new design capable of maintaining viable signal-to-noise ratio (SNR) out into the far peripheral retina.

mf-ERG and Stimulus Panel

An LEDs as a light source was chosen because new advancements in LED technology allow for a large number of focused photons to be emitted from a point source. Additionally, LEDs are available in a variety of single peak narrow-bandwidth packages. The stimulus contained 1024 doublet pixels each containing a red (653 nm, half-bandwidth 22 nm, FIG. 2.1c) and a green (527 nm, half-bandwidth 33 nm, FIG. 2.1d) LED. Thus, the new display had 2,048 paired green and red LEDs. LEDs have inherent manufacturing variations in their breakdown resistance. Since the amount of current is proportional to the number of photons per unit time, applying a constant voltage across the LEDs would result in varying photon output. To circumvent these issues and ensure repeatability and linearity, constant current integrated circuit chips (Allegro A6276) were used to drive the LEDs (FIG. 2.1b). These devices are designed to maintain constant current despite fluctuations in anode voltage. To prevent variation in peak wavelength over varied intensities, a pulse frequency modulation (PFM) signal was used (Swanson, Ueno, Smith, & Pokorny, 1987).

Using red and green LEDs, it is possible to isolate responses of L- or M-cones using silent substitution. Integrating the spectral composition of the green LED with the spectral sensitivity curves of the human M- and L-photopigments (FIG. 2.1e) yields that approximately equal quanta are caught by both photopigments (FIG. 2.1f). In contrast, the red LED is six times more effective at stimulating the L photopigment than it is the M (FIG. 2.1f). Isolation of responses that are due to transduction from an introduced L-opsin transgene, M-opsin transgene or S-opsin transgene are straightforward in primates because red, blue or green LEDs can be chosen that are much more effective for the L-opsin M-opsin or S-opsin transgene respectively than for the endogenous pigments of the untreated dichromatic primates. In the case of Squirrel monkeys, they have S-cones maximally sensitive near 430 nm, and they can express any of several variants of middle-to-long wavelength opsin including L or M. The monkey used in validation experiments had M-cones sensitive near 532 nm, in addition to his S-cones. Thus, following the administration of the L-opsin transgene via subretinal injection, the mf-ERGs of squirrel monkey were predicted to show elevations in mf-ERG amplitude to red light in regions corresponding areas of the retina transduced, and distal areas would show progressively lower amplitudes to the L-cone isolating stimulus.

Resolution of the stimulator was 1024 LED over a larger stimulating area of about 150 degrees of visual field. Sensitivity of the measurement can be increased by summing more retinal responses per unit area and by using ultra-bright LEDs. Other new techniques that were used to prevent peripheral SNR fall-off included the use of trapezoidal shaped printed circuit boards that when placed edge-to-edge created a geodesic dome (FIG. 2.1a). The advantage of this design was that LEDs were held equidistantly from and pointing toward a single focal point where the subject's pupil was positioned. Any variation in directionality caused by imperfect sphericity was corrected by aiming each LED individually. In the typical usage, LEDs from areas of the dome shaped stimulator were summed so that there were 37 individual segments, which together subtended the 150° of visual angle, thus allowing a wide-field functional map of an area covering almost the entire retina to be produced.

There are two mathematical methodologies available to code and decode the topographical regions on the recording electrode: One is a cross-correlation technique called m-sequence and the other is a frequency encoding technique called cyclic summation. Cyclic summation is preferred in our application because it has been empirically shown to provide higher signal-to-noise ratio than m-sequence (Lindenberg, Horn, & Korth, 2003). Also, cyclic summation cannot be done using any kind of conventional CRT or LCD video display. Cyclic summation requires independent control of every segment of the display. Conventional video displays update the entire screen with every video frame typically at 60 Hz. In cyclic summation, each segment being analyzed is updating at a slightly different frequency. Typically, the "center frequency" is 30 Hz but each segment fractionally different from 30 Hz, i.e., 30.00 Hz, 30.10 Hz, 30.20 ... etc. In the analysis, responses to different areas of the retina to different segment frequencies are used to generate a map of retinal responses which are read out as electrophysiological "activity." For example, after gene therapy using an L opsin gene in a primate retina containing only M and S cones, areas of retina that express the newly introduced L opsin will have higher electrical activity in response to the red LED light relative to the green light than areas of the retina not expressing the transgene. This allows the effectiveness of the gene therapy in terms of areas responding their time course to be monitored with an objective measure.

In practice, we define the following parameters; $f_c$=center frequency, T=total time, Q=number of segments, and n=0 ... (Q−1). The number of cycles per segment is given by $$cycles_n = f_c \cdot T - \left[\frac{Q-1}{2} + n\right]. \quad (2.1)$$

Then, $f_n$ represents the frequencies at which each segment is encoded into the stimulus is $$f_n = \frac{cycles_n}{T}. \quad (2.2)$$

Finally, by windowing and summing the recorded retinal waveform, defined as w(t), region specific signal, $Activity_n$, can be extracted in equation 2.3, $$Activity_n = \sum_{n=0}^{(Q-1)} \sum_{m=0}^{(cycles_n-1)} w\left(\frac{m}{f_n} \ldots \frac{(m+1)}{f_n}\right). \quad (2.3)$$

For our purposes, $f_c$=30 Hz, T=40 seconds, and Q=37. In the retina, an additional advantage of the cyclic summation method are that the intensity and temporal frequency of the LEDs can be specified to isolate cone photoreceptor responses and silence rod photoreceptor responses.

Repeatability, Linearity, and SNR

Measurements for repeatability and linearity were made using a UDT S370 Optometer (UDT Instruments, San Diego, Calif.). LED outputs were measured in microwatts (uW) at seven different intensity settings, in random order. Three complete sets of data were taken on three separate days. All measurements were taken after the instrument became equilibrated with the ambient room temperature, which reflects normal operation of the instrument.

Signal-to-noise ratio was measured using a human subject by first placing an opaque material in front of the stimulus and running successive mf-ERGs. Voltages received during the blocked trials were taken as the noise of the instrument. Signal was then measured by performing mf-ERGs on four human subjects with normal trichromatic color vision. To compare SNR as a function of eccentricity, signal and noise were broken into different eccentric rings. Best subject and the average of all subjects were calculated for each ring. Tests involving human subjects were done in accordance with the principles embodied in the Declaration of Helsinki.

Viral Vector and Subretinal Injections

To validate whether the instrument operated as expected, a mixture of two recombinant adeno-associated viruses was injected sub-retinally in a gerbil (Meriones unguiculatus) and a squirrel monkey (Saimiri sciureus). One virus, rAAV.CHOPS2053.GFP, carried a gene for green fluorescent protein (GFP) and the other virus, rAAV.CHOPS2053.RHLOPS, coded for human L-opsin. The L-opsin virus was identical to the GFP virus except that a Not I restriction fragment containing the coding sequence for green fluorescent protein was replaced with a 1.2 kb Not I restriction fragment containing recombinant human L opsin cDNA. The opsin gene encoded a human L pigment that is predicted from the deduced amino acid sequence to be maximally sensitive to 562 nm light. In order to provide a method for visualizing transduced cone photoreceptors using immunohistochemistry in future experiments, the sequence of the human L opsin transgene was changed so that the last 12 amino acids matched the known epitope for the monoclonal antibody OS-2. This antibody was previously shown to specifically label S or UV cones in mammalian and primate retina. The C-terminal 12 amino acids of human S opsin were demonstrated to be the epitope. The substitution of the C-terminal 12 amino acids of S-opsin into L-opsin is not predicted to change the spectral sensitivity of the L-opsin trans-gene product.

Subretinal injections were performed. Briefly, gerbils were anesthetized using a combination of Ketamine (50 mg/kg) and Xylazine (2 mg/kg), and it received two 5 uL subretinal injections of a 1:1 (volume:volume) mixture of rAAV.CHOPS2053.GFP and rAAV.CHOPS2053.RHLOPS that were placed in the superior retinal area. A color mf-ERG was then performed on this animal at 6 months post-injection. Squirrel monkeys was anesthetized using 15 mg/kg ketamine and 2 mg/kg xylazine, and they received two 100 uL subretinal injections of a virus mixture containing 110 uL of rAAV.CHOPS2053.GFP and 220 uL of rAAV.CHOPS2053.RHLOPS. Both injections were positioned near the fovea, with the first injection placed superiorly, and the second injection placed in the inferotemporal region of the retina. A color mf-ERG was performed on this animal about 42 weeks, or 10.5 months post-injection. All of these procedures were conducted in accordance with the experimental animal care and usage guidelines of the United States National Institutes of Health.

Fundus Exams

Both the gerbil and squirrel monkey had fundus images taken at multiple time points post-injection to observe expression of the GFP transgene over time. Fundus images were obtained using the fluorescein angiography mode of the RetCam II digital imaging system (Massie Laboratories, Pleasanton, Calif. For the gerbil, images were taken with a lens designed for detecting retinopathy in premature infants, which provides a 130° field of view, and for the monkey, a high magnification 30° lens was used. Thus, multiple fundus images from the squirrel monkey were pieced together into a montage, in order to show a comparable retinal area.

Results

Measures of repeatability, linearity, and signal-to-noise ratio (SNR) were performed to evaluate the wide-field color ERG system. More properly, given n=2 . . . 8, m=1/2$^n$, and t=[0, ~3.5, 7] days, then intensity, $I_m(t)$, is said to be repeatable if $$s = 3 \cdot \sqrt{\frac{1}{2} \sum_{t=1}^{3} (I_m(t) - \overline{I_m(t)})^2} \leq \varepsilon \quad (2.4)$$

where ε is defined as $$\varepsilon = 0.05 \cdot \max(photon_m). \quad (2.5)$$

The instrument was said to be linear if Pearson's $R^2$ was greater than 0.95. And finally, signal (in SNR) was is calculated by averaging response from four subjects, and noise was taken as the residual signal while an opaque material blocked stimulus.

Repeatability and linearity are demonstrated in FIG. 2.2. Each data point is an average of optometer measurements for the particular intensity setting taken on three separate days; error bars are the standard deviations with a 99.7% confidence interval. Pearson's R correlation was calculated and the coefficient of determination ($R^2$) values is shown. The red LEDs shared 0.9987 total variance and the green LEDs shared 0.9996 total variance demonstrating system is linear and repeatable over time. SNR values are shown in Table 2.1. The SNR was high for the inner segments of the stimulus panel; it decreased in more peripheral regions but remained high enough to allow measurements into the far periphery.

Because the GFP-coding virus and the L-opsin-coding virus were injected together at the same locations, fluorescence fundus images could be registered with mf-ERG data from the same animal in order to validate the redesigned wide-field color mf-ERG system. Areas of high GFP expression corresponded well to areas of high mf-ERG voltage in response to the L-cone isolating red stimulus (FIG. 2.3). Animals were insensitive to the red 653 nm wave-length light prior to injection, verifying that the signal measured in animals post-injection is true signal coming from the introduced L-opsin transgene product. In the squirrel monkey, the red-light mf-ERG data showed high voltage in the regions that corresponded to the fluorescence fundus images.

To evaluate whether the concave surface of the newly developed stimulator produces ERG amplitudes that are relatively constant with retinal eccentricity an experiment was performed in which flicker ERG responses were measured under two different conditions. In FIG. 2.4, the circles represent ERG responses from an LED traveling down a linear path while the subject fixated forward. On the same graph, triangles represent ERG responses from an LED traveling on a rotating boom while the subject fixated forward. The boom held the LEDs perpendicular to the cornea. Results from this experiment demonstrate the increase in signal given by the convex stimulator, compared to a traditional flat-panel LCD screen or CRT monitor. The curved stimulus design, in addition to the use of ultra-bright LEDs as the light source, increased the SNR sufficiently high in the far periphery to ensure viable signals were recorded from cone photoreceptors.

In the conventional mf-ERG, the signal amplitudes are greatly reduced in the periphery because the illumination from a flat screen falls off roughly as the cosine with increasing eccentricity. In our design, the redesigned stimulus had concave structure holding the LEDs such that the inner surface pointed perpendicular to the stimulated retinal area. In addition, similar to traditional mf-ERG stimulators, the number of LEDs in each segment was increased with eccentricity to compensate for the decrease in cone density.

If 40% of cones express the transgene the increase in red sensitivity should be that expected from a spectral ERG in which 20% of the total ERG contribution is from L opsin while 80% is from M opsin. This is consistent with the observed red sensitivity in both monkeys and gerbils.

This is the first time that measurements from cones in the far peripheral retina have been achieved. Results from these experiments indicate that the wide-field color mf-ERG system is a valid technique for measuring the topography of opsin expression in living subjects, and it will serve as an important tool for evaluating success of gene therapy in humans.

REFERENCES FOR EXAMPLE 2

Sutter, E. E. (1991). The Fast m-Transform: A Fast Computation of Cross-Correlations with Binary m-Sequences. *SIAM Journal on Computing*, 20(4), 686-694.

Swanson, W. H., Ueno, T., Smith, V. C., & Pokorny, J. (1987). Temporal modulation sensitivity and pulse-detection thresholds for chromatic and luminance perturbations. *Journal of the Optical Society of America A—Optics, Image Science and Vision*, 4(10), 13.

Lindenberg, T., Horn, F. K., & Korth, M. (2003). Cyclic summation versus m-sequence technique in the multifocal ERG. *Graefes Archive of Clinical Experimental Ophthalmology.*, 241(6), 505-510.

We claim:

1. A method for treating blue cone monochromacy in a primate, comprising administering to the eye of a primate suffering from blue cone monochromacy a recombinant adeno-associated virus (AAV) gene delivery vector comprising
   (a) a promoter region, wherein the promoter region comprises an M opsin promoter sequence comprising the nucleic acid sequence of SEQ ID NO:2; and
   (b) a gene encoding a therapeutic protein comprising the amino acid sequence of SEQ ID NO: 11;
   wherein in vivo expression of the therapeutic protein in cone cells of the primate serves to restore visual capacity in the primate.

2. The method of claim 1, wherein the visual capacity is selected from the group consisting of: a reduction or slowing of vision loss; improved visual acuity; and a decrease in abnormal sensitivity to bright lights.

3. The method of claim 2, wherein the primate's response to the treatment is monitored.

4. The method of claim 1, wherein the gene delivery vector further comprises an enhancer element upstream of the promoter, wherein the enhancer element comprises the nucleic acid sequence of SEQ ID NO: 51, and wherein the gene is operatively linked to the enhancer element.

5. The method of claim 1, wherein the gene delivery vector further comprises an intron comprising a splice donor/acceptor region, wherein the intron is located downstream of the promoter region and is located upstream of the gene.

* * * * *

SEQUENCE LISTING

```
<160> NUMBER OF SEQ ID NOS: 51

<210> SEQ ID NO 1
<211> LENGTH: 494
<212> TYPE: DNA
<213> ORGANISM: Artificial Sequence
<220> FEATURE:
<223> OTHER INFORMATION: Synthetic

<400> SEQUENCE: 1
ggatccggtt ccaggcctcg gccctaaata gtctccctgg gctttcaaga gaaccacatg      60
agaaaggagg attcgggctc tgagcagttt caccacccac ccccagtct gcaaatcctg     120 acccgtgggt ccacctgccc caaaggcgga cgcaggacga tagaagggaa cagagaacac     180
ataaacacag agagggccac agcggctccc acagtcaccg ccaccttcct ggcggggatg     240
ggtggggcgt ctgagtttgg ttcccagcaa atccctctga gccgcccttg cgggctcgcc     300
tcaggagcag gggagcaaga ggtgggagga ggaggtctaa gtcccaggcc caattaagag     360
atcaggtagt gtagggtttg ggagctttta aggtgaagag gcccgggctg atcccacagg     420
ccagtataaa gcgccgtgac cctcaggtga tgcgccaggg ccggctgccg tcggggacag     480
ggctttccat agcc                                                      494

<210> SEQ ID NO 2
<211> LENGTH: 494
<212> TYPE: DNA
<213> ORGANISM: Artificial Sequence
<220> FEATURE:
<223> OTHER INFORMATION: Synthetic

<400> SEQUENCE: 2
ttatttagta gaaacggggt ttcaccatgt tagtcaggct ggtcgggaac tcctgacctc      60
aggagatcta cccgccttgg cctcccaaag tgctgggatt acaggcgtgt gccactgtgc     120
ccagccactt ttttttagac agagtcttgg tctgttgccc aggctagagt tcagtggcgc     180
catctcagct cactgcaacc tccgcctccc agattcaagc gattctcctg cctcgacctc     240
ccagtagctg ggattacagg tttccagcaa atccctctga gccgccccg ggggctcgcc     300
```

| | |
|---|---|
| tcaggagcaa ggaagcaagg ggtgggagga ggaggtctaa gtcccaggcc caattaagag | 360 |
| atcagatggt gtaggatttg ggagctttta aggtgaagag gcccgggctg atcccactgg | 420 |
| ccggtataaa gcaccgtgac cctcaggtga cgcaccaggg ccggctgccg tcggggacag | 480 |
| ggctttccat agcc | 494 |

<210> SEQ ID NO 3
<211> LENGTH: 568
<212> TYPE: DNA
<213> ORGANISM: Artificial Sequence
<220> FEATURE:
<223> OTHER INFORMATION: Synthetic

<400> SEQUENCE: 3

| | |
|---|---|
| ctaggcattg tcaagttgcc taagtcctgt tccatcaagg ctgtttactg atgtgcttcc | 60 |
| agggcactcc ccactcccag ccctttcctg cagcccaggg ctggttccta gcctctcagc | 120 |
| agacttaaga tgggcacctt ccacaaaggg gcagatgagt tgaggaaaac ttaactgata | 180 |
| cagttgtgcc agaagccaaa ataagaggcg tgccctttct atagcccccat taaaagaaca | 240 |
| aaaaagtgga agcatcttca gtgaatatgg gtcagcacct cccagacctc agggagtcca | 300 |
| cttctgttca tcccagcacc cagcattgca tatccagatt atttgagccc aatctcttat | 360 |
| cctctgaaga acacaatcgg cttttggggcc acaaaaggtt taggtagtgg tttagggatt | 420 |
| tctaatccca aactttgtcc ttgggaggtt taggattagt attgatcatt cacagagccc | 480 |
| aagtgttttt agaggagggg ttttgtgggg tgggaggatc acctataaga ggactcagag | 540 |
| gggggtgtgg ggcatccatg agaaaaat | 568 |

<210> SEQ ID NO 4
<211> LENGTH: 1555
<212> TYPE: DNA
<213> ORGANISM: Artificial Sequence
<220> FEATURE:
<223> OTHER INFORMATION: Synthetic

<400> SEQUENCE: 4

| | |
|---|---|
| ccagggtgag attatgaggc tgagctgaga atatcaagac tgtaccgagt aggggggcctt | 60 |
| ggcaagtgtg gagagcccgg cagctggggc agagggcgga gtacggtgtg cgtttacgga | 120 |
| cctcttcaaa cgaggtagga aggtcagaag tcaaaaaggg aacaaatgat gtttaaccac | 180 |
| acaaaaatga aaatccaatg gttggatatc cattccaaat acacaaaggc aacggataag | 240 |
| tgatccgggc caggcacaga aggccatgca cccgtaggat tgcactcaga gctcccaaat | 300 |
| gcataggaat agaagggtgg gtgcaggagg ctgagggggtg gggaaagggc atgggtgttt | 360 |
| catgaggaca gagcttccgt ttcatgcaat gaaaagagtt tggagacgga tggtggtgac | 420 |
| tggactatac acttacacac ggtagcgatg gtacactttg tattatgtat attttaccac | 480 |
| gatcttttta aagtgtcaaa ggcaaatggc caaatggttc cttgtcctat agctgtagca | 540 |
| gccatcggct gttagtgaca aagcccctga gtcaagatga cagcagcccc cataactcct | 600 |
| aatcggctct cccgcgtgga gtcatttagg agtagtcgca ttagagacaa gtccaacatc | 660 |
| taatcttcca ccctggccag ggccccagct ggcagcgagg gtgggagact ccgggcagag | 720 |
| cagagggcgc tgacattggg gcccggcctg gcttgggtcc ctctggcctt tccccagggg | 780 |
| ccctcttttcc ttggggcttt cttgggccgc cactgctccc gctcctctcc cccatccca | 840 |
| cccccctcacc cctcgttct tcatatcctt ctctagtgct ccctccactt tcatccaccc | 900 |
| ttctgcaaga gtgtgggacc acaaatgagt tttcacctgg cctggggaca cacgtgcccc | 960 |

| cacaggtgct gagtgacttt ctaggacagt aatctgcttt aggctaaaat gggacttgat | 1020 |
| cttctgttag ccctaatcat caattagcag agccggtgaa ggtgcagaac ctaccgcctt | 1080 |
| tccaggcctc ctcccacctc tgccacctcc actctccttc ctgggatgtg ggggctggca | 1140 |
| cacgtgtggc ccagggcatt ggtgggattg cactgagctg ggtcattagc gtaatcctgg | 1200 |
| acaagggcag acagggcgag cggagggcca gctccggggc tcaggcaagg ctgggggctt | 1260 |
| cccccagaca ccccactcct cctctgctgg accccactt cataggcac ttcgtgttct | 1320 |
| caaagggctt ccaaatagca tggtggcctt ggatgcccag ggaagcctca gagttgctta | 1380 |
| tctccctcta gacagaaggg gaatctcggt caagagggag aggtcgccct gttcaaggcc | 1440 |
| acccagccag ctcatggcgg taatgggaca aggctggcca gccatcccac cctcagaagg | 1500 |
| gacccggtgg ggcaggtgat ctcagaggag gctcacttct gggtctcaca ttctt | 1555 |

<210> SEQ ID NO 5
<211> LENGTH: 189
<212> TYPE: DNA
<213> ORGANISM: Artificial Sequence
<220> FEATURE:
<223> OTHER INFORMATION: Synthetic

<400> SEQUENCE: 5

| gatccggtac tcgaggaact gaaaaaccag aaagttaact ggtaagttta gtcttttgt | 60 |
| cttttatttc aggtcccgga tccggtggtg gtgcaaatca aagaactgct cctcagtgga | 120 |
| tgttgccttt acttctaggc ctgtacggaa gtgttacttc tgctctaaaa gctgcggaat | 180 |
| tgtacccgc | 189 |

<210> SEQ ID NO 6
<211> LENGTH: 1114
<212> TYPE: DNA
<213> ORGANISM: Homo sapiens

<400> SEQUENCE: 6

| atgagaaaaa tgtcggagga agagttttat ctgttcaaaa atatctcttc agtggggccg | 60 |
| tgggatgggc ctcagtacca cattgcccct gtctgggcct tctacctcca ggcagctttc | 120 |
| atgggcactg tcttccttat agggttccca ctcaatgcca tggtgctggt ggccacactg | 180 |
| cgctacaaaa agttgcggca gccccctcaac tacattctgg tcaacgtgtc cttcggaggc | 240 |
| ttcctcctct gcatcttctc tgtcttccct gtcttcgtcg ccagctgtaa cggatacttc | 300 |
| gtcttcggtc gccatgtttg tgctttggag ggcttcctgg gcactgtagc aggtctggtt | 360 |
| acaggatggt cactggcctt cctggccttt gagcgctaca ttgtcatctg taagcccttc | 420 |
| ggcaacttcc gcttcagctc caagcatgca ctgacggtgg tcctggctac ctggaccatt | 480 |
| ggtattggcg tctccatccc acccttcttt ggctggagcc ggttcatccc tgagggcctg | 540 |
| cagtgttcct gtggccctga ctggtacacc gtgggcacca ataccgcag cgagtcctat | 600 |
| acgtggttcc tcttcatctt ctgcttcatt gtgcctctct ccctcatctg cttctcctac | 660 |
| actcagctgc tgagggccct gaaagctgtt gcagctcagc agcaggagtc agctacgacc | 720 |
| cagaaggctg aacgggaggt gagccgcatg gtggttgtga tggtaggatc cttctgtgtc | 780 |
| tgctacgtgc cctacgcggc cttcgccatg tacatggtca acaaccgtaa ccatgggctg | 840 |
| gacttacggc ttgtcaccat tccttcattc ttctccaaga gtgcttgcat ctacaatccc | 900 |
| atcatctact gcttcatgaa taagcagttc caagcttgca tcatgaagat ggtgtgtggg | 960 |

```
aaggccatga cagatgaatc cgacacatgc agctcccaga aaacagaagt ttctactgtc   1020
tcgtctaccc aagttggccc caactgagga cccaatattg gcctgtttgc aacagctaga   1080
attaaatttt acttttaaaa aaaaaaaaaa aaaa                               1114
```

<210> SEQ ID NO 7
<211> LENGTH: 348
<212> TYPE: PRT
<213> ORGANISM: Homo sapiens

<400> SEQUENCE: 7

```
Met Arg Lys Met Ser Glu Glu Phe Tyr Leu Phe Lys Asn Ile Ser
1               5                   10                  15

Ser Val Gly Pro Trp Asp Gly Pro Gln Tyr His Ile Ala Pro Val Trp
            20                  25                  30

Ala Phe Tyr Leu Gln Ala Ala Phe Met Gly Thr Val Phe Leu Ile Gly
            35                  40                  45

Phe Pro Leu Asn Ala Met Val Leu Val Ala Thr Leu Arg Tyr Lys Lys
50                  55                  60

Leu Arg Gln Pro Leu Asn Tyr Ile Leu Val Asn Val Ser Phe Gly Gly
65                  70                  75                  80

Phe Leu Leu Cys Ile Phe Ser Val Phe Pro Val Phe Val Ala Ser Cys
                85                  90                  95

Asn Gly Tyr Phe Val Phe Gly Arg His Val Cys Ala Leu Glu Gly Phe
            100                 105                 110

Leu Gly Thr Val Ala Gly Leu Val Thr Gly Trp Ser Leu Ala Phe Leu
            115                 120                 125

Ala Phe Glu Arg Tyr Ile Val Ile Cys Lys Pro Phe Gly Asn Phe Arg
            130                 135                 140

Phe Ser Ser Lys His Ala Leu Thr Val Val Leu Ala Thr Trp Thr Ile
145                 150                 155                 160

Gly Ile Gly Val Ser Ile Pro Pro Phe Phe Gly Trp Ser Arg Phe Ile
                165                 170                 175

Pro Glu Gly Leu Gln Cys Ser Cys Gly Pro Asp Trp Tyr Thr Val Gly
            180                 185                 190

Thr Lys Tyr Arg Ser Glu Ser Tyr Thr Trp Phe Leu Phe Ile Phe Cys
            195                 200                 205

Phe Ile Val Pro Leu Ser Leu Ile Cys Phe Ser Tyr Thr Gln Leu Leu
210                 215                 220

Arg Ala Leu Lys Ala Val Ala Ala Gln Gln Gln Glu Ser Ala Thr Thr
225                 230                 235                 240

Gln Lys Ala Glu Arg Glu Val Ser Arg Met Val Val Met Val
                245                 250                 255

Ser Phe Cys Val Cys Tyr Val Pro Tyr Ala Ala Phe Ala Met Tyr Met
            260                 265                 270

Val Asn Asn Arg Asn His Gly Leu Asp Leu Arg Leu Val Thr Ile Pro
            275                 280                 285

Ser Phe Phe Ser Lys Ser Ala Cys Ile Tyr Asn Pro Ile Ile Tyr Cys
290                 295                 300

Phe Met Asn Lys Gln Phe Gln Ala Cys Ile Met Lys Met Val Cys Gly
305                 310                 315                 320

Lys Ala Met Thr Asp Glu Ser Asp Thr Cys Ser Ser Gln Lys Thr Glu
                325                 330                 335

Val Ser Thr Val Ser Ser Thr Gln Val Gly Pro Asn
            340                 345
```

<210> SEQ ID NO 8
<211> LENGTH: 1998
<212> TYPE: DNA
<213> ORGANISM: Homo sapiens

<400> SEQUENCE: 8

```
cccactggcc ggtataaagc accgtgaccc tcaggtgacg caccagggcc ggctgccgtc      60
ggggacaggg cttccatag ccatggccca gcagtggagc ctccaaaggc tcgcaggccg     120
ccatccgcag gacagctatg aggacagcac ccagtccagc atcttcacct acaccaacag     180
caactccacc agaggcccct tcgaaggccc gaattaccac atcgctccca gatgggtgta     240
ccacctcacc agtgtctgga tgatctttgt ggtcattgca tccgtcttca caaatgggct     300
tgtgctggcg gccaccatga gttcaagaa gctgcgccac ccgctgaact ggatcctggt     360
gaacctggcg gtcgctgacc tggcagagac cgtcatcgcc agcactatca gcgttgtgaa     420
ccaggtctat ggctacttcg tgctgggcca ccctatgtgt gtcctggagg ctacaccgt      480
ctccctgtgt gggatcacag gtctctggtc tctggccatc atttcctggg agagatggat     540
ggtggtctgc aagcccttg gcaatgtgag atttgatgcc aagctggcca tcgtgggcat     600
tgccttctcc tggatctggg ctgctgtgtg gacagccccg cccatctttg gttggagcag     660
gtactggccc cacggcctga agacttcatg cggcccagac gtgttcagcg gcagctcgta     720
ccccggggtg cagtcttaca tgattgtcct catggtcacc tgctgcatca ccccactcag     780
catcatcgtg ctctgctacc tccaagtgtg gctggccatc cgagcggtgg caaagcagca     840
gaaagagtct gaatccaccc agaaggcaga aaggaagtg acgcgcatgg tggtggtgat     900
ggtcctggca ttctgcttct gctgggaccc atacgcctc ttcgcatgct ttgctgctgc     960
caaccctgc taccccttcc accctttgat ggctgccctg ccggccttct tgccaaaag    1020
tgccactatc tacaaccccg ttatctatgt ctttatgaac cggcagtttc gaaactgcat    1080
cttgcagctt ttcgggaaga aggttgacga tggctctgaa ctctccagcg cctccaaaac    1140
ggaggtctca tctgtgtcct cggtatcgcc tgcatgaggt ctgcctccta cccatcccgc    1200
ccaccggggc tttggccacc tctcctttcc ccctccttct ccatcccgt aaaataaatg    1260
taatttatct ttgccaaaac caacaaagtc acagaggctt tcactgcagt gtgggaccac    1320
ctgagcctct gcgtgtgcag gcactgggtc tcgagggt gcaaggggga taagaggag    1380
agagcgcttc atagacttta agttttcccg agcctcatgt ctaccgatgg cgtgaaagga    1440
tcctggcaaa acagaagtgt gaggcaggtg ggcgtctata tccattcac caggctggtg    1500
gttacataat cggcaagcaa gagctgtgga ggggcttgct ggatgccctc agcacccagg    1560
aggagggagg gagctagcaa gctaaggcag gtggccctcc tggccccta aggtccatct    1620
gctggaggcc cagagtcctt ggagtacagt ctacacctgg aggggaccca ttcctgccag    1680
tctgtggcag gatggcgcg ccacctctgc caggccagga cccaagccc gatcagcatc    1740
agcatggtgc aggtgcacag gcgtgagctg atcagtgacg aggggcaggc acacaaggtg    1800
gagacaaaga ccaagaggac ggttgccagt gagaggcgcg gactcaggaa cttgaacaac    1860
atctgcgggg gacggctttg gaggtgctcc gctgcctcca gttgggtgac ttgctgtagc    1920
atctccagct tggatattcg gctcttgaag gtctccgtga tctcctgcag gagacgaaaa    1980
tgcacgcacc agaagtca                                                  1998
```

<210> SEQ ID NO 9

-continued

```
<211> LENGTH: 364
<212> TYPE: PRT
<213> ORGANISM: Homo sapiens

<400> SEQUENCE: 9

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
50                  55                  60

Ile Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Val Val
            100                 105                 110

Asn Gln Val Tyr Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
130                 135                 140

Ala Ile Ile Ser Trp Glu Arg Trp Met Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ala Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
210                 215                 220

Val Thr Cys Cys Ile Thr Pro Leu Ser Ile Ile Val Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270

Met Val Leu Ala Phe Cys Phe Cys Trp Gly Pro Tyr Ala Phe Phe Ala
        275                 280                 285

Cys Phe Ala Ala Ala Asn Pro Gly Tyr Pro Phe His Pro Leu Met Ala
290                 295                 300

Ala Leu Pro Ala Phe Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Val Ser Pro Ala
        355                 360

<210> SEQ ID NO 10
<211> LENGTH: 1234
<212> TYPE: DNA
```

<213> ORGANISM: Homo sapiens

<400> SEQUENCE: 10

| | | |
|---|---|---|
| cggctgccgt cggggacagg gctttccata gccatggccc agcagtggag cctccaaagg | 60 |
| ctcgcaggcc gccatccgca ggacagctat gaggacagca cccagtccag catcttcacc | 120 |
| tacaccaaca gcaactccac cagaggcccc ttcgaaggcc cgaattacca catcgctccc | 180 |
| agatgggtgt accacctcac cagtgtctgg atgatctttg tggtcactgc atccgtcttc | 240 |
| acaaatgggc ttgtgctggc ggccaccatg aagttcaaga agctgcgcca cccgctgaac | 300 |
| tggatcctgg tgaacctggc ggtcgctgac ctagcagaga ccgtcatcgc cagcactatc | 360 |
| agcattgtga accaggtctc tggctacttc gtgctgggcc acccatgtg tgtcctggag | 420 |
| ggctacaccg tctccctgtg tgggatcaca ggtctctggt ctctggccat catttcctgg | 480 |
| gagaggtggc tggtggtgtg caagcccttt ggcaatgtga gatttgatgc caagctggcc | 540 |
| atcgtgggca ttgccttctc ctggatctgg tctgctgtgt ggacagcccc gcccatcttt | 600 |
| ggttggagca ggtactggcc ccacggcctg aagacttcat gcggcccaga cgtgttcagc | 660 |
| ggcagctcgt accccggggt gcagtcttac atgattgtcc tcatggtcac ctgctgcatc | 720 |
| atcccactcg ctatcatcat gctctgctac ctccaagtgt ggctggccat ccgagcggtg | 780 |
| gcaaagcagc agaaagagtc tgaatccacc cagaaggcag agaaggaagt gacgcgcatg | 840 |
| gtggtggtga tgatctttgc gtactgcgtc tgctggggac cctacacctt cttcgcatgc | 900 |
| tttgctgctg ccaaccctgg ttacgccttc accctttga tggctgccct gccggcctac | 960 |
| tttgccaaaa gtgccactat ctacaacccc gttatctatg tctttatgaa ccggcagttt | 1020 |
| cgaaactgca tcttgcagct tttcgggaag aaggttgacg atggctctga actctccagc | 1080 |
| gcctccaaaa cggaggtctc atctgtgtcc tcggtatcgc ctgcatgagg tctgcctcct | 1140 |
| acccatcccg cccaccgggg cttggccac ctctcctttc ccctccttc tccatccctg | 1200 |
| taaaataaat gtaatttatc tttgccaaaa ccaa | 1234 |

<210> SEQ ID NO 11
<211> LENGTH: 364
<212> TYPE: PRT
<213> ORGANISM: Homo sapiens

<400> SEQUENCE: 11

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Thr Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Ile Val
            100                 105                 110

Asn Gln Val Ser Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu

```
                      130                 135                 140
        Ala Ile Ile Ser Trp Glu Arg Trp Leu Val Val Cys Lys Pro Phe Gly
        145                 150                 155                 160

Asn Val Arg Phe Asp Ala Lys Leu Ala Ile Val Gly Ile Ala Phe Ser
                        165                 170                 175

Trp Ile Trp Ser Ala Val Trp Thr Ala Pro Pro Ile Phe Gly Trp Ser
                        180                 185                 190

Arg Tyr Trp Pro His Gly Leu Lys Thr Ser Cys Gly Pro Asp Val Phe
                        195                 200                 205

Ser Gly Ser Ser Tyr Pro Gly Val Gln Ser Tyr Met Ile Val Leu Met
                        210                 215                 220

Val Thr Cys Cys Ile Ile Pro Leu Ala Ile Ile Met Leu Cys Tyr Leu
        225                 230                 235                 240

Gln Val Trp Leu Ala Ile Arg Ala Val Ala Lys Gln Gln Lys Glu Ser
                        245                 250                 255

Glu Ser Thr Gln Lys Ala Glu Lys Glu Val Thr Arg Met Val Val Val
                        260                 265                 270

Met Ile Phe Ala Tyr Cys Val Cys Trp Gly Pro Tyr Thr Phe Phe Ala
                        275                 280                 285

Cys Phe Ala Ala Ala Asn Pro Gly Tyr Ala Phe His Pro Leu Met Ala
                        290                 295                 300

Ala Leu Pro Ala Tyr Phe Ala Lys Ser Ala Thr Ile Tyr Asn Pro Val
        305                 310                 315                 320

Ile Tyr Val Phe Met Asn Arg Gln Phe Arg Asn Cys Ile Leu Gln Leu
                        325                 330                 335

Phe Gly Lys Lys Val Asp Asp Gly Ser Glu Leu Ser Ser Ala Ser Lys
                        340                 345                 350

Thr Glu Val Ser Ser Val Ser Ser Val Ser Pro Ala
                        355                 360

<210> SEQ ID NO 12
<211> LENGTH: 7326
<212> TYPE: DNA
<213> ORGANISM: Homo sapiens

<400> SEQUENCE: 12
aggacacagc gtccggagcc agaggcgctc ttaacggcgt ttatgtcctt tgctgtctga     60
ggggcctcag ctctgaccaa tctggtcttc gtgtggtcat tagcatgggc ttcgtgagac    120
agatacagct tttgctctgg aagaactgga ccctgcggaa aaggcaaaag attcgctttg    180
tggtggaact cgtgtggcct ttatctttat ttctggtctt gatctggtta aggaatgcca    240
acccgctcta cagccatcat gaatgccatt tccccaacaa ggcgatgccc tcagcaggaa    300
tgctgccgtg gctccagggg atcttctgca atgtgaacaa tccctgtttt caaagcccca    360
ccccaggaga atctcctgga attgtgtcaa actataacaa ctccatcttg gcaagggtat    420
atcgagattt tcaagaactc ctcatgaatg caccagagag ccagcacctt ggccgtattt    480
ggacagagct acacatcttg tcccaattca tggacaccct ccggactcac ccggagagaa    540
ttgcaggaag aggaatacga ataagggata tcttgaaaga tgaagaaaca ctgacactat    600
ttctcattaa aaacatcggc ctgtctgact cagtggtcta ccttctgatc aactctcaag    660
tccgtccaga gcagttcgct catggagtcc cggacctggc gctgaaggac atcgcctgca    720
gcgaggccct cctggagcgc ttcatcatct tcagccagag acgcggggca agacggtgc     780 gctatgccct gtgctccctc tcccagggca ccctacagtg gatagaagac actctgtatg    840
```

```
ccaacgtgga cttcttcaag ctcttccgtg tgcttcccac actcctagac agccgttctc    900
aaggtatcaa tctgagatct tggggaggaa tattatctga tatgtcacca agaattcaag    960
agtttatcca tcggccgagt atgcaggact tgctgtgggt gaccaggccc ctcatgcaga   1020
atggtggtcc agagaccttt acaaagctga tgggcatcct gtctgacctc ctgtgtggct   1080
accccgaggg aggtggctct cgggtgctct ccttcaactg gtatgaagac aataactata   1140
aggcctttct ggggattgac tccacaagga aggatcctat ctattcttat gacagaagaa   1200
caacatcctt ttgtaatgca ttgatccaga gcctggagtc aaatccttta accaaaatcg   1260
cttggagggc ggcaaagcct ttgctgatgg gaaaaatcct gtacactcct gattcacctg   1320
cagcacgaag gatactgaag aatgccaact caacttttga gaactggaa cacgttagga    1380
agttggtcaa agcctgggaa gaagtagggc cccagatctg gtacttcttt gacaacagca   1440
cacagatgaa catgatcaga gatacccctgg ggaacccaac agtaaaagac tttttgaata   1500
ggcagcttgg tgaagaaggt attactgctg aagccatcct aaacttcctc tacaagggcc   1560
ctcgggaaag ccaggctgac gacatggcca acttcgactg gagggacata tttaacatca   1620
ctgatcgcac cctccgcctg gtcaatcaat acctggagtg cttggtcctg gataagtttg   1680
aaagctacaa tgatgaaact cagctcaccc aacgtgccct ctctctactg gaggaaaaca   1740
tgttctgggc cggagtggta ttccctgaca tgtatccctg gaccagctct ctaccacccc   1800
acgtgaagta agatccga atggacatag acgtggtgga gaaaaccaat aagattaaag    1860
acaggtattg ggattctggt cccagagctg atcccgtgga agatttccgg tacatctggg   1920
gcgggtttgc ctatctgcag gacatggttg aacaggggat cacaaggagc caggtgcagg   1980
cggaggctcc agttggaatc tacctccagc agatgcccta cccctgcttc gtggacgatt   2040
cttttcatgat catcctgaac cgctgtttcc ctatcttcat ggtgctggca tggatctact   2100
ctgtctccat gactgtgaag agcatcgtct ggagaagga gttgcgactg aaggagacct   2160
tgaaaaatca gggtgtctcc aatgcagtga tttggtgtac ctggttcctg acagcttct   2220
ccatcatgtc gatgagcatc ttcctcctga cgatattcat catgcatgga agaatcctac   2280
attacagcga cccattcatc ctcttcctgt tcttgttggc tttctccact gccaccatca   2340
tgctgtgctt tctgctcagc accttcttct ccaaggccag tctggcagca gcctgtagtg   2400
gtgtcatcta tttcacccctc tacctgccac acatcctgtg cttcgcctgg caggaccgca   2460
tgaccgctga gctgaagaag gctgtgagct actgtctccc ggtggcattt ggatttggca   2520
ctgagtacct ggttcgcttt gaagagcaag gcctggggct gcagtggagc aacatcggga   2580
acagtcccac ggaaggggac gaattcagct tcctgctgtc catgcagatg atgctccttg   2640
atgctgctgt ctatggctta ctcgcttggt accttgatca ggtgtttcca ggagactatg   2700
gaaccccact tccttggtac tttcttctac aagagtcgta ttggcttggc ggtgaagggt   2760
gttcaaccag agaagaaaga gcctggaaa agaccgagcc cctaacagag gaaacggagg   2820
atccagagca cccagaagga atacacgact ccttctttga acgtgagcat ccagggtggg   2880
ttcctggggt atgcgtgaag aatctggtaa agatttttga gccctgtggc cggccagctg   2940
tggaccgtct gaacatcacc ttctacgaga accagatcac cgcattcctg gccacaatg   3000
gagctgggaa aaccaccacc ttgtccatcc tgacgggtct gttgccacca acctctggga   3060
ctgtgctcgt tggggaagg acattgaaa ccagcctgga tgcagtccgg cagagccttg   3120
gcatgtgtcc acagcacaac atcctgttcc accacctcac ggtggctgag cacatgctgt   3180
```

```
tctatgccca gctgaaagga aagtcccagg aggaggccca gctggagatg aagccatgt    3240
tggaggacac aggcctccac cacaagcgga atgaagaggc tcaggaccta tcaggtggca    3300
tgcagagaaa gctgtcggtt gccattgcct ttgtgggaga tgccaaggtg gtgattctgg    3360
acgaacccac ctctggggtg gacccttact cgagacgctc aatctgggat ctgctcctga    3420
agtatcgctc aggcagaacc atcatcatgt ccactcacca catggacgag gccgacctcc    3480
ttggggaccg cattgccatc attgcccagg aaggctcta ctgctcaggc accccactct    3540
tcctgaagaa ctgctttggc acaggcttgt acttaacctt ggtgcgcaag atgaaaaaca    3600
tccagagcca aggaaaggc agtgagggga cctgcagctg ctcgtctaag gtttctcca    3660
ccacgtgtcc agcccacgtc gatgacctaa ctccagaaca agtcctggat ggggatgtaa    3720
atgagctgat ggatgtagtt ctccaccatg ttccagaggc aaagctggtg gagtgcattg    3780
gtcaagaact tatcttcctt cttccaaata agaacttcaa gcacagagca tatgccagcc    3840
ttttcagaga gctggaggag acgctggctg accttggtct cagcagtttt ggaatttctg    3900
acactcccct ggaagagatt tttctgaagg tcacggagga ttctgattca ggacctctgt    3960
ttgcgggtgg cgctcagcag aaaagagaaa acgtcaaccc ccgacacccc tgcttgggtc    4020
ccagagagaa ggctggacag acaccccagg actccaatgt ctgctcccca ggggcgccgg    4080
ctgctcaccc agagggccag cctcccccag agccagagtg cccaggcccg cagctcaaca    4140
cggggacaca gctggtcctc cagcatgtgc aggcgctgct ggtcaagaga ttccaacaca    4200
ccatccgcag ccacaaggac ttcctggcgc agatcgtgct cccggctacc tttgtgtttt    4260
tggctctgat gctttctatt gttatccctc cttttggcga ataccccgct ttgacccttc    4320
accctggat atatgggcag cagtacacct tcttcagcat ggatgaacca ggcagtgagc    4380
agttcacggt acttgcagac gtcctcctga ataagccagg cttggcaac cgctgcctga    4440
aggaagggtg gcttccggag taccctgtg gcaactcaac accctggaag actccttctg    4500
tgtccccaaa catcacccag ctgttccaga agcagaaatg gacacaggtc aacccttcac    4560
catcctgcag gtgcagcacc agggagaagc tcaccatgct gccagagtgc cccgagggtg    4620
ccggggcct cccgccccc cagagaacac agcgcagcac ggaaattcta caagacctga    4680
cggacaggaa catctccgac ttcttggtaa aaacgtatcc tgctcttata agaagcagct    4740
taaagagcaa attctgggtc aatgaacaga ggtatggagg aatttccatt ggaggaaagc    4800
tcccagtcgt ccccatcacg ggggaagcac ttgttgggtt tttaagcgac cttggccgga    4860
tcatgaatgt gagcggggc cctatcacta gagaggcctc taaagaaata cctgatttcc    4920
ttaaacatct agaaactgaa gacaacatta aggtgtggtt taataacaaa ggctggcatg    4980
ccctggtcag ctttctcaat gtggcccaca cgccatcttt acgggccagc ctgcctaagg    5040
acaggagccc cgaggagtat ggaatcaccg tcattagcca accctgaac ctgaccaagg    5100
agcagctctc agagattaca gtgctgacca cttcagtgga tgctgtggtt gccatctgcg    5160
tgattttctc catgtccttc gtcccagcca gctttgtcct ttatttgatc caggagcggg    5220
tgaacaaatc caagcaccct cagtttatca gtggagtgag ccccaccacc tactgggtga    5280
ccaacttcct ctgggacatc atgaattatt ccgtgagtgc tgggctggtg gtgggcatct    5340
tcatcgggtt tcagaagaaa gcctacactt ctccagaaaa ccttcctgcc cttgtggcac    5400
tgctcctgct gtatgatgg gcggtcattc ccatgatgta cccagcatcc ttcctgtttg    5460
atgtccccag cacagcctat gtggctttat cttgtgctaa tctgttcatc ggcatcaaca    5520
gcagtgctat taccttcatc ttggaattat ttgagaataa ccggacgctg ctcaggttca    5580
```

| | | |
|---|---|---|
| acgccgtgct gaggaagctg ctcattgtct tcccccactt ctgcctgggc cggggcctca | 5640 |
| ttgaccttgc actgagccag gctgtgacag atgtctatgc ccggtttggt gaggagcact | 5700 |
| ctgcaaatcc gttccactgg gacctgattg ggaagaacct gtttgccatg gtggtggaag | 5760 |
| gggtggtgta cttcctcctg accctgctgg tccagcgcca cttcttcctc tcccaatgga | 5820 |
| ttgccgagcc cactaaggag cccattgttg atgaagatga tgatgtggct gaagaaagac | 5880 |
| aaagaattat tactggtgga aataaaactg acatcttaag gctacatgaa ctaaccaaga | 5940 |
| tttatccagg cacctccagc ccagcagtgg acaggctgtg tgtcggagtt cgccctggag | 6000 |
| agtgctttgg cctcctggga gtgaatggtg ccggcaaaac aaccacattc aagatgctca | 6060 |
| ctggggacac cacagtgacc tcaggggatg ccaccgtagc aggcaagagt attttaacca | 6120 |
| atatttctga agtccatcaa aatatgggct actgtcctca gtttgatgca attgatgagc | 6180 |
| tgctcacagg acgagaacat ctttaccttt atgcccggct tcgaggtgta ccagcagaag | 6240 |
| aaatcgaaaa ggttgcaaac tggagtatta gagcctggg cctgactgtc tacgccgact | 6300 |
| gcctggctgg cacgtacagt gggggcaaca gcggaaaact ctccacagcc atcgcactca | 6360 |
| ttggctgccc accgctggtg ctgctggatg agcccaccac agggatggac ccccaggcac | 6420 |
| gccgcatgct gtggaacgtc atcgtgagca tcatcagaga agggagggct gtggtcctca | 6480 |
| catcccacag catggaagaa tgtgaggcac tgtgtacccg gctggccatc atggtaaagg | 6540 |
| gcgcctttcg atgtatgggc accattcagc atctcaagtc caaatttgga gatggctata | 6600 |
| tcgtcacaat gaagatcaaa tccccgaagg acgacctgct tcctgacctg aaccctgtgg | 6660 |
| agcagttctt ccaggggaac ttcccaggca gtgtgcagag ggagaggcac tacaacatgc | 6720 |
| tccagttcca ggtctcctcc tcctcccctg cgaggatctt ccagctcctc ctctcccaca | 6780 |
| aggacagcct gctcatcgag gagtactcag tcacacagac cacactggac caggtgtttg | 6840 |
| taaattttgc taaacagcag actgaaagtc atgacctccc tctgcaccct cgagctgctg | 6900 |
| gagccagtcg acaagcccag gactgatctt tcacaccgct cgttcctgca gccagaaagg | 6960 |
| aactctgggc agctggaggc gcaggagcct gtgcccatat ggtcatccaa atggactggc | 7020 |
| cagcgtaaat gaccccactg cagcagaaaa caaacacacg aggagcatgc agcgaattca | 7080 |
| gaaagaggtc tttcagaagg aaaccgaaac tgacttgctc acctggaaca cctgatggtg | 7140 |
| aaaccaaaca aatacaaaat ccttctccag accccagaac tagaaacccc gggccatccc | 7200 |
| actagcagct ttggcctcca tattgctctc atttcaagca gatctgcttt tctgcatgtt | 7260 |
| tgtctgtgtg tctgcgttgt gtgtgatttt catggaaaaa taaaatgcaa atgcactcat | 7320 |
| cacaaa | 7326 |

<210> SEQ ID NO 13
<211> LENGTH: 2273
<212> TYPE: PRT
<213> ORGANISM: Homo sapiens

<400> SEQUENCE: 13

Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala

```
            50                  55                  60
Gly Met Leu Pro Trp Leu Gln Gly Ile Phe Cys Asn Val Asn Asn Pro
 65                  70                  75                  80

Cys Phe Gln Ser Pro Thr Pro Gly Glu Ser Pro Gly Ile Val Ser Asn
                     85                  90                  95

Tyr Asn Asn Ser Ile Leu Ala Arg Val Tyr Arg Asp Phe Gln Glu Leu
                    100                 105                 110

Leu Met Asn Ala Pro Glu Ser Gln His Leu Gly Arg Ile Trp Thr Glu
                    115                 120                 125

Leu His Ile Leu Ser Gln Phe Met Asp Thr Leu Arg Thr His Pro Glu
                    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                    165                 170                 175

Val Val Tyr Leu Leu Ile Asn Ser Gln Val Arg Pro Glu Gln Phe Ala
                    180                 185                 190

His Gly Val Pro Asp Leu Ala Leu Lys Asp Ile Ala Cys Ser Glu Ala
                    195                 200                 205

Leu Leu Glu Arg Phe Ile Ile Phe Ser Gln Arg Arg Gly Ala Lys Thr
                    210                 215                 220

Val Arg Tyr Ala Leu Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                    245                 250                 255

Leu Pro Thr Leu Leu Asp Ser Arg Ser Gln Gly Ile Asn Leu Arg Ser
                    260                 265                 270

Trp Gly Gly Ile Leu Ser Asp Met Ser Pro Arg Ile Gln Glu Phe Ile
                    275                 280                 285

His Arg Pro Ser Met Gln Asp Leu Leu Trp Val Thr Arg Pro Leu Met
                    290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Ser Arg Val Leu Ser
                    325                 330                 335

Phe Asn Trp Tyr Glu Asp Asn Asn Tyr Lys Ala Phe Leu Gly Ile Asp
                    340                 345                 350

Ser Thr Arg Lys Asp Pro Ile Tyr Ser Tyr Asp Arg Arg Thr Thr Ser
                    355                 360                 365

Phe Cys Asn Ala Leu Ile Gln Ser Leu Glu Ser Asn Pro Leu Thr Lys
                    370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
                    405                 410                 415

Thr Phe Glu Glu Leu Glu His Val Arg Lys Leu Val Lys Ala Trp Glu
                    420                 425                 430

Glu Val Gly Pro Gln Ile Trp Tyr Phe Phe Asp Asn Ser Thr Gln Met
                    435                 440                 445

Asn Met Ile Arg Asp Thr Leu Gly Asn Pro Thr Val Lys Asp Phe Leu
                    450                 455                 460

Asn Arg Gln Leu Gly Glu Glu Gly Ile Thr Ala Glu Ala Ile Leu Asn
465                 470                 475                 480
```

```
Phe Leu Tyr Lys Gly Pro Arg Glu Ser Gln Ala Asp Met Ala Asn
            485                 490                 495

Phe Asp Trp Arg Asp Ile Phe Asn Ile Thr Asp Arg Thr Leu Arg Leu
        500                 505                 510

Val Asn Gln Tyr Leu Glu Cys Leu Val Leu Asp Lys Phe Glu Ser Tyr
            515                 520                 525

Asn Asp Glu Thr Gln Leu Thr Gln Arg Ala Leu Ser Leu Leu Glu Glu
    530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
            565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
        595                 600                 605

Ala Tyr Leu Gln Asp Met Val Glu Gln Gly Ile Thr Arg Ser Gln Val
        610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
            645                 650                 655

Ile Phe Met Val Leu Ala Trp Ile Tyr Ser Val Ser Met Thr Val Lys
            660                 665                 670

Ser Ile Val Leu Glu Lys Glu Leu Arg Leu Lys Glu Thr Leu Lys Asn
        675                 680                 685

Gln Gly Val Ser Asn Ala Val Ile Trp Cys Thr Trp Phe Leu Asp Ser
    690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
            725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
            755                 760                 765

Tyr Phe Thr Leu Tyr Leu Pro His Ile Leu Cys Phe Ala Trp Gln Asp
        770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
            805                 810                 815

Leu Gly Leu Gln Trp Ser Asn Ile Gly Asn Ser Pro Thr Glu Gly Asp
            820                 825                 830

Glu Phe Ser Phe Leu Leu Ser Met Gln Met Met Leu Leu Asp Ala Ala
        835                 840                 845

Val Tyr Gly Leu Leu Ala Trp Tyr Leu Asp Gln Val Phe Pro Gly Asp
850                 855                 860

Tyr Gly Thr Pro Leu Pro Trp Tyr Phe Leu Leu Gln Glu Ser Tyr Trp
865                 870                 875                 880

Leu Gly Gly Glu Gly Cys Ser Thr Arg Glu Glu Arg Ala Leu Glu Lys
            885                 890                 895
```

Thr Glu Pro Leu Thr Glu Glu Thr Glu Asp Pro Glu His Pro Glu Gly
                900                 905                 910

Ile His Asp Ser Phe Phe Glu Arg Glu His Pro Gly Trp Val Pro Gly
            915                 920                 925

Val Cys Val Lys Asn Leu Val Lys Ile Phe Glu Pro Cys Gly Arg Pro
        930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
                965                 970                 975

Thr Gly Leu Leu Pro Pro Thr Ser Gly Thr Val Leu Val Gly Gly Arg
            980                 985                 990

Asp Ile Glu Thr Ser Leu Asp Ala Val Arg Gln Ser Leu Gly Met Cys
        995                 1000                1005

Pro Gln His Asn Ile Leu Phe His His Leu Thr Val Ala Glu His
    1010                1015                1020

Met Leu Phe Tyr Ala Gln Leu Lys Gly Lys Ser Gln Glu Glu Ala
    1025                1030                1035

Gln Leu Glu Met Glu Ala Met Leu Glu Asp Thr Gly Leu His His
    1040                1045                1050

Lys Arg Asn Glu Glu Ala Gln Asp Leu Ser Gly Gly Met Gln Arg
    1055                1060                1065

Lys Leu Ser Val Ala Ile Ala Phe Val Gly Asp Ala Lys Val Val
    1070                1075                1080

Ile Leu Asp Glu Pro Thr Ser Gly Val Asp Pro Tyr Ser Arg Arg
    1085                1090                1095

Ser Ile Trp Asp Leu Leu Leu Lys Tyr Arg Ser Gly Arg Thr Ile
    1100                1105                1110

Ile Met Ser Thr His His Met Asp Glu Ala Asp Leu Leu Gly Asp
    1115                1120                1125

Arg Ile Ala Ile Ile Ala Gln Gly Arg Leu Tyr Cys Ser Gly Thr
    1130                1135                1140

Pro Leu Phe Leu Lys Asn Cys Phe Gly Thr Gly Leu Tyr Leu Thr
    1145                1150                1155

Leu Val Arg Lys Met Lys Asn Ile Gln Ser Gln Arg Lys Gly Ser
    1160                1165                1170

Glu Gly Thr Cys Ser Cys Ser Ser Lys Gly Phe Ser Thr Thr Cys
    1175                1180                1185

Pro Ala His Val Asp Asp Leu Thr Pro Glu Gln Val Leu Asp Gly
    1190                1195                1200

Asp Val Asn Glu Leu Met Asp Val Val Leu His His Val Pro Glu
    1205                1210                1215

Ala Lys Leu Val Glu Cys Ile Gly Gln Glu Leu Ile Phe Leu Leu
    1220                1225                1230

Pro Asn Lys Asn Phe Lys His Arg Ala Tyr Ala Ser Leu Phe Arg
    1235                1240                1245

Glu Leu Glu Glu Thr Leu Ala Asp Leu Gly Leu Ser Ser Phe Gly
    1250                1255                1260

Ile Ser Asp Thr Pro Leu Glu Glu Ile Phe Leu Lys Val Thr Glu
    1265                1270                1275

Asp Ser Asp Ser Gly Pro Leu Phe Ala Gly Gly Ala Gln Gln Lys
    1280                1285                1290

Arg Glu Asn Val Asn Pro Arg His Pro Cys Leu Gly Pro Arg Glu

```
                    1295                1300                1305
Lys Ala Gly Gln Thr Pro Gln Asp Ser Asn Val Cys Ser Pro Gly
    1310                1315                1320

Ala Pro Ala Ala His Pro Glu Gly Gln Pro Pro Glu Pro Glu
    1325                1330                1335

Cys Pro Gly Pro Gln Leu Asn Thr Gly Thr Gln Leu Val Leu Gln
    1340                1345                1350

His Val Gln Ala Leu Leu Val Lys Arg Phe Gln His Thr Ile Arg
    1355                1360                1365

Ser His Lys Asp Phe Leu Ala Gln Ile Val Leu Pro Ala Thr Phe
    1370                1375                1380

Val Phe Leu Ala Leu Met Leu Ser Ile Val Ile Pro Pro Phe Gly
    1385                1390                1395

Glu Tyr Pro Ala Leu Thr Leu His Pro Trp Ile Tyr Gly Gln Gln
    1400                1405                1410

Tyr Thr Phe Phe Ser Met Asp Glu Pro Gly Ser Glu Gln Phe Thr
    1415                1420                1425

Val Leu Ala Asp Val Leu Leu Asn Lys Pro Gly Phe Gly Asn Arg
    1430                1435                1440

Cys Leu Lys Glu Gly Trp Leu Pro Glu Tyr Pro Cys Gly Asn Ser
    1445                1450                1455

Thr Pro Trp Lys Thr Pro Ser Val Ser Pro Asn Ile Thr Gln Leu
    1460                1465                1470

Phe Gln Lys Gln Lys Trp Thr Gln Val Asn Pro Ser Pro Ser Cys
    1475                1480                1485

Arg Cys Ser Thr Arg Glu Lys Leu Thr Met Leu Pro Glu Cys Pro
    1490                1495                1500

Glu Gly Ala Gly Gly Leu Pro Pro Pro Gln Arg Thr Gln Arg Ser
    1505                1510                1515

Thr Glu Ile Leu Gln Asp Leu Thr Asp Arg Asn Ile Ser Asp Phe
    1520                1525                1530

Leu Val Lys Thr Tyr Pro Ala Leu Ile Arg Ser Ser Leu Lys Ser
    1535                1540                1545

Lys Phe Trp Val Asn Glu Gln Arg Tyr Gly Gly Ile Ser Ile Gly
    1550                1555                1560

Gly Lys Leu Pro Val Val Pro Ile Thr Gly Glu Ala Leu Val Gly
    1565                1570                1575

Phe Leu Ser Asp Leu Gly Arg Ile Met Asn Val Ser Gly Gly Pro
    1580                1585                1590

Ile Thr Arg Glu Ala Ser Lys Glu Ile Pro Asp Phe Leu Lys His
    1595                1600                1605

Leu Glu Thr Glu Asp Asn Ile Lys Val Trp Phe Asn Asn Lys Gly
    1610                1615                1620

Trp His Ala Leu Val Ser Phe Leu Asn Val Ala His Asn Ala Ile
    1625                1630                1635

Leu Arg Ala Ser Leu Pro Lys Asp Arg Ser Pro Glu Glu Tyr Gly
    1640                1645                1650

Ile Thr Val Ile Ser Gln Pro Leu Asn Leu Thr Lys Glu Gln Leu
    1655                1660                1665

Ser Glu Ile Thr Val Leu Thr Thr Ser Val Asp Ala Val Val Ala
    1670                1675                1680

Ile Cys Val Ile Phe Ser Met Ser Phe Val Pro Ala Ser Phe Val
    1685                1690                1695
```

```
Leu Tyr Leu Ile Gln Glu Arg Val Asn Lys Ser Lys His Leu Gln
    1700            1705                1710

Phe Ile Ser Gly Val Ser Pro Thr Thr Tyr Trp Val Thr Asn Phe
    1715            1720                1725

Leu Trp Asp Ile Met Asn Tyr Ser Val Ser Ala Gly Leu Val Val
    1730            1735                1740

Gly Ile Phe Ile Gly Phe Gln Lys Lys Ala Tyr Thr Ser Pro Glu
    1745            1750                1755

Asn Leu Pro Ala Leu Val Ala Leu Leu Leu Leu Tyr Gly Trp Ala
    1760            1765                1770

Val Ile Pro Met Met Tyr Pro Ala Ser Phe Leu Phe Asp Val Pro
    1775            1780                1785

Ser Thr Ala Tyr Val Ala Leu Ser Cys Ala Asn Leu Phe Ile Gly
    1790            1795                1800

Ile Asn Ser Ser Ala Ile Thr Phe Ile Leu Glu Leu Phe Glu Asn
    1805            1810                1815

Asn Arg Thr Leu Leu Arg Phe Asn Ala Val Leu Arg Lys Leu Leu
    1820            1825                1830

Ile Val Phe Pro His Phe Cys Leu Gly Arg Gly Leu Ile Asp Leu
    1835            1840                1845

Ala Leu Ser Gln Ala Val Thr Asp Val Tyr Ala Arg Phe Gly Glu
    1850            1855                1860

Glu His Ser Ala Asn Pro Phe His Trp Asp Leu Ile Gly Lys Asn
    1865            1870                1875

Leu Phe Ala Met Val Val Gly Val Val Tyr Phe Leu Leu Thr
    1880            1885                1890

Leu Leu Val Gln Arg His Phe Phe Leu Ser Gln Trp Ile Ala Glu
    1895            1900                1905

Pro Thr Lys Glu Pro Ile Val Asp Glu Asp Asp Val Ala Glu
    1910            1915                1920

Glu Arg Gln Arg Ile Ile Thr Gly Gly Asn Lys Thr Asp Ile Leu
    1925            1930                1935

Arg Leu His Glu Leu Thr Lys Ile Tyr Pro Gly Thr Ser Ser Pro
    1940            1945                1950

Ala Val Asp Arg Leu Cys Val Gly Val Arg Pro Gly Glu Cys Phe
    1955            1960                1965

Gly Leu Leu Gly Val Asn Gly Ala Gly Lys Thr Thr Thr Phe Lys
    1970            1975                1980

Met Leu Thr Gly Asp Thr Thr Val Thr Ser Gly Asp Ala Thr Val
    1985            1990                1995

Ala Gly Lys Ser Ile Leu Thr Asn Ile Ser Glu Val His Gln Asn
    2000            2005                2010

Met Gly Tyr Cys Pro Gln Phe Asp Ala Ile Asp Glu Leu Leu Thr
    2015            2020                2025

Gly Arg Glu His Leu Tyr Leu Tyr Ala Arg Leu Arg Gly Val Pro
    2030            2035                2040

Ala Glu Glu Ile Glu Lys Val Ala Asn Trp Ser Ile Lys Ser Leu
    2045            2050                2055

Gly Leu Thr Val Tyr Ala Asp Cys Leu Ala Gly Thr Tyr Ser Gly
    2060            2065                2070

Gly Asn Lys Arg Lys Leu Ser Thr Ala Ile Ala Leu Ile Gly Cys
    2075            2080                2085
```

| | | | | | | | | | | |
|---|---|---|---|---|---|---|---|---|---|---|
|Pro|Pro|Leu|Val|Leu|Leu|Asp|Glu|Pro|Thr|Thr|Gly|Met|Asp|Pro|
| |2090| | | |2095| | | |2100| | | | | |

Gln Ala Arg Arg Met Leu Trp Asn Val Ile Val Ser Ile Ile Arg
    2105            2110            2115

Glu Gly Arg Ala Val Val Leu Thr Ser His Ser Met Glu Glu Cys
    2120            2125            2130

Glu Ala Leu Cys Thr Arg Leu Ala Ile Met Val Lys Gly Ala Phe
    2135            2140            2145

Arg Cys Met Gly Thr Ile Gln His Leu Lys Ser Lys Phe Gly Asp
    2150            2155            2160

Gly Tyr Ile Val Thr Met Lys Ile Lys Ser Pro Lys Asp Asp Leu
    2165            2170            2175

Leu Pro Asp Leu Asn Pro Val Glu Gln Phe Phe Gln Gly Asn Phe
    2180            2185            2190

Pro Gly Ser Val Gln Arg Glu Arg His Tyr Asn Met Leu Gln Phe
    2195            2200            2205

Gln Val Ser Ser Ser Ser Leu Ala Arg Ile Phe Gln Leu Leu Leu
    2210            2215            2220

Ser His Lys Asp Ser Leu Leu Ile Glu Glu Tyr Ser Val Thr Gln
    2225            2230            2235

Thr Thr Leu Asp Gln Val Phe Val Asn Phe Ala Lys Gln Gln Thr
    2240            2245            2250

Glu Ser His Asp Leu Pro Leu His Pro Arg Ala Ala Gly Ala Ser
    2255            2260            2265

Arg Gln Ala Gln Asp
    2270

<210> SEQ ID NO 14
<211> LENGTH: 2608
<212> TYPE: DNA
<213> ORGANISM: Homo sapiens

<400> SEQUENCE: 14

```
tccttcttca ttctgcagtt ggtgccagaa ctctggatcc tgaactggaa gaaaatgtct      60
atccaggttg agcatcctgc tggtggttac aagaaactgt ttgaaactgt ggaggaactg     120
tcctcgccgc tcacagctca tgtaacaggc aggatccccc tctggctcac cggcagtctc     180
cttcgatgtg ggccaggact ctttgaagtt ggatctgagc cattttacca cctgtttgat     240
gggcaagccc tcctgcacaa gtttgacttt aaagaaggac atgtcacata ccacagaagg     300
ttcatccgca ctgatgctta cgtacgggca atgactgaga aaaggatcgt cataacagaa     360
tttggcacct gtgctttccc agatccctgc aagaatatat tttccaggtt ttttctttac     420
tttcgaggag tagaggttac tgacaatgcc cttgttaatg tctacccagt gggggaagat     480
tactacgctt gcacagagac caactttatt acaaagatta tccagagacc ttggagaca     540
attaagcagg ttgatctttg caactatgtc tctgtcaatg gggccactgc tcaccccca     600
attgaaaatg atggaaccgt ttacaatatt ggtaattgct ttggaaaaaa tttttcaatt    660
gcctacaaca ttgtaaagat cccaccactg caagcagaca aggaagatcc aataagcaag    720
tcagagatcg ttgtacaatt ccctgcagt gaccgattca agccatctta cgttcatagt    780
tttggtctga ctcccaacta tatcgttttt gtggagacac cagtcaaaat taacctgttc    840
aagttccttt cttcatggag ctttgggga gccaactaca tggattgttt tgagtccaat    900
gaaaccatgg gggtttggct tcatattgct gacaaaaaaa ggaaaagta cctcaataat    960
```

| | | | | |
|---|---|---|---|---|
| aaatacagaa cttctccttt caacctcttc catcacatca acacctatga agacaatggg | | | | 1020 |
| tttctgattg tggatctctg ctgctggaaa ggatttgagt ttgtttataa ttacttatat | | | | 1080 |
| ttagccaatt tacgtgagaa ctgggaagag gtgaaaaaaa atgccagaaa ggctccccaa | | | | 1140 |
| cctgaagtta ggagatatgt acttcctttg aatattgaca aggctgacac aggcaagaat | | | | 1200 |
| ttagtcacgc tccccaatac aactgccact gcaattctgt gcagtgacga gactatctgg | | | | 1260 |
| ctggagcctg aagttctctt tcagggcct cgtcaagcat ttgagtttcc tcaaatcaat | | | | 1320 |
| taccagaagt attgtgggaa accttacaca tatgcgtatg gacttggctt gaatcacttt | | | | 1380 |
| gttccagata ggctctgtaa gctgaatgtc aaaactaaag aaacttgggt ttggcaagag | | | | 1440 |
| cctgattcat acccatcaga acccatctt gtttctcacc cagatgcctt ggaagaagat | | | | 1500 |
| gatggtgtag ttctgagtgt ggtggtgagc ccaggagcag gacaaaagcc tgcttatctc | | | | 1560 |
| ctgattctga atgccaagga cttaagtgaa gttgcccggg ctgaagtgga gattaacatc | | | | 1620 |
| cctgtcacct ttcatggact gttcaaaaaa tcttgagcat actccagcaa gatatgtttt | | | | 1680 |
| tggtagcaaa actgagaaaa tcagcttcag gtctgcaatc aaattctgtt caattttagc | | | | 1740 |
| ctgctatatg tcatggtttt aacttgcaga tgcgcacaat tttgcaatgt tttacagaaa | | | | 1800 |
| gcactgagtt gagcaagcaa ttcctttatt taaaaaaaaa agtacgtatt tagataatca | | | | 1860 |
| tacttcctct gtgagacagg ccataactga aaaactctta aatatttagc aatcaaatag | | | | 1920 |
| gaaatgaatg tggacttact aaatggcttt taattcctat tataagagca tattttaggt | | | | 1980 |
| acctatctgc tccaattata tttttaacat ttaaaaacca agtcctctca cacttgattt | | | | 2040 |
| atattatatg tggctttgct gagtcaagga agtatcatgc aataaggctt aattactaaa | | | | 2100 |
| tgtcaaacca aacttttct caaaccaggg actatcatct aagattaatt acagtaatta | | | | 2160 |
| ttttgcgtat acgtaactgc tcaaagatta tgaatcttat gaatgttaac ctttccgttt | | | | 2220 |
| attacaagca agtactatta tttctgattt tataataaga aaatctgtgt ttaatcaact | | | | 2280 |
| gaggcctctc aaccaaataa catctcagag attaagttat atattaaaag cttatgtaac | | | | 2340 |
| ataaaagcaa gtacatatag tagtgactat atttaaaaaa acagcataaa atgcttaaaa | | | | 2400 |
| atgtaatatt tactaaaatc agattatggg ataatgttgc aggattatac tttattgcat | | | | 2460 |
| cttttttgtt taattgtatt taagcattgt gcaatcactt gggaaaaata ttaaattatt | | | | 2520 |
| aacattgagg tattaataca ttttaagcct tttgttttta aatttctttt cttccagaga | | | | 2580 |
| ttgtttaaaa ataaatattg acaaaaat | | | | 2608 |

<210> SEQ ID NO 15
<211> LENGTH: 533
<212> TYPE: PRT
<213> ORGANISM: Homo sapiens

<400> SEQUENCE: 15

```
Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80
```

-continued

```
Arg Arg Phe Ile Arg Thr Asp Ala Tyr Val Arg Ala Met Thr Glu Lys
                85                  90                  95
Arg Ile Val Ile Thr Glu Phe Gly Thr Cys Ala Phe Pro Asp Pro Cys
            100                 105                 110
Lys Asn Ile Phe Ser Arg Phe Phe Ser Tyr Phe Arg Gly Val Glu Val
            115                 120                 125
Thr Asp Asn Ala Leu Val Asn Val Tyr Pro Val Gly Glu Asp Tyr Tyr
130                 135                 140
Ala Cys Thr Glu Thr Asn Phe Ile Thr Lys Ile Asn Pro Glu Thr Leu
145                 150                 155                 160
Glu Thr Ile Lys Gln Val Asp Leu Cys Asn Tyr Val Ser Val Asn Gly
                165                 170                 175
Ala Thr Ala His Pro His Ile Glu Asn Asp Gly Thr Val Tyr Asn Ile
            180                 185                 190
Gly Asn Cys Phe Gly Lys Asn Phe Ser Ile Ala Tyr Asn Ile Val Lys
            195                 200                 205
Ile Pro Pro Leu Gln Ala Asp Lys Glu Asp Pro Ile Ser Lys Ser Glu
            210                 215                 220
Ile Val Val Gln Phe Pro Cys Ser Asp Arg Phe Lys Pro Ser Tyr Val
225                 230                 235                 240
His Ser Phe Gly Leu Thr Pro Asn Tyr Ile Val Phe Val Glu Thr Pro
                245                 250                 255
Val Lys Ile Asn Leu Phe Lys Phe Leu Ser Ser Trp Ser Leu Trp Gly
            260                 265                 270
Ala Asn Tyr Met Asp Cys Phe Glu Ser Asn Glu Thr Met Gly Val Trp
            275                 280                 285
Leu His Ile Ala Asp Lys Lys Arg Lys Lys Tyr Leu Asn Asn Lys Tyr
290                 295                 300
Arg Thr Ser Pro Phe Asn Leu Phe His His Ile Asn Thr Tyr Glu Asp
305                 310                 315                 320
Asn Gly Phe Leu Ile Val Asp Leu Cys Cys Trp Lys Gly Phe Glu Phe
                325                 330                 335
Val Tyr Asn Tyr Leu Tyr Leu Ala Asn Leu Arg Glu Asn Trp Glu Glu
            340                 345                 350
Val Lys Lys Asn Ala Arg Lys Ala Pro Gln Pro Glu Val Arg Arg Tyr
            355                 360                 365
Val Leu Pro Leu Asn Ile Asp Lys Ala Asp Thr Gly Lys Asn Leu Val
            370                 375                 380
Thr Leu Pro Asn Thr Thr Ala Thr Ala Ile Leu Cys Ser Asp Glu Thr
385                 390                 395                 400
Ile Trp Leu Glu Pro Glu Val Leu Phe Ser Gly Pro Arg Gln Ala Phe
                405                 410                 415
Glu Phe Pro Gln Ile Asn Tyr Gln Lys Tyr Cys Gly Lys Pro Tyr Thr
            420                 425                 430
Tyr Ala Tyr Gly Leu Gly Leu Asn His Phe Val Pro Asp Arg Leu Cys
            435                 440                 445
Lys Leu Asn Val Lys Thr Lys Glu Thr Trp Val Trp Gln Glu Pro Asp
450                 455                 460
Ser Tyr Pro Ser Glu Pro Ile Phe Val Ser His Pro Asp Ala Leu Glu
465                 470                 475                 480
Glu Asp Asp Gly Val Val Leu Ser Val Val Ser Pro Gly Ala Gly
                485                 490                 495
Gln Lys Pro Ala Tyr Leu Leu Ile Leu Asn Ala Lys Asp Leu Ser Glu
```

```
          500             505                  510
Val Ala Arg Ala Glu Val Glu Ile Asn Ile Pro Val Thr Phe His Gly
        515                  520                  525
Leu Phe Lys Lys Ser
        530
```

<210> SEQ ID NO 16
<211> LENGTH: 1752
<212> TYPE: DNA
<213> ORGANISM: Homo sapiens

<400> SEQUENCE: 16

```
gagcccgatt taacggaaac tgtgggcggt gagaagttcc ttatgacaca ctaatcccaa      60
cctgctgacc ggaccacgcc tccagcggag ggaacctcta gagctccagg acattcaggt     120
accaggtagc cccaaggagg agctgccgac ctggcaggga caaccaaga ctggggttaa     180
atctcacagc ctgcaagtgg aagagaagaa cttgaaccca ggtccaactt ttgcgccaca     240
gcaggctgcc tcttggtcct gacaggaagt cacaacttgg ccctgacttc ctatcctagg     300
gaaggggccg gctggagagg ccaggacaga gaaagcagat cccttctttt tccaaggact     360
ctgtgtcttc cataggcaac atgtcagaag gggtgggcac gttccgcatg gtacctgaag     420
aggaacagga gctccgtgcc caactggagc agctcacaac caaggaccat ggacctgtct     480
ttggcccgtg cagccagctg ccccgccaca ccttgcagaa ggccaaggat gagctgaacg     540
agagagagga gacccgggag gaggcagtgc gagagctgca ggagatggtg caggcgcagg     600
cggcctcggg ggaggagctg gcggtggccg tggcggagag ggtgcaagag aaggacagcg     660
gcttcttcct gcgcttcatc cgcgcacgga gttcaacgt gggccgtgcc tatgagctgc     720
tcagaggcta tgtgaatttc cggctgcagt accctgagct cttttgacagc ctgtccccag     780
aggctgtccg ctgcaccatt gaagctggct accctggtgt cctctctagt cgggacaagt     840
atggccagt ggtcatgctc ttcaacattg agaactggca agtcaagaa atcacctttg     900
atgagatctt gcaggcatat tgcttcatcc tggagaagct gctggagaat gaggaaactc     960
aaatcaatgg cttctgcatc attgagaact caagggcttt accatgcag caggctgcta    1020
gtctccggac ttcagatctc aggaagatgg tggacatgct ccaggattcc ttcccagccc    1080
ggttcaaagc catccacttc atccaccagc catggtactt caccacgacc tacaatgtgg    1140
tcaagccctt cttgaagagc aagctgcttg agagggtctt tgtccacggg gatgaccttt    1200
ctggtttcta ccaggagatc gatgagaaca tcctgcccct tgacttcggg ggcacgctgc    1260
ccaagtatga tggcaaggcc gttgctgagc agctctttgg ccccaggcc caagctgaga    1320
acacagcctt ctgaaaacat ctcctgccag ctgaactgta gttagaatct ctgggcctct    1380
cctcaactgt cctggaccca aggctaggaa agggctgctt gagatgactg tggtccccc    1440
ttagactccc taagcccgag tgagctcagg tgtcaccctg ttctcaagtt ggggatggg    1500
taataaagga gggggaattc ccttgaacaa gaagaactgg ggatagttat atttccacct    1560
gcccttgaag cttttaagaca gtgattttg tgtaaggttg tatttcaaag actcgaattc    1620
attttctcag tcatttcctt tgtaacagag ttttacgact tagagtctgt gaaacaggc    1680
aaggagcccg ggttaaaata tcccctatt cgccccaaa atgcaataaa agaagataaa    1740
agagagagga ta                                                       1752
```

<210> SEQ ID NO 17
<211> LENGTH: 317

<212> TYPE: PRT
<213> ORGANISM: Homo sapiens

<400> SEQUENCE: 17

Met Ser Glu Gly Val Gly Thr Phe Arg Met Val Pro Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
            35                  40                  45

Lys Asp Glu Leu Asn Glu Arg Glu Thr Arg Glu Glu Ala Val Arg
50                  55                  60

Glu Leu Gln Glu Met Val Gln Ala Gln Ala Ser Gly Glu Glu Leu
65                  70                  75                  80

Ala Val Ala Val Ala Glu Arg Val Gln Glu Lys Asp Ser Gly Phe Phe
                85                  90                  95

Leu Arg Phe Ile Arg Ala Arg Lys Phe Asn Val Gly Arg Ala Tyr Glu
                100                 105                 110

Leu Leu Arg Gly Tyr Val Asn Phe Arg Leu Gln Tyr Pro Glu Leu Phe
            115                 120                 125

Asp Ser Leu Ser Pro Glu Ala Val Arg Cys Thr Ile Glu Ala Gly Tyr
130                 135                 140

Pro Gly Val Leu Ser Ser Arg Asp Lys Tyr Gly Arg Val Val Met Leu
145                 150                 155                 160

Phe Asn Ile Glu Asn Trp Gln Ser Gln Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
            195                 200                 205

Met Gln Gln Ala Ala Ser Leu Arg Thr Ser Asp Leu Arg Lys Met Val
            210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Ser Lys Leu Leu Glu Arg Val Phe Val His Gly Asp Asp
            260                 265                 270

Leu Ser Gly Phe Tyr Gln Glu Ile Asp Glu Asn Ile Leu Pro Ser Asp
            275                 280                 285

Phe Gly Gly Thr Leu Pro Lys Tyr Asp Gly Lys Ala Val Ala Glu Gln
290                 295                 300

Leu Phe Gly Pro Gln Ala Gln Ala Glu Asn Thr Ala Phe
305                 310                 315

<210> SEQ ID NO 18
<211> LENGTH: 3027
<212> TYPE: DNA
<213> ORGANISM: Homo sapiens

<400> SEQUENCE: 18
cagcgttcag gctgccccct cttggctggg aagggcgctg aagaaacaac gcccaggacc      60
aggactatcc cctgctcaag ctgtgattcc gagaccctg ccaccactac tgcattcacg     120
gggatcccag gctagtggga ctcgacatgg gtagccccca gggcagctcc ctacagcttg    180

```
ggccatctgc acttttccca aggccctaag tctccgcctc tgggctcgtt aaggtttggg      240
gtgggagctg tgctgtggga agcaacccgg actacacttg gcaagcatgg cgctactgaa      300
agtcaagttt gaccagaaga agcgggtcaa gttggcccaa gggctctggc tcatgaactg      360
gttctccgtg ttggctggca tcatcatctt cagcctagga ctgttcctga agattgaact      420
ccgaaagagg agcgatgtga tgaataattc tgagagccat tttgtgccca actcattgat      480
agggatgggg gtgctatcct gtgtcttcaa ctcgctggct gggaagatct gctacgacgc      540
cctggaccca gccaagtatg ccagatggaa gccctggctg aagccgtacc tggctatctg      600
tgttctcttc aacatcatcc tcttccttgt ggctctctgc tgctttctgc ttcggggctc      660
gctggagaac accctgggcc aagggctcaa gaacggcatg aagtactacc gggacacaga      720 caccctggc aggtgtttca tgaagaagac catcgacatg ctgcagatcg agttcaaatg      780
ctgcggcaac aacggttttc gggactggtt tgagattcag tggatcagca atcgctacct      840
ggacttttcc tccaaagaag tcaaagatcg aatcaagagc aacgtggatg gcgtaccttg      900 gtggacggc gtccctttca gctgctgcaa tcctagctcg ccacggccct gcatccagta      960
tcagatcacc aacaactcag cacactacag ttacgaccac cagacggagg agctcaacct      1020
gtgggtgcgt ggctgcaggg ctgccctgct gagctactac agcagcctca tgaactccat      1080
gggtgtcgtc acgctcctca tttggctctt cgaggtgacc attacaattg gctgcgcta      1140 cctacagacg tcgctggatg gtgtgtccaa ccccgaggaa tctgagagcg agagccaggg      1200
ctggctgctg gagaggagcg tgccggagac ctggaaggcc tttctggaga gtgtgaagaa      1260
gctgggcaag ggcaaccagg tggaagccga gggcgcagac gcaggccagg ccccagaggc      1320
tggctgaggg ccctggggcc cctcccctcc cgaacactga gaaatagtgc actccaagaa      1380
acgtggatct ccccctcatc caactccgaa agtctgaatc tcccaaggag ggcaccatct      1440
tacagagact ctccctgacg gtggaattta agtttagggt ccctaaaagc atttgacaca      1500
cagttgttga atgactgacc caaaatgtga atgaagctaa tgtgaatgtg agtgaagctc      1560
ccttcaggcc cgctgcccta ggatatgccc tcctggtgac tcggggggctg tctcagacga      1620 ctagcccagg acccatcttt ctcacacgga tttagtccca ccctatggcc actggccgta      1680
tctgagggct gctccccttt tagaatttac ctcttatgag ctccatgttg cttcactcta      1740
tccaaagtgt cacttggtgc ataagcacag aaatctgaaa aatggccatg ttgtcttttt      1800
tttttttttt taatgccaag attgacaggt tggccgtttg cttaatgcca gaagttgggg      1860
gaaagttacg cttttctaag aataatggac tcttaaggca ttgagggctc taaacaggat      1920
tctttaatca tggagcaaga gaatttcaag gcaggggatt ttatccccca ccaaaaacac      1980
agtgaaaggc ctgcttttgt gtcccattca catgccctcg gtcactgagt ctggagtgaa      2040 ccacggggttg aggaagtcag gctgttggcg tgtcccagca ccacaccacc cctaaagtgc      2100
caggtgatct cctgtggctc atcggtgaaa gcagtgggt aggctgctgc cctgctgtgg      2160
aagaggagca acaatcagac atgagtccac cctttggaga ccaggcctca gctcttggtg      2220
ggcccaggga cacccacaca ggtggccatc acagcccat ggacaacact aattgtccac      2280
agcaaagggc aaggaatcct ctgggagctt cttccgtttc ttcccccag atacccatct      2340 tgaaaaacac tatttctgga atgcttctgc atcaaaggag attctttgag atagcccatc      2400
ttcctgagct agcaaataca ggagttttca cttttcttta gaaagagaag ctttcagggg      2460
aaggagagaa tgatttttgct gacttcccaa gccctggtga ccagaccaag gcagggccca      2520
gcataattcc tccagttgga tgaacattca agagagctcg ttcctacctg gctggagacc      2580
```

```
gaggccagaa ggcaaaaacc agaaagggaa cagtccataa cttacctctg cttctgaccg    2640
atggtgtttg ggaataggtt actttggact gagtttgggt tctctgctgt cctaagaact    2700
tcagtgtaga gaaaataaga cttctggtgc tgctggggta tgttctgggc ttaattcccc    2760
caagcagaag accagatcca agatgtttgg acaccctgtc agacgttggt cccaagttta    2820
attagatttc tgaatctcgt tgaggccaag gaatgatcca tactgaaaaa atgctgagcc    2880
agccatcttt ggcaaaggtc cctgagctct tgctatctct caagagtgct gagaaccacg    2940
gtgaaagtgc tgctctaggc ccacaagtgt aactatgctg ttaacagctg tcaatagata    3000
attaaaattc atactgtatg aaaatca                                        3027

<210> SEQ ID NO 19
<211> LENGTH: 346
<212> TYPE: PRT
<213> ORGANISM: Homo sapiens

<400> SEQUENCE: 19

Met Ala Leu Leu Lys Val Lys Phe Asp Gln Lys Lys Arg Val Lys Leu
1               5                   10                  15

Ala Gln Gly Leu Trp Leu Met Asn Trp Phe Ser Val Leu Ala Gly Ile
            20                  25                  30

Ile Ile Phe Ser Leu Gly Leu Phe Leu Lys Ile Glu Leu Arg Lys Arg
        35                  40                  45

Ser Asp Val Met Asn Asn Ser Glu Ser His Phe Val Pro Asn Ser Leu
    50                  55                  60

Ile Gly Met Gly Val Leu Ser Cys Val Phe Asn Ser Leu Ala Gly Lys
65                  70                  75                  80

Ile Cys Tyr Asp Ala Leu Asp Pro Ala Lys Tyr Ala Arg Trp Lys Pro
                85                  90                  95

Trp Leu Lys Pro Tyr Leu Ala Ile Cys Val Leu Phe Asn Ile Ile Leu
            100                 105                 110

Phe Leu Val Ala Leu Cys Cys Phe Leu Leu Arg Gly Ser Leu Glu Asn
        115                 120                 125

Thr Leu Gly Gln Gly Leu Lys Asn Gly Met Lys Tyr Tyr Arg Asp Thr
    130                 135                 140

Asp Thr Pro Gly Arg Cys Phe Met Lys Lys Thr Ile Asp Met Leu Gln
145                 150                 155                 160

Ile Glu Phe Lys Cys Cys Gly Asn Asn Gly Phe Arg Asp Trp Phe Glu
                165                 170                 175

Ile Gln Trp Ile Ser Asn Arg Tyr Leu Asp Phe Ser Ser Lys Glu Val
            180                 185                 190

Lys Asp Arg Ile Lys Ser Asn Val Asp Gly Arg Tyr Leu Val Asp Gly
        195                 200                 205

Val Pro Phe Ser Cys Cys Asn Pro Ser Ser Pro Arg Pro Cys Ile Gln
    210                 215                 220

Tyr Gln Ile Thr Asn Asn Ser Ala His Tyr Ser Tyr Asp His Gln Thr
225                 230                 235                 240

Glu Glu Leu Asn Leu Trp Val Arg Gly Cys Arg Ala Ala Leu Leu Ser
                245                 250                 255

Tyr Tyr Ser Ser Leu Met Asn Ser Met Gly Val Val Thr Leu Leu Ile
            260                 265                 270

Trp Leu Phe Glu Val Thr Ile Thr Ile Gly Leu Arg Tyr Leu Gln Thr
        275                 280                 285
```

```
Ser Leu Asp Gly Val Ser Asn Pro Glu Glu Ser Glu Ser Gln
    290                 295                 300

Gly Trp Leu Leu Glu Arg Ser Val Pro Glu Thr Trp Lys Ala Phe Leu
305                 310                 315                 320

Glu Ser Val Lys Lys Leu Gly Lys Gly Asn Gln Val Glu Ala Glu Gly
                325                 330                 335

Ala Asp Ala Gly Gln Ala Pro Glu Ala Gly
                340                 345

<210> SEQ ID NO 20
<211> LENGTH: 1767
<212> TYPE: DNA
<213> ORGANISM: Homo sapiens

<400> SEQUENCE: 20
```

| | | | | | |
|---|---|---|---|---|---|
| gtcagctggg | tgactcatac | atctgtgaga | ccctccgtat | ggagaccggg | gcgggggtg | 60 |
| ttgcttaatg | cttagaactg | ctgaaactac | cagttcactg | tctcagcact | aatccaactc | 120 |
| tgctccttaa | gtgggatttg | gcttttagac | attgagacct | ggatgctggg | catcctcgct | 180 |
| agatccccta | caaattcccc | acatacgtag | gccaggagcc | tcagcggtgc | ccctttcaggc | 240 |
| tcatctggca | gacggtacc | agcttgctca | gaacaggggg | tggctattca | tcatctcaga | 300 |
| gcatagagac | cctctccttg | ccacccggcc | cttcccacct | ggttggtgac | aaatcacaag | 360 |
| gtggtagaag | ttgccaggga | cagataacat | ggcagccagc | gggaagacca | gcaagtccga | 420 |
| accgaaccat | gttatcttca | agaagatctc | ccgggacaaa | tcggtgacca | tctacctggg | 480 |
| gaacagagac | tacatagacc | atgtcagcca | agtccagcct | gtggatggtg | tcgtgttggt | 540 |
| tgatcctgat | cttgtgaagg | gaaagaaagt | gtatgtcact | ctgacctgcg | ccttccgcta | 600 |
| tggccaagag | gacattgacg | tgatcggctt | gaccttccgc | agggacctgt | acttctcccg | 660 |
| ggtccaggtg | tatcctcctg | tggggccgc | gagcaccccc | acaaaactgc | aagagagcct | 720 |
| gcttaaaaag | ctggggagca | cacgtaccc | ctttctcctg | acgtttcctg | actacttgcc | 780 |
| ctgttcagtg | atgttgcagc | cagctccaca | agattcaggg | aagtcctgtg | gggttgactt | 840 |
| tgaggtcaaa | gcattcgcca | cagacagcac | cgatgccgaa | gaggacaaaa | tccccaagaa | 900 |
| gagctccgtg | cgattactga | tccgcaaagt | acagcatgcc | ccacttgaga | tgggtcccca | 960 |
| gccccgagct | gaggcggcct | ggcagttctt | catgtctgac | aagcccctgc | accttgcggt | 1020 |
| ctctctcaac | aaagagatct | atttccatgg | ggagcccatc | cctgtgaccg | tgactgtcac | 1080 |
| caataacaca | gagaagaccg | tgaagaagat | taaagcattc | gtggaacagg | tggccaatgt | 1140 |
| ggttctctac | tcgagtgatt | attacgtcaa | gcccgtggct | atggaggaag | cgcaagaaaa | 1200 |
| agtgccacca | acagcacttt | tgaccaagac | gctgacgctg | ctgcccttgc | tggctaacaa | 1260 |
| tcgagaaagg | agaggcattg | ccctggatgg | gaaaatcaag | cacgaggaca | caaaccttgc | 1320 |
| ctccagcacc | atcattaagg | agggcataga | ccggaccgtc | ctgggaatcc | tggtgtctta | 1380 |
| ccagatcaag | gtgaagctca | cagtgtcagg | ctttctggga | gagctcacct | ccagtgaagt | 1440 |
| cgccactgag | gtcccattcc | gcctcatgca | ccctcagcct | gaggacccag | ctaaggaaag | 1500 |
| ttatcaggat | gcaaatttag | tttttgagga | gtttgctcgc | cataatctga | agatgcagg | 1560 |
| agaagctgag | gaggggaaga | gagacaagaa | tgacgttgat | gagtgaagat | gtcggctcag | 1620 |
| gatgccggaa | aatgacctgt | agttaccagt | gcaacgagca | aagccccaca | gtttagtcct | 1680 |
| ttggagttat | gctgcgtatg | aaaggatgag | tcttcttccg | agaaataaag | cttgtttgtt | 1740 |
| ctcccctgga | aaaaaaaaaa | aaaaaaa | | | | 1767 |

<210> SEQ ID NO 21
<211> LENGTH: 405
<212> TYPE: PRT
<213> ORGANISM: Homo sapiens

<400> SEQUENCE: 21

```
Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45

Val Leu Val Asp Pro Asp Leu Val Lys Gly Lys Lys Val Tyr Val Thr
    50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
```

370             375             380
His Asn Leu Lys Asp Ala Gly Glu Ala Glu Glu Gly Lys Arg Asp Lys
385             390             395             400

Asn Asp Val Asp Glu
            405

<210> SEQ ID NO 22
<211> LENGTH: 2483
<212> TYPE: DNA
<213> ORGANISM: Homo sapiens

<400> SEQUENCE: 22

| | | | | | |
|---|---|---|---|---|---|
| agttgattgc | aggtcctcct | ggggccagaa | gggtgcctgg | gaggccaggt | tctggggatc | 60 |
| ccctccatcc | agaagaacca | cctgctcact | ctgtcccttc | gcctgctgct | ggaccatgg | 120 |
| gggctggggc | cagtgctgag | gagaagcact | ccagggagct | ggaaaagaag | ctgaaagagg | 180 |
| acgctgagaa | ggatgctcga | accgtgaagc | tgctgcttct | gggtgccggt | gagtccggga | 240 |
| agagcaccat | cgtcaagcag | atgaagatta | tccaccagga | cgggtactcg | ctggaagagt | 300 |
| gcctcgagtt | tatcgccatc | atctacggca | acacgttgca | gtccatcctg | ccatcgtac | 360 |
| gcgccatgac | cacactcaac | atccagtacg | agactctgc | acgccaggac | gacgcccgga | 420 |
| agctgatgca | catggcagac | actatcgagg | agggcacgat | gcccaaggag | atgtcggaca | 480 |
| tcatccagcg | gctgtggaag | gactccggta | tccaggcctg | ttttgagcgc | gcctcggagt | 540 |
| accagctcaa | cgactcggcg | ggctactacc | tctccgacct | ggagcgcctg | gtaaccccgg | 600 |
| gctacgtgcc | caccgagcag | gacgtgctgc | gctcgcgagt | caagaccact | ggcatcatcg | 660 |
| agacgcagtt | ctccttcaag | gatctcaact | tccggatgtt | cgatgtgggc | gggcagcgct | 720 |
| cggagcgcaa | gaagtggatc | cactgcttcg | agggcgtgac | ctgcatcatc | ttcatcgcgg | 780 |
| cgctgagcgc | ctacgacatg | gtgctagtgg | aggacgacga | agtgaaccgc | atgcacgaga | 840 |
| gcctgcacct | gttcaacagc | atctgcaacc | accgctactt | cgccacgacg | tccatcgtgc | 900 |
| tcttccttaa | caagaaggac | gtcttcttcg | agaagatcaa | gaaggcgcac | ctcagcatct | 960 |
| gtttcccgga | ctacgatgga | cccaacacct | acgaggacgc | cggcaactac | atcaaggtgc | 1020 |
| agttcctcga | gctcaacatg | cggcgcgacg | tgaaggagat | ctattcccac | atgacgtgcg | 1080 |
| ccaccgacac | gcagaacgtc | aaatttgtct | tcgacgctgt | caccgacatc | atcatcaagg | 1140 |
| agaacctcaa | agactgtggc | ctcttctgag | gccagggcct | gtgctgcagt | cggggacaag | 1200 |
| gagcttccgt | ctggcaaggc | cggggcacaa | tttgcactcc | cctcagctag | acgcacagac | 1260 |
| tcagcaataa | acctttgcat | caggctccag | ctgtcctttc | ttggtggagg | acttaattat | 1320 |
| cacaagtcat | gggcatttat | taagtgccca | gtgctgggtt | gggcatgaag | tgggaagatg | 1380 |
| gcccctccca | ggaagaagta | cctggcctga | caaggtgggg | cactcttggg | ggtatgggac | 1440 |
| caactcatgg | cttttcacgg | gagttgagga | gagaggagct | gtggaaaata | ttcactggga | 1500 |
| cagtcttgga | tcaagaggga | gttttgaggt | ggaggctcat | tctggcaggg | accgtagtgt | 1560 |
| ctaccagccc | cagaaacatg | ggcttatggc | cacaggagtt | cagtggagca | agagcagggg | 1620 |
| aggagagacg | tggacaggtg | cccaaagcca | gtcggagggc | ctgggctttc | tcagaaggtg | 1680 |
| atggagagtc | ttggaagccc | tcgaggcagg | aacataattg | cagggctggg | attagggtga | 1740 |
| gggaagtgag | gcacactcac | cttgggtgca | acatttaagg | cgatgccaaa | aaatttagta | 1800 |
| accaaggtaa | ataatattag | gataatattt | ttaaaaatca | aatgaatgca | aaaccccaca | 1860 |
| atgaatgaaa | tatcaaaatc | caacagagga | tcaaacagag | gcatgctaag | atatattggg | 1920 |

```
gcttgaagca aagggaaaac tatttgttgc tatatgtttg tagggatttt ttgccagttt    1980
taaaaataca tgtatcataa agtttactat ctcagccact tgccggtgta tagtttggtg    2040
gtgttaagta cattcataat gttgtacaac caccgcaact gttcatctcc agaactcctt    2100
tcctcttgta aaactgtaac tctgtaccca tgaaaaaata accccccatt cctgccttcc    2160
cccggctcct ggcatccacc attctacttt ccatctctat gaatgtgact gctctaagtg    2220
cctcagatgt gtgggtccat gaagtctttg tcttttttgca actggcttat ttcacttagc    2280
atcatgtctt caaggtttat tcatgtgtag catatggcag aatctccttc cttttttaagg    2340 ttgaataata ttccattgta tatattccac actttgttta tttattcatc tattgatgaa    2400
tggttacatc tgccttttgg ctattgtgaa taatgctgct atgaacatgg gtgtacaaat    2460
ctctcaaaaa aaaaaaaaaa aaa                                            2483
```

<210> SEQ ID NO 23
<211> LENGTH: 350
<212> TYPE: PRT
<213> ORGANISM: Homo sapiens

<400> SEQUENCE: 23

```
Met Gly Ala Gly Ala Ser Ala Glu Glu Lys His Ser Arg Glu Leu Glu
1               5                  10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
        35                  40                  45

Met Lys Ile Ile His Gln Asp Gly Tyr Ser Leu Glu Glu Cys Leu Glu
    50                  55                  60

Phe Ile Ala Ile Ile Tyr Gly Asn Thr Leu Gln Ser Ile Leu Ala Ile
65                  70                  75                  80

Val Arg Ala Met Thr Thr Leu Asn Ile Gln Tyr Gly Asp Ser Ala Arg
                85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
        115                 120                 125

Asp Ser Gly Ile Gln Ala Cys Phe Glu Arg Ala Ser Glu Tyr Gln Leu
    130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
        195                 200                 205

His Cys Phe Glu Gly Val Thr Cys Ile Ile Phe Ile Ala Ala Leu Ser
    210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
                245                 250                 255

Thr Thr Ser Ile Val Leu Phe Leu Asn Lys Lys Asp Val Phe Phe Glu
            260                 265                 270
```

```
Lys Ile Lys Lys Ala His Leu Ser Ile Cys Phe Pro Asp Tyr Asp Gly
            275                 280                 285

Pro Asn Thr Tyr Glu Asp Ala Gly Asn Tyr Ile Lys Val Gln Phe Leu
        290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
            340                 345                 350

<210> SEQ ID NO 24
<211> LENGTH: 201
<212> TYPE: PRT
<213> ORGANISM: Homo sapiens

<400> SEQUENCE: 24

Met Gly Asn Val Met Glu Gly Lys Ser Val Glu Glu Leu Ser Ser Thr
1               5                   10                  15

Glu Cys His Gln Trp Tyr Lys Lys Phe Met Thr Glu Cys Pro Ser Gly
            20                  25                  30

Gln Leu Thr Leu Tyr Glu Phe Arg Gln Phe Phe Gly Leu Lys Asn Leu
        35                  40                  45

Ser Pro Ser Ala Ser Gln Tyr Val Glu Gln Met Phe Glu Thr Phe Asp
    50                  55                  60

Phe Asn Lys Asp Gly Tyr Ile Asp Phe Met Glu Tyr Val Ala Ala Leu
65                  70                  75                  80

Ser Leu Val Leu Lys Gly Lys Val Glu Gln Lys Leu Arg Trp Tyr Phe
                85                  90                  95

Lys Leu Tyr Asp Val Asp Gly Asn Gly Cys Ile Asp Arg Asp Glu Leu
            100                 105                 110

Leu Thr Ile Ile Gln Ala Ile Arg Ala Ile Asn Pro Cys Ser Asp Thr
        115                 120                 125

Thr Met Thr Ala Glu Glu Phe Thr Asp Thr Val Phe Ser Lys Ile Asp
    130                 135                 140

Val Asn Gly Asp Gly Glu Leu Ser Leu Glu Glu Phe Ile Glu Gly Val
145                 150                 155                 160

Gln Lys Asp Gln Met Leu Leu Asp Thr Leu Thr Arg Ser Leu Asp Leu
                165                 170                 175

Thr Arg Ile Val Arg Arg Leu Gln Asn Gly Glu Gln Asp Glu Glu Gly
            180                 185                 190

Ala Asp Glu Ala Ala Glu Ala Ala Gly
        195                 200

<210> SEQ ID NO 25
<211> LENGTH: 1103
<212> TYPE: PRT
<213> ORGANISM: Homo sapiens

<400> SEQUENCE: 25

Met Thr Ala Cys Ala Arg Arg Ala Gly Gly Leu Pro Asp Pro Gly Leu
1               5                   10                  15

Cys Gly Pro Ala Trp Trp Ala Pro Ser Leu Pro Arg Leu Pro Arg Ala
            20                  25                  30

Leu Pro Arg Leu Pro Leu Leu Leu Leu Leu Leu Leu Gln Pro Pro
        35                  40                  45
```

```
Ala Leu Ser Ala Val Phe Thr Val Gly Val Leu Gly Pro Trp Ala Cys
         50                  55                  60

Asp Pro Ile Phe Ser Arg Ala Arg Pro Asp Leu Ala Ala Arg Leu Ala
 65                  70                  75                  80

Ala Ala Arg Leu Asn Arg Asp Pro Gly Leu Ala Gly Gly Pro Arg Phe
                 85                  90                  95

Glu Val Ala Leu Leu Pro Glu Pro Cys Arg Thr Pro Gly Ser Leu Gly
                100                 105                 110

Ala Val Ser Ser Ala Leu Ala Arg Val Ser Gly Leu Val Gly Pro Val
             115                 120                 125

Asn Pro Ala Ala Cys Arg Pro Ala Glu Leu Leu Ala Glu Glu Ala Gly
         130                 135                 140

Ile Ala Leu Val Pro Trp Gly Cys Pro Trp Thr Gln Ala Glu Gly Thr
145                 150                 155                 160

Thr Ala Pro Ala Val Thr Pro Ala Ala Asp Ala Leu Tyr Ala Leu Leu
                 165                 170                 175

Arg Ala Phe Gly Trp Ala Arg Val Ala Leu Val Thr Ala Pro Gln Asp
             180                 185                 190

Leu Trp Val Glu Ala Gly Arg Ser Leu Ser Thr Ala Leu Arg Ala Arg
         195                 200                 205

Gly Leu Pro Val Ala Ser Val Thr Ser Met Glu Pro Leu Asp Leu Ser
210                 215                 220

Gly Ala Arg Glu Ala Leu Arg Lys Val Arg Asp Gly Pro Arg Val Thr
225                 230                 235                 240

Ala Val Ile Met Val Met His Ser Val Leu Gly Gly Glu Glu Gln
                 245                 250                 255

Arg Tyr Leu Leu Glu Ala Ala Glu Glu Leu Gly Leu Thr Asp Gly Ser
             260                 265                 270

Leu Val Phe Leu Pro Phe Asp Thr Ile His Tyr Ala Leu Ser Pro Gly
         275                 280                 285

Pro Glu Ala Leu Ala Ala Leu Ala Asn Ser Ser Gln Leu Arg Arg Ala
     290                 295                 300

His Asp Ala Val Leu Thr Leu Thr Arg His Cys Pro Ser Glu Gly Ser
305                 310                 315                 320

Val Leu Asp Ser Leu Arg Arg Ala Gln Glu Arg Glu Leu Pro Ser
                 325                 330                 335

Asp Leu Asn Leu Gln Gln Val Ser Pro Leu Phe Gly Thr Ile Tyr Asp
             340                 345                 350

Ala Val Phe Leu Leu Ala Arg Gly Val Ala Glu Ala Arg Ala Ala Ala
         355                 360                 365

Gly Gly Arg Trp Val Ser Gly Ala Ala Val Ala Arg His Ile Arg Asp
370                 375                 380

Ala Gln Val Pro Gly Phe Cys Gly Asp Leu Gly Gly Asp Glu Glu Pro
385                 390                 395                 400

Pro Phe Val Leu Leu Asp Thr Asp Ala Ala Gly Asp Arg Leu Phe Ala
                 405                 410                 415

Thr Tyr Met Leu Asp Pro Ala Arg Gly Ser Phe Leu Ser Ala Gly Thr
             420                 425                 430

Arg Met His Phe Pro Arg Gly Gly Ser Ala Pro Gly Pro Asp Pro Ser
         435                 440                 445

Cys Trp Phe Asp Pro Asn Ile Cys Gly Gly Gly Leu Glu Pro Gly
450                 455                 460
```

```
Leu Val Phe Leu Gly Phe Leu Val Val Gly Met Gly Leu Ala Gly
465                 470                 475                 480

Ala Phe Leu Ala His Tyr Val Arg His Arg Leu Leu His Met Gln Met
            485                 490                 495

Val Ser Gly Pro Asn Lys Ile Ile Leu Thr Val Asp Asp Ile Thr Phe
            500                 505                 510

Leu His Pro His Gly Gly Thr Ser Arg Lys Val Ala Gln Gly Ser Arg
            515                 520                 525

Ser Ser Leu Gly Ala Arg Ser Met Ser Asp Ile Arg Ser Gly Pro Ser
530                 535                 540

Gln His Leu Asp Ser Pro Asn Ile Gly Val Tyr Glu Gly Asp Arg Val
545                 550                 555                 560

Trp Leu Lys Lys Phe Pro Gly Asp Gln His Ile Ala Ile Arg Pro Ala
            565                 570                 575

Thr Lys Thr Ala Phe Ser Lys Leu Gln Glu Leu Arg His Glu Asn Val
            580                 585                 590

Ala Leu Tyr Leu Gly Leu Phe Leu Ala Arg Gly Ala Glu Gly Pro Ala
            595                 600                 605

Ala Leu Trp Glu Gly Asn Leu Ala Val Val Ser Glu His Cys Thr Arg
            610                 615                 620

Gly Ser Leu Gln Asp Leu Leu Ala Gln Arg Glu Ile Lys Leu Asp Trp
625                 630                 635                 640

Met Phe Lys Ser Ser Leu Leu Leu Asp Leu Ile Lys Gly Ile Arg Tyr
                645                 650                 655

Leu His His Arg Gly Val Ala His Gly Arg Leu Lys Ser Arg Asn Cys
            660                 665                 670

Ile Val Asp Gly Arg Phe Val Leu Lys Ile Thr Asp His Gly His Gly
            675                 680                 685

Arg Leu Leu Glu Ala Gln Lys Val Leu Pro Glu Pro Pro Arg Ala Glu
            690                 695                 700

Asp Gln Leu Trp Thr Ala Pro Glu Leu Leu Arg Asp Pro Ala Leu Glu
705                 710                 715                 720

Arg Arg Gly Thr Leu Ala Gly Asp Val Phe Ser Leu Ala Ile Ile Met
            725                 730                 735

Gln Glu Val Val Cys Arg Ser Ala Pro Tyr Ala Met Leu Glu Leu Thr
            740                 745                 750

Pro Glu Glu Val Val Gln Arg Val Arg Ser Pro Pro Leu Cys Arg
            755                 760                 765

Pro Leu Val Ser Met Asp Gln Ala Pro Val Glu Cys Ile Leu Leu Met
770                 775                 780

Lys Gln Cys Trp Ala Glu Gln Pro Glu Leu Arg Pro Ser Met Asp His
785                 790                 795                 800

Thr Phe Asp Leu Phe Lys Asn Ile Asn Lys Gly Arg Lys Thr Asn Ile
            805                 810                 815

Ile Asp Ser Met Leu Arg Met Leu Glu Gln Tyr Ser Ser Asn Leu Glu
            820                 825                 830

Asp Leu Ile Arg Glu Arg Thr Glu Glu Leu Glu Leu Glu Lys Gln Lys
            835                 840                 845

Thr Asp Arg Leu Leu Thr Gln Met Leu Pro Pro Ser Val Ala Glu Ala
            850                 855                 860

Leu Lys Thr Gly Thr Pro Val Glu Pro Glu Tyr Phe Glu Gln Val Thr
865                 870                 875                 880

Leu Tyr Phe Ser Asp Ile Val Gly Phe Thr Thr Ile Ser Ala Met Ser
```

885                 890                 895
Glu Pro Ile Glu Val Val Asp Leu Leu Asn Asp Leu Tyr Thr Leu Phe
            900                 905                 910

Asp Ala Ile Ile Gly Ser His Asp Val Tyr Lys Val Glu Thr Ile Gly
            915                 920                 925

Asp Ala Tyr Met Val Ala Ser Gly Leu Pro Gln Arg Asn Gly Gln Arg
            930                 935                 940

His Ala Ala Glu Ile Ala Asn Met Ser Leu Asp Ile Leu Ser Ala Val
945                 950                 955                 960

Gly Thr Phe Arg Met Arg His Met Pro Glu Val Pro Val Arg Ile Arg
            965                 970                 975

Ile Gly Leu His Ser Gly Pro Cys Val Ala Gly Val Val Gly Leu Thr
            980                 985                 990

Met Pro Arg Tyr Cys Leu Phe Gly Asp Thr Val Asn Thr Ala Ser Arg
            995                1000                1005

Met Glu Ser Thr Gly Leu Pro Tyr Arg Ile His Val Asn Leu Ser
        1010                1015                1020

Thr Val Gly Ile Leu Arg Ala Leu Asp Ser Gly Tyr Gln Val Glu
        1025                1030                1035

Leu Arg Gly Arg Thr Glu Leu Lys Gly Lys Gly Ala Glu Asp Thr
        1040                1045                1050

Phe Trp Leu Val Gly Arg Arg Gly Phe Asn Lys Pro Ile Pro Lys
        1055                1060                1065

Pro Pro Asp Leu Gln Pro Gly Ser Ser Asn His Gly Ile Ser Leu
        1070                1075                1080

Gln Glu Ile Pro Pro Glu Arg Arg Arg Lys Leu Glu Lys Ala Arg
        1085                1090                1095

Pro Gly Gln Phe Ser
        1100

<210> SEQ ID NO 26
<211> LENGTH: 676
<212> TYPE: PRT
<213> ORGANISM: Homo sapiens

<400> SEQUENCE: 26

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Thr Ser Ser Val Leu Gln Pro
        35                  40                  45

Gly Ile Ala Met Glu Thr Arg Gly Leu Ala Asp Ser Gly Gln Gly Ser
50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Arg Lys Lys Thr Lys Lys Lys Asp Ala Ile Val Val Asp
    130                 135                 140

```
Pro Ser Ser Asn Leu Tyr Tyr Arg Trp Leu Thr Ala Ile Ala Leu Pro
145                 150                 155                 160

Val Phe Tyr Asn Trp Tyr Leu Leu Ile Cys Arg Ala Cys Phe Asp Glu
            165                 170                 175

Leu Gln Ser Glu Tyr Leu Met Leu Trp Leu Val Leu Asp Tyr Ser Ala
        180                 185                 190

Asp Val Leu Tyr Val Leu Asp Val Leu Val Arg Ala Arg Thr Gly Phe
    195                 200                 205

Leu Glu Gln Gly Leu Met Val Ser Asp Thr Asn Arg Leu Trp Gln His
210                 215                 220

Tyr Lys Thr Thr Thr Gln Phe Lys Leu Asp Val Leu Ser Leu Val Pro
225                 230                 235                 240

Thr Asp Leu Ala Tyr Leu Lys Val Gly Thr Asn Tyr Pro Glu Val Arg
            245                 250                 255

Phe Asn Arg Leu Leu Lys Phe Ser Arg Leu Phe Glu Phe Phe Asp Arg
        260                 265                 270

Thr Glu Thr Arg Thr Asn Tyr Pro Asn Met Phe Arg Ile Gly Asn Leu
    275                 280                 285

Val Leu Tyr Ile Leu Ile Ile His Trp Asn Ala Cys Ile Tyr Phe
290                 295                 300

Ala Ile Ser Lys Phe Ile Gly Phe Gly Thr Asp Ser Trp Val Tyr Pro
305                 310                 315                 320

Asn Ile Ser Ile Pro Glu His Gly Arg Leu Ser Arg Lys Tyr Ile Tyr
            325                 330                 335

Ser Leu Tyr Trp Ser Thr Leu Thr Leu Thr Thr Ile Gly Glu Thr Pro
        340                 345                 350

Pro Pro Val Lys Asp Glu Glu Tyr Leu Phe Val Val Asp Phe Leu
    355                 360                 365

Val Gly Val Leu Ile Phe Ala Thr Ile Val Gly Asn Val Gly Ser Met
370                 375                 380

Ile Ser Asn Met Asn Ala Ser Arg Ala Glu Phe Gln Ala Lys Ile Asp
385                 390                 395                 400

Ser Ile Lys Gln Tyr Met Gln Phe Arg Lys Val Thr Lys Asp Leu Glu
            405                 410                 415

Thr Arg Val Ile Arg Trp Phe Asp Tyr Leu Trp Ala Asn Lys Lys Thr
        420                 425                 430

Val Asp Glu Lys Glu Val Leu Lys Ser Leu Pro Asp Lys Leu Lys Ala
    435                 440                 445

Glu Ile Ala Ile Asn Val His Leu Asp Thr Leu Lys Lys Val Arg Ile
450                 455                 460

Phe Gln Asp Cys Glu Ala Gly Leu Leu Val Glu Leu Val Leu Lys Leu
465                 470                 475                 480

Arg Pro Thr Val Phe Ser Pro Gly Asp Tyr Ile Cys Lys Lys Gly Asp
            485                 490                 495

Ile Gly Lys Glu Met Tyr Ile Ile Asn Glu Gly Lys Leu Ala Val Val
        500                 505                 510

Ala Asp Asp Gly Val Thr Gln Phe Val Val Leu Ser Asp Gly Ser Tyr
    515                 520                 525

Phe Gly Glu Ile Ser Ile Leu Asn Ile Lys Gly Ser Lys Ser Gly Asn
530                 535                 540

Arg Arg Thr Ala Asn Ile Arg Ser Ile Gly Tyr Ser Asp Leu Phe Cys
545                 550                 555                 560

Leu Ser Lys Asp Asp Leu Met Glu Ala Leu Thr Glu Tyr Pro Glu Ala
```

Lys Lys Ala Leu Glu Glu Lys Gly Arg Gln Ile Leu Met Lys Asp Asn
565                 570                 575

Leu Ile Asp Glu Glu Leu Ala Arg Ala Gly Asp Pro Lys Asp Leu
    580                 585                 590

Glu Glu Lys Val Glu Gln Leu Gly Ser Ser Leu Asp Thr Leu Gln Thr
595                 600                 605

Arg Phe Ala Arg Leu Leu Ala Glu Tyr Asn Ala Thr Gln Met Lys Met
610                 615                 620

Lys Gln Arg Leu Ser Gln Leu Glu Ser Gln Val Lys Gly Gly Gly Asp
625                 630                 635                 640

Lys Pro Leu Ala Asp Gly Glu Val Pro Gly Asp Ala Thr Lys Thr Glu
        645                 650                 655

Asp Lys Gln Gln
    660                 665                 670

675

<210> SEQ ID NO 27
<211> LENGTH: 694
<212> TYPE: PRT
<213> ORGANISM: Homo sapiens

<400> SEQUENCE: 27

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Ser Ala Trp Pro Leu Ala Lys Cys Asn Thr Asn Thr Ser
130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
            180                 185                 190

Asp Glu Leu Gln Ser Glu Tyr Leu Met Leu Trp Leu Val Leu Asp Tyr
        195                 200                 205

Ser Ala Asp Val Leu Tyr Val Leu Asp Val Leu Val Arg Ala Arg Thr
210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

```
Val Pro Thr Asp Leu Ala Tyr Leu Lys Val Gly Thr Asn Tyr Pro Glu
            260                 265                 270

Val Arg Phe Asn Arg Leu Leu Lys Phe Ser Arg Leu Phe Glu Phe Phe
            275                 280                 285

Asp Arg Thr Glu Thr Arg Thr Asn Tyr Pro Asn Met Phe Arg Ile Gly
            290                 295                 300

Asn Leu Val Leu Tyr Ile Leu Ile Ile His Trp Asn Ala Cys Ile
305                 310                 315                 320

Tyr Phe Ala Ile Ser Lys Phe Ile Gly Phe Gly Thr Asp Ser Trp Val
                325                 330                 335

Tyr Pro Asn Ile Ser Ile Pro Glu His Gly Arg Leu Ser Arg Lys Tyr
                340                 345                 350

Ile Tyr Ser Leu Tyr Trp Ser Thr Leu Thr Leu Thr Thr Ile Gly Glu
                355                 360                 365

Thr Pro Pro Val Lys Asp Glu Glu Tyr Leu Phe Val Val Val Asp
            370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
                420                 425                 430

Leu Glu Thr Arg Val Ile Arg Trp Phe Asp Tyr Leu Trp Ala Asn Lys
            435                 440                 445

Lys Thr Val Asp Glu Lys Glu Val Leu Lys Ser Leu Pro Asp Lys Leu
450                 455                 460

Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys
            500                 505                 510

Gly Asp Ile Gly Lys Glu Met Tyr Ile Ile Asn Glu Gly Lys Leu Ala
            515                 520                 525

Val Val Ala Asp Asp Gly Val Thr Gln Phe Val Val Leu Ser Asp Gly
            530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
            580                 585                 590

Glu Ala Lys Lys Ala Leu Glu Glu Lys Gly Arg Gln Ile Leu Met Lys
            595                 600                 605

Asp Asn Leu Ile Asp Glu Glu Leu Ala Arg Ala Gly Ala Asp Pro Lys
            610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
            660                 665                 670

Gly Asp Lys Pro Leu Ala Asp Gly Glu Val Pro Gly Asp Ala Thr Lys
```

```
                675                 680                 685

Thr Glu Asp Lys Gln Gln
        690

<210> SEQ ID NO 28
<211> LENGTH: 354
<212> TYPE: PRT
<213> ORGANISM: Homo sapiens

<400> SEQUENCE: 28

Met Gly Ser Gly Ala Ser Ala Glu Asp Lys Glu Leu Ala Lys Arg Ser
1               5                   10                  15

Lys Glu Leu Glu Lys Lys Leu Gln Glu Asp Ala Asp Lys Glu Ala Lys
            20                  25                  30

Thr Val Lys Leu Leu Leu Leu Gly Ala Gly Glu Ser Gly Lys Ser Thr
        35                  40                  45

Ile Val Lys Gln Met Lys Ile Ile His Gln Asp Gly Tyr Ser Pro Glu
    50                  55                  60

Glu Cys Leu Glu Phe Lys Ala Ile Ile Tyr Gly Asn Val Leu Gln Ser
65                  70                  75                  80

Ile Leu Ala Ile Ile Arg Ala Met Thr Thr Leu Gly Ile Asp Tyr Ala
                85                  90                  95

Glu Pro Ser Cys Ala Asp Asp Gly Arg Gln Leu Asn Asn Leu Ala Asp
            100                 105                 110

Ser Ile Glu Glu Gly Thr Met Pro Pro Glu Leu Val Glu Val Ile Arg
        115                 120                 125

Arg Leu Trp Lys Asp Gly Gly Val Gln Ala Cys Phe Glu Arg Ala Ala
    130                 135                 140

Glu Tyr Gln Leu Asn Asp Ser Ala Ser Tyr Tyr Leu Asn Gln Leu Glu
145                 150                 155                 160

Arg Ile Thr Asp Pro Glu Tyr Leu Pro Ser Glu Gln Asp Val Leu Arg
                165                 170                 175

Ser Arg Val Lys Thr Thr Gly Ile Ile Glu Thr Lys Phe Ser Val Lys
            180                 185                 190

Asp Leu Asn Phe Arg Met Phe Asp Val Gly Gly Gln Arg Ser Glu Arg
        195                 200                 205

Lys Lys Trp Ile His Cys Phe Glu Gly Val Thr Cys Ile Ile Phe Cys
    210                 215                 220

Ala Ala Leu Ser Ala Tyr Asp Met Val Leu Val Glu Asp Asp Glu Val
225                 230                 235                 240

Asn Arg Met His Glu Ser Leu His Leu Phe Asn Ser Ile Cys Asn His
                245                 250                 255

Lys Phe Phe Ala Ala Thr Ser Ile Val Leu Phe Leu Asn Lys Lys Asp
            260                 265                 270

Leu Phe Glu Glu Lys Ile Lys Lys Val His Leu Ser Ile Cys Phe Pro
        275                 280                 285

Glu Tyr Asp Gly Asn Asn Ser Tyr Asp Ala Gly Asn Tyr Ile Lys
    290                 295                 300

Ser Gln Phe Leu Asp Leu Asn Met Arg Lys Asp Val Lys Glu Ile Tyr
305                 310                 315                 320

Ser His Met Thr Cys Ala Thr Asp Thr Gln Asn Val Lys Phe Val Phe
                325                 330                 335

Asp Ala Val Thr Asp Ile Ile Lys Glu Asn Leu Lys Asp Cys Gly
            340                 345                 350
```

Leu Phe

<210> SEQ ID NO 29
<211> LENGTH: 858
<212> TYPE: PRT
<213> ORGANISM: Homo sapiens

<400> SEQUENCE: 29

Met Gly Glu Ile Asn Gln Val Ala Val Glu Lys Tyr Leu Glu Asn
1               5                   10                  15

Pro Gln Phe Ala Lys Glu Tyr Phe Asp Arg Lys Leu Arg Val Val
                20                  25                  30

Leu Gly Glu Ile Phe Lys Asn Ser Gln Val Pro Val Gln Ser Ser Met
            35                  40                  45

Ser Phe Ser Glu Leu Thr Gln Val Glu Ser Ala Leu Cys Leu Glu
        50                  55                  60

Leu Leu Trp Thr Val Gln Glu Glu Gly Gly Thr Pro Glu Gln Gly Val
65                  70                  75                  80

His Arg Ala Leu Gln Arg Leu Ala His Leu Leu Gln Ala Asp Arg Cys
                85                  90                  95

Ser Met Phe Leu Cys Arg Ser Arg Asn Gly Ile Pro Glu Val Ala Ser
            100                 105                 110

Arg Leu Leu Asp Val Thr Pro Thr Ser Lys Phe Glu Asp Asn Leu Val
        115                 120                 125

Gly Pro Asp Lys Glu Val Val Phe Pro Leu Asp Ile Gly Ile Val Gly
    130                 135                 140

Trp Ala Ala His Thr Lys Lys Thr His Asn Val Pro Val Lys Lys
145                 150                 155                 160

Asn Ser His Phe Ser Asp Phe Met Asp Lys Gln Thr Gly Tyr Val Thr
                165                 170                 175

Lys Asn Leu Leu Ala Thr Pro Ile Val Val Gly Lys Glu Val Leu Ala
            180                 185                 190

Val Ile Met Ala Val Asn Lys Val Asn Ala Ser Glu Phe Ser Lys Gln
        195                 200                 205

Asp Glu Glu Val Phe Ser Lys Tyr Leu Asn Phe Val Ser Ile Ile Leu
    210                 215                 220

Arg Leu His His Thr Ser Tyr Met Tyr Asn Ile Glu Ser Arg Arg Ser
225                 230                 235                 240

Gln Ile Leu Met Trp Ser Ala Asn Lys Val Phe Glu Glu Leu Thr Asp
                245                 250                 255

Val Glu Arg Gln Phe His Lys Ala Leu Tyr Thr Val Arg Ser Tyr Leu
            260                 265                 270

Asn Cys Glu Arg Tyr Ser Ile Gly Leu Leu Asp Met Thr Lys Glu Lys
        275                 280                 285

Glu Phe Tyr Asp Glu Trp Pro Ile Lys Leu Gly Glu Val Glu Pro Tyr
    290                 295                 300

Lys Gly Pro Lys Thr Pro Asp Gly Arg Glu Val Asn Phe Tyr Lys Ile
305                 310                 315                 320

Ile Asp Tyr Ile Leu His Gly Lys Glu Glu Ile Lys Val Ile Pro Thr
                325                 330                 335

Pro Pro Ala Asp His Trp Thr Leu Ile Ser Gly Leu Pro Thr Tyr Val
            340                 345                 350

Ala Glu Asn Gly Phe Ile Cys Asn Met Met Asn Ala Pro Ala Asp Glu
        355                 360                 365

```
Tyr Phe Thr Phe Gln Lys Gly Pro Val Asp Glu Thr Gly Trp Val Ile
    370                 375                 380

Lys Asn Val Leu Ser Leu Pro Ile Val Asn Lys Lys Glu Asp Ile Val
385                 390                 395                 400

Gly Val Ala Thr Phe Tyr Asn Arg Lys Asp Gly Lys Pro Phe Asp Glu
                405                 410                 415

His Asp Glu Tyr Ile Thr Glu Thr Leu Thr Gln Phe Leu Gly Trp Ser
                420                 425                 430

Leu Leu Asn Thr Asp Thr Tyr Asp Lys Met Asn Lys Leu Glu Asn Arg
            435                 440                 445

Lys Asp Ile Ala Gln Glu Met Leu Met Asn Gln Thr Lys Ala Thr Pro
450                 455                 460

Glu Glu Ile Lys Ser Ile Leu Lys Phe Gln Glu Lys Leu Asn Val Asp
465                 470                 475                 480

Val Ile Asp Asp Cys Glu Glu Lys Gln Leu Val Ala Ile Leu Lys Glu
                485                 490                 495

Asp Leu Pro Asp Pro Arg Ser Ala Glu Leu Tyr Glu Phe Arg Phe Ser
                500                 505                 510

Asp Phe Pro Leu Thr Glu His Gly Leu Ile Lys Cys Gly Ile Arg Leu
            515                 520                 525

Phe Phe Glu Ile Asn Val Val Glu Lys Phe Lys Val Pro Val Glu Val
530                 535                 540

Leu Thr Arg Trp Met Tyr Thr Val Arg Lys Gly Tyr Arg Ala Val Thr
545                 550                 555                 560

Tyr His Asn Trp Arg His Gly Phe Asn Val Gly Gln Thr Met Phe Thr
                565                 570                 575

Leu Leu Met Thr Gly Arg Leu Lys Lys Tyr Tyr Thr Asp Leu Glu Ala
            580                 585                 590

Phe Ala Met Leu Ala Ala Ala Phe Cys His Asp Ile Asp His Arg Gly
        595                 600                 605

Thr Asn Asn Leu Tyr Gln Met Lys Ser Thr Ser Pro Leu Ala Arg Leu
610                 615                 620

His Gly Ser Ser Ile Leu Glu Arg His His Leu Glu Tyr Ser Lys Thr
625                 630                 635                 640

Leu Leu Gln Asp Glu Ser Leu Asn Ile Phe Gln Asn Leu Asn Lys Arg
                645                 650                 655

Gln Phe Glu Thr Val Ile His Leu Phe Glu Val Ala Ile Ile Ala Thr
                660                 665                 670

Asp Leu Ala Leu Tyr Phe Lys Lys Arg Thr Met Phe Gln Lys Ile Val
            675                 680                 685

Asp Ala Cys Glu Gln Met Gln Thr Glu Glu Ala Ile Lys Tyr Val
690                 695                 700

Thr Val Asp Pro Thr Lys Lys Glu Ile Ile Met Ala Met Met Met Thr
705                 710                 715                 720

Ala Cys Asp Leu Ser Ala Ile Thr Lys Pro Trp Glu Val Gln Ser Gln
                725                 730                 735

Val Ala Leu Met Val Ala Asn Glu Phe Trp Glu Gln Gly Asp Leu Glu
                740                 745                 750

Arg Thr Val Leu Gln Gln Gln Pro Ile Pro Met Met Asp Arg Asn Lys
            755                 760                 765

Arg Asp Glu Leu Pro Lys Leu Gln Val Gly Phe Ile Asp Phe Val Cys
770                 775                 780

Thr Phe Val Tyr Lys Glu Phe Ser Arg Phe His Lys Glu Ile Thr Pro
```

```
                785                 790                 795                 800
Met Leu Ser Gly Leu Gln Asn Asn Arg Val Glu Trp Lys Ser Leu Ala
                    805                 810                 815

Asp Glu Tyr Asp Ala Lys Met Lys Val Ile Glu Glu Ala Lys Lys
                820                 825                 830

Gln Glu Gly Gly Ala Glu Lys Ala Ala Glu Asp Ser Gly Gly Asp
                835                 840                 845

Asp Lys Lys Ser Lys Thr Cys Leu Met Leu
                850                 855

<210> SEQ ID NO 30
<211> LENGTH: 83
<212> TYPE: PRT
<213> ORGANISM: Homo sapiens

<400> SEQUENCE: 30

Met Ser Asp Asn Thr Thr Leu Pro Ala Pro Ala Ser Asn Gln Gly Pro
1               5                   10                  15

Thr Thr Pro Arg Lys Gly Pro Pro Lys Phe Lys Gln Arg Gln Thr Arg
                    20                  25                  30

Gln Phe Lys Ser Lys Pro Pro Lys Lys Gly Val Lys Gly Phe Gly Asp
                35                  40                  45

Asp Ile Pro Gly Met Glu Gly Leu Gly Thr Asp Ile Thr Val Ile Cys
            50                  55                  60

Pro Trp Glu Ala Phe Ser His Leu Glu Leu His Glu Leu Ala Gln Phe
65                  70                  75                  80

Gly Ile Ile

<210> SEQ ID NO 31
<211> LENGTH: 299
<212> TYPE: PRT
<213> ORGANISM: Homo sapiens

<400> SEQUENCE: 31

Met Met Ala Tyr Met Asn Pro Gly Pro His Tyr Ser Val Asn Ala Leu
1               5                   10                  15

Ala Leu Ser Gly Pro Ser Val Asp Leu Met His Gln Ala Val Pro Tyr
                    20                  25                  30

Pro Ser Ala Pro Arg Lys Gln Arg Arg Glu Arg Thr Thr Phe Thr Arg
                35                  40                  45

Ser Gln Leu Glu Glu Leu Glu Ala Leu Phe Ala Lys Thr Gln Tyr Pro
                50                  55                  60

Asp Val Tyr Ala Arg Glu Glu Val Ala Leu Lys Ile Asn Leu Pro Glu
65                  70                  75                  80

Ser Arg Val Gln Val Trp Phe Lys Asn Arg Arg Ala Lys Cys Arg Gln
                    85                  90                  95

Gln Arg Gln Gln Gln Lys Gln Gln Gln Pro Pro Gly Gly Gln Ala
                    100                 105                 110

Lys Ala Arg Pro Ala Lys Arg Lys Ala Gly Thr Ser Pro Arg Pro Ser
                    115                 120                 125

Thr Asp Val Cys Pro Asp Pro Leu Gly Ile Ser Asp Ser Tyr Ser Pro
                    130                 135                 140

Pro Leu Pro Gly Pro Ser Gly Ser Pro Thr Thr Ala Val Ala Thr Val
145                 150                 155                 160

Ser Ile Trp Ser Pro Ala Ser Glu Ser Pro Leu Pro Glu Ala Gln Arg
                    165                 170                 175
```

```
Ala Gly Leu Val Ala Ser Gly Pro Ser Leu Thr Ser Ala Pro Tyr Ala
            180                 185                 190

Met Thr Tyr Ala Pro Ala Ser Ala Phe Cys Ser Ser Pro Ser Ala Tyr
            195                 200                 205

Gly Ser Pro Ser Ser Tyr Phe Ser Gly Leu Asp Pro Tyr Leu Ser Pro
            210                 215                 220

Met Val Pro Gln Leu Gly Gly Pro Ala Leu Ser Pro Leu Ser Gly Pro
225                 230                 235                 240

Ser Val Gly Pro Ser Leu Ala Gln Ser Pro Thr Ser Leu Ser Gly Gln
                245                 250                 255

Ser Tyr Gly Ala Tyr Ser Pro Val Asp Ser Leu Glu Phe Lys Asp Pro
            260                 265                 270

Thr Gly Thr Trp Lys Phe Thr Tyr Asn Pro Met Asp Pro Leu Asp Tyr
            275                 280                 285

Lys Asp Gln Ser Ala Trp Lys Phe Gln Ile Leu
            290                 295

<210> SEQ ID NO 32
<211> LENGTH: 809
<212> TYPE: PRT
<213> ORGANISM: Homo sapiens

<400> SEQUENCE: 32

Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190

Lys Lys Met Pro Leu Thr Glu Tyr Leu Lys Arg Ile Lys Leu Pro Asn
            195                 200                 205

Ser Ile Asp Ser Tyr Thr Asp Arg Leu Tyr Leu Leu Trp Leu Leu Leu
        210                 215                 220

Val Thr Leu Ala Tyr Asn Trp Asn Cys Trp Phe Ile Pro Leu Arg Leu
225                 230                 235                 240

Val Phe Pro Tyr Gln Thr Ala Asp Asn Ile His Tyr Trp Leu Ile Ala
```

-continued

```
                245                 250                 255
Asp Ile Ile Cys Asp Ile Ile Tyr Leu Tyr Asp Met Leu Phe Ile Gln
            260                 265                 270

Pro Arg Leu Gln Phe Val Arg Gly Gly Asp Ile Ile Val Asp Ser Asn
        275                 280                 285

Glu Leu Arg Lys His Tyr Arg Thr Ser Thr Lys Phe Gln Leu Asp Val
    290                 295                 300

Ala Ser Ile Ile Pro Phe Asp Ile Cys Tyr Leu Phe Gly Phe Asn
305                 310                 315                 320

Pro Met Phe Arg Ala Asn Arg Met Leu Lys Tyr Thr Ser Phe Phe Glu
                325                 330                 335

Phe Asn His His Leu Glu Ser Ile Met Asp Lys Ala Tyr Ile Tyr Arg
            340                 345                 350

Val Ile Arg Thr Thr Gly Tyr Leu Leu Phe Ile Leu His Ile Asn Ala
        355                 360                 365

Cys Val Tyr Tyr Trp Ala Ser Asn Tyr Glu Gly Ile Gly Thr Thr Arg
    370                 375                 380

Trp Val Tyr Asp Gly Glu Gly Asn Glu Tyr Leu Arg Cys Tyr Tyr Trp
385                 390                 395                 400

Ala Val Arg Thr Leu Ile Thr Ile Gly Gly Leu Pro Glu Pro Gln Thr
                405                 410                 415

Leu Phe Glu Ile Val Phe Gln Leu Leu Asn Phe Phe Ser Gly Val Phe
            420                 425                 430

Val Phe Ser Ser Leu Ile Gly Gln Met Arg Asp Val Ile Gly Ala Ala
        435                 440                 445

Thr Ala Asn Gln Asn Tyr Phe Arg Ala Cys Met Asp Asp Thr Ile Ala
    450                 455                 460

Tyr Met Asn Asn Tyr Ser Ile Pro Lys Leu Val Gln Lys Arg Val Arg
465                 470                 475                 480

Thr Trp Tyr Glu Tyr Thr Trp Asp Ser Gln Arg Met Leu Asp Glu Ser
                485                 490                 495

Asp Leu Leu Lys Thr Leu Pro Thr Thr Val Gln Leu Ala Leu Ala Ile
            500                 505                 510

Asp Val Asn Phe Ser Ile Ile Ser Lys Val Asp Leu Phe Lys Gly Cys
        515                 520                 525

Asp Thr Gln Met Ile Tyr Asp Met Leu Leu Arg Leu Lys Ser Val Leu
    530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
            580                 585                 590

Ile Ser Leu Leu Ala Ala Gly Gly Asn Arg Arg Thr Ala Asn Val
        595                 600                 605

Val Ala His Gly Phe Ala Asn Leu Leu Thr Leu Asp Lys Lys Thr Leu
    610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
            660                 665                 670
```

-continued

```
Pro Lys Leu Phe Lys Thr Leu Leu Gly Gly Thr Gly Lys Ala Ser Leu
            675                 680                 685

Ala Arg Leu Leu Lys Leu Lys Arg Glu Gln Ala Ala Gln Lys Lys Glu
    690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Lys Pro Leu Asp
            740                 745                 750

Arg Pro Glu Cys Thr Ala Ser Pro Ile Ala Val Glu Glu Pro His
                755                 760                 765

Ser Val Arg Arg Thr Val Leu Pro Arg Gly Thr Ser Arg Gln Ser Leu
    770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
                805
```

<210> SEQ ID NO 33
<211> LENGTH: 610
<212> TYPE: PRT
<213> ORGANISM: Homo sapiens

<400> SEQUENCE: 33

```
Met Pro Leu Thr Glu Tyr Leu Lys Arg Ile Lys Leu Pro Asn Ser Ile
1               5                   10                  15

Asp Ser Tyr Thr Asp Arg Leu Tyr Leu Leu Trp Leu Leu Leu Val Thr
            20                  25                  30

Leu Ala Tyr Asn Trp Asn Cys Cys Phe Ile Pro Leu Arg Leu Val Phe
        35                  40                  45

Pro Tyr Gln Thr Ala Asp Asn Ile His Tyr Trp Leu Ile Ala Asp Ile
    50                  55                  60

Ile Cys Asp Ile Ile Tyr Leu Tyr Asp Met Leu Phe Ile Gln Pro Arg
65                  70                  75                  80

Leu Gln Phe Val Arg Gly Gly Asp Ile Ile Val Asp Ser Asn Glu Leu
                85                  90                  95

Arg Lys His Tyr Arg Thr Ser Thr Lys Phe Gln Leu Asp Val Ala Ser
            100                 105                 110

Ile Ile Pro Phe Asp Ile Cys Tyr Leu Phe Phe Gly Phe Asn Pro Met
        115                 120                 125

Phe Arg Ala Asn Arg Met Leu Lys Tyr Thr Ser Phe Phe Glu Phe Asn
    130                 135                 140

His His Leu Glu Ser Ile Met Asp Lys Ala Tyr Ile Tyr Arg Val Ile
145                 150                 155                 160

Arg Thr Thr Gly Tyr Leu Leu Phe Ile Leu His Ile Asn Ala Cys Val
                165                 170                 175

Tyr Tyr Trp Ala Ser Asn Tyr Glu Gly Ile Gly Thr Thr Arg Trp Val
            180                 185                 190

Tyr Asp Gly Glu Gly Asn Glu Tyr Leu Arg Cys Tyr Tyr Trp Ala Val
        195                 200                 205

Arg Thr Leu Ile Thr Ile Gly Gly Leu Pro Glu Pro Gln Thr Leu Phe
    210                 215                 220

Glu Ile Val Phe Gln Leu Leu Asn Phe Phe Ser Gly Val Phe Val Phe
```

```
            225                 230                 235                 240
        Ser Ser Leu Ile Gly Gln Met Arg Asp Val Ile Gly Ala Ala Thr Ala
                    245                 250                 255
        Asn Gln Asn Tyr Phe Arg Ala Cys Met Asp Asp Thr Ile Ala Tyr Met
                    260                 265                 270
        Asn Asn Tyr Ser Ile Pro Lys Leu Val Gln Lys Arg Val Arg Thr Trp
                    275                 280                 285
        Tyr Glu Tyr Thr Trp Asp Ser Gln Arg Met Leu Asp Glu Ser Asp Leu
                    290                 295                 300
        Leu Lys Thr Leu Pro Thr Thr Val Gln Leu Ala Leu Ala Ile Asp Val
        305                 310                 315                 320
        Asn Phe Ser Ile Ile Ser Lys Val Asp Leu Phe Lys Gly Cys Asp Thr
                    325                 330                 335
        Gln Met Ile Tyr Asp Met Leu Leu Arg Leu Lys Ser Val Leu Tyr Leu
                    340                 345                 350
        Pro Gly Asp Phe Val Cys Lys Lys Gly Glu Ile Gly Lys Glu Met Tyr
                    355                 360                 365
        Ile Ile Lys His Gly Glu Val Gln Val Leu Gly Gly Pro Asp Gly Thr
                    370                 375                 380
        Lys Val Leu Val Thr Leu Lys Ala Gly Ser Val Leu Ala Ala Gly
        385                 390                 395                 400
        Gly Gly Asn Arg Arg Thr Ala Asn Val Val Ala His Gly Phe Ala Asn
                    405                 410                 415
        Leu Leu Thr Leu Asp Lys Lys Thr Leu Gln Glu Ile Leu Val His Tyr
                    420                 425                 430
        Pro Asp Ser Glu Arg Ile Leu Met Lys Lys Ala Arg Val Leu Leu Lys
                    435                 440                 445
        Gln Lys Ala Lys Thr Ala Glu Ala Thr Pro Pro Arg Lys Asp Leu Ala
                    450                 455                 460
        Leu Leu Phe Pro Pro Lys Glu Thr Pro Lys Leu Phe Lys Thr Leu
        465                 470                 475                 480
        Leu Gly Gly Thr Gly Lys Ala Ser Leu Ala Arg Leu Leu Lys Leu Lys
                    485                 490                 495
        Arg Glu Gln Ala Ala Gln Lys Lys Glu Asn Ser Glu Gly Gly Glu Glu
                    500                 505                 510
        Glu Gly Lys Glu Asn Glu Asp Lys Gln Lys Glu Asn Glu Asp Lys Gln
                    515                 520                 525
        Lys Glu Asn Glu Asp Lys Gly Lys Glu Asn Glu Asp Lys Asp Lys Gly
                    530                 535                 540
        Arg Glu Pro Glu Glu Lys Pro Leu Asp Arg Pro Glu Cys Thr Ala Ser
        545                 550                 555                 560
        Pro Ile Ala Val Glu Glu Pro His Ser Val Arg Arg Thr Val Leu
                    565                 570                 575
        Pro Arg Gly Thr Ser Arg Gln Ser Leu Ile Ile Ser Met Ala Pro Ser
                    580                 585                 590
        Ala Glu Gly Gly Glu Glu Val Leu Thr Ile Glu Val Lys Glu Lys Ala
                    595                 600                 605
        Lys Gln
            610

<210> SEQ ID NO 34
<211> LENGTH: 7100
<212> TYPE: DNA
<213> ORGANISM: Homo sapiens
```

<400> SEQUENCE: 34

```
gacatactga gaataaatcc aaagacatta gtttctttgc acgaaatgag gttacatatc    60
cagtgacatt tatttgagct atttaaacaa cttaaacatc ttttctttt cttaataagg   120
gacgtttcaa gttgtggtct cagccaaaat gagtgatacc ccttctactg ttttttccat   180
cattcatcct acgtcttctg aaggtcaagt tccaccccct cgccatttga gcctcactca   240
tcctgttgtg gccaagcgaa tcagtttcta caagagcgga gaccccaat tcggcggggt   300
cagggtggtg gtcaacccte gctcctttaa gtcctttgat gctctgctgg ataacttgtc   360
caggaaggtg cccctcccct ttggagtgag aacatcagc cccctcggg gcaggcacag   420
catcacgcgc ctggaggagc tggaggacgg cgagtcctac ctatgttccc acggcaggaa   480
ggtgcagcct gtagacctgg acaaagcccg tcggcgcccg cggccctggc tcagcagccg   540
ggccattagc gcgcactcac cgccccaccc cgtagccgtc gctgctcccg gcatgccccg   600
cccccacgg agcctagtgg tcttcaggaa tggcgacccg aagacgaggc gtgcggttct   660
tctgagcagg agggtcaccc agagcttcga ggcatttcta cagcacctga cagaggtcat   720
gcagcgccct gtggtcaagc tgtacgctac ggacggaagg agggttccca gcctccaggc   780
agtgatcctg agctctggag ctgtggtggc ggcaggaagg gagccattta aaccaggaaa   840
ttatgacatc caaaaatact tgcttcctgc tagattacca gggatctctc agcgtgtgta   900
ccccaaggga aatgcaaagt cagaaagcag aaagataagc acacatatgt cttcaagctc   960
aaggtcccag atttattctg tttcttctga gaaaacacat aataatgatt gctacttaga  1020
ctattctttt gttcctgaaa agtacttggc cttagaaaag aatgattctc agaatttacc  1080
aatatatcct tctgaagatg atattgaaa atcaattatt tttaatcaag acggcactat  1140
gacagttgag atgaaagttc gattcagaat aaaagaggaa gaaaccataa aatggacaac  1200
tactgtcagt aaaactggtc cttctaataa tgatgaaaag agtgagatga gttttccagg  1260
aagaacagaa agtcgatcat ctggtttaaa gcttgcagca tgttcattct ctgcagatgt  1320
gtcacctatg gagcgaagca gtaatcaaga gggcagtttg gcagaggaga taaacattca  1380
aatgacagat caagtggctg aaacttgcag ttctgctagt tgggagaatg ctactgtgga  1440
cacagatatc atccagggaa ctcaagacca agcaaagcat cgttttata ggccccctac  1500
acctggacta agaagagtga gacaaaagaa atctgtgatt ggcagtgtga ccttagtatc  1560
tgaaactgag gttcaagaga aaatgattgg acagttttca tatagtgaag aaagggaaag  1620
tggggaaaac aagtctgagt atcacatgtt tacacattct tgcagtaaaa tgtcatcagt  1680
atctaacaaa ccagtacttg ttcagatcaa taacaatgat caaatggagg agtcatcatt  1740
agaaagaaaa aaggaaaaca gtctgcttaa gtcaagtgca ataagtgctg gtgttataga  1800
aattacaagt cagaagatgt tagagatgtc acataataat ggtttgccat caactatatc  1860
aaataactca attgtggagg aagatgtagt tgattgtgtg gtattggaca caaaactgg  1920
tatcaagaac ttcaaaactt atggtaacac caatgatagg ttcagtccta tttcagcaga  1980
tgcaacccat tttcaagta ataactctgg aactgacaaa aatatttctg aggctccagc  2040
ttcagaagca tcctctactg tcactgcaag aattgacaga ctaattaatg aatttgctca  2100
gtgtggttta acaaaacttc caaaaaatga aagaagatt ttgtcatctg ttgccagcaa  2160
aaagaagaaa aaatctcgac agcaagcaat aaattccagg tatcaagatg gacagcttgc  2220
aaccaaagga attcttaata agaatgagag aataaacaca aaaggtagaa ttacaaagga  2280
```

```
aatgatagtg caagattcag atagtcccct taaaggaggg atactttgtg aggaagacct    2340
ccagaaaagt gatactgtaa ttgaatcaaa tactttttgt tccaaaagta atctcaattc    2400
cacgatttcc aagaatttcc atagaaataa attaaatact actcaaaatt ccaaggttca    2460 aggacttttta accaaaagaa aatctagatc actaaataaa ataagcttag gagcacctaa    2520
aaaaagagaa atcggtcaaa gagataaagt gtttcctcac aatgaatcta aatattgcaa    2580
aagtactttt gaaaacaaaa gtttatttca tgtatttaac atccttgagc aaaaacccaa    2640 agattttttat gcaccgcaat ctcaagcaga agtggcatct gggtatttga gaggaatggc    2700
aaagaagagt ttagtttcaa aagttactga ttcacacata actttaaaaa gccagaaaaa    2760
acgtaaaggg gataaagtga agcaagtgc tattttaagt aaacaacatg ctacaaccag    2820
ggcaaattct ttagcttctt tgaaaaaacc tgattttcct gaggctattg ctcatcattc    2880
aattcaaaat tatatacaga gttggttgca gaacataaat ccatatccaa ctttaaagcc    2940
tataaaatca gctccagtat gtagaaatga acgagtgtg gtaaattgta gcaataatag    3000
tttttcaggg aatgatcccc atacaaattc tggaaaaata agtaattttg ttatggaaag    3060
taataagcac ataactaaaa ttgccggttt gacaggagat aatctatgta agagggaga    3120 taagtctttt attgccaatg acactggtga agaagatctc catgagacac aggttggatc    3180
tctgaatgat gcttatttgg ttccctgca tgaacactgt actttgtcac agtcagctat    3240
taatgatcat aatactaaaa gtcatatagc tgctgaaaaa tcaggaccag agaaaaaact    3300
tgtttaccag gaaataaacc tagctagaaa aaggcaaagt gtagaggctg ccattcaagt    3360
agatcctata gaagaggaaa ctccaaaaga cctcttacca gtcctgatgc ttcaccaatt    3420
gcaagcttca gttcctggta ttcacaagac tcagaatgga gttgttcaaa tgccaggttc    3480
acttgcaggt gttcccttc attctgcaat atgtaattca tccactaatc tccttctagc    3540
ttggctcttg gtgctaaacc taagggaag tatgaatagc ttctgtcaag ttgatgctca    3600
caaggctacc aacaaatctt cagaaacact tgcattgttg gagattctaa agcacatagc    3660
tatcacagag gaagctgatg acttgaaagc tgctgttgcc aatttagtgg agtcaactac    3720
aagccacttt ggactcagtg agaaagaaca agacatggtt ccaatagatc tttctgcaaa    3780
ttgttccacg gtcaacattc agagtgttcc taagtgcagt gaaaatgaaa gaacacaagg    3840
aatctcctct ttggatggag gttgctctgc cagtgaggca tgtgccctg aagtctgtgt    3900 tttggaagtg acttgctctc catgtgagat gtgcactgta aataaggctt attctccaaa    3960
agagacatgt aaccccagtg cacttttttt tcctagtgat ggttatggtg tggatcagac    4020
ttctatgaat aaggcttgtt tcctaggaga ggtctgttca cttactgata ctgtgttttc    4080
tgataaggct tgtgctcaaa aggagaacca tacctatgag ggagcttgcc caattgatga    4140
gacctacgtt cctgtcaatg tctgcaatac cattgacttt ttaaactcca agaaaacac    4200 atatactgat aacttggatt caactgaaga gttagaaaga ggtgatgaca ttcagaaaga    4260
tctaaatatt ttgacagacc ctgaatataa aaatggattt aatacattgg tgtcacatca    4320
aaatgtcagt aatttaagct cctgtggcct ttgcctaagt gaaaaagaag cagaacttga    4380
taagaaacat agtctctag atgattttga aaattgttca ctaaggaagt ttcaggatga    4440
aaatgcatat acttcctttg atatggaaga accacggact tctgaagaac aggctcaat    4500 aaccaacagc atgacatcaa gtgaaagaaa catttcagaa ttggaatctt ttgaagaatt    4560
agaaaaccat gacactgata tctttaatac agtggtaaat ggaggagagc aagccactga    4620
agaattaatc caagaagagg tagaggctag taaaactttta gaattgatag acatctctag    4680
```

```
taagaatatt atggaagaaa aaagaatgaa cggtataatt tatgaaataa tcagtaagag    4740
gctggcaaca ccaccatctt tagatttttg ctatgattct aagcaaaata gtgaaaagga    4800
gaccaatgaa ggagaaacta agatggtaaa aatgatggtg aaaactatgg aaactggaag    4860
ttattcagag tcctctcctg atttaaaaaa atgcatcaaa agtccagtga cttctgattg    4920
gtcagactat cggcctgaca gtgacagtga gcagccatat aaaacatcca gtgatgatcc    4980
caatgacagt ggcgaactta cccaagagaa agaatataac ataggatttg ttaaaagggc    5040
aatagaaaaa ctgtacggta aagcagatat tatcaaacca tcttttttc ctgggtctac     5100 ccgcaaatct caggtttgtc cttataattc tgtggaattt cagtgttcca ggaaagcaag    5160
tctttatgat tctgaagggc agtcatttgg ctcttctgaa caggtatcta gtagttcatc    5220
tatgttgcag gaattccagg aggaaagaca agataagtgt gatgttagtg ctgtgaggga    5280
caattattgt aggggtgaca ttgtagaacc tggtacaaaa caaaatgatg atagcagaat    5340
cctcacagac atagaggaag gagtactgat tgacaaaggc aaatggcttc tgaaagaaaa    5400
tcatttgcta aggatgtcat ctgaaaatcc tggcatgtgt ggcaatgcag acaccacatc    5460
agtggacacc ctacttgata taacagcag tgaggtacca tattcacatt ttggtaattt     5520
ggccccaggc ccaacgatgg atgaactctc ctcttcagaa ctcgaggaac tgactcaacc    5580
ccttgaacta aaatgcaatt actttaacat gcctcatggt agtgactcag aaccttttca    5640
tgaggacttg ctggatgttc gcaatgaaac ctgtgccaag gaaagaatag caaatcatca    5700
tacagaggag aagggtagtc atcagtcaga aagagtatgc acatctgtca ctcattcctt    5760
tatttctgct ggtaacaaag tctaccctgt ctctgatgat gctattaaaa accaaccatt    5820
gcctggcagt aatatgattc atggtacact tcaggaagct gactctttgg ataaactgta    5880
tgctctttgt ggtcaacatt gcccaatact aactgttatt atccaaccca tgaatgagga    5940
agaccgagga tttgcatatc gcaaagaatc tgatattgaa aatttcttgg gttttatt     6000 atggatgaaa atacacccat atttacttca gacagacaaa aatgtgttca gggaagagaa    6060
caataaagca agtatgagac aaaatcttat tgataatgcc attggtgata tatttgatca    6120
gttttatttc agtaacacat tgacttgat gggtaaaaga agaaaacaaa aaagaattaa     6180
cttcttgggg ttagaggaag aaggtaattt aaagaaattt caaccagatt tgaaggaaag    6240
gttttgtatg aatttcttgc acacatcatt gttagttgtg ggtaatgtgg attcaaatac    6300
acaagacctc agcggtcaga caaatgaaat ctttaaagca gtcgatgaga ataacaactt    6360
attaaataac agattccagg gctcaagaac aaatctcaac caagtagtaa gagaaaatat    6420
caactgtcat tacttctttg aaatgcttgg tcaagcttgc ctcttagata tttgccaagt    6480
tgagacctcc ttaaatatta gcaacagaaa tatttagaa ctttgtatgt ttagggtga     6540 aaatcttttc atttgggaag aggaagacat attaaattta actgatcttg aaagcagtag    6600
agaacaagaa gatttataat ttcaatatca gcacactcat tctttgtcaa ttcattttt     6660 cccatgagat gaagcacatg tgacgaatac ggactagata acctctaaga attttccact    6720
tcttcaaaat gaacttactc tagaaagctt acccttggat aaccagtttg actttcataa    6780
tgtctctgtt ttttgttttt ccaacaatta cagactcagg ttctcttatt ttggaagttt    6840
ctatctggtt ttgttctgaa cttacatttt tttttttttt ggtatctatg atttttttg     6900 ctcagggcat caaaatgtgc taaggacaag aattatatcc tttttaaaaa atgttgttag    6960
cttggtgtaa aatgtatatt gactgtattg gtgaataaat tgaatagaca taacctcaaa    7020
```

```
gtacttcact tattcttttt aactactgat ttgataaaaa gtatgattat aagatatcca   7080
cgacaatctc atagtttctt                                               7100
```

<210> SEQ ID NO 35
<211> LENGTH: 2156
<212> TYPE: PRT
<213> ORGANISM: Homo sapiens

<400> SEQUENCE: 35

| | | | | | | | | | | | | | | |
|---|---|---|---|---|---|---|---|---|---|---|---|---|---|---|
| Met | Ser | Asp | Thr | Pro | Ser | Thr | Gly | Phe | Ser | Ile | Ile | His | Pro | Thr | Ser |
| 1 | | | | 5 | | | | | 10 | | | | | 15 | |
| Ser | Glu | Gly | Gln | Val | Pro | Pro | Arg | His | Leu | Ser | Leu | Thr | His | Pro | |
| | | | 20 | | | | | 25 | | | | | 30 | | |
| Val | Val | Ala | Lys | Arg | Ile | Ser | Phe | Tyr | Lys | Ser | Gly | Asp | Pro | Gln | Phe |
| | | | 35 | | | | 40 | | | | | 45 | | | |
| Gly | Gly | Val | Arg | Val | Val | Asn | Pro | Arg | Ser | Phe | Lys | Ser | Phe | Asp | |
| | 50 | | | | | 55 | | | | | 60 | | | | |
| Ala | Leu | Leu | Asp | Asn | Leu | Ser | Arg | Lys | Val | Pro | Leu | Pro | Phe | Gly | Val |
| 65 | | | | | 70 | | | | | 75 | | | | | 80 |
| Arg | Asn | Ile | Ser | Thr | Pro | Arg | Gly | Arg | His | Ser | Ile | Thr | Arg | Leu | Glu |
| | | | | 85 | | | | | 90 | | | | | 95 | |
| Glu | Leu | Glu | Asp | Gly | Glu | Ser | Tyr | Leu | Cys | Ser | His | Gly | Arg | Lys | Val |
| | | | 100 | | | | | 105 | | | | | 110 | | |
| Gln | Pro | Val | Asp | Leu | Asp | Lys | Ala | Arg | Arg | Arg | Pro | Arg | Pro | Trp | Leu |
| | | 115 | | | | | 120 | | | | | 125 | | | |
| Ser | Ser | Arg | Ala | Ile | Ser | Ala | His | Ser | Pro | Pro | His | Pro | Val | Ala | Val |
| | 130 | | | | | 135 | | | | | 140 | | | | |
| Ala | Ala | Pro | Gly | Met | Pro | Arg | Pro | Pro | Arg | Ser | Leu | Val | Val | Phe | Arg |
| 145 | | | | | 150 | | | | | 155 | | | | | 160 |
| Asn | Gly | Asp | Pro | Lys | Thr | Arg | Arg | Ala | Val | Leu | Leu | Ser | Arg | Val | |
| | | | | 165 | | | | | 170 | | | | | 175 | |
| Thr | Gln | Ser | Phe | Glu | Ala | Phe | Leu | Gln | His | Leu | Thr | Glu | Val | Met | Gln |
| | | | 180 | | | | | 185 | | | | | 190 | | |
| Arg | Pro | Val | Val | Lys | Leu | Tyr | Ala | Thr | Asp | Gly | Arg | Arg | Val | Pro | Ser |
| | | 195 | | | | | 200 | | | | | 205 | | | |
| Leu | Gln | Ala | Val | Ile | Leu | Ser | Ser | Gly | Ala | Val | Val | Ala | Ala | Gly | Arg |
| | 210 | | | | | 215 | | | | | 220 | | | | |
| Glu | Pro | Phe | Lys | Pro | Gly | Asn | Tyr | Asp | Ile | Gln | Lys | Tyr | Leu | Leu | Pro |
| 225 | | | | | 230 | | | | | 235 | | | | | 240 |
| Ala | Arg | Leu | Pro | Gly | Ile | Ser | Gln | Arg | Val | Tyr | Pro | Lys | Gly | Asn | Ala |
| | | | | 245 | | | | | 250 | | | | | 255 | |
| Lys | Ser | Glu | Ser | Arg | Lys | Ile | Ser | Thr | His | Met | Ser | Ser | Ser | Ser | Arg |
| | | | 260 | | | | | 265 | | | | | 270 | | |
| Ser | Gln | Ile | Tyr | Ser | Val | Ser | Ser | Glu | Lys | Thr | His | Asn | Asn | Asp | Cys |
| | | 275 | | | | | 280 | | | | | 285 | | | |
| Tyr | Leu | Asp | Tyr | Ser | Phe | Val | Pro | Glu | Lys | Tyr | Leu | Ala | Leu | Glu | Lys |
| | 290 | | | | | 295 | | | | | 300 | | | | |
| Asn | Asp | Ser | Gln | Asn | Leu | Pro | Ile | Tyr | Pro | Ser | Glu | Asp | Ile | Glu | |
| 305 | | | | | 310 | | | | | 315 | | | | | 320 |
| Lys | Ser | Ile | Ile | Phe | Asn | Gln | Asp | Gly | Thr | Met | Thr | Val | Glu | Met | Lys |
| | | | | 325 | | | | | 330 | | | | | 335 | |
| Val | Arg | Phe | Arg | Ile | Lys | Glu | Glu | Thr | Ile | Lys | Trp | Thr | Thr | Thr | |
| | | | 340 | | | | | 345 | | | | | 350 | | |
| Val | Ser | Lys | Thr | Gly | Pro | Ser | Asn | Asn | Asp | Glu | Lys | Ser | Glu | Met | Ser |

```
                355                 360                 365
Phe Pro Gly Arg Thr Glu Ser Arg Ser Ser Gly Leu Lys Leu Ala Ala
370                 375                 380

Cys Ser Phe Ser Ala Asp Val Ser Pro Met Glu Arg Ser Ser Asn Gln
385                 390                 395                 400

Glu Gly Ser Leu Ala Glu Ile Asn Ile Gln Met Thr Asp Gln Val
            405                 410                 415

Ala Glu Thr Cys Ser Ser Ala Ser Trp Glu Asn Ala Thr Val Asp Thr
            420                 425                 430

Asp Ile Ile Gln Gly Thr Gln Asp Gln Ala Lys His Arg Phe Tyr Arg
            435                 440                 445

Pro Pro Thr Pro Gly Leu Arg Arg Val Arg Gln Lys Lys Ser Val Ile
450                 455                 460

Gly Ser Val Thr Leu Val Ser Glu Thr Glu Val Gln Glu Lys Met Ile
465                 470                 475                 480

Gly Gln Phe Ser Tyr Ser Glu Glu Arg Glu Ser Gly Glu Asn Lys Ser
            485                 490                 495

Glu Tyr His Met Phe Thr His Ser Cys Ser Lys Met Ser Ser Val Ser
                500                 505                 510

Asn Lys Pro Val Leu Val Gln Ile Asn Asn Asn Asp Gln Met Glu Glu
            515                 520                 525

Ser Ser Leu Glu Arg Lys Lys Glu Asn Ser Leu Leu Lys Ser Ser Ala
530                 535                 540

Ile Ser Ala Gly Val Ile Glu Ile Thr Ser Gln Lys Met Leu Glu Met
545                 550                 555                 560

Ser His Asn Asn Gly Leu Pro Ser Thr Ile Ser Asn Asn Ser Ile Val
            565                 570                 575

Glu Glu Asp Val Val Asp Cys Val Val Leu Asp Asn Lys Thr Gly Ile
            580                 585                 590

Lys Asn Phe Lys Thr Tyr Gly Asn Thr Asn Asp Arg Phe Ser Pro Ile
            595                 600                 605

Ser Ala Asp Ala Thr His Phe Ser Ser Asn Asn Ser Gly Thr Asp Lys
            610                 615                 620

Asn Ile Ser Glu Ala Pro Ala Ser Glu Ala Ser Ser Thr Val Thr Ala
625                 630                 635                 640

Arg Ile Asp Arg Leu Ile Asn Glu Phe Ala Gln Cys Gly Leu Thr Lys
                645                 650                 655

Leu Pro Lys Asn Glu Lys Lys Ile Leu Ser Val Ala Ser Lys
                660                 665                 670

Lys Lys Lys Ser Arg Gln Gln Ala Ile Asn Ser Arg Tyr Gln Asp Gly
            675                 680                 685

Gln Leu Ala Thr Lys Gly Ile Leu Asn Lys Asn Glu Arg Ile Asn Thr
            690                 695                 700

Lys Gly Arg Ile Thr Lys Glu Met Ile Val Gln Asp Ser Asp Ser Pro
705                 710                 715                 720

Leu Lys Gly Gly Ile Leu Cys Glu Glu Asp Leu Gln Lys Ser Asp Thr
                725                 730                 735

Val Ile Glu Ser Asn Thr Phe Cys Ser Lys Ser Asn Leu Asn Ser Thr
            740                 745                 750

Ile Ser Lys Asn Phe His Arg Asn Lys Leu Asn Thr Thr Gln Asn Ser
            755                 760                 765

Lys Val Gln Gly Leu Leu Thr Lys Arg Lys Ser Arg Ser Leu Asn Lys
770                 775                 780
```

Lys Lys

-continued

```
Ile Ser Leu Gly Ala Pro Lys Lys Arg Glu Ile Gly Gln Arg Asp Lys
785                 790                 795                 800

Val Phe Pro His Asn Glu Ser Lys Tyr Cys Lys Ser Thr Phe Glu Asn
            805                 810                 815

Lys Ser Leu Phe His Val Phe Asn Ile Leu Glu Gln Lys Pro Lys Asp
        820                 825                 830

Phe Tyr Ala Pro Gln Ser Gln Ala Glu Val Ala Ser Gly Tyr Leu Arg
    835                 840                 845

Gly Met Ala Lys Lys Ser Leu Val Ser Lys Val Thr Asp Ser His Ile
850                 855                 860

Thr Leu Lys Ser Gln Lys Lys Arg Lys Gly Asp Lys Val Lys Ala Ser
865                 870                 875                 880

Ala Ile Leu Ser Lys Gln His Ala Thr Thr Arg Ala Asn Ser Leu Ala
            885                 890                 895

Ser Leu Lys Lys Pro Asp Phe Pro Glu Ala Ile Ala His His Ser Ile
        900                 905                 910

Gln Asn Tyr Ile Gln Ser Trp Leu Gln Asn Ile Asn Pro Tyr Pro Thr
    915                 920                 925

Leu Lys Pro Ile Lys Ser Ala Pro Val Cys Arg Asn Glu Thr Ser Val
930                 935                 940

Val Asn Cys Ser Asn Asn Ser Phe Ser Gly Asn Asp Pro His Thr Asn
945                 950                 955                 960

Ser Gly Lys Ile Ser Asn Phe Val Met Glu Ser Asn Lys His Ile Thr
            965                 970                 975

Lys Ile Ala Gly Leu Thr Gly Asp Asn Leu Cys Lys Glu Gly Asp Lys
        980                 985                 990

Ser Phe Ile Ala Asn Asp Thr Gly Glu Glu Asp Leu His Glu Thr Gln
    995                 1000                1005

Val Gly Ser Leu Asn Asp Ala Tyr Leu Val Pro Leu His Glu His
    1010                1015                1020

Cys Thr Leu Ser Gln Ser Ala Ile Asn Asp His Asn Thr Lys Ser
    1025                1030                1035

His Ile Ala Ala Glu Lys Ser Gly Pro Glu Lys Lys Leu Val Tyr
    1040                1045                1050

Gln Glu Ile Asn Leu Ala Arg Lys Arg Gln Ser Val Glu Ala Ala
    1055                1060                1065

Ile Gln Val Asp Pro Ile Glu Glu Thr Pro Lys Asp Leu Leu
    1070                1075                1080

Pro Val Leu Met Leu His Gln Leu Gln Ala Ser Val Pro Gly Ile
    1085                1090                1095

His Lys Thr Gln Asn Gly Val Val Gln Met Pro Gly Ser Leu Ala
    1100                1105                1110

Gly Val Pro Phe His Ser Ala Ile Cys Asn Ser Ser Thr Asn Leu
    1115                1120                1125

Leu Leu Ala Trp Leu Leu Val Leu Asn Leu Lys Gly Ser Met Asn
    1130                1135                1140

Ser Phe Cys Gln Val Asp Ala His Lys Ala Thr Asn Lys Ser Ser
    1145                1150                1155

Glu Thr Leu Ala Leu Leu Glu Ile Leu Lys His Ile Ala Ile Thr
    1160                1165                1170

Glu Glu Ala Asp Asp Leu Lys Ala Ala Val Ala Asn Leu Val Glu
    1175                1180                1185
```

-continued

Ser Thr Thr Ser His Phe Gly Leu Ser Glu Lys Glu Gln Asp Met
1190            1195                1200

Val Pro Ile Asp Leu Ser Ala Asn Cys Ser Thr Val Asn Ile Gln
1205            1210                1215

Ser Val Pro Lys Cys Ser Glu Asn Glu Arg Thr Gln Gly Ile Ser
1220            1225                1230

Ser Leu Asp Gly Gly Cys Ser Ala Ser Glu Ala Cys Ala Pro Glu
1235            1240                1245

Val Cys Val Leu Glu Val Thr Cys Ser Pro Cys Glu Met Cys Thr
1250            1255                1260

Val Asn Lys Ala Tyr Ser Pro Lys Glu Thr Cys Asn Pro Ser Asp
1265            1270                1275

Thr Phe Phe Pro Ser Asp Gly Tyr Gly Val Asp Gln Thr Ser Met
1280            1285                1290

Asn Lys Ala Cys Phe Leu Gly Glu Val Cys Ser Leu Thr Asp Thr
1295            1300                1305

Val Phe Ser Asp Lys Ala Cys Ala Gln Lys Glu Asn His Thr Tyr
1310            1315                1320

Glu Gly Ala Cys Pro Ile Asp Glu Thr Tyr Val Pro Val Asn Val
1325            1330                1335

Cys Asn Thr Ile Asp Phe Leu Asn Ser Lys Glu Asn Thr Tyr Thr
1340            1345                1350

Asp Asn Leu Asp Ser Thr Glu Glu Leu Glu Arg Gly Asp Asp Ile
1355            1360                1365

Gln Lys Asp Leu Asn Ile Leu Thr Asp Pro Glu Tyr Lys Asn Gly
1370            1375                1380

Phe Asn Thr Leu Val Ser His Gln Asn Val Ser Asn Leu Ser Ser
1385            1390                1395

Cys Gly Leu Cys Leu Ser Glu Lys Glu Ala Glu Leu Asp Lys Lys
1400            1405                1410

His Ser Ser Leu Asp Asp Phe Glu Asn Cys Ser Leu Arg Lys Phe
1415            1420                1425

Gln Asp Glu Asn Ala Tyr Thr Ser Phe Asp Met Glu Glu Pro Arg
1430            1435                1440

Thr Ser Glu Glu Pro Gly Ser Ile Thr Asn Ser Met Thr Ser Ser
1445            1450                1455

Glu Arg Asn Ile Ser Glu Leu Glu Ser Phe Glu Glu Leu Glu Asn
1460            1465                1470

His Asp Thr Asp Ile Phe Asn Thr Val Val Asn Gly Gly Glu Gln
1475            1480                1485

Ala Thr Glu Glu Leu Ile Gln Glu Glu Val Glu Ala Ser Lys Thr
1490            1495                1500

Leu Glu Leu Ile Asp Ile Ser Ser Lys Asn Ile Met Glu Glu Lys
1505            1510                1515

Arg Met Asn Gly Ile Ile Tyr Glu Ile Ile Ser Lys Arg Leu Ala
1520            1525                1530

Thr Pro Pro Ser Leu Asp Phe Cys Tyr Asp Ser Lys Gln Asn Ser
1535            1540                1545

Glu Lys Glu Thr Asn Glu Gly Glu Thr Lys Met Val Lys Met Met
1550            1555                1560

Val Lys Thr Met Glu Thr Gly Ser Tyr Ser Glu Ser Ser Pro Asp
1565            1570                1575

Leu Lys Lys Cys Ile Lys Ser Pro Val Thr Ser Asp Trp Ser Asp

```
       1580                1585                1590

Tyr Arg Pro Asp Ser Asp Ser Glu Gln Pro Tyr Lys Thr Ser Ser
       1595                1600                1605

Asp Asp Pro Asn Asp Ser Gly Glu Leu Thr Gln Glu Lys Glu Tyr
       1610                1615                1620

Asn Ile Gly Phe Val Lys Arg Ala Ile Glu Lys Leu Tyr Gly Lys
       1625                1630                1635

Ala Asp Ile Ile Lys Pro Ser Phe Phe Pro Gly Ser Thr Arg Lys
       1640                1645                1650

Ser Gln Val Cys Pro Tyr Asn Ser Val Glu Phe Gln Cys Ser Arg
       1655                1660                1665

Lys Ala Ser Leu Tyr Asp Ser Glu Gly Gln Ser Phe Gly Ser Ser
       1670                1675                1680

Glu Gln Val Ser Ser Ser Ser Met Leu Gln Glu Phe Gln Glu
       1685                1690                1695

Glu Arg Gln Asp Lys Cys Asp Val Ser Ala Val Arg Asp Asn Tyr
       1700                1705                1710

Cys Arg Gly Asp Ile Val Glu Pro Gly Thr Lys Gln Asn Asp Asp
       1715                1720                1725

Ser Arg Ile Leu Thr Asp Ile Glu Glu Gly Val Leu Ile Asp Lys
       1730                1735                1740

Gly Lys Trp Leu Leu Lys Glu Asn His Leu Leu Arg Met Ser Ser
       1745                1750                1755

Glu Asn Pro Gly Met Cys Gly Asn Ala Asp Thr Thr Ser Val Asp
       1760                1765                1770

Thr Leu Leu Asp Asn Asn Ser Ser Glu Val Pro Tyr Ser His Phe
       1775                1780                1785

Gly Asn Leu Ala Pro Gly Pro Thr Met Asp Glu Leu Ser Ser Ser
       1790                1795                1800

Glu Leu Glu Glu Leu Thr Gln Pro Leu Glu Leu Lys Cys Asn Tyr
       1805                1810                1815

Phe Asn Met Pro His Gly Ser Asp Ser Glu Pro Phe His Glu Asp
       1820                1825                1830

Leu Leu Asp Val Arg Asn Glu Thr Cys Ala Lys Glu Arg Ile Ala
       1835                1840                1845

Asn His His Thr Glu Glu Lys Gly Ser His Gln Ser Glu Arg Val
       1850                1855                1860

Cys Thr Ser Val Thr His Ser Phe Ile Ser Ala Gly Asn Lys Val
       1865                1870                1875

Tyr Pro Val Ser Asp Asp Ala Ile Lys Asn Gln Pro Leu Pro Gly
       1880                1885                1890

Ser Asn Met Ile His Gly Thr Leu Gln Glu Ala Asp Ser Leu Asp
       1895                1900                1905

Lys Leu Tyr Ala Leu Cys Gly Gln His Cys Pro Ile Leu Thr Val
       1910                1915                1920

Ile Ile Gln Pro Met Asn Glu Glu Asp Arg Gly Phe Ala Tyr Arg
       1925                1930                1935

Lys Glu Ser Asp Ile Glu Asn Phe Leu Gly Phe Tyr Leu Trp Met
       1940                1945                1950

Lys Ile His Pro Tyr Leu Leu Gln Thr Asp Lys Asn Val Phe Arg
       1955                1960                1965

Glu Glu Asn Asn Lys Ala Ser Met Arg Gln Asn Leu Ile Asp Asn
       1970                1975                1980
```

```
Ala Ile Gly Asp Ile Phe Asp Gln Phe Tyr Phe Ser Asn Thr Phe
        1985                1990                1995

Asp Leu Met Gly Lys Arg Arg Lys Gln Lys Arg Ile Asn Phe Leu
    2000                2005                2010

Gly Leu Glu Glu Gly Asn Leu Lys Lys Phe Gln Pro Asp Leu
    2015                2020                2025

Lys Glu Arg Phe Cys Met Asn Phe Leu His Thr Ser Leu Leu Val
    2030                2035                2040

Val Gly Asn Val Asp Ser Asn Thr Gln Asp Leu Ser Gly Gln Thr
    2045                2050                2055

Asn Glu Ile Phe Lys Ala Val Asp Glu Asn Asn Leu Leu Asn
    2060                2065                2070

Asn Arg Phe Gln Gly Ser Arg Thr Asn Leu Asn Gln Val Val Arg
    2075                2080                2085

Glu Asn Ile Asn Cys His Tyr Phe Phe Glu Met Leu Gly Gln Ala
    2090                2095                2100

Cys Leu Leu Asp Ile Cys Gln Val Glu Thr Ser Leu Asn Ile Ser
    2105                2110                2115

Asn Arg Asn Ile Leu Glu Leu Cys Met Phe Glu Gly Glu Asn Leu
    2120                2125                2130

Phe Ile Trp Glu Glu Glu Asp Ile Leu Asn Leu Thr Asp Leu Glu
    2135                2140                2145

Ser Ser Arg Glu Gln Glu Asp Leu
    2150                2155

<210> SEQ ID NO 36
<211> LENGTH: 3950
<212> TYPE: DNA
<213> ORGANISM: Homo sapiens

<400> SEQUENCE: 36
atgtcacatc tggtggaccc tacatcagga gacttgccag ttagagacat agatgctata       60
cctctggtgc taccagcctc aaaaggtaag aatatgaaaa ctcaaccacc cttgagcagg      120
atgaaccggg aggaattgga ggacagtttc tttcgacttc gcaagatca catgttggtg      180 aaggagcttt cttggaagca acaggatgag atcaaaaggc tgaggaccac cttgctgcgg      240
ttgaccgctg ctggccggga cctgcgggtc gcggaggagg cggcgccgct ctcggagacc      300
gcaaggcgcg ggcagaaggc gggatggcgg cagcgcctct ccatgcacca gcgcccccag      360
atgcaccgac tgcaagggca tttccactgc gtcggccctg ccagccccg ccgcgcccag      420 cctcgcgtcc aagtgggaca cagacagctc cacacagccg gtgcaccggt gccggagaaa      480
cccaagaggg ggccaaggga caggctgagc tacacagccc ctccatcgtt taaggagcat      540
gcgacaaatg aaaacagagg tgaagtagcc agtaaaccca gtgaacttgt ttctggttct      600
aacagcataa tttctttcag cagtgtcata agtatggcta aacccattgg tctatgcatg      660
cctaacagtg cccacatcat ggccagcaat accatgcaag tggaagagcc acccaagtct      720
cctgagaaaa tgtggcctaa agatgaaaat tttgaacaga gaagctcatt ggagtgtgct      780
cagaaggctg cagagcttcg agcttccatt aaagagaagg tagagctgat tcgacttaag      840
aagctcttac atgaaagaaa tgcttcattg gttatgacaa agcacaattt aacagaagtt      900
caagaggcat acgaaacctt gctccagaag aatcagggaa tcctgagtgc agcccatgag      960
gccctcctca agcaagtgaa tgagctcagg gcagagctga aggaagaaag caagaaggct     1020
```

```
gtgagcttga agagccaact ggaagatgtg tctatcttgc agatgactct gaaggagttt    1080
caggagagag ttgaagattt ggaaaaagaa cgaaaattgc tgaatgacaa ttatgacaaa    1140
ctcttagaaa gcatgctgga cagcagtgac agctccagtc agccccactg gagcaacgag    1200
ctcatagcgg aacagctaca gcagcaagtc tctcagctgc aggatcagct ggatgctgag    1260
ctggaggaca agagaaaagt tttacttgag ctgtccaggg agaaagccca aaatgaggat    1320
ctgaagcttg aagtcaccaa catacttcag aagcataaac aggaagtaga gctcctccaa    1380
aatgcagcca caatttccca acctcctgac aggcaatctg aaccagccac tcacccagct    1440
gtattgcaag agaacactca gatcgagcca agtgaaccca aaaccaaga agaaaagaaa     1500 ctgtcccagg tgctaaatga gttgcaagta tcacacgcag agaccacatt ggaactagaa    1560
aagaccaggg acatgcttat tctgcagcgc aaaatcaacg tgtgttatca ggaggaactg    1620
gaggcaatga tgacaaaagc tgacaatgat aatagagatc acaaagaaaa gctggagagg    1680
ttgactcgac tactagacct caagaataac cgtatcaagc agctggaagg tattttaaga    1740
agccatgacc ttccaacatc tgaacagctc aaagatgttg cttatggcac ccgaccgttg    1800
tcgttatgtt tggaaacact gccagcccat ggagatgagg ataaagtgga tatttctctg    1860
ctgcatcagg gtgagaatct tttgaactg cacatccacc aggccttcct gacatctgcc     1920
gccctagctc aggctggaga tacccaacct accactttct gcacctattc cttctatgac    1980
tttgaaaccc actgtacccc attatctgtg ggccacagc ccctctatga cttcacctcc      2040
cagtatgtga tggagacaga ttcgcttttc ttacactacc ttcaagaggc ttcagcccgg    2100
cttgacatac accaggccat ggccagtgaa cacagcactc ttgctgcagg atggatttgc    2160
tttgacaggg tgctagagac tgtggagaaa gtccatggct tggccacact gattggagct    2220
ggtggagaag agttcggggt tctagagtac tggatgaggc tgcgtttccc cataaaaccc    2280
agcctacagg cgtgcaataa cgaaagaaa gcccaggtct acctgtcaac cgatgtgctt     2340
ggaggccgga aggcccagga agaggagttc agatcggagt cttgggaacc tcagaacgag    2400
ctgtggattg aaatcaccaa gtgctgtggc ctccggagtc gatggctggg aactcaaccc    2460
agtccatatg ctgtgtaccg cttcttcacc tttctgacc atgacactgc catcattcca      2520
gccagtaaca cccctactt tagagaccag gctcgattcc cagtgcttgt gacctctgac      2580
ctggaccatt atctgagacg ggaggccttg tctatacatg tttttgatga tgaagactta    2640
gagcctggct cgtatcttgg ccgagcccga gtgcctttac tgcctcttgc aaaaaatgaa    2700
tctatcaaag gtgatttaa cctcactgac cctgcagaga aacccaacgg atctattcaa    2760
gtgcaactgg attggaagtt tccctacata ccccctgaga gcttcctgaa accagaagct    2820
cagactaagg ggaaggatac caaggacagt tcaaagatct catctgaaga ggaaaaggct    2880
tcatttcctt cccaggatca gatggcatct cctgaggttc ccattgaagc tggccagtat    2940
cgatctaaga gaaacctcc tcatgggggga gaaagaaagg agaaggagca ccaggttgtg    3000
agctactcaa gaagaaaaca tggcaaaaga ataggtgttc aaggaaagaa tagaatggag    3060
tatcttagcc ttaacatctt aaatggaaat acaccagagc aggtgaatta cactgagtgg    3120
aagttctcag agactaacag cttcataggt gatggcttta aaaatcagca cgaggaagag    3180
gaaatgacat tatcccattc agcactgaaa cagaaggaac ctctacatcc tgtaaatgac    3240
aaagaatcct ctgaacaagg ttctgaagtc agtgaagcac aaactaccga cagtgatgat    3300
gtcatagtgc cacccatgtc tcagaaatat cctaaggcag attcagagaa gatgtgcatt    3360
gaaattgtct ccctggcctt ctacccagag gcagaagtga tgtctgatga gaacataaaa    3420
```

```
caggtgtatg tggagtacaa attctacgac ctacccttgt cggagacaga gactccagtg    3480
tccctaagga agcctagggc aggagaagaa atccactttc actttagcaa ggtaatagac    3540
ctggacccac aggagcagca aggccgaagg cggtttctgt tcgacatgct gaatggacaa    3600
gatcctgatc aaggacattt aaagtttaca gtggtaagtg atcctctgga tgaagaaaag    3660
aaagaatgtg aagaagtggg atatgcatat cttcaactgt ggcagatcct ggagtcagga    3720
agagatattc tagagcaaga gctagacatt gttagccctg aagatctggc taccccaata    3780
ggaaggctga aggtttccct tcaagcagct gctgtcctcc atgctattta caaggagatg    3840
actgaagatt tgttttcatg aaggaacaag tgctattcca atctaaaagt ctctgaggga    3900
accatagtaa aaagtctctt ataaagttag cttgctataa catgaaaaaa                3950
```

<210> SEQ ID NO 37
<211> LENGTH: 1286
<212> TYPE: PRT
<213> ORGANISM: Homo sapiens

<400> SEQUENCE: 37

```
Met Ser His Leu Val Asp Pro Thr Ser Gly Asp Leu Pro Val Arg Asp
1               5                   10                  15

Ile Asp Ala Ile Pro Leu Val Leu Pro Ala Ser Lys Gly Lys Asn Met
            20                  25                  30

Lys Thr Gln Pro Pro Leu Ser Arg Met Asn Arg Glu Glu Leu Glu Asp
        35                  40                  45

Ser Phe Phe Arg Leu Arg Glu Asp His Met Leu Val Lys Glu Leu Ser
    50                  55                  60

Trp Lys Gln Gln Asp Glu Ile Lys Arg Leu Arg Thr Thr Leu Leu Arg
65                  70                  75                  80

Leu Thr Ala Ala Gly Arg Asp Leu Arg Val Ala Glu Ala Ala Pro
                85                  90                  95

Leu Ser Glu Thr Ala Arg Arg Gly Gln Lys Ala Gly Trp Arg Gln Arg
            100                 105                 110

Leu Ser Met His Gln Arg Pro Gln Met His Arg Leu Gln Gly His Phe
        115                 120                 125

His Cys Val Gly Pro Ala Ser Pro Arg Arg Ala Gln Pro Arg Val Gln
    130                 135                 140

Val Gly His Arg Gln Leu His Thr Ala Gly Ala Pro Val Pro Glu Lys
145                 150                 155                 160

Pro Lys Arg Gly Pro Arg Asp Arg Leu Ser Tyr Thr Ala Pro Pro Ser
                165                 170                 175

Phe Lys Glu His Ala Thr Asn Glu Asn Arg Gly Glu Val Ala Ser Lys
            180                 185                 190

Pro Ser Glu Leu Val Ser Gly Ser Asn Ser Ile Ile Ser Phe Ser Ser
        195                 200                 205

Val Ile Ser Met Ala Lys Pro Ile Gly Leu Cys Met Pro Asn Ser Ala
    210                 215                 220

His Ile Met Ala Ser Asn Thr Met Gln Val Glu Pro Pro Lys Ser
225                 230                 235                 240

Pro Glu Lys Met Trp Pro Lys Asp Glu Asn Phe Glu Gln Arg Ser Ser
                245                 250                 255

Leu Glu Cys Ala Gln Lys Ala Ala Glu Leu Arg Ala Ser Ile Lys Glu
            260                 265                 270

Lys Val Glu Leu Ile Arg Leu Lys Lys Leu Leu His Glu Arg Asn Ala
```

```
                275                 280                 285
Ser Leu Val Met Thr Lys Ala Gln Leu Thr Glu Val Gln Glu Ala Tyr
290                 295                 300
Glu Thr Leu Leu Gln Lys Asn Gln Gly Ile Leu Ser Ala Ala His Glu
305                 310                 315                 320
Ala Leu Leu Lys Gln Val Asn Glu Leu Arg Ala Glu Leu Lys Glu Glu
                325                 330                 335
Ser Lys Lys Ala Val Ser Leu Lys Ser Gln Leu Glu Asp Val Ser Ile
                340                 345                 350
Leu Gln Met Thr Leu Lys Glu Phe Gln Glu Arg Val Glu Asp Leu Glu
                355                 360                 365
Lys Glu Arg Lys Leu Leu Asn Asp Asn Tyr Asp Lys Leu Leu Glu Ser
370                 375                 380
Met Leu Asp Ser Ser Asp Ser Ser Gln Pro His Trp Ser Asn Glu
385                 390                 395                 400
Leu Ile Ala Glu Gln Leu Gln Gln Gln Val Ser Gln Leu Gln Asp Gln
                405                 410                 415
Leu Asp Ala Glu Leu Glu Asp Lys Arg Lys Val Leu Leu Glu Leu Ser
                420                 425                 430
Arg Glu Lys Ala Gln Asn Glu Asp Leu Lys Leu Glu Val Thr Asn Ile
                435                 440                 445
Leu Gln Lys His Lys Gln Glu Val Glu Leu Leu Gln Asn Ala Ala Thr
                450                 455                 460
Ile Ser Gln Pro Pro Asp Arg Gln Ser Glu Pro Ala Thr His Pro Ala
465                 470                 475                 480
Val Leu Gln Glu Asn Thr Gln Ile Glu Pro Ser Glu Pro Lys Asn Gln
                485                 490                 495
Glu Glu Lys Lys Leu Ser Gln Val Leu Asn Glu Leu Gln Val Ser His
                500                 505                 510
Ala Glu Thr Thr Leu Glu Leu Glu Lys Thr Arg Asp Met Leu Ile Leu
                515                 520                 525
Gln Arg Lys Ile Asn Val Cys Tyr Gln Glu Glu Leu Glu Ala Met Met
                530                 535                 540
Thr Lys Ala Asp Asn Asp Asn Arg Asp His Lys Glu Lys Leu Glu Arg
545                 550                 555                 560
Leu Thr Arg Leu Leu Asp Leu Lys Asn Asn Arg Ile Lys Gln Leu Glu
                565                 570                 575
Gly Ile Leu Arg Ser His Asp Leu Pro Thr Ser Glu Gln Leu Lys Asp
                580                 585                 590
Val Ala Tyr Gly Thr Arg Pro Leu Ser Leu Cys Leu Glu Thr Leu Pro
                595                 600                 605
Ala His Gly Asp Glu Asp Lys Val Asp Ile Ser Leu Leu His Gln Gly
                610                 615                 620
Glu Asn Leu Phe Glu Leu His Ile His Gln Ala Phe Leu Thr Ser Ala
625                 630                 635                 640
Ala Leu Ala Gln Ala Gly Asp Thr Gln Pro Thr Thr Phe Cys Thr Tyr
                645                 650                 655
Ser Phe Tyr Asp Phe Glu Thr His Cys Thr Pro Leu Ser Val Gly Pro
                660                 665                 670
Gln Pro Leu Tyr Asp Phe Thr Ser Gln Tyr Val Met Glu Thr Asp Ser
                675                 680                 685
Leu Phe Leu His Tyr Leu Gln Glu Ala Ser Ala Arg Leu Asp Ile His
                690                 695                 700
```

```
Gln Ala Met Ala Ser Glu His Ser Thr Leu Ala Ala Gly Trp Ile Cys
705                 710                 715                 720

Phe Asp Arg Val Leu Glu Thr Val Glu Lys Val His Gly Leu Ala Thr
            725                 730                 735

Leu Ile Gly Ala Gly Gly Glu Phe Gly Val Leu Tyr Trp Met
        740                 745                 750

Arg Leu Arg Phe Pro Ile Lys Pro Ser Leu Gln Ala Cys Asn Lys Arg
        755                 760                 765

Lys Lys Ala Gln Val Tyr Leu Ser Thr Asp Val Leu Gly Gly Arg Lys
770                 775                 780

Ala Gln Glu Glu Glu Phe Arg Ser Glu Ser Trp Glu Pro Gln Asn Glu
785                 790                 795                 800

Leu Trp Ile Glu Ile Thr Lys Cys Cys Gly Leu Arg Ser Arg Trp Leu
                805                 810                 815

Gly Thr Gln Pro Ser Pro Tyr Ala Val Tyr Arg Phe Phe Thr Phe Ser
            820                 825                 830

Asp His Asp Thr Ala Ile Ile Pro Ala Ser Asn Asn Pro Tyr Phe Arg
                835                 840                 845

Asp Gln Ala Arg Phe Pro Val Leu Val Thr Ser Asp Leu Asp His Tyr
850                 855                 860

Leu Arg Arg Glu Ala Leu Ser Ile His Val Phe Asp Asp Glu Asp Leu
865                 870                 875                 880

Glu Pro Gly Ser Tyr Leu Gly Arg Ala Arg Val Pro Leu Leu Pro Leu
            885                 890                 895

Ala Lys Asn Glu Ser Ile Lys Gly Asp Phe Asn Leu Thr Asp Pro Ala
                900                 905                 910

Glu Lys Pro Asn Gly Ser Ile Gln Val Gln Leu Asp Trp Lys Phe Pro
                915                 920                 925

Tyr Ile Pro Pro Glu Ser Phe Leu Lys Pro Glu Ala Gln Thr Lys Gly
        930                 935                 940

Lys Asp Thr Lys Asp Ser Ser Lys Ile Ser Ser Glu Glu Glu Lys Ala
945                 950                 955                 960

Ser Phe Pro Ser Gln Asp Gln Met Ala Ser Pro Glu Val Pro Ile Glu
                965                 970                 975

Ala Gly Gln Tyr Arg Ser Lys Arg Lys Pro Pro His Gly Gly Glu Arg
            980                 985                 990

Lys Glu Lys Glu His Gln Val Val Ser Tyr Ser Arg Arg Lys His Gly
            995                 1000                1005

Lys Arg Ile Gly Val Gln Gly Lys Asn Arg Met Glu Tyr Leu Ser
    1010                1015                1020

Leu Asn Ile Leu Asn Gly Asn Thr Pro Glu Gln Val Asn Tyr Thr
    1025                1030                1035

Glu Trp Lys Phe Ser Glu Thr Asn Ser Phe Ile Gly Asp Gly Phe
    1040                1045                1050

Lys Asn Gln His Glu Glu Glu Met Thr Leu Ser His Ser Ala
    1055                1060                1065

Leu Lys Gln Lys Glu Pro Leu His Pro Val Asn Asp Lys Glu Ser
    1070                1075                1080

Ser Glu Gln Gly Ser Glu Val Ser Glu Ala Gln Thr Thr Asp Ser
    1085                1090                1095

Asp Asp Val Ile Val Pro Pro Met Ser Gln Lys Tyr Pro Lys Ala
    1100                1105                1110
```

```
Asp Ser Glu Lys Met Cys Ile Glu Ile Val Ser Leu Ala Phe Tyr
    1115                1120                1125

Pro Glu Ala Glu Val Met Ser Asp Glu Asn Ile Lys Gln Val Tyr
    1130                1135                1140

Val Glu Tyr Lys Phe Tyr Asp Leu Pro Leu Ser Glu Thr Glu Thr
    1145                1150                1155

Pro Val Ser Leu Arg Lys Pro Arg Ala Gly Glu Glu Ile His Phe
    1160                1165                1170

His Phe Ser Lys Val Ile Asp Leu Asp Pro Gln Glu Gln Gln Gly
    1175                1180                1185

Arg Arg Arg Phe Leu Phe Asp Met Leu Asn Gly Gln Asp Pro Asp
    1190                1195                1200

Gln Gly His Leu Lys Phe Thr Val Val Ser Asp Pro Leu Asp Glu
    1205                1210                1215

Glu Lys Lys Glu Cys Glu Glu Val Gly Tyr Ala Tyr Leu Gln Leu
    1220                1225                1230

Trp Gln Ile Leu Glu Ser Gly Arg Asp Ile Leu Glu Gln Glu Leu
    1235                1240                1245

Asp Ile Val Ser Pro Glu Asp Leu Ala Thr Pro Ile Gly Arg Leu
    1250                1255                1260

Lys Val Ser Leu Gln Ala Ala Val Leu His Ala Ile Tyr Lys
    1265                1270                1275

Glu Met Thr Glu Asp Leu Phe Ser
    1280                1285

<210> SEQ ID NO 38
<211> LENGTH: 7221
<212> TYPE: DNA
<213> ORGANISM: Homo sapiens

<400> SEQUENCE: 38
cgggcggcct cttgtgtgag ggcctgtggg attctccgga tatggccgga gtgtttcctt      60
atcgagggcc gggtaacccg gtgcctggcc ctctagcccc gctaccggac tacatgtcgg     120
aggagaagct gcaggagaaa gctcgaaaat ggcagcaatt gcaggccaag cgctatgcag     180
aaaagcggaa gtttgggttt gtggatgccc agaaggaaga catgccccca gaacatgtca     240
gggagatcat tcgagaccat ggagacatga ccaacaggaa gttccgccat gacaaagggg     300
tttacttggg tgccctaaag tacatgcccc acgcagtcct caaactcctg agaacatgc     360
ctatgccttg ggagcagatt cgggatgtgc ccgtgctgta ccacatcact ggagccattt     420
ccttcgtcaa tgagattccc tgggtcattg aacctgtcta catctcccag tgggggtcaa     480
tgtggattat gatgcgccga gaaaaaagag ataggaggca tttcaagaga atgcgttttc     540
cccctttga tgatgaggag ccgcccttgg actatgctga acatcctta atgttgagc      600
cactggaggc cattcagcta gagctggacc ctgaggagga cgcccctgtg ttggactggt     660
tctatgacca ccagccgttg agggacagca ggaagtatgt aaatggctcc acttaccagc     720
gctggcagtt cacactacct atgatgtcaa ctctctaccg cctggctaat cagctcctga     780
cagacttggt ggatgacaac tacttctacc tgtttgattt gaaggccttc tttacgtcca     840
aggcactcaa tatggccatt cctggaggcc ccaaatttga acctcttgtt cgagacatca     900
acctacagga tgaagactgg aatgaattca tgatattaa caagattatc atccggcagc     960
ctatccggac tgagtacaag attgcttttc cttacttgta caacaatctt ccacaccatg    1020
tccacctcac ctggtaccat actcccaatg ttgtattcat caaaactgaa gatcctgact    1080
```

```
tgccagcttt ctactttgac cctttgatca acccaatctc ccataggcac tcagtcaaga    1140
gccaggaacc attgccggat gatgatgagg aatttgagct cccggagttt gtggagccct    1200
tcctgaagga cacacccctc tatacagaca atacagccaa tggcattgcc ctgctctggg    1260
ccccgcggcc cttcaaccta cgctctggtc gcacccgtcg ggccctggac ataccccttg    1320
tcaagaactg gtatcgggag cattgtcctg ccgggcagcc tgtgaaagtg agggtctcct    1380
accagaagct gcttaagtac tatgtgctga atgccctgaa gcatcggccc cctaaggctc    1440
aaaagaagag gtatttgttc cgctccttca aagccaccaa attctttcag tccacaaagc    1500
tggactgggt ggagggttgg ctccaggttt gccgccaggg ctacaacatg ctcaaccttc    1560
tcattcaccg caaaaacctc aactacctgc acctggacta caacttcaac ctcaagcctg    1620
tgaaaacgct caccaccaag gaaagaaaga aatctcgttt tgggaatgct ttccacctgt    1680
gtcgggaagt tctgcgtttg actaagctgg tggtggatag tcacgtgcag tatcggctgg    1740
gcaatgtgga tgccttccag ctggcagatg gattgcagta tatatttgcc catgttgggc    1800
agttgacggg catgtatcga tacaaataca agctgatgcg acagattcgc gtgtgcaagg    1860
acctgaagca tctcatctat tatcgtttca acacaggccc tgtagggaag ggtcctggct    1920
gtggcttctg ggctgccggt tggcgagtct ggctcttttt catgcgtggc attacccctt    1980
tattagagcg atggcttggc aacctcctgg cccggcagtt tgaaggtcga cactcaaagg    2040
gggtggcaaa gacagtaaca aagcagcgag tggagtcaca ttttgacctt gagctgcggg    2100
cagctgtgat gcatgatatt ctggacatga tgcctgaggg gatcaagcag aacaaggccc    2160
ggacaatcct gcagcacctc agtgaagcct ggcgctgctg gaaagccaac attccctgga    2220
aggtccctgg gctgccgacg cccatagaga atatgatcct tcgatacgtg aaggccaagg    2280
ctgactggtg gaccaacact gcccactaca accgagaacg gatccgccga ggggccactg    2340
tggacaagac tgtttgtaaa aagaatctgg gccgcctcac ccggctctat ctgaaggcag    2400
aacaggagcg gcagcacaac tacctgaagg acgggcctta catcacagcg gagaaaacag    2460
tggcagtata taccaccaca gtgcattggt tggaaagccg caggttttca cccatcccat    2520 tcccccact ctcctataag catgacacca agttgctcat cttggcattg gagcggctca    2580
aggaagctta tagtgtgaag tctcggttga accagtctca gagggaggag ctaggtctga    2640
tcgagcaggc ctacgataac ctccacgagg cgctgtcccg cataaagcgt cacctcctca    2700
cacagagagc cttcaaagag gtgggcattg agttcatgga tctgtatagc cacctcgttc    2760
cagtatatga tgttgagccc ctggagaaga taactgatgc ttacctggac cagtacctgt    2820
ggtatgaagc cgacaagcgc cgcctgttcc caccctggat taagcctgca gacacagaac    2880
cacctccact gcttgtttac aagtggtgtc aaggcatcaa taacctgcag gacgtgtggg    2940
agacgagtga aggcgagtgc aatgtcatgc tggaatcccg ctttgagaag atgtatgaga    3000
agatcgactt gactctgctc aacaggctcg tgcgcctcat cgtggaccac aacatagccg    3060
actacatgac agccaagaac aacgtcgtca tcaactataa ggacatgaac catacgaatt    3120
catatgggat catcagagagc ctgcagtttg cctcattcat agtgcagtat tatggcctgg    3180
tgatggattt gcttgtattg ggattgcacc gggccagtga gatggctggg cccctcaga    3240 tgccaaatga cttctctcagt ttccaggaca tagccactga ggctgcccac cccatccgtc    3300
tcttctgcag atacattgat cgcatccata ttttttcag gttcacagca gatgaggctc    3360
gggacctgat tcaacgttac ctgacagagc accctgaccc caataatgaa aacatcgttg    3420
```

```
gctataataa caagaagtgc tggccccgag atgcccgcat gcgcctcatg aaacatgatg    3480
ttaacttagg ccgggcggta ttctgggaca tcaagaaccg cttgccacgg tcagtgacta    3540
cagttcagtg ggagaacagc ttcgtgtctg tgtacagtaa ggacaacccc aacctgctgt    3600
tcaacatgtg tggcttcgag tgccgcatcc tgcctaagtg ccgcaccagc tatgaggagt    3660
tcacccacaa ggacggggtc tggaacctgc agaatgaggt tactaaggag cgcacagctc    3720 agtgttttcct gcgtgtggac gatgagtcaa tgcagcgctt ccacaaccgc gtgcgtcaga    3780
ttctcatggc ctctgggtcc accaccttca ccaagattgt gaataagtgg aatacagctc    3840
tcattggcct tatgacatac tttcgggagg ctgtggtgaa cacccaagag ctcttggact    3900
tactggtgaa gtgtgagcac aaaatccaga cacgtatcaa gattggactc aactccaaga    3960
tgccaagtcg gttcccccccg gttgtgttct acaccccctaa ggagttgggt ggactcggca    4020
tgctctcaat gggccatgtg ctcatccccc aatccgacct caggtggtcc aaacagacag    4080
atgtaggtat cacacacttt cgttcaggaa tgagccatga agaagaccag ctcattccca    4140
acttgtaccg ctacatacag ccatgggaga gcgagttcat tgattctcag cgggtctggg    4200
ctgagtactc actcaagaga caagaggcca ttgctcagaa cagacgcctg actttagaag    4260
acctagaaga ttcatgggat cgtggcattc ctcgaatcaa tacctcttc cagaaggacc    4320 ggcacacact ggcttatgat aagggctggc gtgtcagaac tgactttaag cagtatcagg    4380
ttttgaagca gaatccgttc tggtggacac cagcggca tgatgggaag ctctggaacc    4440
tgaacaacta ccgtacagac atgatccagg ccctgggcgg tgtggaaggc attctggaac    4500
acacactctt taagggcact tacttcccta cctgggaggg gcttttctgg gagaaggcca    4560
gtggctttga ggaatctatg aagtggaaga agctaactaa tgctcagcga tcaggactga    4620
accagattcc caatcgtaga ttcaccctct ggtggtcccc gaccattaat cgagccaatg    4680
tatatgtagg ctttcaggtg cagctagacc tgacgggtat cttcatgcac ggcaagatcc    4740
ccacgctgaa gatctctctc atccagatct tccgagctca cttgtggcag aagatccatg    4800
agagcattgt tatggactta tgtcaggtgt ttgaccagga acttgatgca ctggaaattg    4860
agacagtaca aaaggagaca atccatcccc gaaagtcata taagatgaac tcttcctgtg    4920
cagatatcct gctctttgcc tcctataagt ggaatgtctc ccggccctca ttgctggctg    4980
actccaagga tgtgatggac agcaccacca cccagaaata ctggattgac atccagttgc    5040
gctgggggga ctatgattcc cacgacattg agcgctacgc ccgggccaag ttcctggact    5100
acaccaccga caacatgagt atctacccctt cgcccacagg tgtactcatc gccattgacc    5160
tggcctataa cttgcacagt gcctatggaa actggttccc aggcagcaag cctctcatac    5220
aacaggccat ggccaagatc atgaaggcaa ccctgccct gtatgtgtta cgtgaacgga    5280
tccgcaaggg gctacagctc tattcatctg aacccactga gccttatttg tcttctcaga    5340
actatggtga gctcttctcc aaccagatta tctggtttgt ggatgacacc aacgtctaca    5400
gagtgactat tcacaagacc tttgaaggga acttgacaac caagcccatc aacgagccaa    5460
tcttcatctt caacccacgc acagggcagc tgttcctcaa gataatccac acgtccgtgt    5520
gggcgggaca gaagcgtttg gggcagttgg ctaagtggaa gacagctgag gaggtggccg    5580
ccctgatccg atctctgcct gtggaggagc agcccaagca gatcattgtc accaggaagg    5640
acatgctgga cccactggag gtgcacttac tggacttccc caatattgtc atcaaaggat    5700
cggagctcca actccctttc caggcgtgtc tcaaggtgga aaaattcggg gatctcatcc    5760
ttaaagccac tgagccccag atggttctct tcaacctcta tgacgactgg ctcaagacta    5820
```

```
tttcatctta cacggccttc tcccgtctca tcctgattct gcgtgcccta catgtgaaca   5880
acgatcgggc aaaagtgatc ctgaagccag acaagactac tattacagaa ccacaccaca   5940
tctggcccac tctgactgac gaagaatgga tcaaggtcga ggtgcagctc aaggatctga   6000
tcttggctga ctacggcaag aaaaacaatg tgaacgtggc atcactgaca caatcagaaa   6060
ttcgagacat catcctgggt atggagatct cggcaccgtc acagcagcgg cagcagatcg   6120
ctgagatcga gaagcagacc aaggaacaat cgcagctgac ggcaacacag actcgcactg   6180
tcaacaagca tggcgatgag atcatcacct ccaccaccag caactatgag acccagactt   6240
tctcatccaa gactgagtgg agggtcaggg ccatctctgc tgccaacctg cacctaagga   6300
ccaatcacat ctatgtttca tctgacgaca tcaaggagac tggctacacc tacatccttc   6360
ccaagaatgt gcttaagaag ttcatctgca tatctgacct tcgggcccaa attgcaggat   6420
acctatatgg ggtgagccca ccagataacc cccaggtgaa ggagatccgc tgcattgtga   6480
tggtgccgca gtggggcact caccagaccg tgcacctgcc tggccagctg ccccagcatg   6540
agtacctcaa ggagatggaa cccttaggtt ggatccacac tcagcccaat gagtccccgc   6600
agttatcacc ccaggatgtc accacccatg ccaagatcat ggctgacaac ccatcttggg   6660
atggcgagaa gaccattatc atcacatgca gcttcacgcc aggctcctgt acactgacgg   6720
cctacaagct gaccccctagt ggctacgaat ggggccgcca gaacacagac aagggcaaca   6780
accccaaggg ctacctgcct tcacactatg agagggtgca gatgctgctg tcggaccgtt   6840
tccttggctt cttcatggtc cctgcccagt cctcgtggaa ctacaacttc atgggtgttc   6900
ggcatgaccc caacatgaaa tatgagctac agctggcgaa ccccaaagag ttctaccacg   6960
aggtgcacag gccctctcac ttcctcaact ttgctctcct gcaggagggg gaggtttact   7020
ctgcggatcg ggaggacctg tatgcctgac cgtttccctg cctcctgctt cagcctcccg   7080
aggccgaagc ctcagcccct ccagacaggc cgctgacatt cagcagtttg gcctcttttcc   7140
ctctgtctgt gcttgtgttg ttgaccctcct gatggcttgt catcctgaat aaaatataat   7200
aataaatttt gtataaatag g                                             7221
```

<210> SEQ ID NO 39
<211> LENGTH: 2335
<212> TYPE: PRT
<213> ORGANISM: Homo sapiens

<400> SEQUENCE: 39

```
Met Ala Gly Val Phe Pro Tyr Arg Gly Pro Gly Asn Pro Val Pro Gly
1               5                   10                  15

Pro Leu Ala Pro Leu Pro Asp Tyr Met Ser Glu Glu Lys Leu Gln Glu
            20                  25                  30

Lys Ala Arg Lys Trp Gln Gln Leu Gln Ala Lys Arg Tyr Ala Glu Lys
        35                  40                  45

Arg Lys Phe Gly Phe Val Asp Ala Gln Lys Glu Asp Met Pro Pro Glu
    50                  55                  60

His Val Arg Glu Ile Ile Arg Asp His Gly Asp Met Thr Asn Arg Lys
65                  70                  75                  80

Phe Arg His Asp Lys Arg Val Tyr Leu Gly Ala Leu Lys Tyr Met Pro
                85                  90                  95

His Ala Val Leu Lys Leu Leu Glu Asn Met Pro Met Pro Trp Glu Gln
            100                 105                 110

Ile Arg Asp Val Pro Val Leu Tyr His Ile Thr Gly Ala Ile Ser Phe
```

```
                115                 120                 125
Val Asn Glu Ile Pro Trp Val Ile Glu Pro Val Tyr Ile Ser Gln Trp
130                 135                 140

Gly Ser Met Trp Ile Met Met Arg Arg Glu Lys Arg Asp Arg His
145                 150                 155                 160

Phe Lys Arg Met Arg Phe Pro Pro Phe Asp Glu Glu Pro Pro Leu
                165                 170                 175

Asp Tyr Ala Asp Asn Ile Leu Asn Val Glu Pro Leu Glu Ala Ile Gln
                180                 185                 190

Leu Glu Leu Asp Pro Glu Glu Asp Ala Pro Val Leu Asp Trp Phe Tyr
                195                 200                 205

Asp His Gln Pro Leu Arg Asp Ser Arg Lys Tyr Val Asn Gly Ser Thr
                210                 215                 220

Tyr Gln Arg Trp Gln Phe Thr Leu Pro Met Met Ser Thr Leu Tyr Arg
225                 230                 235                 240

Leu Ala Asn Gln Leu Leu Thr Asp Leu Val Asp Asp Asn Tyr Phe Tyr
                245                 250                 255

Leu Phe Asp Leu Lys Ala Phe Phe Thr Ser Lys Ala Leu Asn Met Ala
                260                 265                 270

Ile Pro Gly Gly Pro Lys Phe Glu Pro Leu Val Arg Asp Ile Asn Leu
                275                 280                 285

Gln Asp Glu Asp Trp Asn Glu Phe Asn Asp Ile Asn Lys Ile Ile Ile
                290                 295                 300

Arg Gln Pro Ile Arg Thr Glu Tyr Lys Ile Ala Phe Pro Tyr Leu Tyr
305                 310                 315                 320

Asn Asn Leu Pro His His Val His Leu Thr Trp Tyr His Thr Pro Asn
                325                 330                 335

Val Val Phe Ile Lys Thr Glu Asp Pro Asp Leu Pro Ala Phe Tyr Phe
                340                 345                 350

Asp Pro Leu Ile Asn Pro Ile Ser His Arg His Ser Val Lys Ser Gln
                355                 360                 365

Glu Pro Leu Pro Asp Asp Glu Glu Phe Glu Leu Pro Glu Phe Val
                370                 375                 380

Glu Pro Phe Leu Lys Asp Thr Pro Leu Tyr Thr Asp Asn Thr Ala Asn
385                 390                 395                 400

Gly Ile Ala Leu Leu Trp Ala Pro Arg Pro Phe Asn Leu Arg Ser Gly
                405                 410                 415

Arg Thr Arg Arg Ala Leu Asp Ile Pro Leu Val Lys Asn Trp Tyr Arg
                420                 425                 430

Glu His Cys Pro Ala Gly Gln Pro Val Lys Val Arg Val Ser Tyr Gln
                435                 440                 445

Lys Leu Leu Lys Tyr Tyr Val Leu Asn Ala Leu Lys His Arg Pro Pro
                450                 455                 460

Lys Ala Gln Lys Lys Arg Tyr Leu Phe Arg Ser Phe Lys Ala Thr Lys
465                 470                 475                 480

Phe Phe Gln Ser Thr Lys Leu Asp Trp Val Glu Gly Trp Leu Gln Val
                485                 490                 495

Cys Arg Gln Gly Tyr Asn Met Leu Asn Leu Leu Ile His Arg Lys Asn
                500                 505                 510

Leu Asn Tyr Leu His Leu Asp Tyr Asn Phe Asn Leu Lys Pro Val Lys
                515                 520                 525

Thr Leu Thr Thr Lys Glu Arg Lys Lys Ser Arg Phe Gly Asn Ala Phe
530                 535                 540
```

His Leu Cys Arg Glu Val Leu Arg Leu Thr Lys Leu Val Val Asp Ser
545                 550                 555                 560

His Val Gln Tyr Arg Leu Gly Asn Val Asp Ala Phe Gln Leu Ala Asp
            565                 570                 575

Gly Leu Gln Tyr Ile Phe Ala His Val Gly Gln Leu Thr Gly Met Tyr
        580                 585                 590

Arg Tyr Lys Tyr Lys Leu Met Arg Gln Ile Arg Val Cys Lys Asp Leu
            595                 600                 605

Lys His Leu Ile Tyr Tyr Arg Phe Asn Thr Gly Pro Val Gly Lys Gly
        610                 615                 620

Pro Gly Cys Gly Phe Trp Ala Ala Gly Trp Arg Val Trp Leu Phe Phe
625                 630                 635                 640

Met Arg Gly Ile Thr Pro Leu Leu Glu Arg Trp Leu Gly Asn Leu Leu
            645                 650                 655

Ala Arg Gln Phe Glu Gly Arg His Ser Lys Gly Val Ala Lys Thr Val
        660                 665                 670

Thr Lys Gln Arg Val Glu Ser His Phe Asp Leu Glu Leu Arg Ala Ala
            675                 680                 685

Val Met His Asp Ile Leu Asp Met Met Pro Glu Gly Ile Lys Gln Asn
        690                 695                 700

Lys Ala Arg Thr Ile Leu Gln His Leu Ser Glu Ala Trp Arg Cys Trp
705                 710                 715                 720

Lys Ala Asn Ile Pro Trp Lys Val Pro Gly Leu Pro Thr Pro Ile Glu
            725                 730                 735

Asn Met Ile Leu Arg Tyr Val Lys Ala Lys Ala Asp Trp Trp Thr Asn
        740                 745                 750

Thr Ala His Tyr Asn Arg Glu Arg Ile Arg Gly Ala Thr Val Asp
            755                 760                 765

Lys Thr Val Cys Lys Lys Asn Leu Gly Arg Leu Thr Arg Leu Tyr Leu
770                 775                 780

Lys Ala Glu Gln Glu Arg Gln His Asn Tyr Leu Lys Asp Gly Pro Tyr
785                 790                 795                 800

Ile Thr Ala Glu Glu Thr Val Ala Val Tyr Thr Thr Thr Val His Trp
            805                 810                 815

Leu Glu Ser Arg Arg Phe Ser Pro Ile Pro Phe Pro Pro Leu Ser Tyr
        820                 825                 830

Lys His Asp Thr Lys Leu Leu Ile Leu Ala Leu Glu Arg Leu Lys Glu
        835                 840                 845

Ala Tyr Ser Val Lys Ser Arg Leu Asn Gln Ser Gln Arg Glu Glu Leu
        850                 855                 860

Gly Leu Ile Glu Gln Ala Tyr Asp Asn Leu His Glu Ala Leu Ser Arg
865                 870                 875                 880

Ile Lys Arg His Leu Leu Thr Gln Arg Ala Phe Lys Glu Val Gly Ile
            885                 890                 895

Glu Phe Met Asp Leu Tyr Ser His Leu Val Pro Val Tyr Asp Val Glu
        900                 905                 910

Pro Leu Glu Lys Ile Thr Asp Ala Tyr Leu Asp Gln Tyr Leu Trp Tyr
        915                 920                 925

Glu Ala Asp Lys Arg Arg Leu Phe Pro Pro Trp Ile Lys Pro Ala Asp
        930                 935                 940

Thr Glu Pro Pro Pro Leu Leu Val Tyr Lys Trp Cys Gln Gly Ile Asn
945                 950                 955                 960

Asn Leu Gln Asp Val Trp Glu Thr Ser Glu Gly Glu Cys Asn Val Met
    965                 970                 975

Leu Glu Ser Arg Phe Glu Lys Met Tyr Glu Lys Ile Asp Leu Thr Leu
            980                 985                 990

Leu Asn Arg Leu Val Arg Leu Ile Val Asp His Asn Ile Ala Asp Tyr
            995                 1000                1005

Met Thr Ala Lys Asn Asn Val Val Ile Asn Tyr Lys Asp Met Asn
    1010                1015                1020

His Thr Asn Ser Tyr Gly Ile Ile Arg Gly Leu Gln Phe Ala Ser
    1025                1030                1035

Phe Ile Val Gln Tyr Tyr Gly Leu Val Met Asp Leu Leu Val Leu
    1040                1045                1050

Gly Leu His Arg Ala Ser Glu Met Ala Gly Pro Pro Gln Met Pro
    1055                1060                1065

Asn Asp Phe Leu Ser Phe Gln Asp Ile Ala Thr Glu Ala Ala His
    1070                1075                1080

Pro Ile Arg Leu Phe Cys Arg Tyr Ile Asp Arg Ile His Ile Phe
    1085                1090                1095

Phe Arg Phe Thr Ala Asp Glu Ala Arg Asp Leu Ile Gln Arg Tyr
    1100                1105                1110

Leu Thr Glu His Pro Asp Pro Asn Asn Glu Asn Ile Val Gly Tyr
    1115                1120                1125

Asn Asn Lys Lys Cys Trp Pro Arg Asp Ala Arg Met Arg Leu Met
    1130                1135                1140

Lys His Asp Val Asn Leu Gly Arg Ala Val Phe Trp Asp Ile Lys
    1145                1150                1155

Asn Arg Leu Pro Arg Ser Val Thr Thr Val Gln Trp Glu Asn Ser
    1160                1165                1170

Phe Val Ser Val Tyr Ser Lys Asp Asn Pro Asn Leu Leu Phe Asn
    1175                1180                1185

Met Cys Gly Phe Glu Cys Arg Ile Leu Pro Lys Cys Arg Thr Ser
    1190                1195                1200

Tyr Glu Glu Phe Thr His Lys Asp Gly Val Trp Asn Leu Gln Asn
    1205                1210                1215

Glu Val Thr Lys Glu Arg Thr Ala Gln Cys Phe Leu Arg Val Asp
    1220                1225                1230

Asp Glu Ser Met Gln Arg Phe His Asn Arg Val Arg Gln Ile Leu
    1235                1240                1245

Met Ala Ser Gly Ser Thr Thr Phe Thr Lys Ile Val Asn Lys Trp
    1250                1255                1260

Asn Thr Ala Leu Ile Gly Leu Met Thr Tyr Phe Arg Glu Ala Val
    1265                1270                1275

Val Asn Thr Gln Glu Leu Leu Asp Leu Leu Val Lys Cys Glu His
    1280                1285                1290

Lys Ile Gln Thr Arg Ile Lys Ile Gly Leu Asn Ser Lys Met Pro
    1295                1300                1305

Ser Arg Phe Pro Pro Val Val Phe Tyr Thr Pro Lys Glu Leu Gly
    1310                1315                1320

Gly Leu Gly Met Leu Ser Met Gly His Val Leu Ile Pro Gln Ser
    1325                1330                1335

Asp Leu Arg Trp Ser Lys Gln Thr Asp Val Gly Ile Thr His Phe
    1340                1345                1350

Arg Ser Gly Met Ser His Glu Glu Asp Gln Leu Ile Pro Asn Leu

-continued

```
              1355                1360                1365
Tyr  Arg  Tyr  Ile  Gln  Pro  Trp  Glu  Ser  Glu  Phe  Ile  Asp  Ser  Gln
              1370                1375                1380
Arg  Val  Trp  Ala  Glu  Tyr  Ser  Leu  Lys  Arg  Gln  Glu  Ala  Ile  Ala
              1385                1390                1395
Gln  Asn  Arg  Arg  Leu  Thr  Leu  Glu  Asp  Leu  Glu  Asp  Ser  Trp  Asp
              1400                1405                1410
Arg  Gly  Ile  Pro  Arg  Ile  Asn  Thr  Leu  Phe  Gln  Lys  Asp  Arg  His
              1415                1420                1425
Thr  Leu  Ala  Tyr  Asp  Lys  Gly  Trp  Arg  Val  Arg  Thr  Asp  Phe  Lys
              1430                1435                1440
Gln  Tyr  Gln  Val  Leu  Lys  Gln  Asn  Pro  Phe  Trp  Trp  Thr  His  Gln
              1445                1450                1455
Arg  His  Asp  Gly  Lys  Leu  Trp  Asn  Leu  Asn  Asn  Tyr  Arg  Thr  Asp
              1460                1465                1470
Met  Ile  Gln  Ala  Leu  Gly  Gly  Val  Glu  Gly  Ile  Leu  Glu  His  Thr
              1475                1480                1485
Leu  Phe  Lys  Gly  Thr  Tyr  Phe  Pro  Thr  Trp  Glu  Gly  Leu  Phe  Trp
              1490                1495                1500
Glu  Lys  Ala  Ser  Gly  Phe  Glu  Glu  Ser  Met  Lys  Trp  Lys  Lys  Leu
              1505                1510                1515
Thr  Asn  Ala  Gln  Arg  Ser  Gly  Leu  Asn  Gln  Ile  Pro  Asn  Arg  Arg
              1520                1525                1530
Phe  Thr  Leu  Trp  Trp  Ser  Pro  Thr  Ile  Asn  Arg  Ala  Asn  Val  Tyr
              1535                1540                1545
Val  Gly  Phe  Gln  Val  Gln  Leu  Asp  Leu  Thr  Gly  Ile  Phe  Met  His
              1550                1555                1560
Gly  Lys  Ile  Pro  Thr  Leu  Lys  Ile  Ser  Leu  Ile  Gln  Ile  Phe  Arg
              1565                1570                1575
Ala  His  Leu  Trp  Gln  Lys  Ile  His  Glu  Ser  Ile  Val  Met  Asp  Leu
              1580                1585                1590
Cys  Gln  Val  Phe  Asp  Gln  Glu  Leu  Asp  Ala  Leu  Glu  Ile  Glu  Thr
              1595                1600                1605
Val  Gln  Lys  Glu  Thr  Ile  His  Pro  Arg  Lys  Ser  Tyr  Lys  Met  Asn
              1610                1615                1620
Ser  Ser  Cys  Ala  Asp  Ile  Leu  Leu  Phe  Ala  Ser  Tyr  Lys  Trp  Asn
              1625                1630                1635
Val  Ser  Arg  Pro  Ser  Leu  Leu  Ala  Asp  Ser  Lys  Asp  Val  Met  Asp
              1640                1645                1650
Ser  Thr  Thr  Thr  Gln  Lys  Tyr  Trp  Ile  Asp  Ile  Gln  Leu  Arg  Trp
              1655                1660                1665
Gly  Asp  Tyr  Asp  Ser  His  Asp  Ile  Glu  Arg  Tyr  Ala  Arg  Ala  Lys
              1670                1675                1680
Phe  Leu  Asp  Tyr  Thr  Thr  Asp  Asn  Met  Ser  Ile  Tyr  Pro  Ser  Pro
              1685                1690                1695
Thr  Gly  Val  Leu  Ile  Ala  Ile  Asp  Leu  Ala  Tyr  Asn  Leu  His  Ser
              1700                1705                1710
Ala  Tyr  Gly  Asn  Trp  Phe  Pro  Gly  Ser  Lys  Pro  Leu  Ile  Gln  Gln
              1715                1720                1725
Ala  Met  Ala  Lys  Ile  Met  Lys  Ala  Asn  Pro  Ala  Leu  Tyr  Val  Leu
              1730                1735                1740
Arg  Glu  Arg  Ile  Arg  Lys  Gly  Leu  Gln  Leu  Tyr  Ser  Ser  Glu  Pro
              1745                1750                1755
```

-continued

Thr Glu Pro Tyr Leu Ser Ser Gln Asn Tyr Gly Glu Leu Phe Ser
    1760            1765            1770

Asn Gln Ile Ile Trp Phe Val Asp Asp Thr Asn Val Tyr Arg Val
    1775            1780            1785

Thr Ile His Lys Thr Phe Glu Gly Asn Leu Thr Thr Lys Pro Ile
    1790            1795            1800

Asn Gly Ala Ile Phe Ile Phe Asn Pro Arg Thr Gly Gln Leu Phe
    1805            1810            1815

Leu Lys Ile Ile His Thr Ser Val Trp Ala Gly Gln Lys Arg Leu
    1820            1825            1830

Gly Gln Leu Ala Lys Trp Lys Thr Ala Glu Glu Val Ala Ala Leu
    1835            1840            1845

Ile Arg Ser Leu Pro Val Glu Glu Gln Pro Lys Gln Ile Ile Val
    1850            1855            1860

Thr Arg Lys Asp Met Leu Asp Pro Leu Glu Val His Leu Leu Asp
    1865            1870            1875

Phe Pro Asn Ile Val Ile Lys Gly Ser Glu Leu Gln Leu Pro Phe
    1880            1885            1890

Gln Ala Cys Leu Lys Val Glu Lys Phe Gly Asp Leu Ile Leu Lys
    1895            1900            1905

Ala Thr Glu Pro Gln Met Val Leu Phe Asn Leu Tyr Asp Asp Trp
    1910            1915            1920

Leu Lys Thr Ile Ser Ser Tyr Thr Ala Phe Ser Arg Leu Ile Leu
    1925            1930            1935

Ile Leu Arg Ala Leu His Val Asn Asn Asp Arg Ala Lys Val Ile
    1940            1945            1950

Leu Lys Pro Asp Lys Thr Thr Ile Thr Glu Pro His His Ile Trp
    1955            1960            1965

Pro Thr Leu Thr Asp Glu Glu Trp Ile Lys Val Glu Val Gln Leu
    1970            1975            1980

Lys Asp Leu Ile Leu Ala Asp Tyr Gly Lys Lys Asn Asn Val Asn
    1985            1990            1995

Val Ala Ser Leu Thr Gln Ser Glu Ile Arg Asp Ile Ile Leu Gly
    2000            2005            2010

Met Glu Ile Ser Ala Pro Ser Gln Gln Arg Gln Gln Ile Ala Glu
    2015            2020            2025

Ile Glu Lys Gln Thr Lys Glu Gln Ser Gln Leu Thr Ala Thr Gln
    2030            2035            2040

Thr Arg Thr Val Asn Lys His Gly Asp Glu Ile Ile Thr Ser Thr
    2045            2050            2055

Thr Ser Asn Tyr Glu Thr Gln Thr Phe Ser Ser Lys Thr Glu Trp
    2060            2065            2070

Arg Val Arg Ala Ile Ser Ala Ala Asn Leu His Leu Arg Thr Asn
    2075            2080            2085

His Ile Tyr Val Ser Ser Asp Asp Ile Lys Glu Thr Gly Tyr Thr
    2090            2095            2100

Tyr Ile Leu Pro Lys Asn Val Leu Lys Lys Phe Ile Cys Ile Ser
    2105            2110            2115

Asp Leu Arg Ala Gln Ile Ala Gly Tyr Leu Tyr Gly Val Ser Pro
    2120            2125            2130

Pro Asp Asn Pro Gln Val Lys Glu Ile Arg Cys Ile Val Met Val
    2135            2140            2145

| | | | | | | | | | | | |
|---|---|---|---|---|---|---|---|---|---|---|---|
| Pro | Gln | Trp | Gly | Thr | His | Gln | Thr | Val | His | Leu | Pro | Gly | Gln | Leu |
| | 2150 | | | | | 2155 | | | | | 2160 | | | |

| Pro | Gln | His | Glu | Tyr | Leu | Lys | Glu | Met | Glu | Pro | Leu | Gly | Trp | Ile |
| 2165 | | | | | 2170 | | | | | 2175 | | | | |

| His | Thr | Gln | Pro | Asn | Glu | Ser | Pro | Gln | Leu | Ser | Pro | Gln | Asp | Val |
| | 2180 | | | | | 2185 | | | | | 2190 | | | |

| Thr | Thr | His | Ala | Lys | Ile | Met | Ala | Asp | Asn | Pro | Ser | Trp | Asp | Gly |
| | 2195 | | | | | 2200 | | | | | 2205 | | | |

| Glu | Lys | Thr | Ile | Ile | Ile | Thr | Cys | Ser | Phe | Thr | Pro | Gly | Ser | Cys |
| | 2210 | | | | | 2215 | | | | | 2220 | | | |

| Thr | Leu | Thr | Ala | Tyr | Lys | Leu | Thr | Pro | Ser | Gly | Tyr | Glu | Trp | Gly |
| | 2225 | | | | | 2230 | | | | | 2235 | | | |

| Arg | Gln | Asn | Thr | Asp | Lys | Gly | Asn | Asn | Pro | Lys | Gly | Tyr | Leu | Pro |
| | 2240 | | | | | 2245 | | | | | 2250 | | | |

| Ser | His | Tyr | Glu | Arg | Val | Gln | Met | Leu | Leu | Ser | Asp | Arg | Phe | Leu |
| | 2255 | | | | | 2260 | | | | | 2265 | | | |

| Gly | Phe | Phe | Met | Val | Pro | Ala | Gln | Ser | Ser | Trp | Asn | Tyr | Asn | Phe |
| | 2270 | | | | | 2275 | | | | | 2280 | | | |

| Met | Gly | Val | Arg | His | Asp | Pro | Asn | Met | Lys | Tyr | Glu | Leu | Gln | Leu |
| | 2285 | | | | | 2290 | | | | | 2295 | | | |

| Ala | Asn | Pro | Lys | Glu | Phe | Tyr | His | Glu | Val | His | Arg | Pro | Ser | His |
| | 2300 | | | | | 2305 | | | | | 2310 | | | |

| Phe | Leu | Asn | Phe | Ala | Leu | Leu | Gln | Glu | Gly | Glu | Val | Tyr | Ser | Ala |
| | 2315 | | | | | 2320 | | | | | 2325 | | | |

| Asp | Arg | Glu | Asp | Leu | Tyr | Ala |
| | 2330 | | | | | 2335 |

<210> SEQ ID NO 40
<211> LENGTH: 7972
<212> TYPE: DNA
<213> ORGANISM: Homo sapiens

<400> SEQUENCE: 40

| | |
|---|---|
| atttgaagtc ctcgttccac gccttctcat catcctgaac accgagctct gggactccgg | 60 |
| cggagaatct aaacgtaaag catcacccac ggtcgtgaac tgtaggctct cctggcatcc | 120 |
| gggatcttat tctggccttg gcggagttgg ggatggtgtc gcctagcagc cgctgccgct | 180 |
| ttggcttgct cgggaccatt tggctggacc cagagtccgc gtggaaccgc gatagggatc | 240 |
| tgtcagggcc cgcggccggg tccagcttgg tggttgcggt agtgagaggc ctccgctggt | 300 |
| tgccaggctt ggtctagagg tggagcacag tgaaagaatt caagatgcca cctaatataa | 360 |
| actggaaaga ataatgaaa gttgacccag atgacctgcc ccgtcaagaa gaactggcag | 420 |
| ataatttatt gatttcctta tccaaggtgg aagtaaatga ctaaaaagt gaaaagcaag | 480 |
| aaaatgtgat acaccttttc agaattactc agtcactaat gaagatgaaa gctcaagaag | 540 |
| tggagctggc tttggaagaa gtagaaaaag ctggagaaga caagcaaaa tttgaaaatc | 600 |
| aattaaaaac taaagtaatg aaactggaaa atgaactgga gatggctcag cagtctgcag | 660 |
| gtggacgaga tactcggttt ttacgtaatg aaatttgcca acttgaaaaa caattagaac | 720 |
| aaaaagatag agaattggag gacatggaaa aggagttgga gaaagagaag aaagttaatg | 780 |
| agcaattggc tcttcgaaat gaggaggcag aaaatgaaaa cagcaaatta agaagagaga | 840 |
| acaaacgtct aaagaaaaag aatgaacaac tttgtcagga tattattgac taccagaaac | 900 |
| aaatagattc acagaaagaa acacttttat caagaagagg ggaagacagt gactaccgat | 960 |

```
cacagttgtc taaaaaaaac tatgagctta tccaatatct tgatgaaatt cagactttaa    1020
cagaagctaa tgagaaaatt gaagttcaga atcaagaaat gagaaaaaat ttagaagagt    1080
ctgtacagga aatggagaag atgactgatg aatataatag aatgaaagct attgtgcatc    1140
agacagataa tgtaatagat cagttaaaaa agaaaacga tcattatcaa cttcaagtgc     1200
aggagcttac agatcttctg aaatcaaaaa atgaagaaga tgatccaatt atggtagctg    1260
tcaatgcaaa agtagaagaa tggaagctaa ttttgtcttc taaagatgat gaaattattg    1320
agtatcagca aatgttacat aacctaaggg agaaacttaa gaatgctcag cttgatgctg    1380
ataaaagtaa tgttatggct ctacagcagg gtatacagga acgagacagt caaattaaga    1440
tgctcaccga acaagtagaa caatatacaa aagaaatgga aaagaatact tgtattattg    1500
aagatttgaa aaatgagctc caagaaaaca aaggtgcttc aacccttttct caacagactc   1560 atatgaaaat tcagtcaacg ttagacattt taaaagagaa aactaaagag ctgagagaa    1620 cagctgaact ggctgaggct gatgctaggg aaaaggataa agaattagtt gaggctctga   1680
agaggttaaa agattatgaa tcgggagtat atggtttaga agatgctgtc gttgaaataa   1740
agaattgtaa aaaccaaatt aaaataagag atcgagagat tgaaatatta acaaaggaaa   1800
tcaataaact tgaattgaag atcagtgatt tccttgatga aatgaggca cttagagagc    1860 gtgtgggcct tgaaccaaag acaatgattg atttaactga atttagaaat agcaaacact   1920
taaaacagca gcagtacaga gctgaaaacc agattctttt gaaagagatt gaaagtctag   1980
aggaagaacg acttgatctg aaaaaaaaaa ttcgtcaaat ggctcaagaa agaggaaaaa   2040
gaagtgcaac ttcaggatta accactgagg acctgaacct aactgaaaac atttctcaag   2100
gagatagaat aagtgaaaga aaattggatt tattgagcct caaaaatatg agtgaagcac   2160
aatcaaagaa tgaatttctt tcaagagaac taattgaaaa agaaagagat ttagaaagga   2220
gtaggacagt gatagccaaa tttcagaata aattaaaaga attagttgaa gaaaataagc   2280
aacttgaaga aggtatgaaa gaaatattgc aagcaattaa ggaaatgcag aaagatcctg   2340
atgttaaagg aggagaaaca tctctaatta tccctagcct tgaaagacta gttaatgcta   2400
tagaatcaaa gaatgcagaa ggaatctttg atgcgagtct gcatttgaaa gcccaagttg   2460
atcagcttac cggaagaaat gaagaattaa gacaggagct cagggaatct cggaaagagg   2520
ctataaatta ttcacagcag ttggcaaaag ctaatttaaa gatagaccat cttgaaaaag   2580
aaactagtct tttacgacaa tcagaaggat cgaatgttgt ttttaaagga attgacttac   2640
ctgatgggat agcaccatct agtgccagta tcattaattc tcagaatgaa tatttaatac   2700
atttgttaca ggaactagaa aataaagaaa aaagttaaa gaatttagaa gattctcttg   2760
aagattacaa cagaaaattt gctgtaattc gtcatcaaca aagtttgttg tataaagaat   2820
acctaagtga aaaggagacc tggaaaacag aatctaaaac aataaaagag gaaagagaa    2880 aacttgagga tcaagtccaa caagatgcta taaaagtaaa agaatataat aatttgctca   2940
atgctcttca gatggattcg gatgaaatga aaaaaatact tgcagaaaat agtaggaaaa   3000
ttactgtttt gcaagtgaat gaaaaatcac ttataaggca atatacaacc ttagtagaat   3060
tggagcgaca acttagaaaa gaaaatgaga agcaaaagaa tgaattgttg tcaatggagg   3120
ctgaagtttg tgaaaaaatt gggtgtttgc aaagatttaa ggaaatggcc attttcaaga   3180
ttgcagctct ccaaaaagtt gtagataata gtgtttcttt gtctgaacta gaactggcta   3240
ataaacagta caatgaactg actgctaagt acagggacat cttgcaaaaa gataatatgc   3300
ttgttcaaag aacaagtaac ttggaacacc tggagtgtga aaacatctcc ttaaaagaac   3360
```

```
aagtggagtc tataaataaa gaactggaga ttaccaagga aaaacttcac actattgaac    3420
aagcctggga acaggaaact aaattaggta atgaatctag catggataag gcaaagaaat    3480
caataaccaa cagtgacatt gtttccattt caaaaaaaat aactatgctg gaaatgaagg    3540
aattaaatga aaggcagcgg gctgaacatt gtcaaaaaat gtatgaacac ttacggactt    3600
cgttaaagca aatggaggaa cgtaattttg aattggaaac caaatttgct gagcttacca    3660
aaatcaattt ggatgcacag aaggtggaac agatgttaag agatgaatta gctgatagtg    3720
tgagcaaggc agtaagtgat gctgataggc aacggattct agaattagag aagaatgaaa    3780
tggaactaaa agttgaagtg tcaaaactga gagagatttc tgatattgcc agaagacaag    3840
ttgaaatttt gaatgcacaa caacaatcta gggacaagga agtagagtcc ctcagaatgc    3900
aactgctaga ctatcaggca cagtctgatg aaaagtcgct cattgccaag ttgcaccaac    3960
ataatgtctc tcttcaactg agtgaggcta ctgctcttgg taagttggag tcaattacat    4020
ctaaactgca gaagatggag gcctacaact tgcgcttaga gcagaaactt gatgaaaaag    4080
aacaggctct ctattatgct cgtttggagg aagaaacag agcaaaacat ctgcgccaaa    4140
caattcagtc tctacgacga cagtttagtg gagctttacc cttggcacaa caggaaaagt    4200
tctccaaaac aatgattcaa ctacaaaatg acaaacttaa gataatgcaa gaaatgaaaa    4260
attctcaaca gaacataga aatatggaga acaaaacatt ggagatggaa ttaaaattaa    4320
agggcctgga agagttaata agcactttaa aggataccaa aggagcccaa aagtaatca    4380 actggcatat gaaaatagaa gaacttcgtc ttcaagaact taaactaaat cgggaattag    4440
tcaaggataa agaagaaata aaatatttga ataacataat ttctgaatat gaacgtacaa    4500
tcagcagtct tgaagaagaa attgtgcaac agaacaagtt tcatgaagaa agacaaatgg    4560
cctgggatca aagagaagtt gacctggaac gccaactaga catttttgac cgtcagcaaa    4620
atgaaatact aaatgcggca caaaagtttg aagaagctac aggatcaatc cctgacccta    4680
gtttgcccct tccaaatcaa cttgagatcg ctctaaggaa aattaaggag aacattcgaa    4740
taattctaga aacacgggca acttgcaaat cactagaaga gaaactaaaa gagaaagaat    4800
ctgctttaag gttagcagaa caaaatatac tgtcaagaga caaagtaatc aatgaactga    4860
ggcttcgatt gcctgccact gcagaaagag aaaagctcat agctgagcta ggcagaaaag    4920
agatggaacc aaaatctcac cacacattga aaattgctca tcaaaccatt gcaaacatgc    4980
aagcaaggtt aaatcaaaaa gaagaagtat taagaagta tcaacgtctt ctagaaaaag    5040
ccagagagga gcaaagagaa attgtgaaga acatgagga agaccttcat attcttcatc    5100
acagattaga actacaggct gatagttcac taaataaatt caaacaaacg gcttgggatt    5160
taatgaaaca gtctcccact ccagttccta ccaacaagca ttttattcgt ctggctgaga    5220
tggaacagac agtagcagaa caagatgact ctctttcctc actcttggtc aaactaaaga    5280
aagtatcaca agatttggag agacaaagag aaatcactga attaaaagta aaagaatttg    5340
aaaatatcaa attacagctt caagaaaacc atgaagatga agtgaaaaaa gtaaaagcgg    5400
aagtagagga tttaaagtat cttctggacc agtcacaaaa ggagtcacag tgtttaaaat    5460
ctgaacttca ggctcaaaaa gaagcaaatt caagagctcc aacaactaca atgagaaatc    5520
tagtagaacg gctaaagagc caattagcct tgaaggagaa acaacagaaa gcacttagtc    5580
gggcactttt agaactccgg gcagaaatga cagcagctgc tgaagaacgt attatttctg    5640
caacttctca aaaagaggcc catctcaatg ttcaacaaat cgttgatcga catactagag    5700
```

```
agctaaagac acaagttgaa gatttaaatg aaaatctttt aaaattgaaa gaagcactta    5760
aaacaagtaa aaacagagaa aactcactaa ctgataattt gaatgactta aataatgaac    5820
tgcaaaagaa acaaaaagcc tataataaaa tacttagaga gaaagaggaa attgatcaag    5880
agaatgatga actgaaaagg caaattaaaa gactaaccag tggattacag ggcaaacccc    5940
tgacagataa taaacaaagt ctaattgaag aactccaaag gaaagttaaa aaactagaga    6000
accaattaga gggaaaggtg gaggaagtag acctaaaacc tatgaaagaa aagaatgcta    6060
aagaagaatt aattaggtgg gaagaaggta aaaagtggca agccaaaata gaaggaattc    6120
gaaacaagtt aaaagagaaa gagggggaag tctttacttt aacaaagcag ttgaatactt    6180
tgaaggatct ttttgccaaa gccgataaag agaaacttac tttgcagagg aaactaaaaa    6240
caactggcat gactgttgat caggttttgg gaatacgagc tttggagtca gaaaaagaat    6300
tggaagaatt aaaaaagaga aatcttgact tagaaaatga tatattgtat atgagggccc    6360
accaagctct tcctcgagat tctgttgtag aagatttaca tttacaaaat agatacctcc    6420
aagaaaaact tcatgcttta gaaaaacagt tttcaaagga tacatattct aagccttcaa    6480
tttcaggaat agagtcagat gatcattgtc agagagaaca ggagcttcag aaggaaaact    6540
tgaagttgtc atctgaaaat attgaactga aatttcagct tgaacaagca aataaagatt    6600
tgccaagatt aaagaatcaa gtcagagatt tgaaggaaat gtgtgaattt cttaagaaag    6660
aaaaagcaga agttcagcgg aaacttggcc atgttagagg gtctggtaga agtggaagaa    6720
caatcccaga actggaaaaa accattggtt taatgaaaaa agtagttgaa aaagtccaga    6780
gagaaaatga acagttgaaa aaagcatcag gaatattgac tagtgaaaaa atggctaata    6840
ttgagcagga aaatgaaaaa ttgaaggctg aattagaaaa acttaaagct catcttgggc    6900
atcagttgag catgcactat gaatccaaga ccaaaggcac agaaaaaatt attgctgaaa    6960
atgaaaggct tcgtaaagaa cttaaaaaag aaactgatgc tgcagagaaa ttacggatag    7020
caaagaataa tttagagata ttaaatgaga agatgacagt tcaactagaa gagactggta    7080
agagattgca gtttgcagaa agcagaggtc cacagcttga aggtgctgac agtaagagct    7140
ggaaatccat tgtggttaca agaatgtatg aaaccaagtt aaaagaattg gaaactgata    7200
ttgccaaaaa aaatcaaagc attactgacc ttaaacagct tgtaaaagaa gcaacagaga    7260
gagaacaaaa agttaacaaa tacaatgaag accttgaaca acagattaag attcttaaac    7320
atgttcctga aggtgctgag acagagcaag gccttaaacg ggagcttcaa gttcttagat    7380
tagctaatca tcagctggat aaagagaaag cagaattaat ccatcagata gaagctaaca    7440
aggaccaaag tggagctgaa agcaccatac ctgatgctga tcaactaaag gaaaaaataa    7500
aagatctaga gacacagctc aaaatgtcag atctagaaaa gcagcatttg aaggaggaaa    7560
taaagaagct gaaaaaagaa ctggaaaatt ttgatccttc attttttgaa gaaattgaag    7620
atcttaagta taattacaag gaagaagtga agaagaatat tctcttagaa gagaaggtaa    7680
aaaaacttc agaacaattg ggagttgaat aactagccc tgttgctgct tctgaagagt    7740
ttgaagatga agaagaaagt cctgttaatt tccccattta ctaaaggtca cctataaact    7800
ttgtttcatt taactatttta ttaactttat aagttaaata tacttggaaa taagcagttc    7860
tccgaactgt agtatttcct tctcactacc ttgtacctttt atacttagat tggaattctt    7920
aataaataaa attatatgaa attttcaact tattaaaaaa aaaaaaaaaa aa            7972
```

```
<210> SEQ ID NO 41
<211> LENGTH: 2479
```

```
<212> TYPE: PRT
<213> ORGANISM: Homo sapiens

<400> SEQUENCE: 41

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
                20                  25                  30

Ser Lys Val Glu Val Asn Glu Leu Lys Ser Lys Gln Glu Asn Val
            35                  40                  45

Ile His Leu Phe Arg Ile Thr Gln Ser Leu Met Lys Met Lys Ala Gln
    50                  55                  60

Glu Val Glu Leu Ala Leu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Cys Ile
370                 375                 380

Ile Glu Asp Leu Lys Asn Glu Leu Gln Arg Asn Lys Gly Ala Ser Thr
385                 390                 395                 400
```

```
Leu Ser Gln Gln Thr His Met Lys Ile Gln Ser Thr Leu Asp Ile Leu
                405                 410                 415
Lys Glu Lys Thr Lys Glu Ala Glu Arg Thr Ala Glu Leu Ala Glu Ala
            420                 425                 430
Asp Ala Arg Glu Lys Asp Lys Glu Leu Val Glu Ala Leu Lys Arg Leu
        435                 440                 445
Lys Asp Tyr Glu Ser Gly Val Tyr Gly Leu Glu Asp Ala Val Val Glu
    450                 455                 460
Ile Lys Asn Cys Lys Asn Gln Ile Lys Ile Arg Asp Arg Glu Ile Glu
465                 470                 475                 480
Ile Leu Thr Lys Glu Ile Asn Lys Leu Glu Leu Lys Ile Ser Asp Phe
            485                 490                 495
Leu Asp Glu Asn Glu Ala Leu Arg Glu Arg Val Gly Leu Glu Pro Lys
        500                 505                 510
Thr Met Ile Asp Leu Thr Glu Phe Arg Asn Ser Lys His Leu Lys Gln
    515                 520                 525
Gln Gln Tyr Arg Ala Glu Asn Gln Ile Leu Leu Lys Glu Ile Glu Ser
    530                 535                 540
Leu Glu Glu Glu Arg Leu Asp Leu Lys Lys Lys Ile Arg Gln Met Ala
545                 550                 555                 560
Gln Glu Arg Gly Lys Arg Ser Ala Thr Ser Gly Leu Thr Thr Glu Asp
            565                 570                 575
Leu Asn Leu Thr Glu Asn Ile Ser Gln Gly Asp Arg Ile Ser Glu Arg
        580                 585                 590
Lys Leu Asp Leu Leu Ser Leu Lys Asn Met Ser Glu Ala Gln Ser Lys
    595                 600                 605
Asn Glu Phe Leu Ser Arg Glu Leu Ile Glu Lys Glu Arg Asp Leu Glu
    610                 615                 620
Arg Ser Arg Thr Val Ile Ala Lys Phe Gln Asn Lys Leu Lys Glu Leu
625                 630                 635                 640
Val Glu Glu Asn Lys Gln Leu Glu Glu Gly Met Lys Glu Ile Leu Gln
            645                 650                 655
Ala Ile Lys Glu Met Gln Lys Asp Pro Asp Val Lys Gly Gly Glu Thr
        660                 665                 670
Ser Leu Ile Ile Pro Ser Leu Glu Arg Leu Val Asn Ala Ile Glu Ser
    675                 680                 685
Lys Asn Ala Glu Gly Ile Phe Asp Ala Ser Leu His Leu Lys Ala Gln
    690                 695                 700
Val Asp Gln Leu Thr Gly Arg Asn Glu Glu Leu Arg Gln Glu Leu Arg
705                 710                 715                 720
Glu Ser Arg Lys Glu Ala Ile Asn Tyr Ser Gln Gln Leu Ala Lys Ala
            725                 730                 735
Asn Leu Lys Ile Asp His Leu Glu Lys Glu Thr Ser Leu Leu Arg Gln
        740                 745                 750
Ser Glu Gly Ser Asn Val Val Phe Lys Gly Ile Asp Leu Pro Asp Gly
    755                 760                 765
Ile Ala Pro Ser Ser Ala Ser Ile Ile Asn Ser Gln Asn Glu Tyr Leu
    770                 775                 780
Ile His Leu Leu Gln Glu Leu Glu Asn Lys Glu Lys Lys Leu Lys Asn
785                 790                 795                 800
Leu Glu Asp Ser Leu Glu Asp Tyr Asn Arg Lys Phe Ala Val Ile Arg
            805                 810                 815
```

His Gln Gln Ser Leu Leu Tyr Lys Glu Tyr Leu Ser Glu Lys Glu Thr
              820                 825                 830

Trp Lys Thr Glu Ser Lys Thr Ile Lys Glu Glu Lys Arg Lys Leu Glu
              835                 840                 845

Asp Gln Val Gln Gln Asp Ala Ile Lys Val Lys Glu Tyr Asn Asn Leu
              850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
              885                 890                 895

Ile Arg Gln Tyr Thr Thr Leu Val Glu Leu Glu Arg Gln Leu Arg Lys
              900                 905                 910

Glu Asn Glu Lys Gln Lys Asn Glu Leu Leu Ser Met Glu Ala Glu Val
              915                 920                 925

Cys Glu Lys Ile Gly Cys Leu Gln Arg Phe Lys Glu Met Ala Ile Phe
              930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
              965                 970                 975

Arg Asp Ile Leu Gln Lys Asp Asn Met Leu Val Gln Arg Thr Ser Asn
              980                 985                 990

Leu Glu His Leu Glu Cys Glu Asn Ile Ser Leu Lys Glu Gln Val Glu
              995                1000                1005

Ser Ile Asn Lys Glu Leu Glu Ile Thr Lys Glu Lys Leu His Thr
              1010                1015                1020

Ile Glu Gln Ala Trp Glu Gln Glu Thr Lys Leu Gly Asn Glu Ser
              1025                1030                1035

Ser Met Asp Lys Ala Lys Lys Ser Ile Thr Asn Ser Asp Ile Val
              1040                1045                1050

Ser Ile Ser Lys Lys Ile Thr Met Leu Glu Met Lys Glu Leu Asn
              1055                1060                1065

Glu Arg Gln Arg Ala Glu His Cys Gln Lys Met Tyr Glu His Leu
              1070                1075                1080

Arg Thr Ser Leu Lys Gln Met Glu Glu Arg Asn Phe Glu Leu Glu
              1085                1090                1095

Thr Lys Phe Ala Glu Leu Thr Lys Ile Asn Leu Asp Ala Gln Lys
              1100                1105                1110

Val Glu Gln Met Leu Arg Asp Glu Leu Ala Asp Ser Val Ser Lys
              1115                1120                1125

Ala Val Ser Asp Ala Asp Arg Gln Arg Ile Leu Glu Leu Glu Lys
              1130                1135                1140

Asn Glu Met Glu Leu Lys Val Glu Val Ser Lys Leu Arg Glu Ile
              1145                1150                1155

Ser Asp Ile Ala Arg Arg Gln Val Glu Ile Leu Asn Ala Gln Gln
              1160                1165                1170

Gln Ser Arg Asp Lys Glu Val Glu Ser Leu Arg Met Gln Leu Leu
              1175                1180                1185

Asp Tyr Gln Ala Gln Ser Asp Glu Lys Ser Leu Ile Ala Lys Leu
              1190                1195                1200

His Gln His Asn Val Ser Leu Gln Leu Ser Glu Ala Thr Ala Leu
              1205                1210                1215

Gly Lys Leu Glu Ser Ile Thr Ser Lys Leu Gln Lys Met Glu Ala

```
            1220                1225               1230
Tyr Asn Leu Arg Leu Glu Gln Lys Leu Asp Glu Lys Glu Gln Ala
        1235                1240               1245

Leu Tyr Tyr Ala Arg Leu Glu Gly Arg Asn Arg Ala Lys His Leu
        1250                1255               1260

Arg Gln Thr Ile Gln Ser Leu Arg Arg Gln Phe Ser Gly Ala Leu
        1265                1270               1275

Pro Leu Ala Gln Gln Glu Lys Phe Ser Lys Thr Met Ile Gln Leu
        1280                1285               1290

Gln Asn Asp Lys Leu Lys Ile Met Gln Glu Met Lys Asn Ser Gln
        1295                1300               1305

Gln Glu His Arg Asn Met Glu Asn Lys Thr Leu Glu Met Glu Leu
        1310                1315               1320

Lys Leu Lys Gly Leu Glu Glu Leu Ile Ser Thr Leu Lys Asp Thr
        1325                1330               1335

Lys Gly Ala Gln Lys Val Ile Asn Trp His Met Lys Ile Glu Glu
        1340                1345               1350

Leu Arg Leu Gln Glu Leu Lys Leu Asn Arg Glu Leu Val Lys Asp
        1355                1360               1365

Lys Glu Glu Ile Lys Tyr Leu Asn Asn Ile Ile Ser Glu Tyr Glu
        1370                1375               1380

Arg Thr Ile Ser Ser Leu Glu Glu Glu Ile Val Gln Gln Asn Lys
        1385                1390               1395

Phe His Glu Glu Arg Gln Met Ala Trp Asp Gln Arg Glu Val Asp
        1400                1405               1410

Leu Glu Arg Gln Leu Asp Ile Phe Asp Arg Gln Gln Asn Glu Ile
        1415                1420               1425

Leu Asn Ala Ala Gln Lys Phe Glu Glu Ala Thr Gly Ser Ile Pro
        1430                1435               1440

Asp Pro Ser Leu Pro Leu Pro Asn Gln Leu Glu Ile Ala Leu Arg
        1445                1450               1455

Lys Ile Lys Glu Asn Ile Arg Ile Ile Leu Glu Thr Arg Ala Thr
        1460                1465               1470

Cys Lys Ser Leu Glu Glu Lys Leu Lys Glu Lys Glu Ser Ala Leu
        1475                1480               1485

Arg Leu Ala Glu Gln Asn Ile Leu Ser Arg Asp Lys Val Ile Asn
        1490                1495               1500

Glu Leu Arg Leu Arg Leu Pro Ala Thr Ala Glu Arg Glu Lys Leu
        1505                1510               1515

Ile Ala Glu Leu Gly Arg Lys Glu Met Glu Pro Lys Ser His His
        1520                1525               1530

Thr Leu Lys Ile Ala His Gln Thr Ile Ala Asn Met Gln Ala Arg
        1535                1540               1545

Leu Asn Gln Lys Glu Glu Val Leu Lys Lys Tyr Gln Arg Leu Leu
        1550                1555               1560

Glu Lys Ala Arg Glu Glu Gln Arg Glu Ile Val Lys Lys His Glu
        1565                1570               1575

Glu Asp Leu His Ile Leu His His Arg Leu Glu Leu Gln Ala Asp
        1580                1585               1590

Ser Ser Leu Asn Lys Phe Lys Gln Thr Ala Trp Asp Leu Met Lys
        1595                1600               1605

Gln Ser Pro Thr Pro Val Pro Thr Asn Lys His Phe Ile Arg Leu
        1610                1615               1620
```

```
Ala Glu Met Glu Gln Thr Val Ala Glu Gln Asp Asp Ser Leu Ser
    1625            1630            1635

Ser Leu Leu Val Lys Leu Lys Lys Val Ser Gln Asp Leu Glu Arg
    1640            1645            1650

Gln Arg Glu Ile Thr Glu Leu Lys Val Lys Glu Phe Glu Asn Ile
    1655            1660            1665

Lys Leu Gln Leu Gln Glu Asn His Glu Asp Glu Val Lys Lys Val
    1670            1675            1680

Lys Ala Glu Val Glu Asp Leu Lys Tyr Leu Leu Asp Gln Ser Gln
    1685            1690            1695

Lys Glu Ser Gln Cys Leu Lys Ser Glu Leu Gln Ala Gln Lys Glu
    1700            1705            1710

Ala Asn Ser Arg Ala Pro Thr Thr Thr Met Arg Asn Leu Val Glu
    1715            1720            1725

Arg Leu Lys Ser Gln Leu Ala Leu Lys Glu Lys Gln Gln Lys Ala
    1730            1735            1740

Leu Ser Arg Ala Leu Leu Glu Leu Arg Ala Glu Met Thr Ala Ala
    1745            1750            1755

Ala Glu Glu Arg Ile Ile Ser Ala Thr Ser Gln Lys Glu Ala His
    1760            1765            1770

Leu Asn Val Gln Gln Ile Val Asp Arg His Thr Arg Glu Leu Lys
    1775            1780            1785

Thr Gln Val Glu Asp Leu Asn Glu Asn Leu Leu Lys Leu Lys Glu
    1790            1795            1800

Ala Leu Lys Thr Ser Lys Asn Arg Glu Asn Ser Leu Thr Asp Asn
    1805            1810            1815

Leu Asn Asp Leu Asn Asn Glu Leu Gln Lys Lys Gln Lys Ala Tyr
    1820            1825            1830

Asn Lys Ile Leu Arg Glu Lys Glu Glu Ile Asp Gln Glu Asn Asp
    1835            1840            1845

Glu Leu Lys Arg Gln Ile Lys Arg Leu Thr Ser Gly Leu Gln Gly
    1850            1855            1860

Lys Pro Leu Thr Asp Asn Lys Gln Ser Leu Ile Glu Glu Leu Gln
    1865            1870            1875

Arg Lys Val Lys Lys Leu Glu Asn Gln Leu Glu Gly Lys Val Glu
    1880            1885            1890

Glu Val Asp Leu Lys Pro Met Lys Glu Lys Asn Ala Lys Glu Glu
    1895            1900            1905

Leu Ile Arg Trp Glu Glu Gly Lys Lys Trp Gln Ala Lys Ile Glu
    1910            1915            1920

Gly Ile Arg Asn Lys Leu Lys Glu Lys Glu Gly Glu Val Phe Thr
    1925            1930            1935

Leu Thr Lys Gln Leu Asn Thr Leu Lys Asp Leu Phe Ala Lys Ala
    1940            1945            1950

Asp Lys Glu Lys Leu Thr Leu Gln Arg Lys Leu Lys Thr Thr Gly
    1955            1960            1965

Met Thr Val Asp Gln Val Leu Gly Ile Arg Ala Leu Glu Ser Glu
    1970            1975            1980

Lys Glu Leu Glu Glu Leu Lys Lys Arg Asn Leu Asp Leu Glu Asn
    1985            1990            1995

Asp Ile Leu Tyr Met Arg Ala His Gln Ala Leu Pro Arg Asp Ser
    2000            2005            2010
```

-continued

| | | | | | | | | | | | | |
|---|---|---|---|---|---|---|---|---|---|---|---|---|
|Val|Val|Glu|Asp|Leu|His|Leu|Gln|Asn|Arg|Tyr|Leu|Gln Glu Lys|
|2015| | | | |2020| | | | |2025| | |

Leu His Ala Leu Glu Lys Gln Phe Ser Lys Asp Thr Tyr Ser Lys
    2030                2035                2040

Pro Ser Ile Ser Gly Ile Glu Ser Asp Asp His Cys Gln Arg Glu
    2045                2050                2055

Gln Glu Leu Gln Lys Glu Asn Leu Lys Leu Ser Ser Glu Asn Ile
    2060                2065                2070

Glu Leu Lys Phe Gln Leu Glu Gln Ala Asn Lys Asp Leu Pro Arg
    2075                2080                2085

Leu Lys Asn Gln Val Arg Asp Leu Lys Glu Met Cys Glu Phe Leu
    2090                2095                2100

Lys Lys Glu Lys Ala Glu Val Gln Arg Lys Leu Gly His Val Arg
    2105                2110                2115

Gly Ser Gly Arg Ser Gly Lys Thr Ile Pro Glu Leu Glu Lys Thr
    2120                2125                2130

Ile Gly Leu Met Lys Lys Val Val Glu Lys Val Gln Arg Glu Asn
    2135                2140                2145

Glu Gln Leu Lys Lys Ala Ser Gly Ile Leu Thr Ser Glu Lys Met
    2150                2155                2160

Ala Asn Ile Glu Gln Glu Asn Glu Lys Leu Lys Ala Glu Leu Glu
    2165                2170                2175

Lys Leu Lys Ala His Leu Gly His Gln Leu Ser Met His Tyr Glu
    2180                2185                2190

Ser Lys Thr Lys Gly Thr Glu Lys Ile Ile Ala Glu Asn Glu Arg
    2195                2200                2205

Leu Arg Lys Glu Leu Lys Lys Glu Thr Asp Ala Ala Glu Lys Leu
    2210                2215                2220

Arg Ile Ala Lys Asn Asn Leu Glu Ile Leu Asn Glu Lys Met Thr
    2225                2230                2235

Val Gln Leu Glu Glu Thr Gly Lys Arg Leu Gln Phe Ala Glu Ser
    2240                2245                2250

Arg Gly Pro Gln Leu Glu Gly Ala Asp Ser Lys Ser Trp Lys Ser
    2255                2260                2265

Ile Val Val Thr Arg Met Tyr Glu Thr Lys Leu Lys Glu Leu Glu
    2270                2275                2280

Thr Asp Ile Ala Lys Lys Asn Gln Ser Ile Thr Asp Leu Lys Gln
    2285                2290                2295

Leu Val Lys Glu Ala Thr Glu Arg Glu Gln Lys Val Asn Lys Tyr
    2300                2305                2310

Asn Glu Asp Leu Glu Gln Gln Ile Lys Ile Leu Lys His Val Pro
    2315                2320                2325

Glu Gly Ala Glu Thr Glu Gln Gly Leu Lys Arg Glu Leu Gln Val
    2330                2335                2340

Leu Arg Leu Ala Asn His Gln Leu Asp Lys Glu Lys Ala Glu Leu
    2345                2350                2355

Ile His Gln Ile Glu Ala Asn Lys Asp Gln Ser Gly Ala Glu Ser
    2360                2365                2370

Thr Ile Pro Asp Ala Asp Gln Leu Lys Glu Lys Ile Lys Asp Leu
    2375                2380                2385

Glu Thr Gln Leu Lys Met Ser Asp Leu Glu Lys Gln His Leu Lys
    2390                2395                2400

Glu Glu Ile Lys Lys Leu Lys Lys Glu Leu Glu Asn Phe Asp Pro

|     |      |     |     |     |     |     |     |     |     |     |
|-----|------|-----|-----|-----|-----|-----|-----|-----|-----|-----|
|     | 2405 |     |     | 2410 |     |     | 2415 |     |     |     |
| Ser | Phe | Phe | Glu | Glu | Ile | Glu | Asp | Leu | Lys | Tyr | Asn | Tyr | Lys | Glu |
|     | 2420 |     |     |     | 2425 |     |     |     | 2430 |     |

Glu Val Lys Lys Asn Ile Leu Leu Glu Glu Lys Val Lys Lys Leu
    2435            2440                2445

Ser Glu Gln Leu Gly Val Glu Leu Thr Ser Pro Val Ala Ala Ser
    2450            2455                2460

Glu Glu Phe Glu Asp Glu Glu Ser Pro Val Asn Phe Pro Ile
    2465            2470                2475

Tyr

<210> SEQ ID NO 42
<211> LENGTH: 2625
<212> TYPE: DNA
<213> ORGANISM: Homo sapiens

<400> SEQUENCE: 42

```
actcgaccgg gctgcgctca ctgcccagcc ggggccccgg gagcctccag gctcccgccc      60
gccctgagct gcggcctccg catggagggg ccactcactc caccaccgct gcagggaggc     120
ggagccgccg ctgttccgga gcccggagcc cggcaacacc cggacacga gacggcggcg      180
cagcggtaca gcgcccgact gctgcaggcc ggctacgagc ccgagagccc tagattggac     240
ctcgctacac acccgacgac accccgttca gaactatctt cagtggtctt actggcaggt     300
gttggtgtcc agatggatcg ccttcgcagg gctagcatgg cggactacct gatcagcggc     360
ggcaccggct acgtgcccga ggatgggctc accgcgcagc agctcttcgc cagcgccgac     420
ggcctcacct acaacgactt cctgattctc ccaggattca tagacttcat agctgatgag     480
gtggacctga cctcagccct gacccggaag atcacgctga agacgccact gatctcctcc     540
cccatggaca ctgtgacaga ggctgacatg gccattgcca tggctctgat gggaggtatt     600
ggtttcattc accacaactg cacccccgag ttccaggcca acgaggtgcg gaaggtcaag     660
aagtttgaac agggcttcat cacggaccct gtggtgctga gccctcgca cactgtgggc     720
gatgtgctgg aggccaagat gcggcatggc ttctctggca tccccatcac tgagacgggc     780
accatgggca gcaagctggt gggcatcgtc acctcccgag acatcgactt tcttgctgag     840
aaggaccaca ccaccctcct cagtgaggtg atgacgccaa ggattgaact ggtggtggct     900
ccagcaggtg tgacgttgaa agaggcaaat gagatcctgc agcgtagcaa gaaagggaag     960
ctgcctatcg tcaatgattg cgatgagctg gtggccatca tcgcccgcac cgacctgaag    1020
aagaaccgag actaccctct ggcctccaag gattcccaga gcagctgct ctgtggggca     1080
gctgtgggca cccgtgagga tgacaaatac cgtctggacc tgctcaccca ggcgggcgtc    1140
gacgtcatag tcttggactc gtcccaaggg aattcggtgt atcagatcgc catggtgcat    1200
tacatcaaac agaagtaccc ccacctccag gtgattgggg ggaacgtggt gacagcagcc    1260
caggccaaga acctgattga tgctggtgtg gacgggctgc gcgtgggcat gggctgcggc    1320
tccatctgca tcacccagga agtgatggcc tgtggtcggc ccagggcac tgctgtgtac    1380
aaggtggctg agtatgcccg cgcctttggt gtgcccatca tagccgatgg cggcatccag    1440
accgtgggac acgtggtcaa ggccctggcc cttggagcct ccacagtgat gatgggctcc    1500
ctgctggccg ccactacgga ggcccctggc gagtacttct ctcagacgg ggtgcggctc    1560
aagaagtacc ggggcatggg ctcactggat gccatggaga gagcagcag cagccagaaa    1620
cgatacttca gcgaggggga taaagtgaag atcgcgcagg gtgtctcggg ctccatccag    1680
```

-continued

```
gacaaaggat ccattcagaa gttcgtgccc tacctcatag caggcatcca acacggctgc    1740
caggatatcg gggcccgcag cctgtctgtc cttcggtcca tgatgtactc aggagagctc    1800
aagtttgaga agcggaccat gtcggcccag attgagggtg gtgtccatgg cctgcactct    1860
tacgaaaagc ggctgtactg aggacagcgg tggaggccga ggtggtggag gggatgcacc    1920
ccagtgtcca cttttgggca cagcctccct ccataactga gtggtccaca gatttgcact    1980
acgggttctc cagctccttt ccaggcagag aggaggggag gtcctgaggg gactgctgcc    2040
cctcactcgg catcccctgc agagtcagga ctgctcccgg ggccaggctg ccctgggagc    2100 cccctccga gccagccag ccaggctctc aggccctgcg cctgcctcag gtctttcttg       2160
ctgcagcctg ctccagcctg ccccacccc aggggcagg cggcccctcc tggcttctcc       2220
tgtagggcac ctcccgccc ctagcctccc aggaaatggt gctctcctgg ccctgcctct     2280
ggcccttccc gggccgctgc ccctcagcca tgtggcactt ctgagctcct gacctaggcc    2340
aaggggaggt ctctgccccc ttccccggcc ctgggctacc cttgggtcct gctcctcagg    2400
ccgctcccct gtccctggcc atgggtagga gactgccctg gtcatggccg cctgcctgtc    2460
attcctgact caccaccgtc cccaggtgaa ccattcctcc cttctcctca gctgcagtcg    2520
aaggctttaa ctttgcacac ttgggatcac agttgcgtca ttgtgtatta aatacttgga    2580
ataaatcaag caggtctcaa cgcctccact aaaaaaaaaa aaaaa                    2625
```

<210> SEQ ID NO 43
<211> LENGTH: 599
<212> TYPE: PRT
<213> ORGANISM: Homo sapiens

<400> SEQUENCE: 43

```
Met Glu Gly Pro Leu Thr Pro Pro Leu Gln Gly Gly Ala Ala
1               5                   10                  15

Ala Val Pro Glu Pro Gly Ala Arg Gln His Pro Gly His Glu Thr Ala
                20                  25                  30

Ala Gln Arg Tyr Ser Ala Arg Leu Leu Gln Ala Gly Tyr Glu Pro Glu
            35                  40                  45

Ser Pro Arg Leu Asp Leu Ala Thr His Pro Thr Thr Pro Arg Ser Glu
        50                  55                  60

Leu Ser Ser Val Val Leu Leu Ala Gly Val Gly Val Gln Met Asp Arg
65                  70                  75                  80

Leu Arg Arg Ala Ser Met Ala Asp Tyr Leu Ile Ser Gly Gly Thr Gly
                85                  90                  95

Tyr Val Pro Glu Asp Gly Leu Thr Ala Gln Gln Leu Phe Ala Ser Ala
            100                 105                 110

Asp Gly Leu Thr Tyr Asn Asp Phe Leu Ile Leu Pro Gly Phe Ile Asp
        115                 120                 125

Phe Ile Ala Asp Glu Val Asp Leu Thr Ser Ala Leu Thr Arg Lys Ile
    130                 135                 140

Thr Leu Lys Thr Pro Leu Ile Ser Ser Pro Met Asp Thr Val Thr Glu
145                 150                 155                 160

Ala Asp Met Ala Ile Ala Met Ala Leu Met Gly Gly Ile Gly Phe Ile
                165                 170                 175

His His Asn Cys Thr Pro Glu Phe Gln Ala Asn Glu Val Arg Lys Val
            180                 185                 190

Lys Lys Phe Glu Gln Gly Phe Ile Thr Asp Pro Val Val Leu Ser Pro
        195                 200                 205
```

-continued

Ser His Thr Val Gly Asp Val Leu Glu Ala Lys Met Arg His Gly Phe
210                215                220

Ser Gly Ile Pro Ile Thr Glu Thr Gly Thr Met Gly Ser Lys Leu Val
225                230                235                240

Gly Ile Val Thr Ser Arg Asp Ile Asp Phe Leu Ala Glu Lys Asp His
                245                250                255

Thr Thr Leu Leu Ser Glu Val Met Thr Pro Arg Ile Glu Leu Val Val
                260                265                270

Ala Pro Ala Gly Val Thr Leu Lys Glu Ala Asn Glu Ile Leu Gln Arg
                275                280                285

Ser Lys Lys Gly Lys Leu Pro Ile Val Asn Asp Cys Asp Glu Leu Val
290                295                300

Ala Ile Ile Ala Arg Thr Asp Leu Lys Lys Asn Arg Asp Tyr Pro Leu
305                310                315                320

Ala Ser Lys Asp Ser Gln Lys Gln Leu Leu Cys Gly Ala Ala Val Gly
                325                330                335

Thr Arg Glu Asp Asp Lys Tyr Arg Leu Asp Leu Leu Thr Gln Ala Gly
                340                345                350

Val Asp Val Ile Val Leu Asp Ser Ser Gln Gly Asn Ser Val Tyr Gln
                355                360                365

Ile Ala Met Val His Tyr Ile Lys Gln Lys Tyr Pro His Leu Gln Val
                370                375                380

Ile Gly Gly Asn Val Val Thr Ala Ala Gln Ala Lys Asn Leu Ile Asp
385                390                395                400

Ala Gly Val Asp Gly Leu Arg Val Gly Met Gly Cys Gly Ser Ile Cys
                405                410                415

Ile Thr Gln Glu Val Met Ala Cys Gly Arg Pro Gln Gly Thr Ala Val
                420                425                430

Tyr Lys Val Ala Glu Tyr Ala Arg Arg Phe Gly Val Pro Ile Ile Ala
                435                440                445

Asp Gly Gly Ile Gln Thr Val Gly His Val Val Lys Ala Leu Ala Leu
                450                455                460

Gly Ala Ser Thr Val Met Met Gly Ser Leu Leu Ala Ala Thr Thr Glu
465                470                475                480

Ala Pro Gly Glu Tyr Phe Phe Ser Asp Gly Val Arg Leu Lys Lys Tyr
                485                490                495

Arg Gly Met Gly Ser Leu Asp Ala Met Glu Lys Ser Ser Ser Ser Gln
                500                505                510

Lys Arg Tyr Phe Ser Glu Gly Asp Lys Val Lys Ile Ala Gln Gly Val
                515                520                525

Ser Gly Ser Ile Gln Asp Lys Gly Ser Ile Gln Lys Phe Val Pro Tyr
530                535                540

Leu Ile Ala Gly Ile Gln His Gly Cys Gln Asp Ile Gly Ala Arg Ser
545                550                555                560

Leu Ser Val Leu Arg Ser Met Met Tyr Ser Gly Glu Leu Lys Phe Glu
                565                570                575

Lys Arg Thr Met Ser Ala Gln Ile Glu Gly Gly Val His Gly Leu His
                580                585                590

Ser Tyr Glu Lys Arg Leu Tyr
595

<210> SEQ ID NO 44
<211> LENGTH: 2981

<212> TYPE: DNA
<213> ORGANISM: Homo sapiens

<400> SEQUENCE: 44

```
gctgggtaaa tcccagagtc tcagccgcct aagtgtcttc cccggaggtg agattatctc    60
cgcctgtgct ggacacctcc ctttctcctg cagccatgga tgccgctctg ctcctgaacg   120
tggaaggggt caagaaaacc attctgcacg ggggcacggg cgagctccca aacttcatca   180
ccggatcccg agtgatcttt catttccgca ccatgaaatg tgatgaggag cggacagtca   240
ttgacgacag tcggcaggtg ggccagccca tgcacatcat catcggaaac atgttcaagc   300
tcgaggtctg ggagatcctg cttacctcca tgcgggtgca cgaggtggcc gagttctggt   360
gcgacaccat ccacacgggg gtctacccca tcctatcccg gagcctgagg cagatggccc   420
agggcaagga ccccacagag tggcacgtgc acacgtgcgg gctggccaac atgttcgcct   480
accacacgct gggctacgag gacctggacg agctgcagaa ggagcctcag cctctggtct   540
ttgtgatcga gctgctgcag gttgatgccc cgagtgatta ccagagggag acctggaacc   600
tgagcaatca tgagaagatg aaggcggtgc ccgtcctcca cggagaggga atcggctct    660
tcaagctggg ccgctacgag gaggcctctt ccaagtacca ggaggccatc atctgcctaa   720
ggaacctgca gaccaaggag aagccatggg aggtgcagtg gctgaagctg gagaagatga   780
tcaatactct gatcctcaac tactgccagt gcctgctgaa gaggaggag tactatgagg    840
tgctggagca caccagtgat attctccggc accacccagg catcgtgaag gcctactacg   900
tgcgtgcccg ggctcacgca gaggtgtgga atgaggccga ggccaaggcg gacctccaga   960
aagtgctgga gctggagccg tccatgcaga aggcggtgcg cagggagctg aggctgctgg  1020
agaaccgcat ggcggagaag caggaggagg agcggctgcg ctgccggaac atgctgagcc  1080
agggtgccac gcagcctccc gcagagccac ccacagagcc acccgcacag tcatccacag  1140
agccacctgc agagccaccc acagcaccat ctgcagagct gtccgcaggg ccccctgcag  1200
agccagccac agagccaccc ccgtccccag ggcactcgct gcagcactga gcccctgag    1260
gcccacagcc acccaggcag ggagcaagtg gcctggtcac ttctggttcg attgaccagg  1320
atcgtggtgt cacttttaa aatttaaaat taattttga aatcaaagtc agacacaccc    1380
atggtaaaaa aaaaaaaaaa aacaatccca agggtacaga agagcttatg aataaaagta  1440
gttttctcct ctaccctct cattccttcc gtgccatggt tttaattgac cctgttttta    1500
attcttctgg tagttttctc tatttccaag taatctgttt aaatcagttt ctagatttta  1560
ccccatgtca atgacaaatg aggatttgat gctctgatcc tttctcatgc ctgataccccc 1620
tccctgtctc cccattttgg atagttacat ttggggtca tctcggtgat ttttgtaact    1680
ttacgcagga cacttagagc tctctagaat cccactgact ttagtgggtc ttgatgtagg  1740
gtgggcaagc ccgacactg gagcttagcc tgagagggtt cttggcctcc cccaggaaag    1800
atttcaaagg caagcgccag tggtagggta gaagaaaaca gctgtggtcg ggcacggtgg  1860
ctcacgccta taatcccagc actttgggag gccgaggcgg gtggatcacc tgaggtcagg  1920
agttccagac cagcctggcc aacatggtga aacctcatct ctactaaaaa tacaaaaaaa  1980
ctagctgggc gtggtggcgg gcgcctataa tcccagctac ttgggaggct gaggcaggag  2040
aattgattga acctgggagg cggaggttgc agtgagccaa gatcacgtca ttgcactcca  2100
gcctggtcaa caagagtaaa acttcatctc aaaaaacaaa acaaaacaaa acaacaaca   2160
aaaaacaaaa gaaaaacaaa caaaaccaaa accaaaacag ctgtattgaa gctgcagtgt  2220
```

```
tgcagctctg tgactgccct gcagagcagg gctaccccat aggcagcgag cagcagctca    2280
gggcagttct gcagtcagat ttatacccac ttttaattac atgtagatta aggagctgca    2340
tatacaaaga tttctaggga aggagtagta acttctgggt cctggggtct ttgccacgga    2400
acagggcagt atgccagggt gttgccacgg caatggtaaa ctgacatggc accctggggg    2460
tcatgcctta gggaaagccg cttccactcg cccctgtttt agctcatctt caagttagtc    2520
tggtgtccaa gctccaccgc ctgcctcagt ctggtgacct ccttctgtgt ctgatgagca    2580
tggcagcgtt gggaccttcc ccttccaact ctctccctcc tcttcgtcct ccctaaagga    2640
cgggtacgag gaggggctat cacgccagcg acatcctcta gcaccaccca ggtgtgtggg    2700
gtggggcagg ggggcgacga agtatccagc ccagggccac gtagtcaact gccaagggct    2760
tcctgggctt ctcttctgcc ccagagcttg tctccaccca gcaggggttc ccccagcgct    2820
aactgtatcc ctaaagttct gatgtacttt acttttccat cttccttgtt gttaacatct    2880
accttctgct ctgtaagcaa aactaaatct tctgtgcttt gtccataggt tgattctaca    2940
atctgaaaat caataaacag catttgcatg aaaaaaaaaa a                        2981
```

<210> SEQ ID NO 45
<211> LENGTH: 384
<212> TYPE: PRT
<213> ORGANISM: Homo sapiens

<400> SEQUENCE: 45

```
Met Asp Ala Ala Leu Leu Asn Val Glu Gly Val Lys Lys Thr Ile
1               5                   10                  15

Leu His Gly Gly Thr Gly Glu Leu Pro Asn Phe Ile Thr Gly Ser Arg
            20                  25                  30

Val Ile Phe His Phe Arg Thr Met Lys Cys Asp Glu Glu Arg Thr Val
        35                  40                  45

Ile Asp Asp Ser Arg Gln Val Gly Gln Pro Met His Ile Ile Ile Gly
    50                  55                  60

Asn Met Phe Lys Leu Glu Val Trp Glu Ile Leu Leu Thr Ser Met Arg
65                  70                  75                  80

Val His Glu Val Ala Glu Phe Trp Cys Asp Thr Ile His Thr Gly Val
                85                  90                  95

Tyr Pro Ile Leu Ser Arg Ser Leu Arg Gln Met Ala Gln Gly Lys Asp
            100                 105                 110

Pro Thr Glu Trp His Val His Thr Cys Gly Leu Ala Asn Met Phe Ala
        115                 120                 125

Tyr His Thr Leu Gly Tyr Glu Asp Leu Asp Glu Leu Gln Lys Glu Pro
    130                 135                 140

Gln Pro Leu Val Phe Val Ile Glu Leu Leu Gln Val Asp Ala Pro Ser
145                 150                 155                 160

Asp Tyr Gln Arg Glu Thr Trp Asn Leu Ser Asn His Glu Lys Met Lys
                165                 170                 175

Ala Val Pro Val Leu His Gly Glu Gly Asn Arg Leu Phe Lys Leu Gly
            180                 185                 190

Arg Tyr Glu Glu Ala Ser Ser Lys Tyr Gln Glu Ala Ile Ile Cys Leu
        195                 200                 205

Arg Asn Leu Gln Thr Lys Glu Lys Pro Trp Glu Val Gln Trp Leu Lys
    210                 215                 220

Leu Glu Lys Met Ile Asn Thr Leu Ile Leu Asn Tyr Cys Gln Cys Leu
225                 230                 235                 240
```

-continued

| Leu | Lys | Lys | Glu | Glu | Tyr | Tyr | Glu | Val | Leu | Glu | His | Thr | Ser | Asp | Ile |
| | | | 245 | | | | | 250 | | | | | 255 | | |

| Leu | Arg | His | His | Pro | Gly | Ile | Val | Lys | Ala | Tyr | Tyr | Val | Arg | Ala | Arg |
| | | | 260 | | | | | 265 | | | | | 270 | | |

| Ala | His | Ala | Glu | Val | Trp | Asn | Glu | Ala | Glu | Ala | Lys | Ala | Asp | Leu | Gln |
| | | | 275 | | | | | 280 | | | | | 285 | | |

| Lys | Val | Leu | Glu | Leu | Glu | Pro | Ser | Met | Gln | Lys | Ala | Val | Arg | Arg | Glu |
| | | | 290 | | | | | 295 | | | | | 300 | | |

| Leu | Arg | Leu | Leu | Glu | Asn | Arg | Met | Ala | Glu | Lys | Gln | Glu | Glu | Glu | Arg |
| 305 | | | | | 310 | | | | | 315 | | | | | 320 |

| Leu | Arg | Cys | Arg | Asn | Met | Leu | Ser | Gln | Gly | Ala | Thr | Gln | Pro | Pro | Ala |
| | | | 325 | | | | | 330 | | | | | 335 | | |

| Glu | Pro | Pro | Thr | Glu | Pro | Pro | Ala | Gln | Ser | Ser | Thr | Glu | Pro | Pro | Ala |
| | | | 340 | | | | | 345 | | | | | 350 | | |

| Glu | Pro | Pro | Thr | Ala | Pro | Ser | Ala | Glu | Leu | Ser | Ala | Gly | Pro | Pro | Ala |
| | | | 355 | | | | | 360 | | | | | 365 | | |

| Glu | Pro | Ala | Thr | Glu | Pro | Pro | Ser | Pro | Gly | His | Ser | Leu | Gln | His | |
| | | | 370 | | | | | 375 | | | | | 380 | | |

<210> SEQ ID NO 46
<211> LENGTH: 1934
<212> TYPE: DNA
<213> ORGANISM: Homo sapiens

<400> SEQUENCE: 46

| gggcacaagc aatcctccct tctcagcttc ctgagtggcc aggactacag aggactgtat | 60 |
| gctgttctta aggactctct gcttcctgga caagctcaag ctaaggacta catctcccag | 120 |
| caggctgtgc tctgacagct cttggattta aataggattc tgggctctgc tcagagtcag | 180 |
| gctgctgctc agcacccagg acggagagga gcagagaagc agcagaagca gccaagagct | 240 |
| ggagccagac caggaacctg agccagagct ggggttgaag ctggagcagc agcaaaagca | 300 |
| acagcagcta cagaagttgg aacgatgctg gtcaccttgg gactgctcac ctccttcttc | 360 |
| tcgttcctgt atatggtagc tccatccatc aggaagttct ttgctggtgg agtgtgtaga | 420 |
| acaaatgtgc agcttcctgg caaggtagtg gtgatcactg cgccaacac gggcattggc | 480 |
| aaggagacgg ccagagagct cgctagccga ggagcccgag tctatattgc ctgcagagat | 540 |
| gtactgaagg gggagtctgc tgccagtgaa atccgagtgg atacaaagaa ctcccaggtg | 600 |
| ctggtgcgga aattggacct atccgacacc aaatctatcc gagcctttgc tgagggcttt | 660 |
| ctggcagagg aaaagcagct ccatattctg atcaacaatg cgggagtaat gatgtgtcca | 720 |
| tattccaaga cagctgatgg ctttgaaacc cacctgggag tcaaccacct gggccacttc | 780 |
| ctcctcacct acctgctcct ggagcggcta aaggtgtctg cccctgcacg ggtggttaat | 840 |
| gtgtcctcgg tggctcacca cattggcaag attcccttcc acgacctcca gagcgagaag | 900 |
| cgctacagca ggggttttgc ctattgccac agcaagctgg ccaatgtgct ttttactcgt | 960 |
| gagctggcca agaggctcca aggcaccggg gtcaccacct acgcagtgca cccaggcgtc | 1020 |
| gtccgctctg agctggtccg gcactcctcc ctgctctgcc tgctctggcg gctcttctcc | 1080 |
| ccctttgtca agacggcacg ggagggggcg cagaccagcc tgcactgcgc cctggctgag | 1140 |
| ggcctggagc ccctgagtgg caagtacttc agtgactgca gaggacctgg tgtgtctcca | 1200 |
| agggcccgaa ataacaaaac agctgagcgc tatggaatg tcagctgtga gcttctagga | 1260 |
| atccggtggg agtagctggt ggaagagctg cagctttatc aggcccaatc catgccataa | 1320 |

-continued

```
tgaacaggga ccaaggagaa ggccaaccct aaaggattgt cctcttggcc agctggtgct    1380
gcgaatcctg cctgctctga tcctcttgac ccttctggga atgtttgcac acctgacact    1440
cttgtgagac tggcttatgg catgagttgt ggacacctat agagtgttct tctctaagac    1500
ctggaaagtc agcaaccctc tgggggcagc aggactgggc agatcccagg ctgggcatgg    1560
gggtggcaga agagcccgag aaattgggtc agttccctca tcagcaccag aggctcagct    1620
gaggcaagaa gagcaccatc actgccatt tctagggct atacactcca actcttggtt    1680
gatctctttc ttttaaaaa tatttgccac caccctggag tctagaccaa cacacaaaga    1740
tcctggctaa ccctggccta tttagattcc ttcctctcac ctggaccttc ccatttcaat    1800
catgcagatg gtttctttt gtaaagagtt ccgtttgcct ttcaattttt agagaaaata    1860
aagactgcat tcatctcaaa aaaaaaaaaa aaaaaaaaaa aaaaaaaaaa aaaaaaaaaa    1920
aaaaaaaaaa aaaa                                                      1934
```

<210> SEQ ID NO 47
<211> LENGTH: 316
<212> TYPE: PRT
<213> ORGANISM: Homo sapiens

<400> SEQUENCE: 47

```
Met Leu Val Thr Leu Gly Leu Leu Thr Ser Phe Phe Ser Phe Leu Tyr
1               5                   10                  15

Met Val Ala Pro Ser Ile Arg Lys Phe Phe Ala Gly Gly Val Cys Arg
            20                  25                  30

Thr Asn Val Gln Leu Pro Gly Lys Val Val Ile Thr Gly Ala Asn
        35                  40                  45

Thr Gly Ile Gly Lys Glu Thr Ala Arg Glu Leu Ala Ser Arg Gly Ala
    50                  55                  60

Arg Val Tyr Ile Ala Cys Arg Asp Val Leu Lys Gly Glu Ser Ala Ala
65                  70                  75                  80

Ser Glu Ile Arg Val Asp Thr Lys Asn Ser Gln Val Leu Val Arg Lys
                85                  90                  95

Leu Asp Leu Ser Asp Thr Lys Ser Ile Arg Ala Phe Ala Glu Gly Phe
            100                 105                 110

Leu Ala Glu Glu Lys Gln Leu His Ile Leu Asn Asn Ala Gly Val
        115                 120                 125

Met Met Cys Pro Tyr Ser Lys Thr Ala Asp Gly Phe Glu Thr His Leu
    130                 135                 140

Gly Val Asn His Leu Gly His Phe Leu Leu Thr Tyr Leu Leu Leu Glu
145                 150                 155                 160

Arg Leu Lys Val Ser Ala Pro Ala Arg Val Val Asn Val Ser Ser Val
                165                 170                 175

Ala His His Ile Gly Lys Ile Pro Phe His Asp Leu Gln Ser Glu Lys
            180                 185                 190

Arg Tyr Ser Arg Gly Phe Ala Tyr Cys His Ser Lys Leu Ala Asn Val
        195                 200                 205

Leu Phe Thr Arg Glu Leu Ala Lys Arg Leu Gln Gly Thr Gly Val Thr
    210                 215                 220

Thr Tyr Ala Val His Pro Gly Val Val Arg Ser Glu Leu Val Arg His
225                 230                 235                 240

Ser Ser Leu Leu Cys Leu Leu Trp Arg Leu Phe Ser Pro Phe Val Lys
                245                 250                 255

Thr Ala Arg Glu Gly Ala Gln Thr Ser Leu His Cys Ala Leu Ala Glu
```

|  | 260 |  |  |  | 265 |  |  |  | 270 |  |  |
|---|---|---|---|---|---|---|---|---|---|---|---|

Gly Leu Glu Pro Leu Ser Gly Lys Tyr Phe Ser Asp Cys Lys Arg Thr
              275                 280                 285

Trp Val Ser Pro Arg Ala Arg Asn Asn Lys Thr Ala Glu Arg Leu Trp
         290                 295                 300

Asn Val Ser Cys Glu Leu Leu Gly Ile Arg Trp Glu
305                 310                 315

<210> SEQ ID NO 48
<211> LENGTH: 4729
<212> TYPE: DNA
<213> ORGANISM: Homo sapiens

<400> SEQUENCE: 48

| | | | | | |
|---|---|---|---|---|---|
| agtctaggcc | tccgcctccg | ttaccctgga | gcccaggtta | ccgccgctgc | cacccaggag | 60 |
| ccccgatcct | cgcctctgtc | ccatccttgt | gttcaaacct | cccgcatctc | ggcaacctcg | 120 |
| gcacccgccc | ggcagcctcc | gcaggaacca | ggcacccgct | ctttggcggt | cagacgccga | 180 |
| ggccccagct | gggagtttgg | tcctaagagg | gaaggcaagg | aggcgggacg | ccgcatcggc | 240 |
| tctgctgaag | agcctgcggg | ttggaggtgg | gctttgaagt | gggcgtggag | acggcggggg | 300 |
| aggtggaggt | gcgagtataa | atgatcaacc | agaaattatc | ttcaaaggaa | taaaaccaga | 360 |
| agtatgtaaa | taaaaagccc | aagataaaga | aacagaaaag | ctgacactac | atgaagcaga | 420 |
| gggcaaaaaa | gtttatcttc | tggatgccaa | tgtgaattgt | ggtctacaaa | tacattgtgg | 480 |
| agaaaataga | ttgcacagaa | atgaatatta | tcaggatctg | aagactgtga | aaatgttttt | 540 |
| cagtattgtc | atagtctcct | ctggagaaaa | taatctgtga | aattatgtga | atagagacca | 600 |
| ttttcaaaa | caatgggga | aagagcagga | agtccaggta | ctgatcaaga | agaaaggca | 660 |
| ggcaaacacc | attattctta | cttatctgat | tttgaaacgc | cacagtcttc | tggccgatca | 720 |
| tcgctggtca | gttcttcacc | tgcaagtgtt | aggagaaaaa | atcctaaaag | acaaacttca | 780 |
| gatggccaag | tacatcacca | agccctcgg | aaaccaagcc | ctaagggtct | accaaacaga | 840 |
| aagggagtcc | gagtgggatt | tcgctcccag | agcctcaata | gagagccact | tcggaaagat | 900 |
| actgatcttg | ttacaaaacg | gattctgtct | gcaagactgc | taaaaatcaa | tgagttgcag | 960 |
| aatgaagtat | ctgaactcca | ggtcaagtta | gctgagctgc | taaaagaaaa | taaatctttg | 1020 |
| aaaaggcttc | agtacagaca | ggagaaagcc | ctgaataagt | ttgaagatgc | cgaaaatgaa | 1080 |
| atctcacaac | ttatatttcg | tcataacaat | gagattacag | cactcaaaga | acgcttaaga | 1140 |
| aaatctcaag | agaagaacg | ggcaactgag | aaaagggtaa | agatacaga | aagtgaacta | 1200 |
| tttaggacaa | aattttcctt | acagaaactg | aaagagatct | ctgaagctag | acacctacct | 1260 |
| gaacgagatg | atttggcaaa | gaaactagtt | tcagcgagagt | taaagttaga | tgacaccgag | 1320 |
| agaagaatta | aggagctatc | gaaaaaccctt | gaactgagta | ctaacagttt | ccaacgacag | 1380 |
| ttgcttgctg | aaaggaaaag | ggcatatgag | gctcatgatg | aaaataaagt | tcttcaaaag | 1440 |
| gaggtacagc | gactatatca | caaattaaag | gaaaaggaga | gagaactgga | tataaaaaat | 1500 |
| atatattcta | atcgtctgcc | aaagtcctct | ccaaataaag | agaagaact | tgcattaaga | 1560 |
| aaaaatgctg | catgccagag | tgattttgca | gacctgtgta | caaaggagt | acaaaccatg | 1620 |
| gaagacttca | agccagaaga | atatcccttta | actccagaaa | caattatgtg | ttacgaaaac | 1680 |
| aaatgggaag | aaccaggaca | tcttactttg | gacttgcaat | ctcaaaagca | agacaggcat | 1740 |
| ggagaagcag | ggattctaaa | cccaattatg | gaaagagaag | aaaaatttgt | tacagatgaa | 1800 |

```
gaactccatg tcgtaaaaca ggaggttgaa aagctggagg atgaatggga aagagaagaa    1860
cttgataaaa agcaaaaaga aaaggcatct ttactggaaa gagaagaaaa gccagagtgg    1920
gaaactggaa ggtaccaact aggaatgtat ccaattcaga atatggataa attgcaagga    1980
gaggaagaag aaagactgaa gagagaaatg ctacttgcta aactgaatga aattgacaga    2040
gaactccaag attctcgaaa tctaaaatac cctgttttgc cattgttacc tgattttgaa    2100
tcaaaactac actccccaga gagaagcccc aaaacataca ggttctctga atcctcagag    2160
agattattta atgggcatca tttgcaagac atcagtttct caactccaaa aggagaaggt    2220
cagaattcag gaaatgttag aagtccagcc tcccctaatg agttcgcatt tggtagctac    2280
gtgccttcgt ttgcaaaaac atcagagagg tcaaatccat ttagtcaaaa aagtagtttt    2340
ttggatttcc aaagaaacag tatggaaaaa cttagtaaag atggtgtaga tttaattaca    2400
agaaaagaga aaaagctaa tttgatggaa cagttatttg gtgccagtgg tagcagcacc    2460
atttcctcca aaagcagtga cccaaattct gtggcttcca gtaaaggaga cattgaccct    2520
ctaaattttc tccctgggaa taaggcagc agagatcaag aacatgatga agatgaaggc    2580
tttttcctca gtgaaggaag aagttttaat ccaaataggc accgattaaa acatgcagac    2640
gataaaccag cagtaaaagc agctgattct gtagaagatg aaattgaaga agtagcactg    2700
agatgactga ctagagtata catttttttct aattgtaaat attgaaatat tttaatacag    2760
tatttattat aaacatttag acttttaat gctaaatgt ccttattaag gaatgatttt    2820
taatagctaa atacaatgca gttaaaaaga agtagatcat acatacacca catagatagt    2880
ttgccaagaa tgaaggaggc ttttttgaat gaaaccaaaa ataaaaatat gtcttgaaaa    2940
atgaaataga tttaactct tcatccagtg ctatggcaag tttaactgca ctggaggtgg    3000 tattccttt ctacttttat tcctatttat gtatttattt ttaatcatat tctcactgtg    3060
ctaaatacag tcttcccact aattgttgaa tgaaaattaa gggtgaaagt ctgtgttggg    3120
aagtgtagct ccggatggtg gagaaccagt gcttcttagg agcccttccc tttatggata    3180
gggccagggg tccctatctt acgtggcagt cctaagctac tcttgagtga tagcagtcac    3240
aacattggga tttcccattc ctctgaaagt acccacagct aaacactact catttcccaa    3300
tttcagtatt tactgaaatc acttacctac aattctgtta gaatattatg ttgagttcgg    3360 aagcatttc tctgtttgca aggacagtta gttgctctct gtcatagccc gcagaagctt    3420
ggctacagtg taattcctct ccttgttctc ctacactctt tgtatctcag tgactgggtg    3480
taagatttca tgccaaatgc aaggaatagt ggaaatacat accaactgca agaatagaa    3540 aaactttatc ccaatatatt atagaaagat cttcagttca attatgtcca gagtaatata    3600
atttggcaat gttaatgctt ttaagatttg aacttgtcct caaaccaagg agacaacaat    3660
agtgtaatac tattggactt acaggattag ttttaaagca actttgaata gaagtgtttc    3720
agacatagga cttctgcctt gttgactaga gtggatagtt ttctgtttaa atgcattggt    3780
cttttggctg tttgtaattc acttcagctt atagagaagt tgatgacctt ggatcatgct    3840
gggtatgatt ggtctttaaa aagcagtaat ataccaccag cccaaggaga aacattgtt    3900 aaaatgaaga gtggtggaaa tagtgtgttg ggaagaataa aaaatttaga ttggcactta    3960
ttctaaagtg agctgttttt ttcaagaatt tactagcatt tgctcgtagt atgatttctg    4020
acgccagtca tatatactga tgaggggaag gagttactgt gttattctga gttcttataa    4080
atgcatatta ttgaatttca ttgcatgact atttgtcaag acttacctgg ttaggtctcc    4140
aattaaaaga tgtaccacct gtcatcttct aaattgtgtt cctttcattt attgggaaca    4200
```

-continued

```
gaatctctca aaagtgctaa actatattaa aaagttttct taatagattt gtatgtctga    4260
tatgtataac catttactat aatatgttgc aaatcattct aatatatgta aaacaatatt    4320
atttgtaatg cagttattgg taaaatatta tgtaatgtta attttgttcc tagctgctaa    4380
tttttctgcc aaaagtattc taattttcag gttgttttaa aggcttttaa aacttttag    4440 ttaagttttt tattcacgtc atttaaatta gttttttgct tttttctac ctgataatct    4500 ctttaacaag atgcaacaag acagaattat taaaattaaa cctaaagtta agttacagat    4560
ttaaaggcat tatgatatta agcattaaaa ttggagatta aaatgtacaa aacagggttt    4620
tccttatgaa caaaccttac agggtaaatt gttttttttt ctaaatgtca ttaaatttat    4680
ttgtactcag aactgttact aataaaaatt aaaaatgcaa aaaaaaaaa                4729
```

<210> SEQ ID NO 49
<211> LENGTH: 697
<212> TYPE: PRT
<213> ORGANISM: Homo sapiens

<400> SEQUENCE: 49

```
Met Gly Glu Arg Ala Gly Ser Pro Gly Thr Asp Gln Glu Arg Lys Ala
1               5                   10                  15

Gly Lys His His Tyr Ser Tyr Leu Ser Asp Phe Glu Thr Pro Gln Ser
            20                  25                  30

Ser Gly Arg Ser Ser Leu Val Ser Ser Pro Ala Ser Val Arg Arg
        35                  40                  45

Lys Asn Pro Lys Arg Gln Thr Ser Asp Gly Gln Val His His Gln Ala
    50                  55                  60

Pro Arg Lys Pro Ser Pro Lys Gly Leu Pro Asn Arg Lys Gly Val Arg
65                  70                  75                  80

Val Gly Phe Arg Ser Gln Ser Leu Asn Arg Glu Pro Leu Arg Lys Asp
                85                  90                  95

Thr Asp Leu Val Thr Lys Arg Ile Leu Ser Ala Arg Leu Leu Lys Ile
            100                 105                 110

Asn Glu Leu Gln Asn Glu Val Ser Glu Leu Gln Val Lys Leu Ala Glu
        115                 120                 125

Leu Leu Lys Glu Asn Lys Ser Leu Lys Arg Leu Gln Tyr Arg Gln Glu
    130                 135                 140

Lys Ala Leu Asn Lys Phe Glu Asp Ala Glu Asn Glu Ile Ser Gln Leu
145                 150                 155                 160

Ile Phe Arg His Asn Asn Glu Ile Thr Ala Leu Lys Glu Arg Leu Arg
                165                 170                 175

Lys Ser Gln Glu Lys Glu Arg Ala Thr Glu Lys Arg Val Lys Asp Thr
            180                 185                 190

Glu Ser Glu Leu Phe Arg Thr Lys Phe Ser Leu Gln Lys Leu Lys Glu
        195                 200                 205

Ile Ser Glu Ala Arg His Leu Pro Glu Arg Asp Leu Ala Lys Lys
    210                 215                 220

Leu Val Ser Ala Glu Leu Lys Leu Asp Asp Thr Glu Arg Arg Ile Lys
225                 230                 235                 240

Glu Leu Ser Lys Asn Leu Glu Leu Ser Thr Asn Ser Phe Gln Arg Gln
                245                 250                 255

Leu Leu Ala Glu Arg Lys Arg Ala Tyr Glu Ala His Asp Glu Asn Lys
            260                 265                 270

Val Leu Gln Lys Glu Val Gln Arg Leu Tyr His Lys Leu Lys Glu Lys
```

```
            275                 280                 285
Glu Arg Glu Leu Asp Ile Lys Asn Ile Tyr Ser Asn Arg Leu Pro Lys
            290                 295                 300

Ser Ser Pro Asn Lys Glu Lys Glu Leu Ala Leu Arg Lys Asn Ala Ala
305                 310                 315                 320

Cys Gln Ser Asp Phe Ala Asp Leu Cys Thr Lys Gly Val Gln Thr Met
                325                 330                 335

Glu Asp Phe Lys Pro Glu Glu Tyr Pro Leu Thr Pro Glu Thr Ile Met
            340                 345                 350

Cys Tyr Glu Asn Lys Trp Glu Pro Gly His Leu Thr Leu Asp Leu
            355                 360                 365

Gln Ser Gln Lys Gln Asp Arg His Gly Glu Ala Gly Ile Leu Asn Pro
            370                 375                 380

Ile Met Glu Arg Glu Glu Lys Phe Val Thr Asp Glu Glu Leu His Val
385                 390                 395                 400

Val Lys Gln Glu Val Glu Lys Leu Glu Asp Glu Trp Glu Arg Glu Glu
                405                 410                 415

Leu Asp Lys Lys Gln Lys Glu Lys Ala Ser Leu Leu Glu Arg Glu Glu
            420                 425                 430

Lys Pro Glu Trp Glu Thr Gly Arg Tyr Gln Leu Gly Met Tyr Pro Ile
            435                 440                 445

Gln Asn Met Asp Lys Leu Gln Gly Glu Glu Glu Arg Leu Lys Arg
            450                 455                 460

Glu Met Leu Leu Ala Lys Leu Asn Glu Ile Asp Arg Glu Leu Gln Asp
465                 470                 475                 480

Ser Arg Asn Leu Lys Tyr Pro Val Leu Pro Leu Leu Pro Asp Phe Glu
                485                 490                 495

Ser Lys Leu His Ser Pro Glu Arg Ser Pro Lys Thr Tyr Arg Phe Ser
            500                 505                 510

Glu Ser Ser Glu Arg Leu Phe Asn Gly His His Leu Gln Asp Ile Ser
            515                 520                 525

Phe Ser Thr Pro Lys Gly Glu Gly Gln Asn Ser Gly Asn Val Arg Ser
530                 535                 540

Pro Ala Ser Pro Asn Glu Phe Ala Phe Gly Ser Tyr Val Pro Ser Phe
545                 550                 555                 560

Ala Lys Thr Ser Glu Arg Ser Asn Pro Phe Ser Gln Lys Ser Ser Phe
                565                 570                 575

Leu Asp Phe Gln Arg Asn Ser Met Glu Lys Leu Ser Lys Asp Gly Val
            580                 585                 590

Asp Leu Ile Thr Arg Lys Glu Lys Ala Asn Leu Met Glu Gln Leu
            595                 600                 605

Phe Gly Ala Ser Gly Ser Thr Ile Ser Ser Lys Ser Ser Asp Pro
            610                 615                 620

Asn Ser Val Ala Ser Ser Lys Gly Asp Ile Asp Pro Leu Asn Phe Leu
625                 630                 635                 640

Pro Gly Asn Lys Gly Ser Arg Asp Gln Glu His Asp Glu Asp Glu Gly
                645                 650                 655

Phe Phe Leu Ser Glu Gly Arg Ser Phe Asn Pro Asn Arg His Arg Leu
            660                 665                 670

Lys His Ala Asp Asp Lys Pro Ala Val Lys Ala Ala Asp Ser Val Glu
            675                 680                 685

Asp Glu Ile Glu Glu Val Ala Leu Arg
            690                 695
```

<210> SEQ ID NO 50
<211> LENGTH: 3771
<212> TYPE: DNA
<213> ORGANISM: Homo sapiens

<400> SEQUENCE: 50

| | | | | | | |
|---|---|---|---|---|---|---|
| ccagggtgag | attatgaggc | tgagctgaga | atatcaagac | tgtaccgagt | aggggggcctt | 60 |
| ggcaagtgtg | gagagcccgg | cagctggggc | agagggcgga | gtacggtgtg | cgtttacgga | 120 |
| cctcttcaaa | cgaggtagga | aggtcagaag | tcaaaaaggg | aacaaatgat | gtttaaccac | 180 |
| acaaaaatga | aaatccaatg | gttggatatc | cattccaaat | acacaaaggc | aacggataag | 240 |
| tgatccgggc | caggcacaga | aggccatgca | cccgtaggat | tgcactcaga | gctcccaaat | 300 |
| gcataggaat | agaaggggtgg | gtgcaggagg | ctgaggggtg | gggaaagggc | atgggtgttt | 360 |
| catgaggaca | gagcttccgt | ttcatgcaat | gaaaagagtt | tggagacgga | tggtggtgac | 420 |
| tggactatac | acttacacac | ggtagcgatg | gtacactttg | tattatgtat | attttaccac | 480 |
| gatcttttta | aagtgtcaaa | ggcaaatggc | caaatggttc | cttgtcctat | agctgtagca | 540 |
| gccatcggct | gttagtgaca | aagcccctga | gtcaagatga | cagcagcccc | cataactcct | 600 |
| aatcggctct | cccgcgtgga | gtcatttagg | agtagtcgca | ttagagacaa | gtccaacatc | 660 |
| taatcttcca | ccctggccag | ggccccagct | ggcagcgagg | gtgggagact | ccgggcagag | 720 |
| cagagggcgc | tgacattggg | gcccggcctg | gcttgggtcc | ctctggcctt | tccccagggg | 780 |
| ccctcttttcc | ttggggctttt | cttggccgc | cactgctccc | gctcctctcc | ccccatccca | 840 |
| ccccctcacc | ccctcgttct | tcatatcctt | ctctagtgct | ccctccactt | tcatccaccc | 900 |
| ttctgcaaga | gtgtgggacc | acaaatgagt | tttcacctgg | cctggggaca | cacgtgcccc | 960 |
| cacaggtgct | gagtgacttt | ctaggacagt | aatctgcttt | aggctaaaat | gggacttgat | 1020 |
| cttctgttag | ccctaatcat | caattagcag | agccggtgaa | ggtgcagaac | ctaccgcctt | 1080 |
| tccaggcctc | ctcccacctc | tgccacctcc | actctccttc | ctgggatgtg | ggggctggca | 1140 |
| cacgtgtggc | ccagggcatt | ggtgggattg | cactgagctg | ggtcattagc | gtaatcctgg | 1200 |
| acaagggcag | acagggcgag | cggagggcca | gctccggggc | tcaggcaagg | ctgggggctt | 1260 |
| cccccagaca | ccccactcct | cctctgctgg | accccccactt | cataggcac | ttcgtgttct | 1320 |
| caaagggctt | ccaaatagca | tggtggcctt | ggatgcccag | ggaagcctca | gagttgctta | 1380 |
| tctccctcta | gacagaaggg | gaatctcggt | caagagggag | aggtcgccct | gttcaaggcc | 1440 |
| acccagccag | ctcatggcgg | taatgggaca | aggctggcca | gccatcccac | cctcagaagg | 1500 |
| gacccggtgg | ggcaggtgat | ctcagaggag | gctcacttct | gggtctcaca | ttcttggatc | 1560 |
| cggttccagg | cctcggccct | aaatagtctc | cctgggcttt | caagagaacc | acatgagaaa | 1620 |
| ggaggattcg | ggctctgagc | agtttcacca | cccaccccccc | agtctgcaaa | tcctgacccg | 1680 |
| tgggtccacc | tgccccaaag | gcggacgcag | gacagtagaa | gggaacagag | aacacataaa | 1740 |
| cacagagagg | gccacagcgg | ctcccacagt | caccgccacc | ttcctggcgg | ggatgggtgg | 1800 |
| ggcgtctgag | tttggttccc | agcaaatccc | tctgagccgc | ccttgcgggc | tcgcctcagg | 1860 |
| agcagggggag | caagagtgg | gaggaggagg | tctaagtccc | aggcccaatt | aagagatcag | 1920 |
| gtagtgtagg | gtttgggagc | ttttaaggtg | aagaggcccg | ggctgatccc | acaggccagt | 1980 |
| ataaagcgcc | gtgaccctca | ggtgatgcgc | cagggccggc | tgccgtcggg | gacagggctt | 2040 |
| tccatagcca | tgctagagga | tccggtactc | gaggaactga | aaaaccagaa | agttaactgg | 2100 |

| | |
|---|---|
| taagtttagt cttttgtct tttatttcag gtcccggatc cggtggtggt gcaaatcaaa | 2160 |
| gaactgctcc tcagtggatg ttgcctttac ttctaggcct gtacggaagt gttacttctg | 2220 |
| ctctaaaagc tgcggaattg tacccgcggc cgcgggacag ggcttccat agccatggcc | 2280 |
| cagcagtgga gcctccaaag gctcgcaggc cgccatccgc aggacagcta tgaggacagc | 2340 |
| acccagtcca gcatcttcac ctacaccaac agcaactcca ccagaggccc cttcgaaggc | 2400 |
| ccgaattacc acatcgctcc cagatgggtg taccacctca ccagtgtctg gatgatcttt | 2460 |
| gtggtcactg catccgtctt cacaaatggg cttgtgctgg cggccaccat gaagttcaag | 2520 |
| aagctgcgcc acccgctgaa ctggatcctg gtgaacctgg cggtcgctga cctagcagag | 2580 |
| accgtcatcg ccagcactat cagcattgtg aaccaggtct ctggctactt cgtgctgggc | 2640 |
| caccctatgt gtgtcctgga gggctacacc gtctccctgt gtgggatcac aggtctctgg | 2700 |
| tctctggcca tcatttcctg ggagagatgg atggtggtc gcaagccctt tggcaatgtg | 2760 |
| agatttgatg ccaagctggc catcgtgggc attgccttct cctggatctg gtctgctgtg | 2820 |
| tggacagccc cgcccatctt tggttggagc aggtactggc cccacggcct gaagacttca | 2880 |
| tgcggcccag acgtgttcag cggcagctcg tacccgggg tgcagtctta catgattgtc | 2940 |
| ctcatggtca cctgctgcat catcccactc gctatcatca tgctctgcta cctccaagtg | 3000 |
| tggctggcca tccgagcggt ggcaaagcag cagaaagagt ctgaatccac ccagaaggca | 3060 |
| gagaaggaag tgacgcgcat ggtggtgtg atgatctttg cgtactgcgt ctgctgggga | 3120 |
| ccctacacct tcttcgcatg ctttgctgct gccaaccctg gttacgcctt ccaccctttg | 3180 |
| atggctgccc tgccggccta ctttgccaaa agtgccacta tctacaaccc cgttatctat | 3240 |
| gtctttatga accggcagtt tcgaaactgc atcttgcagc ttttcgggaa gaaggttgac | 3300 |
| gatggctctg aactctccag cgcctccaaa acggaggtct caactgtgtc ctcgacccag | 3360 |
| gtagggccta actgaggtct gcctcctacc catcccgccc accggggctt tggccacctc | 3420 |
| tcctttcccc ctccttctcc atccctgtaa aataaatgta atttatcttt gccaaaacca | 3480 |
| aaaaaaacgg aattcgtaat catgtcatag ctgtttcctg tgtgaaattg ttatccgctc | 3540 |
| acaattccac acaacatacg aggcggccgc gcggatccag acatgataag atacattgat | 3600 |
| gagtttggac aaaccacaac tagaatgcag tgaaaaaaat gctttatttg tgaaatttgt | 3660 |
| gatgctattg ctttatttgt aaccattata agctgcaata aacaagttaa caacaacaat | 3720 |
| tgcattcatt ttatgtttca ggttcagggg gaggtgtggg aggttttta g | 3771 |

<210> SEQ ID NO 51
<211> LENGTH: 36
<212> TYPE: DNA
<213> ORGANISM: Artificial Sequence
<220> FEATURE:
<223> OTHER INFORMATION: Synthetic
<400> SEQUENCE: 51

| | |
|---|---|
| gacttgatct tctgttagcc ctaatcatca attagc | 36 |